(12) United States Patent　　(10) Patent No.: US 8,048,661 B2
Burgard et al.　　(45) Date of Patent: Nov. 1, 2011

(54) MICROBIAL ORGANISMS COMPRISING EXOGENOUS NUCLEIC ACIDS ENCODING REDUCTIVE TCA PATHWAY ENZYMES

(75) Inventors: Anthony P. Burgard, San Diego, CA (US); Robin E. Osterhout, San Diego, CA (US); Jun Sun, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 13/011,796

(22) Filed: Jan. 21, 2011

(65) Prior Publication Data

US 2011/0201089 A1　　Aug. 18, 2011

Related U.S. Application Data

(60) Provisional application No. 61/307,437, filed on Feb. 23, 2010, provisional application No. 61/314,570, filed on Mar. 16, 2010.

(51) Int. Cl.
　　*C12N 9/00* (2006.01)
　　*C12N 1/20* (2006.01)
(52) U.S. Cl. .................................. 435/183; 435/252.3
(58) Field of Classification Search ............... 435/252.3, 435/183
　　See application file for complete search history.

(56) References Cited

U.S. PATENT DOCUMENTS

| | | |
|---|---|---|
| 3,513,209 A | 5/1970 | Clement |
| 3,912,586 A | 10/1975 | Kaneyuki et al. |
| 3,965,182 A | 6/1976 | Worrel |
| 4,048,196 A | 9/1977 | Broecker et al. |
| 4,082,788 A | 4/1978 | Mims |
| 4,190,495 A | 2/1980 | Curtiss |
| 4,228,949 A | 10/1980 | Jackson |
| 4,240,578 A | 12/1980 | Jackson |
| 4,301,077 A | 11/1981 | Pesa et al. |
| 4,430,430 A | 2/1984 | Momose et al. |
| 4,624,920 A | 11/1986 | Inoue et al. |
| 4,652,685 A | 3/1987 | Cawse et al. |
| 4,871,667 A | 10/1989 | Imada et al. |
| 4,876,331 A | 10/1989 | Doi |
| 5,079,143 A | 1/1992 | Klein et al. |
| 5,143,833 A | 9/1992 | Datta |
| 5,143,834 A | 9/1992 | Glassner et al. |
| 5,164,309 A | 11/1992 | Gottschalk et al. |
| 5,168,055 A | 12/1992 | Datta et al. |
| 5,173,429 A | 12/1992 | Gaddy et al. |
| 5,182,199 A | 1/1993 | Hartley |
| 5,192,673 A | 3/1993 | Jain et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,403,721 A | 4/1995 | Ward, Jr. et al. |
| 5,413,922 A | 5/1995 | Matsuyama et al. |
| 5,416,020 A | 5/1995 | Severson et al. |
| 5,457,040 A | 10/1995 | Jarry et al. |
| 5,461,139 A | 10/1995 | Gonda et al. |
| 5,475,086 A | 12/1995 | Tobin et al. |
| 5,478,952 A | 12/1995 | Schwartz |
| 5,487,987 A | 1/1996 | Frost et al. |
| 5,502,273 A | 3/1996 | Bright et al. |
| 5,504,004 A | 4/1996 | Guettler et al. |
| 5,512,465 A | 4/1996 | Matsuyama et al. |
| 5,516,883 A | 5/1996 | Hori et al. |
| 5,521,075 A | 5/1996 | Guettler et al. |
| 5,534,432 A | 7/1996 | Peoples et al. |
| 5,563,239 A | 10/1996 | Hubbs et al. |
| 5,573,931 A | 11/1996 | Guettler et al. |
| 5,602,321 A | 2/1997 | John |
| 5,610,041 A | 3/1997 | Somerville et al. |
| 5,616,496 A | 4/1997 | Frost et al. |
| 5,650,555 A | 7/1997 | Somerville et al. |
| 5,663,063 A | 9/1997 | Peoples et al. |

(Continued)

FOREIGN PATENT DOCUMENTS

CN　　1 358 841　　7/2002

(Continued)

OTHER PUBLICATIONS

Kim et al. 2006; Both subunits of ATP-citrate lyase from *Chlorobium tepidum* contribute to catalytic activity. J Bacteriology 188(18): 6544-6552.* Yamamoto et al. 2003. Characterization of two different 2-oxoglutarate:ferredoxin oxidoreductasees from *Hydrogenobacter thermophilus* TK-6. Biochem Biophys Res Commun 312: 1297-1302.*
Mileni et al. 2006; Heterologous production in Wolinella succinogenes and characterization of the quinol:fumarate reducase enzymes from *Helicobacter pylori* and *Campylobacter jejuni*. Biochem J 395: 191-201.*
Abe et al., "Biosynthesis from gluconate of a random copolyester consisting of 3-hydroxybutyrate and medium-chain-length 3-hydroxyalkanoates by *Pseudomonas* sp. 61-3," *Int. J. Biol. Macromol.* 16(3):115-119 (1994).
Allen et al., "DNA sequence of the putA gene from *Salmonella typhimurium*: a bifunctional membrane-associated dehydrogenase that binds DNA," *Nucleic Acids Res.* 21:1676 (1993).
Amarasingham and Davis, "Regulation of alpha-ketoglutarate dehydrogenase formation in *Escherichia coli*," *J. Biol. Chem.* 240: 3664-3668 (1965).

(Continued)

*Primary Examiner* — Karen Carlson
(74) *Attorney, Agent, or Firm* — Jones Day

(57) ABSTRACT

A non-naturally occurring microbial organism includes a microbial organism having a reductive TCA or Wood-Ljungdahl pathway in which at least one exogenous nucleic acid encoding these pathway enzymes is expressed in a sufficient amount to enhance carbon flux through acetyl-CoA. A method for enhancing carbon flux through acetyl-CoA includes culturing theses non-naturally occurring microbial organisms under conditions and for a sufficient period of time to produce a product having acetyl-CoA as a building block. Another non-naturally occurring microbial organism includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. A method for enhancing the availability of reducing equivalents in the presence of carbon monoxide or hydrogen includes culturing this organism for a sufficient period of time to produce a product.

8 Claims, 22 Drawing Sheets

U.S. PATENT DOCUMENTS

| | | | |
|---|---|---|---|
| 5,674,978 A | 10/1997 | Tobin et al. |
| 5,686,276 A | 11/1997 | Lafend et al. |
| 5,700,934 A | 12/1997 | Wolters et al. |
| 5,705,626 A | 1/1998 | Tobin et al. |
| 5,747,311 A | 5/1998 | Jewell |
| 5,750,848 A | 5/1998 | Krüger et al. |
| 5,770,435 A | 6/1998 | Donnelly et al. |
| 5,807,722 A | 9/1998 | Gaddy et al. |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,133,014 A | 10/2000 | Mukouyama et al. |
| 6,136,577 A | 10/2000 | Gaddy et al. |
| 6,156,852 A | 12/2000 | Asrar et al. |
| 6,159,738 A | 12/2000 | Donnelly et al. |
| 6,194,572 B1 | 2/2001 | Buijs et al. |
| 6,204,341 B1 | 3/2001 | Asrar et al. |
| 6,214,592 B1 | 4/2001 | Crouzet et al. |
| 6,228,623 B1 | 5/2001 | Asrar et al. |
| 6,248,862 B1 | 6/2001 | Asrar et al. |
| 6,274,790 B1 | 8/2001 | Kunst et al. |
| 6,277,586 B1 | 8/2001 | Tobin et al. |
| 6,280,986 B1 | 8/2001 | Hespell et al. |
| RE37,393 E | 9/2001 | Donnelly et al. |
| 6,316,262 B1 | 11/2001 | Huisman et al. |
| 6,329,183 B1 | 12/2001 | Skraly et al. |
| 6,340,581 B1 | 1/2002 | Gaddy et al. |
| RE37,543 E | 2/2002 | Krüger et al. |
| 6,353,100 B1 | 3/2002 | Guit et al. |
| 6,361,983 B1 | 3/2002 | Ames |
| 6,432,686 B1 | 8/2002 | Bulthuis et al. |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,455,284 B1 | 9/2002 | Gokarn et al. |
| 6,485,947 B1 | 11/2002 | Rajgarhia et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,660,857 B2 | 12/2003 | Agterberg et al. |
| 6,682,906 B1 | 1/2004 | Tobin et al. |
| 6,686,194 B1 | 2/2004 | Mutzel et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,743,610 B2 | 6/2004 | Donnelly et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,838,176 B2 | 1/2005 | Goto et al. |
| 6,852,517 B1 | 2/2005 | Suthers et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,241,594 B2 | 7/2007 | Lee et al. |
| 7,244,610 B2 | 7/2007 | San et al. |
| 7,256,016 B2 | 8/2007 | San et al. |
| 7,256,021 B2 | 8/2007 | Hermann |
| 7,262,046 B2 | 8/2007 | Ka-Yiu et al. |
| 7,285,402 B2 | 10/2007 | Gaddy et al. |
| 7,309,597 B2 | 12/2007 | Liao et al. |
| 7,314,974 B2 | 1/2008 | Cao et al. |
| 7,371,558 B2 | 5/2008 | Cervin et al. |
| 7,393,676 B2 | 7/2008 | Gokarn et al. |
| 7,432,091 B2 | 10/2008 | Yukawa et al. |
| 7,491,520 B2 | 2/2009 | Raemakers-Franken et al. |
| 7,504,250 B2 | 3/2009 | Emptage et al. |
| 7,569,380 B2 | 8/2009 | San et al. |
| 2002/0012939 A1 | 1/2002 | Palsson |
| 2002/0040123 A1 | 4/2002 | Patil et al. |
| 2002/0106358 A1 | 8/2002 | Hopwood et al. |
| 2002/0164729 A1 | 11/2002 | Skraly et al. |
| 2002/0168654 A1 | 11/2002 | Maranas et al. |
| 2003/0028915 A1 | 2/2003 | Tilton et al. |
| 2003/0032153 A1 | 2/2003 | Yamamoto et al. |
| 2003/0059792 A1 | 3/2003 | Palsson et al. |
| 2003/0087381 A1 | 5/2003 | Gokarn |
| 2003/0113886 A1 | 6/2003 | Brzostowicz et al. |
| 2003/0182678 A1 | 9/2003 | Mitsky et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0079482 A1 | 4/2005 | Maranas et al. |
| 2005/0090645 A1 | 4/2005 | Asakura |
| 2005/0164342 A1 | 7/2005 | Tobin |
| 2005/0170480 A1 | 8/2005 | Huisman |
| 2005/0239179 A1 | 10/2005 | Skraly et al. |
| 2005/0250135 A1 | 11/2005 | Klaenhammer et al. |
| 2005/0287655 A1 | 12/2005 | Tabata et al. |
| 2006/0035348 A1 | 2/2006 | Gulevich et al. |
| 2006/0041152 A1 | 2/2006 | Cantrell et al. |
| 2006/0046288 A1 | 3/2006 | Ka-Yiu et al. |
| 2006/0073577 A1 | 4/2006 | Ka-Yiu et al. |
| 2006/0084155 A1 | 4/2006 | Huisman et al. |
| 2006/0099578 A1 | 5/2006 | Wallace et al. |
| 2006/0110810 A1 | 5/2006 | Rajgarhia et al. |
| 2006/0134760 A1 | 6/2006 | Rieping |
| 2006/0141594 A1 | 6/2006 | San et al. |
| 2006/0172399 A1 | 8/2006 | Nomoto et al. |
| 2006/0281156 A1 | 12/2006 | Aoyama et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto |
| 2007/0092957 A1 | 4/2007 | Donaldson et al. |
| 2007/0111294 A1 | 5/2007 | Burgard et al. |
| 2007/0117191 A1 | 5/2007 | Kamachi et al. |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274522 A1 | 11/2008 | Bramucci et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |

| | | | |
|---|---|---|---|
| 2009/0047718 A1 | 2/2009 | Blaschek et al. | |
| 2009/0047719 A1 | 2/2009 | Burgard et al. | |
| 2009/0068207 A1 | 3/2009 | Breitbart et al. | |
| 2009/0075351 A1 | 3/2009 | Burk et al. | |
| 2009/0100536 A1 | 4/2009 | Adams et al. | |
| 2009/0158452 A1 | 6/2009 | Johnson et al. | |
| 2009/0191593 A1 | 7/2009 | Burk et al. | |
| 2009/0246842 A1 | 10/2009 | Hawkins et al. | |
| 2009/0253192 A1 | 10/2009 | Emptage et al. | |
| 2009/0305364 A1 | 12/2009 | Burgard et al. | |
| 2010/0009419 A1 | 1/2010 | Burk et al. | |
| 2010/0099925 A1 | 4/2010 | Kharas | |
| 2010/0184171 A1 | 7/2010 | Jantama et al. | |
| 2010/0304453 A1 | 12/2010 | Trawick et al. | |
| 2011/0045575 A1 | 2/2011 | Van Dien et al. | |
| 2011/0129904 A1 | 6/2011 | Burgard et al. | |

FOREIGN PATENT DOCUMENTS

| | | | |
|---|---|---|---|
| EP | 0 494 078 | | 7/1992 |
| EP | 1 075 482 A1 | | 2/2001 |
| EP | 1 473 368 | | 11/2004 |
| EP | 1 647 594 A1 | | 4/2006 |
| EP | 2 017 344 | | 1/2009 |
| GB | 1230276 | | 4/1971 |
| GB | 1314126 | | 4/1973 |
| GB | 1344557 | | 1/1974 |
| GB | 1512751 | | 6/1978 |
| JP | 50 006776 | | 1/1975 |
| JP | 62285779 | | 12/1987 |
| KR | 1020060011345 A | | 2/2006 |
| KR | 100676160 B1 | | 1/2007 |
| KR | 100679638 B1 | | 1/2007 |
| KR | 1020070021732 A | | 2/2007 |
| KR | 1020070096348 A | | 10/2007 |
| KR | 10-2009-0025902 | | 3/2009 |
| WO | WO 82/03854 | | 11/1982 |
| WO | WO 91/00917 | | 1/1991 |
| WO | WO 91/13997 | | 9/1991 |
| WO | WO 92/19747 | | 11/1992 |
| WO | WO 93/02187 | | 2/1993 |
| WO | WO 93/02194 | | 4/1993 |
| WO | WO 93/06225 | | 4/1993 |
| WO | WO 94/11519 | | 5/1994 |
| WO | WO 94/12014 | | 6/1994 |
| WO | WO 94/20614 | | 9/1994 |
| WO | WO 94/20615 | | 9/1994 |
| WO | WO 95/11985 | | 5/1995 |
| WO | WO 99/06532 | | 2/1999 |
| WO | WO 99/14313 | | 3/1999 |
| WO | WO 99/58686 | | 11/1999 |
| WO | WO 00/61763 | | 10/2000 |
| WO | WO 01/16346 | | 3/2001 |
| WO | WO 02/42418 | | 5/2002 |
| WO | WO 02/055995 | | 7/2002 |
| WO | WO 02/061115 | | 8/2002 |
| WO | WO 02/090312 | | 11/2002 |
| WO | WO 03/008603 | | 1/2003 |
| WO | WO 03/010322 | | 2/2003 |
| WO | WO 03/106691 | | 12/2003 |
| WO | WO 03/106998 | | 12/2003 |
| WO | WO 2004/018621 | | 3/2004 |
| WO | WO 2004/029235 | | 4/2004 |
| WO | WO 2004/062763 A2 | | 7/2004 |
| WO | WO 2005/026338 | | 3/2005 |
| WO | WO 2005/047498 | | 5/2005 |
| WO | WO 2005/052135 | | 6/2005 |
| WO | WO 2005/068643 | | 7/2005 |
| WO | WO 2006/028063 | | 3/2006 |
| WO | WO 2006/031424 | | 3/2006 |
| WO | WO 2006/034156 | | 3/2006 |
| WO | WO 2007/001982 | | 1/2007 |
| WO | WO 2007/030830 | | 3/2007 |
| WO | WO 2007/050671 A2 | | 5/2007 |
| WO | WO 2007/141208 | | 12/2007 |
| WO | WO 2008/018930 | | 2/2008 |
| WO | WO 2008/024023 | | 2/2008 |
| WO | WO 2008/027742 | | 3/2008 |
| WO | WO 2008/080124 | | 7/2008 |
| WO | WO 2008/089102 A2 | | 7/2008 |
| WO | WO 2008/115840 | | 9/2008 |
| WO | WO 2008/131286 | | 10/2008 |
| WO | WO 2008/137403 | | 11/2008 |
| WO | WO 2008/144626 | | 11/2008 |
| WO | WO 2008/152016 | | 12/2008 |
| WO | WO 2009/011974 | | 1/2009 |
| WO | WO 2009/013160 A2 | | 1/2009 |
| WO | WO 2009/014437 | | 1/2009 |
| WO | WO 2009/023493 | | 2/2009 |
| WO | WO 2009/031766 | | 3/2009 |
| WO | WO 2009/049274 A2 | | 4/2009 |
| WO | WO 2009/094485 A1 | | 7/2009 |
| WO | WO 2009/103026 | | 8/2009 |
| WO | WO 2009/111513 A1 | | 9/2009 |
| WO | WO 2009/113853 | | 9/2009 |
| WO | WO 2009/113855 | | 9/2009 |
| WO | WO 2009/131040 | | 10/2009 |
| WO | WO 2010/006076 | | 1/2010 |
| WO | WO 2010/085731 | | 7/2010 |

OTHER PUBLICATIONS

Amos and McInerey, "Composition of poly-.beta.-hydroxyalkanoate from Syntrophomonas wottei grown on unsaturated fatty acid substrates" *Arch. Microbiol.* 155:103-106 (1991).

Amuro et al., "Isolation and characterization of the two distinct genes for human glutamate dehydrogenase," *Biochem. Biophys. Acta.* 1049:216-218 (1990).

Andre and Jauniaux, "Nucleotide sequence of the yeast UGA1 gene encoding GABA transaminase," *Nucleic Acids Res.* 18:3049 (1990).

Baum et al., "A plant glutamate decarboxylase containing a calmodulin binding domain, Cloning, sequence, and functional analysis" *J. Biol. Chem.* 268:19610-19617 (1993).

Benachenhou-Lahfa et al., "PCR-mediated cloning and sequencing of the gene encoding glutamate dehydrogenase from the archaeon Sulfolobus shilbatae: Identification of putative amino-acid signatures for extremophilic adaptation," *Gene* 140:17-24 (1994).

Blattner et al., "The complete genome sequence of *Escherichia coli* K-12," *Science* 277:1453-1462 (1997).

Botsford et al., "Accumulation of glutamate by *Salmonella typhimurium* in response to osmotic stress," *Appl. Environ. Microbiol.* 60:2568-2574 (1994).

Brandi et al., "Ability of the phototrophic bacterium *Rhodospirillum rubrum* to produce various poly (beta-hydroxyalkanoates): potential sources for biodegradable polyesters," *Int. J. Biol. Macromol.* 11:49-55 (1989).

Bridger et al., "The subunits of succinyl-coenzyme. A synthetase—function and assembly," In Krebs' Citric Acid Cycle—Half a Century and Still Turning, *Biochem. Soc. Symp.* 54:103-111 (1987).

Brosch et al., "Genome plasticity of BCG and impact on vaccine efficacy," *Proc. Natl. Acad. Sci. U.S.A.* 104(13):5596-5601 (2007).

Buck and Guest, "Overexpression and site-directed mutagenesis of the succinyl-CoA synthetase of *Escherichia coli* and nucleotide sequence of a gene (g30) that is adjacent to the suc operon," *Biochem. J.* 260(3):737-747 (1989).

Buck et al., "Cloning and expression of the succinyl-CoA synthetase genes of *Escherichia coli* K12," *J. Gen. Microbiol.* 132(6):1753-1762 (1986).

Bult et al., "Complete genome sequence of the methanogenic archaeon, *Methanococcus jannaschii*," *Science* 273:1058-1073 (1996).

Chavez et al., "The NADP-glutamate dehydrogenase of the cyanobacterium Synechocystis 6803: cloning, transcriptional analysis and disruption of the gdhA gene," *Plant Mol. Biol.* 28:173-188 (1995).

Chen and Lin, "Regulation of the adhE gene, which encodes ethanol dehydrogenase in *Escherichia coli*," *J. Bacteriol.* 173(24):8009-8013 (1991).

Chu et al., "Enzymatically active truncated cat brain glutamate decarboxylase: expression, purification, and absorption spectrum," *Arch. Biochem. Biophys.* 313:287-295 (1994).

Cock et al., "A nuclear gene with many introns encoding ammonium-inducible chloroplastic NADP-specific glutamate dehydrogenase(s) in Chlorella sorokiniana," *Plant Mol. Biol.* 17:1023-1044 (1991).

Cogoni et al., "*Saccharomyces cerevisiae* has a single glutamate synthase gene coding for a plant-like high-molecular-weight polypeptide," *J. Bacteriol.* 177:792-798 (1995).

Cole et al., "Deciphering the biology of *Mycobacterium tuberculosis* from the complete genome sequence " *Nature* 393:537-544 (1998).

Creaghan and Guest, "Succinate dehydrogenase-dependent nutritional requirement for succinate in mutants of *Escherichia coli* K12," *J. Gen. Microbiol.* 107(1):1-13 (1978).

Cunningham and Guest, "Transcription and transcript processing in the sdhCDAB-sucABCD operon of *Escherichia coli*," *Microbiology* 144:2113-2123 (1998).

Darlison et al., "Nucleotide sequence of the sucA gene encoding the 2-oxoglutarate dehydrogenase of *Escherichia coli* K12," *Eur. J. Biochem.* 141(2):351-359 (1984).

Deckert et al., "The complete genome of the hyperthermophilic bacterium *Aquifex aeolicus*," *Nature* 392:353-358 (1998).

Diruggiero et al., "Expression and in vitro assembly of recombinant glutamate dehydrogenase from the hyperthermophilic archaeon *Pyrococcus furiosus*," *Appl. Environ. Microbiol.* 61:159-164 (1995).

Doi et al., "Biosynthesis and characterization of poly(3-hydroxybutyrate-co-4-hydroxybutyrate) in *Alcaligenes eutrophus*," *Int. J. Biol. Macromol.* 12:106-111 (1990).

Doi et al., "Nuclear Magnetic Resonance Studies on Unusual Bacterial Copolyesters of 3-Hydroxybutyrate and 4-Hydroxybutyrate," *Macromolecules* 21:2722-2727 (1988).

Doi, "Microbial Synthesis, Physical Properties, and Biodegradability of Polyhydroxyalkanoates," *Macromol. Symp.* 98:585-599 (1995).

Dover et al., "Genetic analysis of the gamma-aminobutyrate utilization pathway in *Escherichia coli* K-12," *J. Bacteriol.* 117(2):494-501 (1974).

Duncan et al., "Purification and properties of NADP-dependent glutamate dehydrogenase from *Ruminococcus flavefaciens* FD-1," *Appl. Environ. Microbiol.* 58:4032-4037 (1992).

Eggen et al., "The glutamate dehydrogenase-encoding gene of the hyperthermophilic archaeon *Pyrococcus furiosus*: sequence, transcription and analysis of the deduced amino acid sequence," *Gene* 132:143-148 (1993).

Ekiel et al., "Acetate and CO2 assimilation by *Methanothrix concilii*," *J. Bacteriol.* 162(3):905-908 (1995).

Evans et al., "A new ferredoxin-dependent carbon reduction cycle in a photosynthetic bacterium," *Proc. Natl. Acad. Sci. U.S.A.* 55(4):928-934 (1966).

Filetici et al., "Sequence of the GLT1 gene from *Saccharomyces cerevisiae* reveals the domain structure of yeast glutamate synthase," *Yeast* 12:1359-1366 (1996).

Follner et al., "Analysis of the PHA granule-associate proteins GA20 and GA11 in *Methylobacterium extorquens* and *Methylobacterium rhodesianum*," *J. Basic Microbiol.* 37(1):11-21 (1997).

Fong and Palsson, "Metabolic gene-deletion strains of *Escherichia coli* evolve to computationally predicted growth phenotypes," *Nat. Genet.* 36(10):1056-1058 (2004).

Fuhrer, et al., "Computational prediction and experimental verification of the gene encoding the NAD+/NADP+-dependent succinate semialdehyde dehydrogenase in *Escherichia coli*," *J. Bacteriol.* 189:8073-8078 (2007).

Gallego et al., "A role for glutamate decarboxylase during tomato ripening: the characterisation of a cDNA encoding a putative glutamate decarboxylase with a calmodulin-binding site," *Plant Mol. Biol.* 27:1143-1151 (1995).

Gerngross and Martin, "Enzyme-catalyzed synthesis of poly((R)-(-)-3-hydroxybutyrate): formation of macroscopic granules in vitro," *Proc. Natl. Acad. Sci. U.S.A.* 92:6279-6783 (1995).

Gerngross, et al., "Overexpression and purification of the soluble polyhydroxyalkanoate synthase from *Alcaligenes eutrophus*: evidence for a required posttranslational modification for catalytic activity," *Biochemistry* 33:9311-9320 (1994).

Girbal, et al., "Regulation of metabolic shifts in Clostridium acetobutylicum ATCC 824," *FEMS Microbiol. Rev.* 17:287-297 (1995).

Gong et al., "Effects of transport properites of ion-exchange membranes on desalination of 1,3-propanediol fermentation broth by electrodialysis," *Desalination* 191:193-199 (2006).

Gonzalez, et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301-308 (1992).

Gregerson, et al., "Molecular characterization of NADH-dependent glutamate synthase from alfalfa nodules," *Plant Cell* 5:215-226 (1993).

Hein, et al., "Biosynthesis of poly(4-hydroxybutyric acid) by recombinant strains of *Escherichia coli*," *FEMS Microbiol. Lett.* 153(2):411-418 (1997).

Hezayen et al., "Biochemical and enzymological properties of the polyhydroxybutyrate synthase from the extremely halophilic archaeon strain 56," *Arch. Biochem. Biophys.* 403(2):284-291 (2002).

Hiramitsu, et al., "Production of Poly(3-hydroxybutyrate-co-4-hydroxybutyrate) by Alcallgenes latus," *Biotechnol Lett.* 15:461-464 (1993).

Hugler et al., "Autotrophic CO2 fixation via the reductive tricarboxylic acid cycle in different lineages within the phylum Aquificae: evidence for two ways of citrate cleavage," *Environ. Microbiol.* 9:81-92 (2007).

Hugler et al., "Evidence for autotrophic Co2 fixation via the reductive tricarboxylic acid cycle by members of the epsilon subedivision of proteobacteria," *J. Bacteriol.* 187(9):3020-3027.

Jesudason and Marchessault, "Synthetic Poly[(R,S)-.beta.-hydroxyalkanoates] with Butyl and Hexyl Side Chains," *Macromolecules* 27:2595-2602 (1994).

Johnston et al., "Complete nucleotide sequence of *Saccharomyces cerevisiae* chromosome VIII," *Science* 265:2077-2082 (1994).

Jones et al., "Purification and characterization of D-b-hydroxybutyrate dehydrogenase expressed in *Escherichia coli*," *Biochem. Cell Biol.* 71(7-8):406-410 (1993).

Kanao et al., "Kinetic and biochemical analyses on the reaction mechanism of a bacterial ATP-citrate lyase," *Eur. J. Biochem.* 269(14):3409-3416 (2002).

Kaneko et al., "Sequence analysis of the genome of the unicellular cyanobacterium *Synechocystis* sp. strain PCC6803, II. Sequence determination of the entire genome and assignment of potential protein-coding regions," *DNA Res.* 3:109-136 (1996).

Kato et al., "Open reading frame 3 of the barotolerant bacterium strain DSS12 is complementary with cydD in *Escherichia coli*: cydD functions are required for cell stability at high pressure," *J. Biochem.* 120:301-305 (1996).

Kato et al., "Production of a novel copolyester of 3-hydroxybutyric acid with a medium-chainlength 3-hydroxyalkanoic acids by *Pseudomonas* sp. 61-3 from sugars," *Appl. Microbiol. Biotechnol.* 45:363-370 (1996).

Kim and Tabita, "Both subunits of ATP-citrate lyase from *Chlorobium tepidum* contribute to catalytic activity," *J. Bacteriol.* 188(18):6544-6552 (2006).

Kimura et al., "Production of Poly(3-hydroxybutyrate-co-4-hydroxybutyrate) by Pseudomonas acidovorans," *Biotechnol. Lett.* 14(6):445-450 (1992).

Kinnaird et al., "The complete nucleotide sequence of the *Neurospora crassa* am (NADP-specific glutamate dehydrogenase) gene," *Gene* 26:253-260 (1983).

Kirby et al., "Purification and properties of rabbit brain and liver 4-aminobutyrate aminotransferases isolated by monoclonal-antibody Immunoadsorbent chromatography," *Biochem. J.* 230:481-488 (1985).

Kizer et al., "Application of Functional Genomics to Pathway Optimization for Increased Isoprenoid Production," *Appl. Environ. Microbiol.* 74(10):3229-3241 (2008).

Klenk et al., "The complete genome sequence of the hyperthermophilic, sulphate-reducing archaeon *Archaeoglobus fulgidus*," *Nature* 390:364-370 (1997).

Kunioka et al., "New bacterial copolyesters produced in *Alcaligenes eutrophus* from organic acids," *Polym. Commun.* 29:174-176 (1988).

Kwon et al., "Brain 4-aminobutyrate aminotransferase. Isolation and sequence of a cDNA encoding the enzyme," *J. Biol. Chem.* 267:7215-7216 (1992).

Lageveen, et al., "Formation of Polyesters by Pseudomonas oleovorans: Effect of Substrates on Formation and Composition of Poly-(R)-3-Hydroxyalkanoates and Poly-(R)-3-Hydroxyalkenoates," *Appl. Environ. Microbiol.* 54:2924-2932 (1988).

Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," *Appl. Microbiol. Biotechnol.* 42: 901-909 (1995).

Lee et al., "Enhanced biosynthesis of P(3HB-3HV) and P(3HB-4HB) by amplification of the cloned PHB biosynthesis genes in *Alcaligenes eutrophus*," *Biotechnol. Lett.* 19:771-774 (1997).

Lemoigne and Rouklehman, "Fermentation b-Hydroxybutyrique," *Annales des Fermentations* 5:527-536 (1925).

Liebergese II and Steinbuchel, "Cloning and nucleotide sequences of genes relevant for biosynthesis of poly(3-hydroxybutyric acid) in Chromatium vinosum strain D," *Eur. J. Biochem.* 209(1):135-150 (1992).

Liu and Steinbuchel, "Exploitation of butyrate kinase and phosphotransbutyrylase from Clostridium acetobutylicum for the in vitro biosynthesis of poly (hydroxyalkanoic acid)," *Appl. Microbiol. Biotechnol.* 53(5):545-552 (2000).

Lu et al., "Enhanced production of poly(3-hydroxybutyrate-co-3-hydroxyhexanoate) via manipulating the fatty acid beta-oxidation pathway in *E. coli*," *FEMS Microbiol. Lett.* 221(1):97-101 (2003).

Lu et al., "Molecular cloning of polyhydroxyalkanoate synthesis operon from Aeromonas hydrophilia and its expression in *Escherichia coli*," *Biotechnol. Prog.* 20(5):1332-1336 (2004).

Mahadevan et al., "Application of metabolic modeling to drive bioprocess development for the production of value-added chemicals," *Biotechnol. Bioprocess Eng.* 10(5):408-417 (2005).

Majumdar et al., "Functional consequences of substitution in the active site (phosphor) histidine residue of *Escherichia coli* succinyl-CoA synthetase," *Biochim. Biophys. Acta.* 1076:86-90 (1991).

Mandel and Ghosh, "Isolation of a glutamate synthase (GOGAT)-negative, pleiotropically N utilization-defective mutant of Azospirillum brasilense: cloning and partial characterization of GOGAT structural gene," *J. Bacteriol.* 175:8024-8029 (1993).

Mat-Jan et al., "Anaerobic growth defects resulting from gene fusions affecting succinyl-CoA synthetase in *Escherichia coli* K12," *Mol. Gen. Genet.* 215:276-280 (1989).

McLaggan et al., "Interdependence of K+ and glutamate accumulation during osmotic adaptation of *Escherichia coli*," *J. Biol. Chem.* 269:1911-1917 (1994).

Metzer and Halpern, "In vivo cloning and characterization of the gabCTDP gene cluster of *Escherichia coli* K-12," *J. Bacteriol.* 172:3250-3256 (1990).

Metzer et al., "Isolation and properties of *Escherichia coli* K-12 mutants impaired in the utilization of gamma-aminobutyrate," *J. Bacteriol.* 137(3):1111-1118 (1979).

Miles and Guest, "Molecular genetic aspects of the citric acid cycle of *Escherichia coli*," *Biochem. Soc. Symp.* 54:45-65 (1987).

Miller and Brenchly, "Cloning and characterization of gdhA, the structural gene for glutamate dehydrogenase of *Salmonella typhimurium*," *J. Bacteriol.* 157:171-178 (1984).

Miyamoto and Katsuki, "Possible physiological roles of aspartase, NAS- and NADP-requiring glutamate dehydrogenases of *Pseudomonas fluorescens*," *J. Biochem.* 112:52-56 (1992).

Mountain et al., "The Klebsiella aerogenes glutamate dehydrogenase (gdnA) gene: cloning, high-level expression and hybrid enzyme formation in *Escherichia coli*," *Mol. Gen. Genet.* 199:141-145 (1985).

Nagasu et al., "Nucleotide Sequence of the GDH gene coding for the NADP-specific glutamate dehydrogenase of *Saccharomyces cerevisiae*," *Gene* 37:247-253 (1985).

Nexant, "1,4-Butanediol/THF—PERP Program New Report Alert," Nexant ChemSystems PERP Report 02/03-7, p. 1-5 (Jan. 2004).

Niu, et al., "Benzene-free synthesis of adipic acid," *Biotechnol. Prog.* 18:201-211 (2002).

Oliver et al., "Determination of the nucleotide sequence for the glutamate synthase structural genes of *Escherichia coli* K-12," *Gene* 60:1-11 (1987).

Park et al., "Aerobic regulation of the sucABCD genes of *Escherichia coli*, which encode alpha-ketoglutarate dehydrogenase and succinyl coenzyme A synthetase: roles of ArcA, Fnr, and the upstream sdhCDAB promoter," *J. Bacteriol.* 179:4138-4142 (1997).

Park et al., "Isolation and characterization of recombinant mitochondrial 4-aminobutyrate aminotransferase," *J. Biol. Chem.* 268:7636-7639 (1993).

Pelanda et al., "glutamate synthase genes of the diazotroph Azospirillum brasillense. Cloning, sequencing, and analysis of functional domains," *J. Biol. Chem.* 268:3099-3106 (1993).

Poirier et al., "Polyhydroxybutyrate, a Biodegradable Thermoplastic Produced in Transgenic Plants," *Science* 256:520-523 (1992).

Presecan et al., "The Bacillus subtillis genome from gerBC (311 degrees) to licR (334 degrees)," *Microbiology* 143:3313-3328 (1997).

Qiu et al., "Metabolic engineering for the production of copolyesters consisting of 3-hydroxybutyrate and 3-hydroxyhexanoate by *Aeromonas hydrophilia*," *Macromol. Biosci.* 4(3):225-261 (2004).

Radhakrishnan et al., "Applications of metabolic modeling to drive bioprocess development for the production of value-aded chemicals," *Biotechnol. Bioprocess. Eng.* 10:408-417 (2005).

Redenbach et al., "A set of ordered cosmids and a detailed genetic and physical map for the 8 Mb Streptomyces coelicolor A3(2) chromosome," *Mol. Microbiol.* 21:77-96 (1996).

Reed et al., "An expanded genome-scale model of *Escherichia coli* K-12 (iJR904 GSM/GPR)," *Genome Biol.* 4(9):R54 (2003).

Reitzer, "Ammonia Assimillation and the Biosynthesis of Glutamine, Glutamate, Aspartate, Asparagine, l-Alanine, and d-Alanine," In Neidhardt (Ed.), *Escherichia Coli and Salmonella: Cellular and Molecular Biology*, ASM PressL Washington, DC, P. 391-407 (1996).

Ribeiro et al., "Microbial reduction of α-acetyl-γ-butyrolactone," *Tetrahedron: Asymmetry*, 17(6):984-988 (2006).

Saito et al., "Microbial Synthesis and properties of Poly(3-hydroxybutyrate-co-4-hydroxybutyrate)," *Polym. Int.* 39:169-174 (1996).

Sakakibara et al., "Isolation and characterization of a cDNA that encodes maize glutamate dehydrogenase," *Plant Cell Physiol.* 36:789-797 (1995).

Sanchez et al., "Properties and functions of two succinic-semialdehyde dehydrogenases from *Pseudomonas putida* "*Biochim. Biophys. Acta.* 953(3):249-257 (1988).

Sanchez et al., "Purification and properties of two succinic semialdehyde dehydrogenases from *Klebsiella pneumoniae*," *Biochim. Biophys. Acta.* 990(3):225-231 (1989).

Shiraki et al., "Fermentative production of (R)-(-)-(3) hydroxybutyrate using 3-hydroxybutyrate dehydrogenase null mutant of *Ralstonia eutropha* and recombinant *Escherichia coli*," *J. Biosci. Bioeng.* 102(6):529-534 (2006).

Siebers et al., "Reconstruction of the central carbohydrate metabolism of Thermoproteus tenax by use of genomic and biochemical data" *J. Bacteriol.* 186(7):2179-2194 (2004).

Skinner and Cooper, "An *Escherichia coli* mutant defective in the NAD-dependent succinate semialdehyde dehydrogenase," *Arch. Microbiol.* 132(3):270-275 (1982).

Smith et al., "Complete genome sequence of Methanobacterium thermoautotrophicum deltaH: functional analysis and comparative genomics," *J. Bacteriol.* 179:7135-7155 (1997).

Snedecor et al., "Selection, expression, and nucleotide sequencing of the glutamate dehydrogenase gene of Peptostreptococcus asaccharolyticus" *J. Bacteriol.* 173:6162-6167.

Song et al., "Construction of recombinant *Escherichia coli* strains producing poly (4-hydroxybutyric acid) homopolyester from glucose," *Wei Sheng Wu Xue Bao* 45(3):382-386 (2005). (In Chinese, includes English abstract).

Spencer and Guest, "Transcription analysis of the sucAB, aceEF and lpd genes of *Escherichia coli*," *Mol. Gen. Genetics* 200:145-154 (1985).

Spencer et al., "Nucleotide sequence of the sucB gene encoding the dihydrolipoamide succinyltransferase of *Escherichia coli* K12 and homology with the corresponding acetyltransferase " *Eur. J. Biochem.* 141(2):361-374 (1984).

Steinbuchel and Schlegel, "Physiology and molecular genetics of poly(beta-hydroxy-alkanoic acid) synthesis in *Alcaligenes eutrophus*," *Mol. Microbiol.* 5(3):535-542 (1991).

Steinbuchel and Valentin, "Diversity of bacterial polyhydroxyalkanoic acids," *FEMS Microbiol. Lett.* 128:219-228 (1995).
Steinbuchel et al., "A *Pseudomonas* strain accumulating polyesters of 3-hydroxybutyric acid and medium-chain-length 3-hydroxyalkanoic acids " *Appl. Microbiol. Biotechnol.* 37:691-697 (1992).
Syntichaki et al., "The amino-acid sequence similarity of plant glutamate dehydrogenase to the extremophilic archaeal enzyme conforms to its stress-related function," *Gene.* 168:87-92 (1996).
Teller et al., "The glutamate dehydrogenase gene of Clostridium symbiosum, Cloning by polymerase chain reaction sequence analysis and over-expression in *Escherichia coli* " *Eur. J. Biochem.* 206:151-159 (1992).
Thakur et al., "Changes in the Electroencephalographic and .gamma.-Aminobutyric Acid Transaminsase and Succinic Semialdehyde Dehydrogenase in the Allergen Induced Rat Brain," *Biochem. Int.* 16:235-243 (1998).
Tomb et al., "The complete genome sequence of the gastric pathogen *Helicobacter pylori*," *Nature* 388:539-547 (1997).
Tzimagiorgis et al., "Molecular cloning, structure and expression analysis of a full-length mouse brain glutamate dehydrogenase cDNA " *Biochem. Biophys. Acta.* 1089:250-253 (1991).
Tzimagiorgis et al., "Structure and expression analysis of a member of the human glutamate dehydrogenase (GLUD) gene gamily mapped to chromosome 10p11.2," *Hum. Genet.* 91:433-438 (1993).
Umeda et al., "Cloning and sequence analysis of the poly(3-hydroxyalkanoic acid)-synthesis genes of *Pseudomonas acidophila* " *Appl. Biochem. Biotechnol.* 70-72:341-352 (1998).
Valentin et al., "Indentification of 4-hydroxyhexanoic acid as a new constituent of biosynthetic polyhydroxyalkanoic acids from bacteria," *Appl. Microbiol. Biotechnol.* 40:710-716 (1994).
Valentin et al., "Identification of 4-hydroxyvaleric acid as a constituent of biosynthetic polyhydroxyalkanoic acids from bacteria," *Appl. Microbiol. Biotechnol.* 36:507-514 (1992).
Valentin et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.* 46:261-267 (1996).
Valentin et al., "Poly(3-hydroxybutyrate-co-4-hydroxybutyrate) formation from gamma-aminobutyrate and glutamate," *Biotechnol Bioeng.* 67(3):291-299 (2000).
Valentin et al., "Production of poly(3-hydroxybutyrate-co-4-hydroxybutyrate) in recombinant *Escherichia coli* grown on glucose," *J. Biotechnol.* 58:33-38 (1997).
Valle et al., "Complete nucleotide sequence of the glutamate dehydrogenase gene from *Escherichia coli* K-12 " *Gene* 27:193-199 (1984).
Valle et al., "Nucleotide sequence of the promotor and amino-terminal coding region of the glutamate dehydrogenase structural gene of *Escherichia coli*," *Gene* 23:199-209 (1983).
Van der Rest et al., "Functions of the membrane-associated and cytoplasmic malate dehydrogenases in the citric acid cycle of *Escherichia coli*," *J. Bacteriol.* 182(24):6892-6899.
Wang et al., "Isolation of poly-3-hydroxybutyrate metabolism genes from complex microbial communities by phenotypic complementation of bacterial mutants " *Appl. Environ. Microbiol.* 72(1):384-391 (2006).
Ward et al., "Molecular analysis of the role of two aromatic aminotransferases and a broad-specificity aspartate aminotransferase in the aromatic amino acid metabolism of *Pyrococcus furiosus*," *Archaea* 1:133-141 (2002).
Werpy et al., "Top Value Added Chemicals from Biomass. vol. I—Results of Screening for Potential Candidates from Sugars and Synthesis Gas," DOE Report (2004).
Wilkie and Warren, "Recombinant Expression, Purification, and Characterization of Three Isoenzymes of Aspartate Aminotrannsferase from *Arabidopsis thaliana*," *Protein Expr. Purif.* 12:381-389 (1998).
Willadsen and Buckel, "Assay of 4-hydroxybutyryl-CoA dehydrasate from Clostridium aminobutyricum," *FEMS Microbiol. Lett.* 70:187-191 (1990).
Williams et al., "Biodegradable plastics from plants," *CHEMTECH* 26:38-44 (1996).

Wolff et al., "Dehydrogenases involved in the conversion of succinate to 4-hydroxybutanoate by *Clostridium kluyveri*," *Appl. Environ. Microbio.* 59:1876-1882 (1993).
Yang et al., "Continuous cultivation of *Lactobacillus rhamnosus* with cell recycling using an acoustic cell settler," *Biotechnol. Bioprocess. Eng.* 7(6):357-361 (2002).
Yee et al., "Isolation and characterization of a NADP-dependent glutamate dehydrogenase gene from the primitive eucaryote *Giardia lamblia*," *J. Biol. Chem.* 267:7539-7544 (1992).
Yu et al., "sucAB and sucCD are mutually essential genes in *Escherichia coli* " *FEMS Microbiol. Lett.* 254(2):245-250 (2006).
Zhang, et al., "Kinetic and mechanistic characterization of the polyhydroxybutyrate synthase from *Ralstonia eutropha* " *Biomacromolecules* 1(2):244-251 (2000).
Zhou et al., "Functional replacement of the *Escherichia coli* D-(−)-lactate dehydrogenase gene (ldhA) with the L-(+)-lactate dehydrogenase gene (IdhL) from *Pediococcus acidilactici*," *Appl. Environ. Micro.* 69:2237-2244 (2003).
Two pages from URL: openwetware.org/wiki/Synthetic_Biology:BioBricks, Synthetic Biology:BioBricks, portal for information relating to the Registry of Standard Biological Parts (Printed Dec. 21, 2009).
Four pages from URL: shigen.nig.ac.jp/ecoli/pec/genes.List.DetailAction.do (Printed Dec. 21, 2009).
Two pages from URL: scientificamerican.com/article.cfm?id=turning-bacteria-into-plastic-factories-replacing-fossil-fuels (Printed Feb. 17, 2011).
Two pages from URL: www.genome.jp/dbget-bin/www_bget?cdf:CD2966 (Printed Dec. 21, 2009).
Two pages from URL: www.genome.jp/dbget-bin/www_bget?cpe:CPE2531 (Printed Dec. 21, 2009).
Two pages from URL: www.genome.jp/dbget-bin/www_bget?ctc:CTC01366 (Printed Dec. 21, 2009).
Two pages from URL: www.genome.jp/dbget-bin/www_bget?cth:Cthe_0423 (Printed Mar. 4, 2010).
Genbank Accession No. BAB21376.1 GI:12407237 (May 8, 2001).
Genbank Accession No. BAB21375.1 GI:12407235 (May 8, 2001).
Genbank Accession No. AAM72321.1 GI:21647054 (Mar. 12, 2010).
Genbank Accession No. AAM72322.1 GI:21647055 (Mar. 12, 2010).
Genbank Accession No. AB150076.1 GI:114054981 (Jan. 4, 2007).
Genbank Accession No. AB150075.1 GI:114054980 (Jan. 4, 2007).
Genbank Accession No. AB150085.1 GI:114055040 (Jan. 4, 2007).
Genbank Accession No. AB150084.1 GI:114055039 (Jan. 4, 2007).
Genbank Accession No. AAX76834.1 GI:62199504 (Apr. 24, 2005).
Genbank Accession No. AAX76835.1 GI:62199506 (Apr. 24, 2005).
Genbank Accession No. XP_504787.1 GI:50554757 (Oct. 29, 2008).
Genbank Accession No. XP_503231.1 GI:50551515 (Oct. 29, 2008).
Genbank Accession No. NP_596202.1 GI:19112994 (Oct. 20, 2010).
Genbank Accession No. NP_593246.1 GI:19114158 (Oct. 20, 2010).
Genbank Accession No. CAB76165.1 GI:7160185 (Nov. 14, 2006).
Genbank Accession No. CAB76164.1 GI:7160184 (Nov. 14, 2006).
Genbank Accession No. CBF86850.1 GI:259487849 (Sep. 24, 2009).
Genbank Accession No. CBF86848.1 GI:259487848 (Oct. 2, 2009).
Genbank Accession No. BAD17844.1 GI:46849514 (Jun. 9, 2007).
Genbank Accession No. BAD17846.1 GI:46849517 (Jun. 9, 2007).
Genbank Accession No. AAC07285.1 GI:2983723 (Mar. 9, 2010).
Genbank Accession No. AAC07686.1 GI:2984152 (Mar. 9, 2010).
Genbank Accession No. BAD17841.1 GI:46849510 (Jun. 9, 2007).
Genbank Accession No. AAC06486.1 GI:2982866 (Mar. 9, 2010).
Genbank Accession No. NP_661284.1 GI:21673219 (Mar. 30, 2010).
Genbank Accession No. NP_661173.1 GI:21673108 (Mar. 30, 2010).
Genbank Accession No. AAM73055.1 GI:21647851 (Mar. 12, 2010).
Genbank Accession No. NP_012838.1 Gi:6322765 (Jun. 3, 2010).

Genbank Accession No. NP_014515.2 Gi:116006499 (Aug. 17, 2010).
Genbank Accession No. NP_010205.1 Gi:6320125 (Jun. 3, 2010).
Genbank Accession No. NP_417703.1 Gi:16131126 (Oct. 25, 2010).
Genbank Accession No. NP_416129.1 Gi:16129570 (Oct. 25, 2010).
Genbank Accession No. NP_418546.1 Gi:16131948 (Oct. 14, 2010).
Genbank Accession No. NP_416128.1 Gi:16129569 (Oct. 14, 2010).
Genbank Accession No. NP_015061.1 Gi:6324993 (May 17, 2010).
Genbank Accession No. Q8NRN8.1 GI:39931596 (Nov. 2, 2010).
Genbank Accession No. O69294.1 GI:9789756 (Aug. 10, 2010).
Genbank Accession No. P84127 GI:75427690 (Oct. 31, 2006).
Genbank Accession No. P14408.1 GI:120605 (Nov. 30, 2010).
Genbank Accession No. YP_001211906.1 GI:147677691 (Aug. 21, 2010).
Genbank Accession No. CAD36475.1 GI:21615553 (Apr. 15, 2005).
Genbank Accession No. AAC25556.1 GI:3288810 (Jul. 20, 2004).
Genbank Accession No. P76459.1 GI:2492994 (Nov. 30, 2010).
Genbank Accession No. P76458.1 GI:2492990 (Nov. 30, 2010).
Genbank Accession No. P38942.2 GI:1705614 (Feb. 5, 2008).
Genbank Accession No. EDK35586.1 GI:146349050 (Feb. 21, 2008).
Genbank Accession No. NP_570103.1 GI:18543355 (Nov. 10, 2010).
Genbank Accession No. CAA57199.1 GI:559392 (Mar. 22, 1995).
Genbank Accession No. NP_418376.1 GI:16131779 (Oct. 14, 2010).
Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).
Abe et al., "Discovery of amide (peptide) bond synthetic activity in Acyl-CoA synthetase," *J. Biol. Chem.* 283(17):11312-11321 (2008).
Aberhart and Hsu, "Stereospecific hydrogen loss in the conversion of [$^2$H$_7$] isobutyrate to β-hydroxyisobutyrate in *Pseudomonas putida*. The stereochemistry of β-hydroxyisobutyrate dehydrogenase," *J. Chem. Soc.* [Perkin1] 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Phyl.* 46:1724-1734 (2005).
Abo-Dalo et al., "A novel member of the GCN5-related *N*-acetyltransferase superfamily from *Caenorhabditis elegans* preferentially catalyses the *N*-acetylation of thialysine [*S*-(2-aminoethyl)-L-cysteine]," *Biochem. J.* 384:129-137 (2004).
Adams and Kletzin, "Oxidoreductase-type enzymes and redox proteins involved in fermentative metabolisms of hyperthermophilic Archaea," *Adv. Protein Chem.* 48:101-180 (1996).
Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).
Agnihotri and Liu, "Enoyl-CoA Hydratase: Reaction, Mechanism, and Inhibition," *Bioorg. Med. Chem.* 11(1):9-20 (2003).
Ahmed and Lewis, "Fermentation of Biomass-Generated Synthesis Gas: Effects of Nitric Oxide," *Biotechol. Bioeng.* 97:1080-1086 (2007).
Ahmed et al., "Effects of biomass-generated producer gas constituents on cell growth, product distribution and hydrogenase activity of *Clostridium carboxidivorans* P7$^T$," *Biomass Bioenergy* 30(7):665-672 (2006).
Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).
Akatsuka et al., "The Serratia marcescens bioH gene encodes an esterase," *Gene* 302(1-2):185-192 (2003).
Akhtar and Jones, "Construction of a synthetic YdbK-dependent pyruvate:H$_2$ pathway in *Escherichia coli* BL21(DE3)," *Metab. Eng.* 11(3):139-147 (2009).

Alam et al., "Anaerobic Fermentation Balance of *Escherichia coli* as Observed by in Vivo Nuclear Magnetic Resonance Spectroscopy," *J. Bacteriol.* 171(11):6213-6217.
Alber et al., "3-Hydroxypropionyl-Coenzyme A synthetase from Metallosphaera sedula, an enzyme involved in autotrophic CO$_2$ fixation," *J. Bacteriol.* 190:1383-1389 (2008).
Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).
Alber et al., "Propionyl-Coenzyme A synthase from *Chloroflexus aurantiacus*, a key enzyme of the 3-hydroxypropionate cycle for autotrophic CO$_2$ fixation," *J. Biol. Chem.* 277:12137-12143 (2002).
Alber et al., "Study of an alternate glyoxylate cycle for acetate assimilation by Rhodobacter sphaeroides," *Mol. Microbiol.* 61(2):297-309 (2006).
Alberty, Biochemical thermodynamics. *Biochim. Biophys. Acta* 1207:1-11 (1994).
Aldor and Keasling, "Metabolic engineering of poly(3-hydroxybutyrate-co-3-hydroxyvalerate) composition in recombinant *Salmonella enterica* serovar typhimurium," *Biotechnol. Bioeng.* 76(2):108-114 (2001).
Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).
Aldrich Catalog, Sigma-Aldrich Company, Milwaukee, WI, p. 481 (2002).
Aldrich et al., "Cloning and complete nucleotide sequence determination of the catB gene encoding cis,cis-muconate lactonizing enzyme," *Gene* 52:185-195 (1987).
Alexeeva et al., "Requirement of ArcA for redox regulation in *Escherichia coli* under microaerobic but not anaerobic or aerobic conditions," *J. Bacteriol.* 185(1):204-209 (2003).
Alexson et al., "NADH-sensitive propionyl-CoA hydrolase in brown-adipose-tissue mitochondria of the rat," *Biochim. Biophys. Acta* 1005(1):13-19 (1989).
Alhapel et al., "Molecular and functional analysis of nicotinate catabolism in Eubacterium barkeri," *Proc. Natl. Acad. Sci. U.S.A.* 103(33):12341-12346 (2006).
Alper et al., "Construction of lycopene-overproducing *E. coli* strains by combining systematic and combinatorial gene knockout targets," *Nat. Biotechnol.* 23(5):612-616 (2005).
Alper et al., "Identifying gene targets for the metabolic engineering of lycopene biosynthesis in *Escherichi coli*," *Metab. Eng.* 7(3):155-164 (2005).
Alper et al., "Engineering yeast transcription machinery for improved ethanol tolerance and production," *Science* 314(5805):1565-1568 (2006).
Altamirano et al., "Decoupling cell growth and product formation in Chinese hamster ovary cells throguh metabolic control," *Biotechnol. Bioeng.* 76(4):351-360 (2001).
Altmiller and Wanger, "Purification and properties of dihydroxy acid dehydratase from soluble and mitochondrial fractions of *Neurospora crassa*," *Arch. Biochem. Biophys.* 138:160-170 (1970).
Amann et al., "Tightly regulated tac promoter vectors useful for the expression of unfused and fused proteins in *Escherichia coli*," *Gene* 69:301-315 (1988).
Andersen and Hansen, "Cloning of the lysA gene from *Mycobacterium tuberculosis*," *Gene* 124(1):105-109 (1993).
Andersen et al., "A gene duplication led to specialized γ-aminobutyrate and β-alanine aminotransferase in yeast," *FEBS J.* 274:1804-1817 (2007).
Anderson and Dawes, "Occurrence, metabolism, metabolic role, and industrial uses of bacterial polyhydroxyalkanoates," *Microbiol. Rev.* 54(4):450-472 (1990).
Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).
Andersson et al., "Effect of different carbon sources on the production of succinic acid using metabolically engineered *Escherichia coli*," *Biotechnol. Prog.* 23(2):381-388 (2007).

Andreesen and Ljungdahl, "Formate Dehydrogenase of *Clostridium thermoaceticum*: Incorporation of Selenium-75, and the Effects of Selenite, Molybate, and Tungstate on the Enzyme," *J. Bacteriol.* 116(2):867-873 (1973).

Aneja and Charles, "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).

Angrand et al., "Simplified generation of targeting constructs using ET recombination," *Nucleic Acids Res.* 27(17):e16 (1999).

Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68:557-562 (2000).

Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).

Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel enzyme, citryl-CoA lyase, catalysing the second step of the citrate cleavage reaction in *Hydrogenobacter thermophilus* TK-6," *Mol. Microbiol.* 52(3):763-770 (2004).

Aoshima et al., "A novel enzyme, citryl-CoA synthetase, catalysing the first step of the citrate cleavage reaction in *Hydrogenobacter thermophilus* TK-6," *Mol. Microbiol.* 52(3):751-761 (2004).

Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of Enzymes Which Generate or Use Acetoacetyl Thioesters in Rat Liver," *J. Biol. Chem.* 258(8):4725-4733 (1983).

Arendsen et al., "Nitrate-Dependent Regulation of Acetate Biosynthesis and Nitrate Respiration by *Clostridium thermoaceticum*," *J. Bacteriol.* 181:1489-1495 (1999).

Argyrou and Blanchard, "Kinetic and chemical mechanism of *Mycobacterium tuberculosis* 1-deoxy-D-xylulose-5-phosphate isomeroreductase," *Biochemistry* 43:4375-4384 (2004).

Arikawa et al., "Soluble fumarate reductase isoenzymes from *Saccharomyces cerevisiae* are required for anaerobic growth," *FEMS Microbiol. Lett.* 165:111-116.

Aristidou et al., "Metabolic Engineering of *Escherichia coli* to Enhance Recombinant Protein Production through Acetate Reduction," *Biotechnol. Prog.* 11(4):475-478.

Aristidou et al., "Metabolic flux analysis of *Escherichia coli* expressing the *Bacillus subtilis* Acetolactate Synthase in Batch and Continuous Cultures," *Biotechnol. Bioeng.* 63(6):737-749 (1999).

Armstrong et al., "Steroselectivity and sterospecificity of the α,β-dihydroxyacid dehydratase from *Salmonella typhimurium*," *Biochim. Biophys. Acta* 498:282-293.

Arps et al., "Genetics of serine pathway enzymes in *Methylobacterium extorquens* AM1: phosphoenolpyruvate carboxylase and malyl Coenzyme A lyase," *J. Bacteriol.* 175:3776-3783 (1993).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.* 22(1-3):95-101 (2005).

Asanuma et al., "Characterization and transcription of the genes encoding enzymes involved in butyrate production in Butyrivibrio fibrisolvens," *Curr. Microbiol.* 45:203-207 (2003).

Asuncion et al., "Overexpression, purification, crystallization and data collection of 3-methylaspartase from *Clostridium tetanomorphum*," *Acta. Crystallogr. D. Biol. Crystallogr.* 57(Pt 5):731-733 (2001).

Asuncion et al., "The structure of 3-methylaspartase from *Clostridium tetanomorphum* functions via the common enolase chemical step," *J. Biol. Chem.* 277(10):8306-8311 (2002).

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Atteia et al., "Pyruvate formate-lyase and a novel route of eukaryotic ATP synthesis in Chlamydomonas mitochondria," *J. Biol. Chem.* 281:9909-9918 (2006).

Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).

Baba et al., "Construction of *Escherichia coli* K-12 in-frame, single-gene knockout mutants: the Keio collection," *Mol. Syst. Biol.* 2:2006.0008 (2006).

Bachmann and Townsend, "β-Lactam-Lactamsynthetase: a new biosynthetic enzyme," *Proc. Natl. Acad. Sci. U.S.A.* 95(16):9082-9086 (1998).

Bai et al., "Lewis-acid assisted cross metathesis of acrylonitrile with functionalized olefins catalyzed by phosphine-free ruthenium carbene complex," *Org. Biomol. Chem.* 3:4139-4142 (2005).

Bailey et al., "Identification, cloning, purification, and enzymatic characterization of *Mycobacterium tuberculosis* 1-deoxy-D-xylulose 5-phosphate synthase," *Glycobiology* 12:813-820 (2002).

Baird et al., "Enzymes involved in acetoacetate formation in various bovine tissues," *Biochem. J.* 117(4):703-709 (1970).

Baker and van der Drift, "Purification and properties of L-erythro-3,5-diaminohexanoate dehydrogenase from *Clostridium sticklandii*," *Biochemistry* 13(2):292-299 (1974).

Baker et al., "Purification and properties of L-erythro-3,5-diaminohexanoate dehydrogenase from a lysine-fermenting *Clostridium*," *J. Biol. Chem.* 247:7724-7734.

Bakker et al., "Stoichiometry and compartmentation of NADH metabolism in *Saccharomyces cerevisiae*," *FEMS Microbiol. Rev.* 25:15-37 (2001).

Banerji et al., "The cloning and characterization of the arom gene of Pneumocystis carinii," *J. Gen. Microbiol.* 139:2901-2914 (1993).

Barber et al., "Structure and regulation of acetyl-CoA carboxylase genes of metazoa," *Biochimica. Biophysica. Acta* 1733:1-28 (2005).

Barker and Frost, "Microbial synthesis of *p*-hydroxybenzoic acid from glucose," *Biotechnol. Bioeng.* 76:376-390 (2001).

Barker et al., "Butyryl-CoA:Acetoacetate CoA-transferase from Lysine-fermenting clostridium," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick et al., "Quantitative analysis of ribosome binding sites in *E.coli*," *Nucleic Acids Res.* 22(7):1287-1295 (1994).

Barrowman et al., "Immunological comparison of microbial TPP-dependent non-oxidative α-keto acid decarboxylase," *FEMS Microbiol. Lett.* 34:57-60 (1986).

Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).

Barthelmebs et al., "Inducible metabolism of phenolic acids in *Pedicoccus pentosaecus* is encoded by an autoregulated operon which involves a new class of negative transcriptional regulator," *J. Bacteriol.* 182:6724-6731 (2000).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).

Basset et al., "Folate synthesis in plants: the p-aminobenzoate branch is initiated by a bifunctional PabA-PabB protein that is targeted to plastids," *Proc. Natl. Acad. Sci. U. S. A* 101:1496-1501 (2004).

Battaile et al., "Structures of isobutyryl-CoA dehydrogenase and enzyme-product complex: Comparison with isovaleryl- and short-chain acyl-CoA dehydrogenases," *J. Biol. Chem.* 279:16526-16534 (2004).

Baudin et al., "A simple and efficient method for direct gene deletion in *Saccharomyces cerevisiae*," *Nucleic Acids Res.* 21(14):3329-3330 (1993).

Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).

Beatrix et al., "The biotin-dependent sodium ion pump glutaconyl-CoA decarboxylase from *Fusobacterium nucleatum* (subsp. nucleatum). Comparison with the glutaconyl-CoA decarboxylases from gram-positive bacteria," *Arch. Microbiol.* 154(4):362-369 (1990).

Beckers et al., "Large-scale mutational analysis for the annotation of the mouse genome," *Curr. Opin. Chem. Biol.* 6:17-23 (2001).

Benner et al., "Stereospecificity and sterochemical infidelity of acetoacetate decarboxylase (AAD)," *J. Am. Chem. So.* 103:993-994 (1981).

Benning et al., "New reactions in the crotonase superfamily: Structure of methylmalonyl CoA decarboxylase from *Escherichia coli*," *Biochemistry* 39:4630-4639 (2000).

Berg et al., "A 3-Hydroxypropionate/4-Hydroxybutyrate Autotrophic Carbon Dioxide Assimilation Pathway in Archaea," *Science* 318(5857) 1782-1786 (2007).

Bergquist and Gibbs, "Degenerate oligonucleotide gene shuffling," *Meth. Mol. Biol.* 352:191-204 (2007).

Bergquist et al., "Degenerate oligonucleotide gene shuffling (DOGS) and random drift mutagenesis (RNDM): Two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).

Berman and Magasanik, "The pathway of myo-inositol degradation in Aerobacter aerogenes," *J. Biol. Chem.* 241(4):800-806 (1966).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Berrios-Rivera et al., "Metabolic Engineering of *Escherichia coli*: Increase of NADH Availability by Overexpressing an $NAD^+$-Dependent Formate Dehydrogenase," *Metab Eng.* 4(3):217-229 (2002).

Berthold et al., "Structure of the branched-chain keto acid decarboxylase (KdcA) from Lactococcus lacti prvides insights into structural basis for the chemoselective enantioselective carboligation reaction," *Acta. Crystallogr. D. Biol. Crystallogr.* 63(Pt 12):1217-1224 (2007).

Biellmann et al., "Aspartate-β-semialdehyde dehydrogenase from *Escherichia coli*. Purification and general properties," *Eur. J. Biochem.* 104(1):53-58 (1980).

Binieda et al., "Purification, characterization, DNA sequence and cloning of a pimeloyl-CoA synthetase from *Pseudomonas mendocina* 35," *Biochem. J.* 340:793-801 (1999).

Binstock and Schulz, "Fatty acid oxidation complex from *Escherichia coli*," *Methods Enzymol.* 71(Pt C):403-411 (1981).

Birch et al., "Cloning, sequencing, and expression of the gene encoding methylmalonyl-Coenzyme A mutase from Streptomyces cinnamonensis," *J. Bacteriol.* 175(11):3511-3519 (1993).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Bisswanger, "Substrate specificity of the Pyruvate Dehydrogenase Complex from *Escherichia coli*," *J. Biol. Chem.* 256(2):815-822 (1981).

Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase," *Acta. Crystalloqr. D. Biol. Crystallogr.* 60(Pt 8):1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).

Blazquez et al., "Identification and analysis of a glutaryl-CoA dehydrogenase-encoding gene and its cognate transcriptional regulator from Azoarcus sp. CIB," *Environ. Microbiol.* 10(2):474-482 (2008).

Blombach et al., "Corynebacterium glutamicum tailored for high-yield L-valine production," *Appl. Microbiol. Biotechnol.* 79(3):471-479 (2008).

Blomqvist et al., "Characterization of the genes of the 2,3-butanediol operons from Klebsiella terrigena and *Enterobacter aerogenes*," *J. Bacteriol.* 175:1392-1404.

Bobik and Rasche, "HPLC assay for methylmalonyl-CoA epimerase," *Anal. Bioanal. Chem.* 375(3):344-349 (2003).

Bobik and Rasche, "Identification of the human methylmalonyl-CoA racemase gene based on the analysis of prokaryotic gene arrangements. Implications for decoding the human genome," *J. Biol. Chem.* 276(40):37194-37198 (2001).

Bobik et al., "Propanediol Utilization Genes (pdu) of *Salmonella typhimurium*: Three Genes for the Propanediol Dehydratase," *J. Bacteriol.* 179(21):6633-6639 (1997).

Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867.

Boiangiu et al., "Sodium Ion Pumps and Hydrogen Production in Glutamate Fermenting Anaerobic Bacteria," *J. Mol. Microbiol. Biotechnol.* 10:105-119 (2005).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).

Bonnarme et al., "Itaconate biosynthesis in *Aspergillus terreus*," *J. Bacteriol.* 177(12):3573-3578 (1995).

Bonner and Bloch, "Purification and properties of fatty acyl thioesterase I from *Escherichia coli*," *J. Biol. Chem.* 247(10):3123-3133 (1972).

Boronin et al., "Plasmids specifying ε-caprolactam degradation in *Pseudomonas* strains," *FEMS Microbiol Lett.* 22(3):167-170 (1984).

Bose et al., "Genetic analysis of the methanol- and methylamine-specific methyltransferase 2 genes of *Methanosarcina acetivorans* C2A," *J. Bacteriol.* 190(11):4017-4026 (2008).

Bott et al., "Methylmalonyl-CoA decarboxylase from Propionigenium modestum. Cloning and sequencing of the structural genes and purification of the enzyme complex," *Eur. J. Biochem.* 250:590-599 (1997).

Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).

Bottomley et al., "Cloning, sequencing, expression, purification and preliminary characterization of type II dehydroquinase from *Helicobacter pylori*," *Biochem. J.* 319:559-565 (1996).

Bower et al., "Cloning, sequencing, and characterization of the *Bacillus subtilis* biotin biosynthetic operon," *J. Bacteriol.* 178(14):4122-4130 (1996).

Boylan and Dekker, "L-Threonine Dehydrogenase of *Escherichia Coli* K-12," *Biochem. Biophys. Res. Commun.* 85(1):190-197 (1978).

Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).

Brachmann et al., "Designer deletion strains derived from *Saccharomyces cerevisiae* S288C: a useful set of strains and plasmids for PCR-mediated gene disruption and other applications," *Yeast* 14(2):115-132 (1998).

Bradford, "A rapid and sensitive method for the quantitation of microgram quantities of protein utilizing the principle of protein-dye binding," *Anal. Biochem.* 72:248-254 (1976).

Branlant, "Nucleotide sequence of *Escherichia coli* gap gene. Different evolutionary behavior of the $NAD^+$-binding domain and of the catalytic domain of D-glyceraldehyde-3-phosphate dehydrogenase," *Eur. J. Biochem.* 150:61-66 (1985).

Bräsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," *Arch. Microbiol.* 182(4):277-287 (2004).

Braune et al., "The sodium ion translocating glutaconyl-CoA decarboxylase from Acidaminococcus fermentans: cloning and function on the genes forming a second operon," *Mol. Microbiol.* 31(2):473-487 (1999).

Bravo et al., "Reliable, sensitive, rapid and quantitative enzyme-based assay for gamma-hydroxybutyric acid (GHB)," *J. Forensic Sci.* 49:379-387 (2004).

Bredwell et al., "Reactor Design Issues for Synthesis-Gas Fermentations," *Biotechnol. Prog.* 15(5):834-844 (1999).

Breese et al., "Genes coding for the benzoyl-CoA pathway of anaerobic aromatic metabolism in the bacterium Thauera aromatica," *Eur. J. Biochem.* 256(1):148-154.

Breitkreuz et al., "A novel γ-hydroxybutyrate dehydrogenase: Identification and expression of an Arabidopsis cDNA and potential role under oxygen deficiency," *J. Biol. Chem.* 278(42):41552-41556 (2003).

Bremer, "Pyruvate Dehydrogenase, Substrate Specificity and Product Inhibition," *Eur. J. Biochem.* 8:535-540 (1969).

Brey et al., "Cloning of multiple genes involved with cobalamin (Vitamin $B_{12}$) biosynthesis in *Bacillus megaterium*," *J. Bacteriol.* 167:623-630 (1986).

Bro et al., "In silico aided metabloic engineering of *Saccharomyces cerevisiae* for improved bioethanol production," *Metab. Eng.* 8(2):102-111 (2006).

Brooke et al., "GAMS: S User's Guide. GAMS Development Corporation," (1998).

Broun et al., "Catalytic plasticity of fatty acid modification enzymes underlying chemical diversity of plant lipids," *Science* 282:1315-1317 (1998).

Brown et al., "A role for *pabAB*, a p-aminobenzoate synthase gene of *Streptomyces venezuelae* ISP5230, in chloramphenicol biosynthesis," *Microbiol.* 142 ( Pt 6):1345-1355 (1996).

Brown et al., "Comparative structural analysis and kinetic properties of lactate dehydrogenases from the four species of human malarial parasites," *Biochemistry* 43:6219-6229 (2004).

Browner et al., "Sequence analysis, biogenesis, and mitochondrial import of the α-subunit of rat liver propionyl-CoA carboxylase," *J. Biol. Chem.* 264:12680-12685 (1989).

Bu and Tobin, "The exon-intron organization of the genes (GAD1 and GAD2) encoding two human glutamate decarboxylases ($GAD_{67}$ and $GAD_{65}$) suggests that they derive from a common ancestral GAD," *Genomics* 21:222-228 (1994).

Bu et al., "Two human glutamate decarboxylases, 65-kDa GAD and 67-kDa GAD, are each encoded by a single gene," *Proc. Natl. Acad. Sci. U.S.A.* 89:2115-2119 (1992).

Buchanan et al., "An extremely thermostable aldolase from Sulfolobus solfataricus with specificity for non-phosphorylated substrates," *Biochem. J.* 343:563-570 (1999).

Buck et al., "Primary structure of the succinyl-CoA synthetase of *Escherichia coli*," *Biochem.* 24(22):6245-6252 (1985).

Buckel and Barker, "Two pathways of glutamate fermentation by anaerobic bacteria," *J. Bacteriol.* 117(3):1248-1260 (1974).

Buckel and Golding, "Radical enzymes in anaerobes," *Annu. Rev. Microbiol.* 60:27-49 (2006).

Buckel and Golding, "Radical species in the catalytic pathways of enzymes from anaerobes," *FEMS Microbiol. Rev.* 22(5):523-541 (1999).

Buckel et al., "ATP-Driven electron transfer in enzymatic radical reactions," *Curr. Opin. Chem. Biol.* 8:462-467 (2004).

Buckel et al., "Glutaconate CoA-Transferase from Acidaminococcus fermentans," *Eur. J. Biochem.* 118:315-321 (1981).

Buckel et al., "Radical-mediated dehydration reactions in anaerobic bacteria," *Biol. Chem.* 386:951-959 (2005).

Buckel, "Sodium ion-translocating decarboxylases," *Biochimica. Biophysica. Acta* 1505:15-27 (2001).

Bueding and Yale, "Production of α-methylbutyric acid by bacteria-free *Ascaris lumbricoides*," *J. Biol. Chem.* 193:411-423 (1951).

Bühler and Simon, "On the kinetics and mechanism of enoate reductase," *Hoppe Seylers Z. Physiol. Chem.* 363(6):609-625 (1982).

Bunch et al., "The *IdhA* gene encoding the fermentative lactate dehydrogenase of *Escherichia coli*," *Microbiol.* 143:187-195 (1997).

Burgard and Maranas, "Probing the performance limits of the *Escherichia coli* metabolic network subject to gene additions or deletions," *Biotechnol. Bioeng.* 74:364-375 (2001).

Burgard et al., "Minimal Reaction Sets for *Escherichia coli* Metabolism under Different Growth Requirements and Uptake Environments," *Biotechnol. Prog.* 17:791-797 (2001).

Burgard et al., "Optknock: a bilevel programming framework for identifying gene knockout strategies for microbial strain optimization," *Biotechnol. Bioeng.* 84(6):647-657 (2003).

Burke et al., "The Isolation, Characterization, and Sequence of the Pyruvate Kinase Gene of *Saccharomyces cerevisiae*," *J. Biol. Chem.* 258(4):2193-2201 (1983).

Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).

Buu et al., "Functional characterization and localization of acetyl-CoA hydrolase, Ach1p, in *Saccharomyces cerevisiae*," *J. Biol. Chem.* 278:17203-17209 (2003).

Buzenet et al., "Purification and properties of 4-Aminobutyrate 2-Ketoglutarate Aminotransferase From Pig Liver," *Biochimica. Biophysica. Acta* 522:400-411 (1978).

Byrnes et al., "Thermodynamics of reactions catalyzed by anthranilate synthase," *Biophys. Chem.* 84:45-64 (2000).

Cahyanto et al., "Regulation of aspartokinase, asparate semialdehyde dehydrogenase, dihydrodipicolinate synthease and dihydropdipicolinate reductase in *Lactobacillus plantarum*," *Microbiology* 152 (Pt 1): 105-112 (2006).

Caldovic and Tuchman, "N-Acetylglutamate and its changing role through evolution," *Biochem. J.* 372:279-290 (2003).

Calhoun et al., "Threonine deaminase from *Escherichia coli*. I. Purification and properties," *J. Biol. Chem.* 248(10):3511-3516 (1973).

Camara et al., "Characterization of a Gene Cluster Involved in 4-Chlorocatechol Degradation by *Pseudomonas reinekei* MT1," *J. Bacteriol.* 191(15):4905-4915.

Campbell and Cronan, Jr., "The enigmatic *Escherichia coli* fadE gene is yafH," *J. Bacteriol.* 184(13):3759-3764 (2002).

Campbell et al., "A complete shikimate pathway in *Toxoplasma gondii*: an ancient eukaryotic innovation," *Int. J. Parasitol.* 34:5-13 (2004).

Campbell et al., "A new *Escherichia coli* metabolic competency: growth on fatty acids by a novel anaerobic β-oxidation pathway," *Mol. Microbiol.* 47(3):793-805 (2003).

Canovas et al., "Characterization of the genes for the biosynthesis of the compatible solute ectoine in the moderately haliphilic bacterium Halomonas elongata DSM 3043," *Syst. Appl. Microbiol.* 21:487-497 (1998).

Cao et al., "Simultaneous Production and recovery of Fumaric Acid from Immobilized *Rhizopus oryzae* with a Rotary biofilm Contactor and an Adsorption Column," *Appl. Environ. Microbiol.* 62(8):2926-2931 (1996).

Carlini et al., "Guerbet condensation of methanol with n-propanol to isobutyl alcohol over heterogeneous copper chromite/Mg-Al mixed oxides catalysts," *J. Mol. Catal. A. Chem.* 220:215-220 (2004).

Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A. Chem.* 206:409-418 (2003).

Carlini et al., "Selective synthesis of isobutanol by means of the Guebet reaction Part 1. Methanol/n-propanol condensation by using copper based catalytic systems," *J. Mol. Catal. A. Chem.* 184:273-280 (2002).

Carlini et al., "Selective synthesis of isobutanol by means of the Guerbet reaction Part 2. Reaction of methanol/ethanol and methanol/ethanol/n-propanol mixtures over copper based MeONa catalytic systems," *J. Mol. Catal. A. Chem.* 200:137-146 (2003).

Carpenter et al., "Structure of dehydroquinate synthase reveals an active site capable of multistep catalysis," *Nature* 394:299-302 (1998).

Carretero-Pau let et al., "Expression and molecular analysis of the Arabidopsis DXR gene encoding1-deoxy-D-xylulose 5-phosphate reductoisomerase, the firszt committed enzyme of the 2-C-methyl-D-erythritiol 4-phosphate pathway," *Plant Physiol.* 129:1581-1591 (2002).

Carta et al., "Production of fumaric acid by fermentation of enzymatic hydrolysates derived from *Cassava bagasse*," *Biores. Tech.* 68:23-28 (1999).

Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).

Cary et al., "Cloning and expression of *Clostridium acetobutylicum* phosphotransbutyrylase and butyrate kinase genes in *Escherichia coli*," *J. Bacteriol.* 170(10):4613-4618 (1988).

Casero and Pegg, "Spermidine/spermine $N^1$-acetyltransferase-the turning point in polyamine metabolism," *FASEB J.* 7:653-661 (1993).

Caspi et al., "MetaCyc: a multiorganism database of metabolic pathways and enzymes," *Nucleic Acids Res.* 34(Database issue):D511-D516 (2006).

Cavin et al., "Gene cloning, transcriptional analysis, purification, and characterization of phenolic acid decarboxylase from *Bacillus subtilis*," *Appl. Environ. Microbiol.* 64(4):1466-1471 (1998).

Cha and Bruce, "Stereo- and regiospecific cis,cis-muconate cycloisomerization by *Rhodococcus rhodochrous* N75," *FEMS Microbiol. Lett.* 224:29-34 (2003).

Cha and Parks, Jr., "Succinic Thiokinase. I. Purification of the Enzyme from Pig Heart," *J. Biol. Chem.* 239:1961-1967 (1964).

Chandra et al. "Pyruvate decarboxylase: a key enzyme for the oxidative metabolism of lactic acid by Acetobacter pasteurianus," *Arch. Microbiol.* 176:443-451 (2001).

Chang et al., "p-Aminobenzoic acid and chloramphenicol biosynthesis in *Streptomyces venezuelae*: gene sets for a key enzyme, 4-amino-4-deoxychorismate synthase," *Microbiology* 147:2113-2126 (2001).

Chang et al., "Effects of deletions at the carboxyl terminus of Zymomonas mobills pyruvate decarboxylase on the kinetic properties and substrate specificity," *Biochemistry* 39(31):9430-9437 (2000).

Chao and Ramsdell, "The effects of wall populations on coexistence of bacteria in the liquid phase of chemostat cultures," *J. Gen. Microbiol.* 131(5):1229-1236 (1985).

Chaparro-Riggers et al., "Comparison of Three Enoate Reductases and their Potential Use for Biotransformations," *Adv. Synth. Catal.* 349:1521-1531 (2007).

Charles et al., "The isolation and nucleotide sequence of the complex AROM locus of *Aspergillus nidulans*," *Nucleic Acids Res.* 14:2201-2213 (1986).

Charrier et al., "A novel class of CoA-transferase involved in short-chain fatty acid metabolism in butyrate-producing human colonic bacteria," *Microbiology* 152:179-185 (2006).

Chatterjee et al., "A general model for selectively in olefin cross methathesis," *J. Am. Chem. Soc.* 125(37):11360-11370 (2003).

Chatterjee et al., "Mutation of the ptsG Gene Results in Increased Production of Succinate in Fermentation of Glucose by *Escherichia coli*," *Appl. Env. Microbiol.* 67:148-154 (2001).

Chaudhuri et al., "Identification of the active-site lysine residues of two biosynthetic 3-dehydroquinases," *Biochem. J.* 275:1-6 (1991).

Chen and Hiu, "Acetone-Butanol-Isopropanol Production by *Clostridium beijerinckii* (Synonym, *Clostridium butylicum*)," *Biotechnology Letters* 8(5):371-376 (1986).

Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).

Chen et al., "The control region of the pdu/cob regulon in *Salmonella typhimurium*," *J. Bacteriol.* 176:5474-5482 (1994).

Cheng et al., "Genetic Analysis of a Gene Cluser for Cyclohexanol Oxidation in Acinetobacter sp. Strain SE19 by In Vitro Transportation," *J. Bacteriol.* 182(17):4744-4751 (2000).

Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).

Cheng et al., "Mammalian Wax Biosynthesis. II. Expression cloning of wax synthase cDNAs encoding a member of the acyltransferase enzyme family," *J. Biol. Chem.* 279(36):37798-37807 (2004).

Cheng et al., "Structural basis for shikimate-binding specificity of *Helicobacter pylori* shikimate kinase," *J. Bacteriol.* 187:8156-8163 (2005).

Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).

Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).

Cho et al., "Critical residues for the Coenzyme specificity of $NAD^+$-dependent 15-hydroxyprostaglandin dehydrogenase," *Arch. Biochem. Biophys.* 419:139-146 (2003).

Choi et al, "Olefin Metathesis Involving Ruthenium Enoic Carbene Complexes," *J. Am. Chem. Soc.* 123(42):10417-10418 (2001).

Choi et al., "Enhanced production of cis,cis-muconate in a cell-recycle bioreactor," *J. Ferment. Bioeng.* 84:70-76 (1997).

Choi-Rhee and Cronan, "The biotin carboxylase-biotin carboxyl carrier protein complex of *Escherichia coli* acetyl-CoA carboxylase," *J. Biol. Chem.* 278:30806-30812 (2003).

Chopra et al., "Expression, purification, and biochemical characterization of *Mycobacterium tuberculosis* aspartate decarboxylase, PanD," *Protein Expr. Purif.* 25:533-540 (2002).

Chou et al., "Effect of Modulated Glucose Uptake on High-Level Recombinant Protein Production in a Dense *Escherichia coli* Culture," *Biotechnol. Prog.* 10:644-647 (1994).

Chowdhury et al., "3-Hydroxyisobutyrate dehydrogenase from *Pseudomonas putida* E23: purification and characterization," *Biosci. Biotechnol. Biochem.* 60(12):2043-2047 (1996).

Chowdhury et al., "Cloning and overexpression of the 3-hydroxyisobutyrate dehydrogenase gene from *Pseudomonas putida* E23," *Biosci. Biotechnol. Biochem.* 67(2):438-441 (2003).

Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).

Chuakrut et al., "Characterization of a bifunctional archael acyl Coenzyme A carboxylase," *J. Bacteriol.* 185:938-947 (2003).

Clark and Ljungdahl, "Purification and properties of 5,10-methylenetetrahydrofolate reductase from *Clostridium formicoaceticum*," *Methods Enzymol.* 122:392-399 (1986).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark et al., "Mutants of *Escherichia coli* defective in acid fermentation," *Appl. Biochem. Biotechnol.* 17:163-173 (1988).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-Hydroxyacid Dehydrogenase With New Substrate Specificity," *Biochem. Biophys. Res. Commun.* 148:15-23 (1987).

Clausen et al., "PAD1 encodes phenylarcrylic acid decarboxylase which confers resistance to cinnamic acid in *Saccharomyces cerevisiae*," *Gene* 142:107-112 (1994).

Coco et al., "DNA shuffling method for generating highly recombined genes and evolved enzymes," *Nat. Biotechnol.* 19:354-359 (2001).

Coggins et al., "The arom multifunctional enzyme from *Neurospora crassa*," *Methods Enzymol.* 142:325-341 (1987).

Colby and Chen, "Purification and properties of 3-hydroxybutyryl-Coenzyme A dehydrogenase from *Clostridium beijerinckii* ("*Clostridium butylicum*") NRRL B593," *Appl. Environ. Microbiol.* 58:3297-3302 (1992).

Coleman, "Expression of a glutamate decarboxylase homologue is required for normal oxidative stress tolerance in *Saccharomyces cerevisiae*," *J. Biol. Chem.* 276:244-250. (2001).

Conrad et al., "D- and L-Isoleucine Metabolism and Regulation of Their Pathways in *Pseudomonas putida*," *J. Bacteriol.* 118(1):103-111 (1974).

Cooper, "Glutamate-γ-aminobutyrate transaminase," *Methods Enzymol.* 113:80-82 (1985).

Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1991).

Cox et al., "Development of a metabolic network design and optimization framework incorporating implementation constraints: A succinate production case study," *Metab. Eng.* 8(1):46-57 (2006).

Craney et al., "A synthetic luxCDABE gene cluster optimized for expression in high-GC bacteria," *Nucleic Acids Res.* 35(6):e46 (2007).

Cukalovic et al., "Feasibility of production method for succinic acid derivatives: a marriage of renewable resources and chemical technology," *Biofuels Bioprod. Bioref.* 2:505-529 (2008).

Cunningham et al., "Transcriptional regulation of the aconitase genes (acnA and acnB) of *Escherichia coli*," *Microbiology* 143(Pt 12):3795-3805 (1997).

Dai et al., "Highly Selective Diels-Alder Reactions of directly Connected Enzyne Dienphiles," *J. Am. Chem. Soc.* 129:645-657 (2007).

Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).

Dal et al., "Transcriptional Organization of Genes for Protocatechuate and quinate Degradation from Acinetobacter sp. Strain ADP1," *Appl. Environ. Microbiol.* 71(2):1025-1034 (2005).

Dangel et al., "Anaerobic metabolism of cyclohexanol by denitrifying bacteria," *Arch. Microbiol.* 150(4):358-362 (1988).

Dangel et al., "Enzyme reactions involved in anaerobic cyclohexanol metabolism by a dentitrifying *Psedomonas* species," *Arch. Microbiol.* 152:273-279 (1989).

D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*," *J. Biol. Chem.* 266(35):23953-23958 (1991).

Das et al., "Characterization of a corrinoid protein involved in the C1 metabolism of strict anaerobic bacterium *Moorella thermoacetica*," *Proteins* 67(1):167-176 (2007).

Datar et al., "Fermentation of biomass-generated producer gas to ethanol," *Biotechnol. Bioeng.* 86(5):587-594 (2004).

Datsenko et al., "One-step inactivation of chromosomal genes in *Escherichia coli* K-12 using PCR products," *Proc. Natl. Acad. Sci. U.S.A.* 97:6640-6645 (2000).

Datta et al., "Covalent structure of biodegradative threonine dehydratase of *Escherichi coli*: homology with other dehydratases," *Proc. Natl. Acad. Sci. U.S.A.* 84(2):393-397 (1987).

Davey and Trudgill, "The metabolism of trans-cyclohexan-1,2-diol by an Acinetobacter species," *Eur. J. Biochem.* 74(1):115-127 (1977).

Davids et al, "Characterization of the N-acetyltransferases respectively responsible for arylalkylamine and diamine acetylation in *Ascaris suum*," *Mol. Biochem. Parasitol.* 64(2):341-344 (1994).

Davie et al., "Expression and assembly of a functional E1 component (α2β2) of mammalian branched-chain α-ketoacid dehydrogenase complex in *Escherichia coli*," *J. Biol. Chem.* 267:16601-16606 (1992).

De Biase et al., "Isolation, overexpression, and biochemical characterization of the two isoforms of glutamic acid decarboxylase from *Escherichia coli*," *Protein Expr. Purif.* 8:430-438 (1996).

de Bok et al., "Two W-containing formate dehydrogenases ($CO_2$-reductases) involving syntrophic propionate oxidation by *Syntrophobacter fumaroxidans*," *Eur. J. Biochem.* 270:2476-2485 (2003).

de Crecy et al., "Development of a novel continuous culture device for experimental evolution of bacterial populations," *Appl. Microbiol. Biotechnol.* 77(2): 489-496 (2007).

de la Torre et al., "Identification and functional analysis of a prokaryotic-type aspartate aminotransferase: implications for plant amino acid metabolism," *Plant. J.* 46(3):414-425 (2006).

de Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).

de Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).

de Smidt et al., "The alcohol dehydrogenases of *Saccharomyces cerevisiae*: a comprehensive review," *FEMS Yeast Rev.* 7:967-978 (2008).

Deana, "Substrate specificity of a dicarboxyl-CoA: dicarboxylic acid Coenzyme A transferase from rat liver mitochondria," *Biochem. Int.* 26(4):767-773 (1992).

DeFeyter and Pittard, "Purification and properties of shikimate kinase II from *Escherichia coli* K-12," *J. Bacteriol.* 165:331-333 (1986).

Del Campillo-Campbell et al., "Biotin-requiring Mutants of *Escherichia coli* K-12," *J. Bacteriol.* 94(6):2065-2066 (1967).

Deno, "The Diels-Alder Reaction with α,β,γ,δ-Unsaturated Acids," *J. Am. Chem. Soc.* 72:4057-4059 (1950).

Department of Energy, "Top value added chemicals from biomass. Volume I—Results of Screening for Potential Candidates from Sugars and Synthesis Gas," *Biomass*, Aug. 2004.

Desvaux, "*Clostridium cellulolyticum*: model organism of mesophilic cellulolytic clostridia," *FEMS Microbiol. Rev.* 29(4):741-764 (2005).

Devos et al., "Practical limits of function prediction," *Proteins* 41:98-107 (2000).

Di Gennaro, "Styrene lower catabolic pathway in *Pseudomonas fluorescens* ST: identification and characterization of genes for phenylacetic acid degradation," *Arch. Microbiol.* 188(2):117-125 (2007).

Diao et al., "Crystal structure of butyrate kinase 2 from *Thermotoga maritima*, a member of the ASKHA superfamily of phosphotransferases," *J. Bacteriol.* 191:2521-2529 (2009).

Diao et al., "Crystallization of the butyrate kinase 2 from *Thermotoga maritima* mediated by vapor diffusion of acetic acid," *Acta. Crystallogr. D. Biol. Crystallogr.* 59(Pt 6):1100-1102 (2003).

Dias et al., "Well-Defined Ruthenium Olefin Metathesis Catalyst: Mechanism and Activity," *J. Am. Chem. Soc.* 119(17):3887-3897 (1997).

Diaz et al., "Gene cloning, heterologous overexpression and optimized refolding of the NAD-glutamate dehydrogenase from *Haloferax mediterranei*," *Extremophiles* 10:105-115 (2006).

Diderichsen et al., "Cloning of aldB, Which Encodes α-Acetolactate Decarboxylase, an Exoenzyme from *Bacillus brevis*," *J. Bacteriol.* 172(8):4315-4321 (1990).

Dittrich et al., "Redistribution of Metabolic Fluxes in the Central Aerobic Metabolic Pathway of *E. coli* Mutant Strains with Deletion of the *ackA-pta* and *poxB* Pathways for the Synthesis of Isoamyl Acetate," *Biotechnol Prog.* 21(2):627-631 (2005).

Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).

Do et al., "Growth of *Rhodospirillum rubrum* on synthesis gas: conversion of CO to $H_2$ and Poly-β-hydroxyalkanoate," *Biotechnol. Bioeng.* 97(2):279-286 (2007).

Dobbek et al., "Crystal structure of a carbon monoxide dehydrogenase reveals a [Ni-4Fe-5S] cluster," *Science* 293(5533):1281-1285 (2001).

Dombek and Ingram, "Ethanol production during batch fermentation with *Saccharomyces cerevisiae*: Changes in glycolytic enzymes and internal pH," *Appl. Environ. Microbiol.* 53:1286-1291 (1987).

Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).

Donnelly and Cooper, "Two succinic semialdehyde dehydrogenases are induced when *Escherichia coli* K-12 Is grown on γ-aminobutyrate," *J. Bacteriol.* 145:1425-1427 (1981).

Donnelly et al., "A novel fermentation pathway in an *Escherichia coli* mutant producing succinic acid, acetic acid, and ethanol," *App. Biochem. Biotech.* 70-72:187-198 (1998).

Doten et al., "Cloning and Genetic Organization of the pca Gene cluster from *Acinetobacter calcoaceticus*," *J. Bacteriol.* 169(7):3168-3174 (1987).

Doyle et al., "Structural Basis for a Change in substrate Specificity: Crystal Structure of S113E Isocitrate Dehydrogenase in a Complex with Isopropylmalate, $Mg^{2+}$ and $^{NAPD}$," *Biochemistry* 40:4234-4241 (2001).

Drake and Daniel, "Physiology of the thermophilic acetogen *Moorella thermoacetica*," *Res. Microbiol.* 155(10):869-883 (2004).

Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).

Drake, "Demonstration of hydrogenase in extracts of the homoacetate-fermenting bacterium *Clostridium thermoaceticum*," *J. Bacteriol.* 150(2):702-709 (1982).

Draths and Frost, "Environmentally compatible synthesis of adipic acid from D-glucose," *J. Am. Chem. Soc.* 116:399-400 (1994).

Drevland et al., "Enzymology and Evolution of the Pyruvate Pathway to 2-Oxobutyrate in *Methanocaldococcus jannachii*," *J. Bacteriol.* 189(12):4391-4400 (2007).

Drewke et al., "4-O-Phosphoryl-L-threonine, a substrate of the pdxC(serC) gene product involved in vitamin $B_6$ biosynthesis," *FEBS Lett.* 390:179-182 (1996).

Drewke et al., "Ethanol formation in adh) mutants reveals the existence of a novel acetaldehyde-reducing activity in *Saccharomyces cerevisiae*," *J. Bacteriol.* 172:3909-3917 (1990).

Driscoll and Taber, "Sequence Organization and Regulation of the *Bacillus subtilis* menBE Operon," *J. Bacteriol.* 174(15):5063-5071 (1992).

Drummond and Stern, "Enzymes of ketone body metabolism. II. Properties of an acetoacetate-synthesizing enzyme prepared from ox liver," *J. Biol. Chem.* 235:318-325 (1960).

Du et al., "Succinic acid production from wheat using a biorefining strategy," *Appl. Microbiol. Biotechnol.* 76:1263-1270 (2007).

Duarte et al., "Reconstruction and validation of *Saccharomyces cerevisiae* iND750, a fully compartmentalized genome-scale metabolic model," *Genome Res.* 14(7):1298-1309 (2004).

Duckworth et al., "The Binding of Reduced Nicotinamide Adenine Dinucleotide to Citrate Synthase of *Escherichia coli* K12," *Biochemistry* 15(1):108-114 (1976).

Duncan et al., "The pentafunctional arom enzyme of *Saccharomyces cerevisiae* is a mosaic of monofunctional domains," *Biochem. J.* 246:375-386 (1987).

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Duncombe and Frerman, "Molecular and catalytic properties of the acetoacetyl-Coenzyme A thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anaerobic mitochondria of the parasitic nematode *Ascaris suum*," *J. Biol. Chem.* 268(30):22391-22396 (1993).

Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).

Durre and Bahl, "Microbial Production of Acetone/Butanol/Isopropanol," In Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Dürre et al., "Solventogenic enzymes of *Clostridium acetobutylicum*: catalytic properties, genetic organization, and transcriptional regulation," *FEMS Microbiol. Rev.* 17:251-262 (1995).

Dürre, "Biobutanol: an attractive biofuel," *Biotechnol. J.* 2(12):1525-1534 (2007).

Dürre, "New insights and novel developments in clostridial acetone/butanol/isopropanol fermentation," *Appl. Microbiol. Biotechnol.* 49:639-648 (1998).

Dusch et al., "Expression of the Corynebacterium glutamicum panD gene encoding L-aspartate-α-decarboxylase leads to pantothenate overproduction in *Escherichia coli*," *Appl. Environ. Microbiol.* 65(4)1530-1539 (1999).

Dutscho et al., "Cloning and sequencing of the genes of 2-hydroxyglutaryl-CoA dehydratase from *Acidaminococcus fermentans*," *Eur. J. Biochem.* 181(3):741-746 (1989).

Dwiarti et al., "Purification and characterization of cis-aconitic acid decarboxylase from Aspergillus terreus TN484-M1," *J. Biosci Bioeng.* 94(1):29-33 (2002).

Dwyer et al., "Proton Abstraction reaction, Steady-State kinetics, and Oxidation-Reduction Potential of Human Glutaryl—CoA Dehydrogenase," *Biochemistry* 39:11488-11499 (2000).

Dykhuizen, "Chemostats used for studying natural selection and adaptive evolution," *Methods. Enzymol.* 224:613-631 (1993).

Eberhard and Gerlt, "Evolution of Function in the Crotonase Superfamily: The Stereochemical course of the Reaction catalyzed by 2-Ketocyclohexanecarboxyl—CoA Hydrolase," *J. Am. Chem. Soc.* 126:7188-7189 (2004).

Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol.* 55:296-300 (2001).

Edwards and Palsson, "Metabolic flux balance analysis and the in silico analysis of *Escherichia coli* K-12 gene deletions," *BMC Bioinform.* 1:1 (2000).

Edwards and Palsson, "Systems properties of the Haemophilus influenzae Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).

Edwards et al., "Metabolic modelling of microbes: the flux-balance approach," *Environ. Microbiol.* 4(3):133-140 (2002).

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Egland et al., "A cluster of bacterial genes for anaerobic benzene ring biodegradation," *Proc. Natl. Acad. Sci. U.S.A.* 94:6484-6489 (1997).

Eikmanns et al., "The phosphoenolpyruvate carboxylase gene of *Corynebacterium glutamicum*: Molecular cloning, nucleotide sequence, and expression." *Mol. Gen. Genet.* 218:330-339 (1989).

Elshahed et al., "Metabolism of Benzoate, Cyclohex-1-ene Carboxylate, and Cyclohexane Carboxylate by "*Syntrophus aciditrophicus*" Strain SB in Syntrophic Association with $H_2$-Using Microorganisms," *Appl. Environ. Microbiol.* 67(4):1728-1738 (2001).

Engel, "Butyryl-CoA Dehydrogenase from *Megasphaera elsdenii*," *Methods Enzymol.* 71:359-366 (1981).

Enomoto et al., "Cloning and sequencing of the gene encoding the soluble fumarate reductase from *Saccharomyces cerevisiae*," *DNA Res*. 3:263-267 (1996).

Ensign and Ludden, "Characterization of the CO Oxidation/$H_2$ Evolution System of *Rhodospirillum rubrum*. Role of a 22-kDa iron-sulfur protein in mediating electron transfer between carbon monoxide dehydrogenase and hydrogenase," *J. Biol. Chem*. 266(27)18395-18403 (1991).

Estévez et al., "X-ray crystallographic and kinetic correlation of a clinically observed human fumarase mutation," *Protein Sci*. 11(6):1552-1557 (2002).

Eulberg et al., "Characterization of a protocatechuate catabolic gene cluster from *Rhodococcus opacus* 1CP: evidence for a merged enzyme with 4-carboxymuconolactone-cecarboxylating and 3-oxoadipate enol-lactone-hydrolyzing activity," *J. Bacteriol*. 180:1072-1081 (1998).

Evans et al., "[$^{13}$C]propionate oxidatin in wild-type and citrate synthase mutant *Escherichia coli*: evidence for multiple pathways of propionate utilization," *Biochem. J*. 291(Pt 3):927-932 (1993).

Ezeji et al., "Butanol fermentation research: upstream and downstream manipulations," *Chem. Rec*. 4(5):305-314 (2004).

Faehnle et al., "A New Branch in the Family: Structure of Aspartate-β-semialdehyde Dehydrogenase from *Methanococcus jannaschii*," *J. Mol. Biol*. 353:1055-1068 (2005).

Feist et al., "The growing scope of applications of genome-scale metabolic reconstructions using *Escherichia coli*," *Nat. Biotechnol*. 26(6):659-667 (2008).

Feldberg and Datta, "L-threonine deaminase of *Rhodospirillum rubrum*. Purification and characterization," *Eur. J. Biochem*. 21(3):438-446 (1971).

Fell and Small, "Fat Synthesis in Adipose Tissue. An Examination of Stoichiometric Constraints," *Biochem. J*. 238(3):781-786 (1986).

Fernandez-Canon and Penalva, "Characterization of a fungal maleylacetoacetate isomerase gene and indentification of its human homologue," *J. Biol. Chem*. 273:329-337 (1998).

Fernandez-Valverde et al., "Purification of *Pseudomonas putida* Acyl Coenzyme A Ligase Active with a Range of aliphatic and Aromatic substrates," *Appl. Environ. Microbiol*. 59(4):1149-1154 (1993).

Fischer and Sauer, "Metabolic flux profiling of *Escherichi coli* mutants in central carbon metabolism using GC-MS," *Eur. J. Biochem*. 270(5):880-891 (2003).

Fish and Blumenthal, "2-Keto-3-deoxy-D-glucarate aldolase," *Methods Enzymol*. 9:529-534 (1966).

Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem*. 241:4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibria," *J. Biol. Chem*. 241:4842-4847 (1966).

Fitzgerald and Flanagan, "Characterization and sequence analysis of the human ornithine decarboxylase gene," *DNA* 8:(9):623-634 (1989).

Flint et al., "The role and properties of the iron-sulfur cluster in *Escherichia coli* dihydroxy-acid dehydratase," *J. Biol. Chem*. 268:14732-14742 (1993).

Flint, "Initial kinetic and mechanistic characterization of *Escherichia coli* fumarase A," *Arch. Biochem. Biophy*. 311(2):509-516 (1994).

Fochi, "Selective catalytic dehydrogenation of 1,4-cyclohexadiene to benzene. 1. Radical anions derived from stransition-metal arene complexes as promoters," *Orqanometallics* 7:2255-2256 (1988).

Fomine and Tlenkopatchev, "Cross-methathesis of dimethyl maleate and ethylene catalyzed by second generation ruthenium carbene complexes: B3LYP and MPW1K comparison study," *J. Org. Chem*. 691:5189-5196 (2006).

Fong and Palsson, "Metabolic gene-deletion strains of *Escherichia coli* evolve to computationally predicted growth phenotypes," *Nat. Genet*. 36(10):1056-1058.

Fong et al., "Description and Interpretation of Adaptive Evolution of *Escherichia coli* K-12 MG1655 by Using a Genome-Scale in Silico Metabolic Model," *J. Bacteriol*. 185(21):6400-6408 (2003).

Fong et al., "In Silico design and adaptive evolution of *Escherichia coli* for production of lactic acid," *Biotechnol. Bioeng*. 91(5):643-648 (2005).

Fonknechten et al., "A conserved gene cluster rules anaerobic oxidative degradation of L-ornithine," *J. Bacteriol*. 191(9):3162-3167 (2009).

Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol*. 184:821-830 (2002).

Fontaine et al., "A New Type of Glucose Fermentation by *Clostridium thermoaceticum* N.Sp.," *J. Bacteriol*. 43(6):701-715 (1942).

Ford et al., "Molecular properties of the lyst1+ gene and the regulation of α-aminoadipate reductase in *Schizosaccharomyces pombe*," *Curr. Genet*. 28:131-137 (1995).

Forouhar et al., "Structural and Functional Evidence for *Bacillus subtilis* PaiA as a Novel $N^1$-Spermidine/spermine Acetyltransferase," *J. Biol. Chem*. 280(48):40328-40336 (2005).

Forster et al., "Genome-scale reconstruction of the *Saccharomyces cerevisiae* metabolic network," *Genome Res*. 13(2):244-253 (2003).

Fox et al., "Characterization of the region encoding the CO-induced hydrogenase of *Rhodospirillum rubrum*," *J. Bacteriol*. 178(21):6200-6208 (1996).

Freiberg et al., "Identification and characterization of the first class of potent bacterial acetyl-CoA carboxylase inhibitors with antibacterial activity," *J. Biol. Chem*. 279:26066-26073 (2004).

Freidrich et al., "The complete stereochemistry of the enzymatic dehydration of 4-hydroxybutyryl Coenzyme A to crontonyl Coenzyme A," *Angew. Chem. Int. Ed*. 47:3254-3257 (2008).

Frerman and Duncombe, "Studies on the subunits of *Escherichia coli* Coenzyme A transferase. Reconstitution of an active enzyme," *Biochim. Biophys. Acta* 580(2):289-297 (1979).

Fries et al., "Reaction Mechanism of the heterotetrameric (α2β2) E1 Component of 2-Oxo Acid Dehydrogenase Multienzyme Complexes," *Biochemistry* 42:6996-7002 (2003).

Frost and Draths, "Synthesis of adipic acid from biomass-derived carbon sources," *Biotechnol Adv*. 15(1):294 (1997).

Frost et al., "Dehydroquinate synthase from *Escherichia coli*: purification, cloning, and construction of overproducers of the enzyme," *Biochemistry* 23:4470-4475 (1984).

Frost, "Redefining chemical manufacture. Replacing petroleum with plant-derived feedstocks," *Ind. Biotechnol*. 1(1):23-24 (2005).

Fu et al., "Crystal structures of human glutaryl-CoA dehydrogenase with and without an alternate substrate: structural bases of dehydrogenation and decarboxylation reactions," *Biochemistry* 43(30):9674-9684 (2004).

Fujii et al., "Characterization of L-lysine 6-aminotransferase and its structural gene from *Flavobacterium lutescens* IFO3084," *J. Biochem*. 128:391-397 (2000).

Fujii et al., "Error-prone rolling circle amplification: the simplest random mutagenesis protocol," *Nat. Protoc*. 1:2493-2497 (2006).

Fujii et al., "One-step random mutagenesis by error-prone rolling circle amplification," *Nucleic Acids Res*. 32:e145 (2004).

Fujii, T. et al. "Molecular Cloning, Sequence Analysis, and Expression of the Yeast Alcohol Acetyltransferase Gene," *Appl. Environ. Microbiol*. 60:2786-2792 (1994).

Fujishiro et al., "Crystallization and Some Properties of Acetylpolyamine Amidohydrolase From *Mycoplana bullata*," *Biochem. Biophys. Res. Commun*. 157(3):1169-1174 (1988).

Fujita et al., "Novel Substrate Specificity of Designer 3-Isopropylmalate Dehydrogenase Derived from *Thermus thermophilus* HB8," *Biosci. Biotechnol. Biochem*. 65(12):2695-2700 (2001).

Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).

Fukuda and Wakagi, "Substrate recognition by 2-oxoacid:ferredoxin oxidoreductase from Sulfolobus sp. Strain 7," *Biochim. Biophys. Acta* 1597:74-80 (2002).

Fukuda et al., "Role of a highly conserved YPITP motif in 2-oxoacid:ferredoxin oxidoreductase Heterologous expression of the gene from Sulfolobus sp. Strain 7, and characterization of the recombinant and variant enzymes," *Eur. J. Biochem.* 268:5639-5646 (2001).

Fukui et al., "Engineering of Ralstonia eutropha for production of poly(3-hydroxybutyrate-co-3-hydroxyhexanoate) from fructose and solid-state properties of the copolymer," *Biomacromolecules* 3(3):618-624 (2002).

Fukumura et al, "Hydrolysis of cyclic and linear oligomers of 6-aminocaproic acid by a bacterial cell extract," *J. Biochem.* 59(6):531-536 (1966).

Fukumura et al., "Purification and properties of a novel enzyme, L-α-amino-ε-caprolactamase from *Cryptococcus laurentii*," *FEBS Lett.* 89(2):298-300 (1978).

Fuller and Leadlay, "Proton transfer in methylmalonyl-CoA epimerase from *Propionibacterium shermanii*. The reaction of (2R)-methylmalonyl-CoA in tritiated water," *Biochem. J.* 213(3):643-650 (1983).

Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).

Furukawa et al., "Increased alcohol acetyltransferase activity by inositol limitation in *Saccharomyces cerevisiae* in sake mash," *J. Biosci. Bioeng.* 96(4):380-386 (2003).

Galagan et al., "The genome of *M. acetivorans* reveals extensive metabolic and physiological diversity," *Genome Res.* 12(4):532-542 (2002).

Gallagher et al., "The crystal structure of chorismate lyase shows a new fold and a tightly retained product," *Proteins* 44:304-311 (2001).

Gangloff et al., "Molecular cloning of the Yeast *Mitochondrial aconitase* Gene (AC01) and Evidence of a Synergistic Regulation of Expression by Glucose plus Glutamate," *Mol. Cell. Biol.* 10(7):3551-3561 (1990).

Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys Acta.* 1255(2):154-160 (1995).

Garvie, "Bacterial lactate dehydrogenases," *Microbiol. Rev.* 44:106-139 (1980).

Gay et al., "Cloning Structural Gene sacB, Which Codes for Exoenzyme Levansucrase of *Bacillus subtilis*: Expression of the Gene in *Escherichia coli*," *J. Bacteriol.* 153(3):1424-1431 (1983).

Genda et al., "Purification and characterization of fumarase from *Corynebacterium glutamicum*," *Biosci. Biotechnol. Biochem.* 70:1102-1109 (2006).

Gerhardt et al. "Fermentation of 4-aminobutyrate by *Clostridium aminobutyricum*: cloning of two genes involved in the formation dehydration of 4-hydroxybutyrl-CoA," *Arch. Microbiol.* 174:189-199 (2000).

Gerischer and Dürre, "mRNA Analysis of the *adc* Gene Region of *Clostridium acetobutylicum* during the Shift to Solventogenesis," *J. Bacteriol.* 174(2):426-433 (1992).

Gescher et al., "Genes coding for a new pathway of aerobic benzoate metabolism in *Azoarcus evansii*," *J Bacteriol.* 184(22):6301-6315 (2002).

Giaever et al., "Functional profiling of the *Saccharomyces cerevisiae* genome," *Nature* 418(6896):387-391 (2002).

Gibbs et al., "Degenerate olignucleotide gene shuffling (DOGS): a method for enhancing the frequence of recombination with family shuffling," *Gene* 271:13-20.

Gibson (née Thomas) et al., "Cross metathesis of the amino acid homoallylglycine," *Chem. Commun.* 1107-1108 (1997).

Gibson and McAlister-Henn, "Physical and genetic interactions of cytosolic malate dehydrogenase with other gluconeogenic enzymes," *J. Biol. Chem.* 278:25628-25636 (2003).

Giesel and Simon, "On the occurrence of enoate reductase and 2-oxo-carboxylate reductase in clostridia and some observations on the amino acid fermentation by *Peptostreptococcus anaerobius*," *Arch. Microbiol.* 135(1):51-57 (1983).

Gillyon et al., "Putrescine Breakdown in the Yeast *Candida boidinii*: Subcellular Location of Some of the Enzymes Involved and Properties of Two Acetamidoaldehyde Dehydrogenases," *J. of Gen. Microbiol.* 133:2477-2485 (1987).

Glasemacher et al., "Purification and properties of acetyl-CoA synthetase (ADP-forming), an archaeal enzyme of acetate formation and ATP synthesis, from the hyperthermophile *Pyrococcus furiosus*," *Eur. J. Biochem.* 244:561-567 (1997).

Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).

Goda et al., "Cloning, sequencing, and expression in *Escherichia coli* of the *Clostridium tetanomorphum* gene encoding β-methylaspartase and characterization of the recombinant protein," *Biochemistry* 31(44):10747-10756 (1992).

Gokarn et al., "Expression of pyruvate carboxylase enhances succinate production in *Escherichia coli* without affecting glucose uptake," *Biotechnol. Lett.* 20:795-798 (1998).

Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).

Gokarn, et al., "The physiological effects and metabolic alterations caused by the expression of *Rhizobium etli* pyruvate carboxylase in *Escherichia coli*," *Appl. Microbiol. Biotechnol.* 56(1-2):188-195 (2001).

Gokulan et al., "Crystal structure of *Mycobacterium tuberculosis* diaminipimelate decarboxylase, an essential enzyme in bacterial lysine biosynthesis," *J. Biol. Chem.* 278(20):18588-18596 (2003).

Goldberg et al., "Improved Conversion of Fumarate to Succinate by *Escherichia coli* Strains Amplified for Fumarate Reductase," *Appl. Environ. Microbiol.* 45:1838-1847.

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

González and Robb, "Genetic analysis of Carboxydothermus hydrogenoformans carbon monoxide dehydrogenase genes cooF and cooS," *FEMS Microbiol. Lett.* 191(2):243-247 (2000).

Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).

Gonzalez-Pajuelo et al., "Metabolic engineering of *Clostridium acetobutylicum* for the industrial production of 1,3-propanediol from glycerol," *Met. Eng.* 7:329-336 (2005).

Gordon and Doelle, "Purification, properties and immunological relationship of L(+)-lactate dehydrogenase from *Lactobacillus casei*," *Eur. J. Biochem.* 67:543-555 (1976).

Goupil et al., "Imbalance of Leucine Flux in *Lactococcus lactis* and Its Use for the Isolation of Diacetyl-Overproducing Strains," *Appl. Environ. Microbiol.* 62(7):2636-2640 (1996).

Goupil-Feuillerat et al., "Transcriptional and Translational Regulation of α-Acetolactate Decarboxylase of *Lactococcus lactis* subsp. Lactis," *J. Bacteriol.* 182(19):5399-5408 (2000).

Gourley et al., "The two types of 3-dehydroquinase have distinct structures but catalyze the same overall reaction," *Nat. Struct. Biol.* 6:521-525 (1999).

Grant and Patel. "The non-oxidative decarboxylation of p-hydroxybenzoic acid, gentisic acid, protocatechuic acid and gallic acid by *Klebsiella aerogenes* (*Aerobacter aerogenes*)," *Antonie Van Leeuwenhoek* 35:325-343 (1969).

Green and Bennett, "Genetic manipulation of acid and solvent formation in clostridium acetobutylicum ATCC 824," *Biotechnol. Bioeng.* 58(2-3):215-221 (1998).

Green and Nichols, "p-Aminobenzoate biosynthesis in *Escherichia coli*. Purification of aminodeoxychorismate lyase and cloning of pabC," *J. Biol. Chem.* 266:12971-12975 (1991).

Green et al., "Catabolism of α-ketoglutarate by a sucA mutant of *Bradyrhizobium japonicum*: evidence for an alternative tricarboxylic acid cycle," *J. Bacteriol.* 182:2838-2844 (2000).

Green et al., "Characterization and sequence of *Escherichia coli pabC*, the gene encoding aminodeoxychorismate lyase, a pyridoxal phosphate-containing enzyme," *J. Bacteriol.* 174:5317-5323 (1992).

Grethlein and Jain, "Bioprocessing of coal-derived synthesis gases by anaerobic bacteria," *Trends Biotech.* 10:418-423 (1992).

Grolle et al., "Isolation of the dxr gene of *Zymomonas mobilis* and characterization of the 1-deoxy-D-xylulose 5-phosphate reductoisomerase," *FEMS Microbiol. Lett.* 191:131-137 (2000).

Grubbs, "Olefin Meethathesis," *Tetrahedron* 60:7117-7140 (2004).

Gu et al., "Crystal structure of shikimate kinase from *Mycobacterium tuberculosis* reveals the dynamic role of the LID domain in catalysis," *J. Mol. Biol.* 319:779-789 (2002).

Gueldener et al., "A second set of *loxP* marker cassettes for Cre-mediated multiple gene knockouts in budding yeast," *Nucleic Acids Res.* 30(6):e23 (2002).

Guerra et al., "Role of transmembrane segment M8 in the biogenesis and function of yeast plasma-membrane H$^+$-ATPase," *Biochim. Biophys. Acta* 1768:2383-2392 (2007).

Guest et al., "The fumarase genes of *Escherichia coli*: location of the fumB gene and discovery of a new gene (fumC)," *J. Gen. Microbiol.* 131(11):2971-2984 (1985).

Guettler et al., "*Actinobacillus succinogenes* sp. nov., a novel succinic-acid-producing strain from the bovine rumen," *Int. J. Syst. Bacteriol.* 49:207-216 (1999).

Guirard and Snell, "Purification and properties of ornithine decarboxylase from *Lactobacillus* sp. 30a," *J. Biol. Chem.* 255:5960-5964 (1980).

Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from *Schizosaccharomyces pombe*," *Yeast* 21:1279-1288 (2004).

Guo and Bhattacharjee, "Site-directed mutational analysis of the novel catalytic domains of α-aminoadipate reductase (Lys2p) from candida albicans," *Mol. Gen. Gemonics* 269:271-279 (2003).

Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).

Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).

Gutknecht et al., "The dihydroxyacetone kinase of *Escherichia coli* utilizes a phosphoprotein instead of ATP as phosphoryl donor," *EMBO J.* 20(10):2480-2486 (2001).

Guyer et al., "Identification of a sex-factor-affinity site in *E. coli* as γδ," *Cold Spring Harbor Symp. Quant. Biol.* 45:135-140 (1981).

Guzman et al., "Tight regulation, modulation, and high-level expression by vectors containing the arabinose $P_{BAD}$ promoter," *J. Bacteriol.* 177:4121-4130 (1995).

Haarasilta and Oura, "On the activity and regulation of anaplerotic and gluconeogenetic enzymes during the growth process of bakers yeast. The biphasic growth," *Eur. J. Biochem.* 52:1-7 (1975).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).

Hahm et al., "Characterization and evaluation of a *pta* (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hambraeus and Nyberg, "Enzymatic Hydrogenation of trans-2-Nonenal in Barley," *J. Adric. Food Chem.* 53:8714-8721 (2005).

Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).

Han et al., "Biochemical characterization and inhibitor discovery of shikimate dehydrogenase from *Helicobacter pylori*," *FEBS J.* 273:4682-4692 (2006).

Hanai et al., "Engineered synthetic pathway for isopropanol production in *Escherichia coli*," *Appl. Environ. Microbiol.* 73(24):7814-7818 (2007).

Hansford, "Control of mitochondrial substrate oxidation," *Curr. Top Bioenergy* 10:217-278 (1980).

Harder, "Anaerobic degradation of cyclohexane-1,2-diol by a new Azoarcus species," *Arch. Microbiol.* 168:199-204 (1997).

Hardison et al., "Globin Gene Server: A prototype E-Mail Database Server Featuring Extensive Multiple Alignments and Data Compilation for Electronic Genetic Analysis," *Genomics* 21:344-353 (1994).

Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).

Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).

Harrison and Harwood, "The pimFABCDE operon from *Rhodopseudomonas palustris* mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood and Parales, "The β-ketoadipate pathway and the biology of self-identity," *Annu. Rev. Microbiol.* 50:553-590 (1996).

Harwood et al., "Anaerobic metabolism of aromatic compounds via the benzoyl-CoA pathway," *FEMS Microbiol. Rev.* 22:439-458 (1999).

Harwood et al., "Identification of the pcaRKF Gene cluster from *Pseudomonas putida*: Involvement in Chemotaxis, Biodegradation, and Transport of 4-Hydroxybenzoate," *J. Bacteriol.* 176(21):6479-6488 (1994).

Hasan and Nester, "Dehydroquinate synthase in *Bacillus subtilis*. An enzyme associated with chorismate synthase and flavin reductase," *J. Biol. Chem.* 253:4999-5004 (1978).

Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).

Haselbeck and McAlister-Henn, "Isolation, nucleotide sequence, and disruption of the Saccharomyces cerevisiae gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80.

Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from *Serratia marcescens*," *Biosci. Biotechnol. Biochem.* 64:1477-1485 (2000).

Hatakeyama et al., "Gene Cloning and Characterization of Maleate cis-trans Isomerase from *Alcaligenes faecalis*," *Biochem. Biophys. Res. Comm.* 239:74-79 (1997).

Hawes et al., "Primary structure and tissue-specific expression of human β-hydroxyisobutyryl-Coenzyme A hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from Fusobacterium," *J. Nihon. Univ. Sch. Dent.* 28(1):12-21 (1986).

Hayden et al., "Glutamate dehydrogenase of *Halobacterium salinarum*: evidence that the gene sequence currently assigned to the $NADP_+$-dependent enzyme is in fact that of the $NAD^+$-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. U.S.A.* 99(25):15926-15931 (2002).

Hayes et al., "The Biofine Process: Production of Levulinic Acid, Furfural and Formic Acid from Lignocellulosic Feedstocks," In *Biorefineries: Industrial Proceses and Products*, Wiley, Weinheim, Germany, 139-164. (2006).

Haywood and Large, "4-Acetamidobutyrate Deacetylase in the Yeast *Candida boidinii* Grown on Putrescine or Spermidine as Sole Nitrogen, Source and Its Probable Role in Polyamine Catabolism," *J. Gen. Microbiol.* 132:7-14 (1986).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*," *Eur. J Biochem.* 229:77-82 (1995).

Heidlas and Tressl, "Purification and Properties of two oxidoreductases catalyzing the enantioselective reduction of diacetyl and other diketones from baker's yeast," *Eur. J. Biochem.* 188:165-174 (1990).

Heipieper and Isken, "Ethanol tolerance and membrane fatty acid adaptation in adh multiple and null mutants of *Kluyveromyces lactis*," *Res. Microbiol.* 151:(9):777-784 (2000).

Helin et al., "The refined x-ray structure of muconate lactonizing enzyme from *Pseudomonas putida* PRS2000 at 1.85 Å resolution," *J. Mol. Biol.* 254:918-941 (1995).

Heller et al., "Cloning and expression of the gene for the vitamin $B_{12}$ receptor protein in the outer membrane of *Escherichia coli*," *J. Bacteriol.* 161:896-903 (1985).

Hemschemeier et al., "Biochemical and physiological characterization of the pyruvate formate-lyase Pfl1 of *Chlamydomonas reinhardtii*, a typically bacterial enzyme in eukaryotic alga, " *Eukaryot. Cell* 7:518-526 (2008).

Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).

Henning et al., "Identification of novel benzoylformate decarboxylases by growth selection," *Appl. Environ. Microbiol.* 72:7510-7517 (2006).

Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).

Henstra et al., "Microbiology of synthesis gas fermentation for biofuel production," *Curr. Opin. Biotechnol.* 18:200-206 (2007).

Hermes et al., "Searching sequence space by definably random mutagenesis: Improving the catalytic potency of an enzyme," *Proc. Natl. Acad. Sci U.S.A.* 87:696-700 (1990).

Herrmann et al., "Energy Conservation via Electron-Transferring Flavoprotein in Anaerobic Bacteria," *J. Bacteriol.* 190(3):784-791 (2008).

Herrmann et al., "Two β-alanyl-CoA:ammonia lyases in *Clostridium propionicum*," *FEBS J.* 272:813-821 (2005).

Hespell et al., "Stabilization of *pet* Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).

Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).

Hester et al., "Purification of active $E1\alpha_2\beta_2$ of *Pseudomonas putida* branched-chainoxoacid dehydrogenase," *Eur. J. Biochem.* 233:828-836 (1995).

Hetzel et al., "Acryloyl-CoA reductase from *Clostridium propionicum*. An enzyme complex of pripionyl-CoA dehydrogenase and electron-transferring flavoprotein," *Eur. J. Biochem.* 270:902-910 (2003).

Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression," *Appl. Environ. Microbiol.* 70(2):937-942 (2004).

Hibbert et al., "Directed evolution of biocatalytic processes," *Biomol. Eng.* 22:11-19 (2005).

Highbarger et al., "Mechanism of the reaction catalyzed by acetoacetate decarboxylase. Importance of lysine 116 in determining the $pK_a$ of active-site lysine 115," *Biochemistry* 35(1):41-46 (1996).

Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).

Hill et al., "PCR based gene engineering of the Vibrio harveyi lux operon and the *Escherichia coli* trp operon provides for biochemically functional native and fused gene products," *Mol. Gen. Genet.* 226:41-48 (1991).

Hillmer and Gottschalk, "Particulate Nature of Enzymes Involved in the Fermentation of Ethanol and Acetate by *Clostridium Kluyveri*," *FEBS Lett.* 21(3):351-354 (1974).

Hillmer and Gottschalk, "Solubilization and partial characterization of particulate dehydrogenases from *Clostridium kluyveri*," *Biochim. Biophys. Acta* 334:12-23 (1974).

Hirano et al., "Purification and characerization of the Alcohol Dehydrogenase with a Broad Substrate Specificy Originated from 2-Phenylethanol-Assimilating Brevibacterium sp. KU 1309," *J. Biosci. Bioeng.* 100(3): 318-322 (2005).

Hirata et al., "Stereochemistry of reduction of the endocyclic double bond of (-31 )-carvone with the enzyme preparation from cultured cells of *Nicotiana tabacum*," *Phytochemistry* 28(12):3331-3333 (1989).

Hiser et al., "ERG10 from *Saccharomyces cerevisiae* encodes acetoacetyl-CoA thiolase," *J. Biol. Chem.* 269:31383-31389 (1994).

Ho et al., "Regulation of serine biosynthesis in *Arabidopsis*. Crucial role of plastidic 3-phosphoglycerate dehydrogenase in non-photosynthetic tissues," *J. Biol. Chem.* 274:397-402 (1999).

Hoang et al., "A broad-host-range Flp-FRT recombination system for site-specific excision of chromosomally-located DNA sequences: application for isolation of unmarked *Pseudomonas aeruginosa* mutants," *Gene* 212(1):77-86 (1998).

Hoffmann and Dimroth, "Sterochemistry of the methylmalonyl-CoA decarboxylation reaction," *FEBS Lett.* 220:121-125 (1987).

Hoffmeister et al., "Mitochondrial trans-2-enoyl-CoA reductase of wax ester fermentation from *Euglena gracilis* defines a new family of enzymes involved in lipid synthesis," *Biol. Chem.* 280(6):4329-4338 (2005).

Hofmeister and Buckel, "(R)-lactyl-CoA dehydratase from *Clostridium propionicum*. Stereochemistry of the dehydration of (R)-2-hydroxybutyryl-CoA to crotonly-CoA," *Eur. J. Biochem.* 206(2):547-552 (1992).

Hofmeister et al., "Cloning and expression of the two genes coding for L-serine dehydratase from *Peptostreptococcus asaccharolyticus*: relationship of the iron-sulfur protein to both L-serine dehydratases from *Escherichia coli*," *J. Bacteriol.* 179(15):4937-4941 (1997).

Hogan et al., "Improved Specificity toward Substrates with Positively Charged Side chains by Site-Directed Mutagenesis of the L-Lactate Dehydrogenase of *Bacillus stearothermophilus*," *Biochemistry* 34:4225-4230 (1995).

Holloway and Marsh, "Adenosylcobalamin-dependent glutamate mutase from *Clostridium tetanomorphum*. Overexpression in *Escherichia coli*, purification, and characterization of the recombinant enzyme," *J. Biol. Chem.* 269(32):20425-20430 (1994).

Holms, "The central metabolic pathways in *Escherichia coli*: relationship between flux and control at a branch point, efficiency of conversion to biomass, and excretion of acetate," *Curr. Top Cell. Regul.* 28:69-105 (1986).

Hong and Lee, "Metabolic flux analysis for succinic acid production by recombinant *Escherichia coli* with amplified malic enzyme activity," *Biotechnol. Bioeng.* 74(2):89-95 (2001).

Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).

Hong et al., "The genome sequence of the capnophilic rumen bacterium *Mannheimia succiniciproducens*." *Nat. Biotechnol.* 22(10):1275-1281 (2004).

Hong et al., "Importance of redox balance on the production of succinic acid by metabolically engineered *Escherichia coli*," *Appl. Microbiol. Biotechnol.* 58:286-290 (2002).

Horswill and Escalante-Semerena, "In vitro conversion of propionate to pyruvate by Salmonella enterica enzymes: 2-methylcitrate dehydratase (PrpD) and aconitas Enzymes catalyze the conversion of 2-methylcitrate to 2-methyl isocitrate," *Biochemistry* 40(15):4703-4713 (2001).

Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).

Howard et al., "Titanium Metallacarbene-Metallacylobutane Reactions: Stepwise Metathesis," *J. Am. Chem. Soc.* 102:6876-6878 (1980).

Hsu et al., "Expression of an aromatic-dependent decarboxylase which provides growth-essential $CO_2$ equivalents for the acetogenic (Wood) pathway of *Clostridium thermoaceticum*," *J. Bacteriol.* 172:5901-5907 (1990).

Hu et al., "The catalytic intermediate stabilized by a "down" active site loop for diaminopimelate decarboxylase from *Helicobacter pylori*. Enzymatic characterization with crystal structure analysis," *J. Biol. Chem.* 283(30):21284-21293 (2008).

Huang et al., "Genetic characterization of the resorcinol catabolic pathway in *Corynebacterium glutamicum*," *Appl. Environ. Microbiol.* 72:7238-7245 (2006).

Huang et al., "Purification and characterization of a ferulic acid decarboxylase from *Pseudomonas fluorescens*," *J. Bacteriol.* 176:5912-5918 (1994).

Huang et al., "Identification and characterization of a second butyrate kinase from *Clostridium acetobutylicum* ATCC 824," *J. Mol. Microbiol. Biotechnol.* 2(1):33-38 (2000).

Hübner et al., "The mechanism of substrate activation of pyruvate decarboxylase: A first approach," *Eur. J. Biochem.* 92:175-181 (1978).

Huder and Dimroth, "Sequence of the sodium ion pump methylmalonyl-CoA decarboxylase from *Veillonella parvula*," *J. Biol. Chem.* 268:24564-24571 (1993).

Hughes et al., "Cloning and expression of pca genes from *Pseudomonas putida* in *Escherichia coli*," *J. Gen. Microbiol.* 134:2877-2887 (1988).

Hughes et al., "Evidence for isofunctional enzymes in the degradation of phenol, m-and p-toluate, and p-cresol via catechol meta-cleavage pathways in *Alcaligenes eutrophus*," *J. Bacteriol.* 158(1):79-83 (1984).

Hugler et al., "Malonyl-Coenzyme A Reductase from *Chloroflexus aurantiacus*, a Key Enzyme of the 3-Hydroxypropionate Cycle for Autotrophic CO2 Fixation," *J. Bacteriol.* 184(9):2404-2410 (2002).

Huh et al., "Global analysis of protein localization in budding yeast," *Nature* 425:686-691 (2003).

Huisman and Lalonde, "Enzyme evolution for chemical process applications," In R.N. Patel (ed.), *Biocatalysis in the pharmaceutical and biotechnology industries*,CRC Press, p. 717-742 (2007).

Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).

Hustede et al., "Cloning of poly(3-hydroxybutyric acid) synthase genes of *Rhodobacter sphaeroides* and *Rhodospirillum rubum* and heterologous expression in *Alcaligenes eutrophys*," *FEMS Microbiol. Lett.* 93:285-290 (1992).

Ibarra et al., "*Escherichia coli* K-12 undergoes adaptive evolution to achieve in silico predicted optimal growth," *Nature* 420(6912):186-189 (2002).

Ichikawa et al., "Catalytic reaction of 1,3-butanediol over solid acids," *J. Mol. Catalysis A Chem.* 256:106-112 (2006).

Ichikawa et al., "PIO study on 1,3-butanediol dehydration over $CeO_2$ (1 1 1) surface," *J. Mol. Catalysis A Chem.* 231:181-189 (2005).

Iffland et al., "Directed Molecular Evolution of Cytochrome *c* Peroxidase," *Biochemistry* 39:10790-10798 (2000).

Ikai and Yamamoto, "Identification and analysis of a gene encoding L-2,4-diaminobutyrate:2-ketoglutarate 4-aminotransferase involved in the 1,3-diaminopropane production pathway in *Acinetobacter baummanni*," *J. Bacteriol.* 179;5118-5125 (1997).

Imai and Ohno, "Measurement of yeast intracellular pH by image processing and the change it undergoes during growth phase," *J.Biotechnol.* 38:165-172 (1995).

Ingoldsby et al., "The discovery of four distinct glutamate dehydrogenase genes in a strain of *Halobacterium salinarum*," *Gene* 349:237-244 (2005).

Ingram and Vreeland, "Differential-Effects of Ethanol and Hexanol on the *Escherichia-coli* Cell-Envelope," *J. Bacteriol.* 144:481-488 (1980).

Inui et al., "Occurrence of Oxygen-Sensitive, NADP+-Dependent Pyruvate-Dehydrogenase in Mitochondria of Euglena-Gracilis," *J. Biochem.* 96:931-934 (1984).

Inui et al., "Pyruvate-NADP+ Oxidoreductase from Euglena-Gracilis—the Kinetic-Properties of the Enzyme," *Arch. Biochem Bipophys.* 274:434-442 (1989).

Inui et al., "Wax Ester Fermentation in euglena-Gracilis," *FEBS Lett.* 150:89-93.

Inui et al., "Fatty acid synthesis in mitochondria of *Euglena gracilis*," *Euro. J. Biochem.* 142(1): 121-126 (1984).

Inui et al., "Production and Composition of Wax Esters by Fermentation of *Euglena gracilis*," *Agr. Biol. Chem.* 47(11):2669-2671 (1983).

Inui et al., "Purification and characterization of pyruvate:NADP+ oxidoreductase in *Euglena gracilis*," *J. Biol. Chem.* 262(19):9130-9135 (1987).

Inui et al., "Pyruvate:NADP+ oxidoreductase from *Euglena gracilis*: mechanism of $O_2$-inactivation of the enzyme and its stability in the aerobe," *Arch. Biochem. Biophys.* 280:292-298 (1990).

Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).

Ishida et al., "Efficient production of $_L$-Lactic acid by metabolically engineered *Saccharomyces cerevisiae* with a genome-integrated $_L$-lactate dehydrogenase gene," *Appl. Envirom. Microbiol.* 71:1964-1970 (2005).

Ishige et al, "Long-chain aldehyde dehydrogenase that participates in n-alkane utilization and wax ester synthesis in *Acinetobacter* sp. strain M-1," *Appl. Environ. Microbiol.* 66:3481-3486 (2000).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2003).

Ito and Yanofsky, "Anthranilate synthetase, an enzyme specified by the tryptophan operon of *Escherichia coli*: Comparative studies on the complex and the subunits," *J. Bacteriol.* 97:734-742 (1969).

Ito et al., "Colistin nephrotoxicity: report of a case with light and electron microscopic studies," *Acta. Pathol. Jpn.* 19:55-67 (1969).

Ito et al., "$_D$-3-hydroxybutyrate dehydrogenase from *Pseudomonas fragi*: molecular cloning of the enzyme gene and crystal structure of the enzyme," *J. Mol. Biol.* 355(4):722-723 (2006).

Iverson et al., "Structure of the *Escherichia coli* fumarate reductase respiratory complex," *Science* 284(5422):1961-1966 (1999).

Iwakura et al., "Studies on regulatory functions of malic enzymes. VI. Purification and molecular properties of NADP-linked malic enzyme from *Escherichia coli* W," *J. Biochem.* 85:1355-1365 (1979).

Izard and Blackwell, "Crystal structures of the metal-dependent 2-dehydro-3-deoxy-galacarate aldolase suggest a novel reaction mechanism," *Embo J.* 19:3849-3856.

Izumi et al., "Structure and Mechanism of HpcG, a Hydratase in the Homoprotocatechuate Degradation Pathway of *Escherichia coli*," *J. Mol. Biol.* 370:899-911 (2007).

Jacobi et al., "The hyp operon gene products are required for the maturation of catalytically active hydrogenase isoenzymes in *Escherichia coli*," *Arch. Microbiol.* 158(6);444-451 (1992).

Jacques et al., "Characterization of yeast homoserine dehydrogenase, an antifungal target: the invariant histidine 309 is important for enzyme integrity," *Biochem. Biophys. Acta.* 1544:28-41 (2001).

Jäger and Färber, "Die Alanatreduktion von β-Carbonyl-oxalylsäure-estern," *Chem. Ber.* 92-2492-2499 (1959).

James and Cronan, "Expression of two *Escherichia coli* acetyl-CoA carboxylase subunits is autoregulated," *J. Biol. Chem.* 279:2520-2527 (2004).

James and Viola, "Production and characterization of bifunctional enzymes. Domain swapping to produce new bifunctional enzymes in the aspartate pathway," *Biochemistry* 41(11) 3720-3725 (2002).

Jansen and Wanders, "$_L$-2-hydroxyglutarate dehydrogenase: identification of a novel enzyme activity in rat and human liver. Implications for $_L$-2-hydroxyglutaric academia," *Biochim. Biophys. Acta* 1225(1):53-56 (1993).

Janssen, "Propanol as an end product of theonine fermentation," *Arch. Microbiol.* 182:482-486 (1993).

Jantama et al., "Combining metabolic engineering and metabolic evolution to develop non recombinant strains of *Escherichia coli* C that produce succinate and malate," *Biotechnol. Bioeng.* 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Javid-Majd and Blanchard, "Mechanistic Analysis of the argE-Encoded N-Acetylornithine Deacetylase," *Biochemistry* 39:1285-1293 (2000).

Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jennert et al., "Gene transfer to *Clostridium cellulolyticum* ATCC 35319," *Microbiol.* 146:3071-3080 (2000).

Jenssen et al., "A literature network of human genes for high-throughput analysis of gene expression," *Nat. Gene.* 28:21-28 (2001).

Jeon et al., "Heterologous expression of the alcohol dehydrogenase (adhl) gene from Geobacillius thermoglucosidasius strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jiang et al., "De Novo Computational Design of Retro-Aldol Enzymes," *Science* 319:1387-1391 (2008).

Jin and Sonenshein, "Characterization of the major citrate synthase of *Bacillus subtilis*," *J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Johnston et al., "Structure of naphthoate synthase (MenB) from Mycobacterium tuberculosis in both native and product-bound forms," *Acta. Crystallogr. D. Biol. Crystallogr.* 61(Pt 9):1199-1206 (2005).

Jojima et al., "Production of isopropanol by metabolically engineered *Escherichia coli*," *Appl. Microbiol. Biotechnol.* 77:1219-1224 (2008).

Jones and Woods, "Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kahng et al., "Characterization of strain HY99, a novel microorganism capable of aerobic and anaerobic degradation of aniline," *FEMS Microbiol. Lett.* 190:215-221 (2000).

Kai et al., "Phospho*enol*pyruvate carboxylase: three-dimensional structure and molecular mechanisms," *Arch. Biochem. Biophys.* 414:170-179 (2003).

Kakimoto et al., "β-aminoisobutyrate-α-ketoglutarate transaminase in relation to β-aminoisobutyric aciduria," *Biochim. Biophys. Acta* 156(2):374-380 (1968).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalpos, "On the mammalian acetone metabolism: from chemistry to clinical implications," *Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1," *J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routes in bacteria," *J. Bacteriol.* 189(3):918-928 (2007).

Kanagawa et al., "Characterization of the 6-aminohexanoate-dimer hydrolase from *Pseudomonas* sp. NK87," *J. Gen. Microbiol.* 139(4):787-795 (1993).

Kanamasa et al., "Cloning and functional characterization of the cis-aconitic acid decarboxylase (CAD) gene from *Aspergillus terreus*," *Appl. Microbiol. Biotechnol.* 80(2):223-229 (2008).

Kanao et al., "Characterization of isocitrate dehydrogenase from the green sulfur bacterium Chlorbium limicola. A carbon dioxide-fixing enzyme in the reductive tricarboxylic acid cycle," *Eur. J. Biochem.* 269(7):1926-1931 (2002).

Kanaujia et al., "Cloning, expression, purification, crystallization and preliminary X-ray crystallographic study of DHNA synthetase from Geobacillus kaustophilus," *Acta. Cyrstallogr. Sect. F. Struct. Biol. Cryst. Commun.* 63(Pt 2):103-105 (2007).

Kanehisa and Goto, "KEGG: Kyoto Encyclopedia of Genes and Genomes database," *Nucleic Acids Res.* 28(1):27-30 (2000).

Kapatral et al., "Genome Sequence and Analysis of the Oral Bacterium *Fusobacterium nucleatum* Strain ATCC 25586," *J. Bacteriol.* 184(7):2005-2018 (2002).

Karyakin et al., "Kinetic properties of $_L$-lysine-2-monooxygenase from *Pseufomonas putida* and its application to biosensors for $_L$-lysine," *Prikladnaya Biokhimiya I Mikrobiologiya* 27:825-832 (1991).

Kasberg et al., "Cloning, characterization, and sequence analysis of the cicE gene encoding the maleylacetate reductase of *Pseufomonas* sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

Kaschabek and Reineke, "Maleylacetate reductase of *Pseufomonas* sp. Strain B13: specificity of substrate conversion and halide elimination," *J. Bacteriol.* 177:320-325 (1995).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).

Kashket and Cao, "Isolation of a Degeneration-Resistant Mutant of clostridium acetobutylicum NCIMB 8052," *Appl. Environ. Microbiol.* 59:4198-4202 (1993).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Katti et al., "Crystal structure of muconolactone isomerase at 3.3 Å resolution," *J. Mol. Biol.* 205:557-571 (1989).

Katz et al., "Screening of two complementary collections of *Saccharomyces cerevisiae* to identify enzymes involved in stereo-selective reductions of specific carbonyl compounds: an alternative to protein purification," *Enzyme Microb. Technol.* 33:163-172 (2003).

Kawabata et al., "The Effect of Growth Temperature on Wax Ester Content and Composition of *Euglena gracilis*," *J. Gen. Microbiol.* 135: 1461-1467 (1989).

Kazahaya et al, "Aerobic Dissimilation of Glucose by Heterolactic Bacteria III. Aldehyde dehydrogenase and alcohol dehydrogenase of luconostoc mesenteroids," *J. Gen. Appl. Microbiol.* 18(1):43-55 (1972).

Kefala et al., "Cloning, expression, purification, crystallization and preliminary x-ray diffraction analysis of LysA (Rv1293) from Mycobacterium tuberculosis," *Acta. Crystallogr. Sect. F. Struct. Biol. Cryst. Commun.* 61(Pt 8):782-784 (2005).

Kellum and Drake, "Effects of cultivation gas phase on hydrogenase of the acetogen *Clostridium thermoaceticum*," *J. Bacteriol.* 160(1):466-469 (1984).

Kenealy et al., "Biochemical Aspects of Fumaric Acid Accumulation by *Rhizopus arrhizus*," *Appl. Environ. Microbiol.* 52:128-133 (1986).

Keng and Viola, "Specificity of Aspartokinase III from *Escherichia coli* and Examination of Important Catalytic Residues," *Arch. Biochem. Biophys.* 335(1):73-81 (1996).

Kenklies et al., "Proline biosynthesis from $_L$-ornithine in Clostridium sticklandii: purification of $\Delta^1$-pyrroline-5-carboxylate reductase, and sequence and expression of encoding gene, proC," *Microbiology* 145(Pt 4):819-826 (1999).

Kerby et al., "Carbon Monoxide-Dependent Growth of *Rhodospirillum rubrum*, " *J. Bacteriol.* 177:2241-2244 (1995).

Kerby et al., "Genetic and physiological characterization of the *Rhodospirillum rubrum* carbon monoxide dehydrogenase system," *J. Bacteriol.* 174(16):5284-5294 (1992).

Kern et al., "Isoamyl alcohol-induced morphological change in *Saccharomyces cerevisiae* involves increases in mitochondria and cell wall chitin content," *FEMS. Yeast Res.* 5:43-49 (2004).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Khan et al., "Molecular Properties and Enhancement of Thermostability by Random Mutagenesis of Glutamate Dehydrogenase from *Bacillus subtilis*," *Biosci. Biotechnol. Biochem* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al, "Effect of Overexpression of *Actinobacillus succinogenes* Phosphoenolpyruvate Carboxykinase on Succinate Production in *Escherichia coli*," *Appl. Env. Microbiol.* 70(2) 1238-1241 (2004).

Kim et al., "2-Hydroxyisocaproyl-CoA dehydratase and its activator from *Clostridium difficile*," *FEBS J.* 272:550-561 (2005).

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).

Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).

Kim et al., "Studies of the hyperthermophile *Thermotoga maritima* by random sequencing of cDNA and genomic libraries. Identification and sequencing of the *trp*EG (D) operon," *J. Mol. Biol.* 231:960-981 (1993).

Kim, "Purification and Properties of a diamine α-Ketoglutarate Transminase from *Escherichia coli*," *J. Biol. Chem.* 239(3):783-786 (1964).

Kino et al. Synthesis of $_{DL}$-tryptophan by modified broad specificity amino acid racemase from *Pseudomonas putida* IFO 12996, *Appl. Microbiol. Biotechnol.* 73:1299-1305 (2007).

Kinoshita et al., "Purification and characterization of 6-aminohexanoic-acid-oligomer hydrolase of Flavobacterium sp. KI72," Eur. J. Biochem. 116(3):547-551 (1981).

Kinoshita, "Purification of two alcohol dehydrogenases from *Zymomonas mobilis* and their properties," *Appl. Microbiol. Biotechnol.* 22:249-254 (1985).

Kisselev L., "Polypeptide release factors in prokaryotes and eukaryotes: same function, different structure," *Structure* 10:8-9 (2002).

Klasson, et al., "Biological conversion of coal and coal-derived synthesis gas," *Fuel* 72(12):1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

Kleanthous et al., "A comparison of the enzymological and biophysical properties of two distinct classes of dehydroquinase enzymes," *Biochem. J.* 282(Pt3):687-695 (1992).

Klyosov, "Kinetics and specificity of human liver aldehyde dehydrogenases toward aliphatic, aromatic, and fused polycyclic aldehydes," *Biochemistry* 35(14):4457-4467 (1996).

Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Knappe et al., "Post-translational activation introduces a free radical into pyruvate formate-lyase," *Proc. Natl. Acad. Sci. U.S.A.* 81:1332-1335 (1984).

Knothe, "'Designer' Biodiesel: Optimizing Fatty Ester Composition to Improve Fuel Properties," *Energy Fuels* 22:1358-1364 (2008).

Kobayashi et al., "Physicochemical, catalytic, and immunochemical properties of fumarases crystallized separately from mitochondrial and cytosolic fractions of rat liver," *J. Biochem.* 89(6):1923-1931 (1981).

Koch and Fuchs, "Enzymatic reduction of benzoyl-CoA to alicyclic compounds, a key reaction in anaerobic aromatic metabolism," *Eur. J. Biochem.* 205:195-202 (1992).

Koch et al., "Products of enzymatic reduction of benzoyl-CoA, a key reaction in anaerobic aromatic metabolism," *Eur. J. Biochem.* 211:649-661 (1993).

Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).

Kollmann-Koch et al.,"Nicotinic acid metabolism. Dimethylmaleate hydratase," *Hoppe Seylers Z Physiol Chem.* 365:s.847-857 (1984).

Koo et al., "Cloning and characterization of the bifunctional alcohol/ acetaldehyde dehydrogenase gene (adhE) in Leuconostoc mesenteroides isolated from kimchi," *Biotechnol. Lett.* 27(7):505-510 (2005).

Korbert et al., "Crystallization of the NADP+-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase α-subunit structure using 3.4 Å MAD and 1.9 Å native data," *Acta. Crystallogr. D. Biol. Crystallogr.* 58(Pt 12):2116-2121 (2002).

Korotkova and Lidstrom, "Connection between poly-β-hydroxybutyrate biosynthesis and growth on $C_1$ and $C_2$ compounds in the methylotroph Methylobacterium extorquens AM1," *J. Bacteriol.* 183(3):1038-1046 (2001).

Korotkova and Lidstrom, "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver $_D$-Methylmalonyl Coenzyme A Hydrolase," *J. Biol. Chem.* 258(18):11415-11421 (1983).

Kowalchuk et al., "Contrasting patterns of evolutionary divergence within the *Acinetobacter calcoaceticus* pca operon," *Gene* 146:23-30 (1994).

Kraus et al., "Biosynthesis and mitochondrial processing of the β subunit of propionyl Coenzyme A carboxylase from rat liver," *J. Biol. Chem.* 258:7245-7248 (1983).

Kreimeyer et al., "Identification of the Last Unknown Genes in the Fermentation Pathway of Lysine," *J. Biol. Chem.* 282(10):7191-7197 (2007).

Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).

Kress et al., "Tungsten(VI) and molybdenum(VI) oxo-alkyl species. Their role in the metathesis of olefins," *J. Chem. Soc. Chem. Commun.* 431-432 (1980).

Kretz et al., "Gene site saturation mutagenesis: a comprehensive mutagenesis approach," *Methods Enzymol.* 388:3-11 (2004).

Krieger et al., "Pyruvate decarboxylase from Kluyveromyces lactis an enzyme with an extraordinary substrate activation behaviour," *Eur. J. Biochem.* 269:3256-3263 (2002).

Krishna et al., "Enzymatic synthesis of isoamyl acetate using immobilized lipase from *Rhizomucor miehei*," *J. Biotechnol.* 87:193-201 (2001).

Kuchta and Abeles, "Lactate Reduction in Clostridium propionicum Purification and properties of lactyl-CoA dehydratase," *J. Biol. Chem.* 260(24):13181-13189 (1985).

Kühnl et al., "Functional analysis of the methylmalonyl-CoA epimerase from *Caenorhabditis elegans*," *FEBS J.* 272(6):1465-1477 (2005).

Kulkarni and Kanekar, "Bioremediation of ε-caprolactum from nylon-6 waste water by use of *Pseudomonas aeruginosa* MCM B-407," *Curr. Microbiol.* 37(3):191-194 (1998).

Kumamaru et al., "Enhanced degradation of polychlorinated biphenyls by directed evolution of biphenyl dioxygenase," *Nat. Biotechnol.* 16:663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kurihara et al., "γ-Glutamyputrescine synthetase in the putrescine utilization pathway of *Escherichia coli* K-12," *J. Biol. Chem.* 283(29)19981-19990 (2008).

Kurihara et al., "A Novel Putrescine Utilization Pathway Involves γ-Glutamylated Intermediates of *Escherichia coli* K-12," *J. Biol. Chem.* 280(6):4602-4608 (2005).

Kuznetsova et al., "Enzyme genomics: Application of general enzymatic screens to discover new enzymes," *FEMS Microbiol. Rev.* 29(2):263-279 (2005).

Kwok and Hanson, "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium Thauera aromatica," *Eur. J. Biochem.* 263(2):420-429 (1999).

Laivenieks et al., "Cloning sequencing, and overexpression of the Anaerobiospirillum succinicproducens phosphoenolpyruvate carboxykinase (*pckA*) gene," *Appl. Environ. Microbiol.* 63:2273-2280 (1997).

Lam and Winkler, "Metabolic Relationships between Pyridoxine (Vitamin $B_6$) and Serine Biosynthesis in *Escherichia coli* K-12," *J. Bacteriol.* 171(11):6518-6528 (1990).

Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).

Lamed and Zeikus, "Novel NADP-linked alcohol-aldehyde/ketone oxidoreductase in thermophilic ethanologenic bacteria," *Biochem. J.* 195:183-190 (1981).

Lardizabal et al., "Purification of a jojoba embryo wax synthase, cloning of its cDNA, and production of high levels of wax in seeds of transgenic arabidopsis," *Plant. Physiol.* 122(3):645-655 (2000).

Lawrence and Roth, "Evolution of Coenzyme $B_{12}$ synthesis among enteric bacteria: evidence for loss and reacquisition of a multigene complex," *Genetics* 142(1):11-24 (1996).

Lawrence and Roth, "The cobalamin (Coenzyme $B_{12}$) biosynthetic genes of *Escherichia coli*," *J. Bacteriol.* 177(22):6371-6380 (1995).

Lebbink et al., "Engineering activity and stability of Thermotoga maritima glutamate dehydrogenase I. Introduction of a six-residue ion-pair network in the hinge region," *J. Mol. Biol.* 280:287-296 (1998).

Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee and Cho, "Identification of essential active-site residues in ornithine decarboxylase of *Nicotiana glutinosa* decarboxylating both L-ornithine and $_L$-lysine," *Biochem. J.* 360:657-665 (2001).

Lee et al., "A new approach to directed gene evolution by recombined extension on truncated templates (RETT)," *J. Molec. Catalysis* 26:119-129 (2003).

Lee et al., "Batch and continuous cultivation of *Anaerobiospirillum succiniciproducens* for the production of succinic acid from whey," *Appl. Microbiol. Biotechnol.* 54(1):23-27 (2000).

Lee et al., "Biological conversion of wood hydrolysate to succinic acid by *Anaerobiospirillum succiniciproducens*," *Biotechnol. Lett.* 25(2):111-114 (2003).

Lee et al., "Biosynthesis of enantiopure (S)-3-hydroxybutyric acid in metabolically engineered *Escherichia coli*," *App. Microbiol. Biotechnol.* 79:633-641 (2008).

Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).

Lee et al., "Cloning and Characterization of Mannheimia succiniciproducens MBEL55E Phosphoenolpyruvate Carboxykinase (*pckA*) Gene," *Biotechnol. Bioprocess Eng.* 7:95-99 (2002).

Lee et al., "Fermentative production of chemicals that can be used for polymer synthesis," *Macromol. Biosci.* 4:157-164 (2004).

Lee et al., "Genome-based metabolic engineering of *Mannheimia succiniciproducens* for succinic acid productiion," *Appl. Environ. Microbiol.* 72(3):1939-1948 (2006).

Lee et al., "Isolation and characterization of a new succinic acid-producing bacterium, *Mannheimia succiniciproducens* MBEL55E, from bovine rumen," *Appl. Microbiol. Biotechnol.* 58(5):663-668 (2002).

Lee et al., "Phylogenetic diversity and the structural basis of substrate specificity in the β/α-barrel fold basic amino acid decarboxylases," *J. Biol. Chem.* 282:27115-27125 (2007).

Lee et al., "Metabolic engineering of *Escherichia coli* for enhanced production of succinic acid, based on genome comparison and in silico gene knockout simulation," *Appl Environ Microbiol.* 71(12):7880-7887 (2005).

Lehtio and Goldman, "The pyruvate format lyase family: sequences, structures and activation," *Protein Eng. Des.Sel.* 17:545-552 (2004).

Lehtio et al., "Crystal structure of glycyl radical enzyme from *Archaeoglobus fulgidus*," *J. Mol. Biol.* 357(1):221-235 (2006).

Lei et al., "A shared binding site for NAD+ and Coenzyme A in an acetaldehyde dehydrogenase involved in bacterial degradation of aromatic compounds," *Biochemistry* 47:6870-6882 (2008).

Lemoine et al., "Microcorrespondence: Monofunctional biosynthetic peptidoglycan transglycosylases," *Mol. Microbiol.* 19(3):639-647 (1996).

Lemonnier and Lane, "Expression of the second lysine decarboxylase gene of *Escherichia coli*," *Microbiology* 144(Pt 3):751-760 (1998).

Lenski and Travisano, "Dynamics of adaptation and diversification: a 10,000-generation experiment with bacterial populations," *Proc. Natl. Acad. Sci. U.S.A.* 91(15):6808-6814 (1994).

Leonardo et al., "Anaerobic Regulation of the adhE gene, Encoding the Fermentative Alcohol Dehydrogenase of *Escherichia coli*," *J. Bacteriol.* 175(3):870-878 (1993).

Lepore et al., "The x-ray crystal structure of lysine-2,3-aminomutase from Clostridium subterminale," *Proc. Natl. Acad. Sci U.S.A.* 102:13819-13824 (2005).

Leppänen et al., "Pyruvate formate lyase is structurally homologous to type I ribonucleotide reductase," *Structure* 7:733-744 (1999).

Lessner et al., "An unconventional pathway for reduction of $CO_2$ to methane in CO-grown *Methanosarcina acetivorans* revealed by proteomics," *Proc. Natl. Acad. Sci. U.S.A.* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Levanon et al., "Effect of Oxygen on the *Escherichia coli* ArcA and FNR Regulation Systems and Metabolic Responses," *Biotechnol. Bioeng.* 89(5):556-564 (2005).

Li and Jordan, "Effects of substitution of tryptophan 412 in the substrate activation pathway of yeast pyruvate decarboxylase," *Biochemistry* 38:10004-10012 (1999).

Li et al., "Properties of Nicotinamide Adenine Dinucleotide Phosphate-Dependent Formate Dehydrogenase from Clostridium thermoaceticum," *J. Bacteriol.* 92(2):405-412 (1966).

Li et al., "Purification, crystallization and preliminary crystallographic studies on 2-dehydro-3-deoxygalactarate aldolase from Leptospira interrogans," *Acta. Crystallogr. Sect. F. Struct. Biol. Cryst. Commun.* 62(Pt 12):1269-1270 (2006).

Li, Guang-Shan, "Development of a reporter system for the study of gene expression for solvent production in *Clostridium beijerinckii* NRRL B592 and *Clostridium acetobutylicum* ATCC 824," Dissertation, Department of Biochemestry, Virginia Polytechnic Institute and State University (Sep. 1998).

Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).

Lin et al., "Functional Expression of Horseradish Peroxidase in *E. coli* by Directed Evolution," *Biotechnol. Prog.* 15:467-471 (1999).

Lin et al., "Effect of carbon sources differing in oxidation state and transport route on succinate production in metabolically engineered *Escherichia coli*," *J. Ind. Microbiol.Biotechnol.* 32:87-93 (2005).

Lin et al., "Fed-batch culture of a metabolically engineered *Escherichia coli* strain designed for high-level succinate production and yield under aerobic conditions," *Biotechnol. Bioeng.* 90:775-779 (2005).

Lin et al., "Genetic Reconstruction of the Aerobic Central Metabolism in *Escherichia coli* for the Absolute Aerobic Production of Succinate," *Biotechnol. Bioeng.* 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in*Escherichia coli*," *Biotechnol. Prog.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, "Metabolic Network Design and Engineering in *Escherichia coli*" Ph.D. Thesis, Rice University, Dept. of Bioengineering (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).

Lingen et al., "Alteration of the substrate specificity of benzoylformate decarboxylase from *Pseudomonas putida* by directed evolution," *Chembiochem.* 4:721-726 (2003).

Lingen et al., "Improving the carboligase activity of benzoylformate decarboxylase from *Pseudomonas putida* by a combination of directed evolution and site-directed mutagenesis," *Protein Eng,* 15:585-593 (2002).

Link et al., "Methods for generating precise deletions and insertions in the genome of wild-type *Eshcerichia coli*: application to open reading frame characterization," *J. Bacteriol.* 179:6228-6237 (1997).

Liou et al., "*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov," *Int. J. Syst. Evol. Microbiol.* 55:(Pt 5):2085-2091 (2005).

Liu et al., "Kinetic and crystallographic analysis of active site mutants of *Escherichia coli* γ-aminobutyrate aminotransferase," *Biochemistry* 44:(8):2982-2992 (2005).

Liu et al., "Microbial production of R-3-hydroxybutyric acid by recombinant *E. coli* harboring genes of phbA, phbB, and tesB,"*Appl. Microbiol. Biotechnol.* 76:811-818 (2007).

Liu et al., "Purification and characterization of ornithine acetyltransferase from *Saccharomyces cerevisiae*," *Eur. J. Biochem.* 228:291-296 (1995).

Liu et al., "Crystal structures of unbound and aminooxyacetate-bound *Escherichia coli* γ-aminobutyrate aminotransferase," *Biochemistry* 43(34):10896-10905 (2004).

Liu et al., "Economical succinic acid production from cane molasses by *Actinobacillus succinogenes*," *Bioresour Technol* 99(6):1736-1742 (2008).

Ljungdahl and Andreesen, "Formate dehydrogenase, a selenium-tungsten enzyme from Clostridium thermoaceticum," *Methods Enzymol.* 53:360-372 (1978).

Ljungdahl and Andreesen, "Tungsten, a component of active formate dehydrogenase from Clostridium thermoacetium," *FEBS Lett.* 54:279-282 (1975).

Ljungdahl, "The Autotrophic Pathway of Acetate Synthesis in Acetogenic Bacteria," *Ann. Rev. Microbiol.* 40:415-450 (1986).

Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle," *Angew Chem Int Ed.* 44(45):7442-7447 (2005).

Lokanath et al., "Crystal structure of novel NADP-dependent 3-hydroxyisobutyrate dehydrogenase from Thermus thermophilus HB8," *J. Mol. Biol.* 352(4):905-917 (2005).

Loke et al., "Active acetyl-CoA synthase from Clostridium thermoaceticum obtained by cloning and heterologous expression of acsAB in *Escherichia coli*," *Proc. Natl. Acad. Sci. U.S.A.* 97:12503-12535 (2000).

Longtine et al., "Additional modules for versatile and economical PCR-based gene deletion and modification in *Saccharomyces cerevisiae*," *Yeast* 14(10): 953-961 (1998).

Lopez-Barragan et al., "The *bzd* gene cluster, coding for anaerobic benzoate catabolism, in *Azoarcus* sp. Strain CIB," *J. Bacteriol.* 186(17):5762-5774 (2004).

Louie and Chan, "Cloning and characterization of the gamma-glutamyl phosphate reductase gene of Campylobacter jejuni," *Mol. Gen. Genet.* 240:29-35 (1993).

Louis et al., "Restricted distribution of the butyrate kinase pathway among butyrate-producing producing bacteria from the human colon," *J. Bacteriol.* 186:2099-2106 (2004).

Lovell et al., "Cloning and expression in *Escherichia coli* of the Clostridium thermoaceticum gene encoding thermostable formyltetrahydrofolate synthetase," *Arch. Microbiol.* 149(4):280-285 (1988).

Lovell et al., "Primary structure of the thermostable formyltetrahydrofolate synthetase from Clostridium thermoaceticum," *Biochemistry* 20(29):5687-5694 (1990).

Low et al., "Mimicking somatic hypermutation: Affinity maturation of antibodies displayed on baceriophage using a bacterial mutator strain," *J. Mol. Biol.* 260(3):359-368 (1996).

Lu et al., "Controlled Poetntial Enzymology of Methyl Transfer Reactions Involved in Acetyl-CoA Synthesis by CO Dehydrogenase and the Corrinoid/Iron-Sulfur Protein from Clostridium thermoaceticum," *J. Biol. Chem.* 265(6):3124-3133 (1990).

Lu et al., "Functional Analysis and Regulation of the Divergent spuABCDEFGH-spuI Operons for Polyamine Uptake and Utilization in *Pseudomonas aeruginosa* PAO1," *J. Bacteriol.* 184(14):3765-3773 (2002).

Lu et al., "Sequence and expression of the gene encoding the corrinoid/iron-sulfur protein from Clostridium thermoaceticum and reconstitution of the recombinant protein to full activity," *J. Biol. Chem.* 268(8):5605-5614 (1993).

Luersen, "Leishmania major thialsine $N_\epsilon$-acetyltransferase: Identification of amino acid residues crucial for substrate binding," *FEBS Lett.* 579:5347-5352 (2005).

Luli and Strohl, "Comparison of Growth, Acetate Production, and Acetate Inhibition of *Escherichia coli* Strains in Batch and Fed-Batch Fermentations," *Appl. Environ. Microbiol.* 56:1004-1011 (1990).

Lupa et al., "Distribution of genes encoding the microbial non-oxidative reversible hydroxyarylic acid decarboxylases/phenol carboxylases," *Genomics* 86:342-351 (2005).

Lupa et al., "Properties of the reversible nonoxidative vanillate/4-hydroxybenzoate decarboxylase from *Bacillus subtilis*," *Can. J. Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Lutz and Bujard, "Independent and tight regulation of transcriptional units in *Escherichia coli* via the LacR/O, the TetR/O and AraC/$I_1$-$I_2$ regulatory elements," *Nucleic Acids Res.* 25(6):1203-1210 (1997).

Lutz et al., "Creating multiple-crossover DNA libraries independent of sequence identity," *Proc. Natl. Acad. Sci U.S.A.* 98:11248-11253 (2001).

Lutz et al., "Dissecting the functional program of *Escherichia coli* promoters: the combined mode of action of Lac repressor and AraC activator," *Nucleic Acids Res.* 29(18):3873-3881 (2001).

Lutz et al., "Rapid generation of incremental truncation libraries for protein enginering using α-phosphothioate nucleotides," *Nucleic Acids Res.* 15;29(4):e16 (2001).

Lynch et al., "SCALEs: multiscale analysis of library enrichment," *Nat. Methods.* 4(1):87-93 (2007).

Lynd et al., "Microbial Cellulose Utilization: Fundamentals and Biotechnology," *Microbiol. Mol. Biol. Rev.* 66:506-577 (2002).

Lynn et al., "Living Ring-Opening Metathesis Polymerization in Aqueous Media Catalyzed by Well-Defined Ruthenium Carbene Complexes," *J. Am. Chem. Soc.* 118(4):784-790 (1996).

Lynn et al., "Living Ring-Opening Metathesis Polymerization in Water," *J. Am. Chem. Soc.* 120(7):1627-1628 (1998).

Ma et al., "Induced rebuilding of aspartase conformation," *Ann. NY Acad. Sci.* 672:60-65 (1992).

Macis et al., "Properties and sequence of the Coenzyme $B_{12}$-dependent glycerol dehydratase of *Clostridium pasteruianum*," *FEMS Microbiol. Lett.* 164:21-28 (1998).

Mack and Buckel, "Conversion of glutaconate CoA-transferase from Acidaminococcus fermentans into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in *Acidaminococcus fermentans*," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The Methanosarcina barkeri genome: comparative analysis with *Methanosarcina acetivorans* and *Methanosarcina mazei* reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).

Mahadevan and Schilling, "The effects of alternate optimal solutions in constraint-based genome-scale metabolic models," *Metab. Eng.* 5(4):264-276 (2003).

Mahan and Csonka, "Genetic analysis of the proBA genes of *Salmonella typhimurium*: physical and genetic analyses of the cloned proB$^+$A$^+$ genes of *Escherichia coli* and of a mutant allele that confers proline overproduction and enhanced osmotolerance," *J. Bacteriol.* 156:1249-1262 (1983).

Mai and Adams, "Purification and characterization of two reversible and ADP-dependent acetyl Coenzyme A synthetases from the hyperthermophilic archaeon *Pyrococcus furiosus*," *J. Bacteriol.* 178:5897-5903 (1996.)

Maicas, S. et al., "NAD(P)H regeneration is the key for heterolactic fermentation of hexoses in *Oenococcus oeni*," *Microbiology* 148: 325-332 (2002).

Maitra and Sprinson, "5-Dehydro-3-deoxy-D-arabino-heptulosonic acid 7-phosphate. An intermediate in the 3-dehydroquinate synthase reaction," *J Biol. Chem.* 253:5426-5430 (1978).

Majewski and Domach, "Simple Constrained-Optimization View of Acete Overflow in *E. Coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170:991-994 (1988).

Marks et al., "Molecular cloning and characterization of (R)-3-hydroxybutyrate dehydrogenase from human heart," *J. Biol. Chem.* 267(22):15459-15463 (1992).

Martin et al., "Engineering a mevalonate pathway in *Escherichia coli* for production of terpenoids," *Nat. Biotechnol.* 21:796-802 (2003).

Martin et al., "Nematode.net update 2008: improvements enabling more efficient data mining and comparative nematode genomics," *Nucleic Acids Res.* 37:D571-D578 (2009).

Martinez-Blanco et al., "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe-4S] cluster and flavin," *Proc. Natl. Acad. Sci. U.S.A.* 101(44):15645-15649 (2004).

Mason and Dufour, "Alcohol acetyltransferases and the significance of ester synthesis in yeast," *Yeast* 16(14):1287-1298 (2000).

Matiasek et al., "Volatile ketone formation in bacteria: release of 3-oxopentanoate by soil pseudomonads during growth on heptanoate," *Curr. Microbiol.* 42:276-281 (2001).

Mat-Jan et al., "Mutants of *Escherichia coli* Deficient in the Fermentative Lactate Dehydrogenase," *J. Bacteriol.* 171(1):342-348 (1989).

Matsumura et al., "Constitutive expression of catABC genes in the aniline-assimilating bacterium *Rhodococcus species* AN-22: production, purification, characterization and gene analysis of CatA, CatB and CatC," *Biochem. J.* 393:219-226 (2006).

Matsushima et al., "An enone reductase from Nicotiana tabacum: cDNA cloning, expression in *Escherichia coli*, and reduction of enones with the recombinant proteins," *Bioorg. Chem.* 36:23-28 (2008).

Matta et al., "Interactions of the antizyme AtoC with regulatory elements of the *Escherichia coli* ato*DAEB* operon," *J. Bacteriol.* 189(17):6324-6332 (2007).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus et al., "Insights into the Evolution of Allosteric Properties. The NADH Binding Site of Hexameric Type II Citrate Synthases," *Biochemistry* 42:5555-5565 (2003).

Mavrovouniotis, Estimation of standard Gibbs energy changes of biotransformations, *J. Biol. Chem.* 266:14440-14445 (1991).

Maynard et al., "Autocatalytic activation of acetyl-CoA synthase," *J. Biol. Inorg. Chem.* 9:316-322 (2004).

Mazur et al., "Cis,cis-muconate lactonizing enzyme from Trichosporon cutaneum: evidence for a novel class of cycloisomerases in eucaryotes," *Biochemistry* 33:1961-1970 (1994).

McAlister-Henn and Thompson, "Isolation and expression of the gene encoding yeast mitochondrial malate dehydrogenase," *J. Bacteriol.* 169:5157-5166 (1987).

McCarthy et al., "Crystal structure of methylmalonyl-Coenzyme a epimerase from *P. shermanii*: a novel enzymatic function on an ancient metal binding scaffold," *Structure* 9(7):637-646 (2001).

McCullough et al., "Enzymatic decarboxylation of the aminobenzoates," *J. Am. Chem. Soc.* 79:628-630 (1957).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McInerney et al., "The genome of Syntrophus aciditrophicus: Life at the thermodynamic limit of microbial growth," *Proc. Natl. Acad. Sci U.S.A.* 104:7600-7607 (2007).

McKinlay et al., "Prospects for a bio-based succinate industry," *Appl. Microbiol. Biotechnol.* 76(4):727-740 (2007).

McPherson and Wootton, "Complete nucleotide sequence of the *Escherichia coli* gdhA gene," *Nucleic Acids Res.* 11:5257-5266 (1983).

McPherson et al., "Multiple interactions of lysine-128 of *Escherichia coli* glutamate dehydrogenase revealed by site-directed mutagenesis studies," *Protein Eng.* 2(2):147-152 (1988).

Meagher, "Purification and partial amino acid sequence of the cyanogen bromide fragments of muconolactone isomerase from *Pseudomonas putida*," *Biochim. Biophys. Acta* 494:33-47 (1977).

Mechichi et al., "Alicycliphilus denitrificans gen. nov., sp. nov., a cyclohexanol-degrading, nitrate-reducing β-proteobacterium," *Int. J. Syst. Evol. Microbiol.* 53:147-152 (2003).

Megraw et al., "Formation of lactyl-Coenzyme A and pyruvyl-Coenzyme A from lactic acid by *Escherichia coli*," *J. Bacteriol.* 90(4):984-988 (1965).

Meinnel et al., "Structural and Biochemical Characterization of the *Escherichia coli* argE Gene Product," *J. Bacteriol.* 174(7):2323-2331 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

Meng and Li, "Cloning, expression and characterization of a thiolase gene from *Clostridium pasteurianum*," *Biotechnol. Lett.* 28(16):1227-1232 (2006).

Menon and Ragsdale, "Mechanism of the Clostridium thermoaceticum pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Merkel and Nichols, "Characterization and sequence of the *Escherichia coli* panBCD gene cluster," *FEMS Microbiol. Lett.* 143(2-3):247-252 (1996).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Metz et al., "Purification of a jojoba embryo fatty acyl-Coenzyme A reductase and expression of its cDNA in high erucic acid rapeseed," Plant Phys. 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Miller et al., "Structure of β-lactam synthetase reveals how to synthesize antibiotics instead of asparagine," *Nat. Struct. Biol.* 8(8):684-689 (2001).

Miller et al., "The catalytic cycle of β-lactam synthetase observed by x-ray crystallographic snapshots," *Proc. Natl. Acad. Sci. U.S.A.* 99(23):14752-14757 (2002).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono and Nagasaki, "Occurrence of L -Lysine ε-Dehydrogenase in *Agrobacterium tumefaciens*," *J. Bacteriol.* 150(1):398-401 (1982).

Misono et al., "Properties of L-lysine epsilon-dehydrogenase from *Agrobacterium tumefaciens*," *J. Biochem.* 105(6):1002-1008 (1989).

Miura et al., "Molecular Cloning of the *nemA* Gene Encoding N-Ethylmaleimide Reductase from *Escherichia Coli*," *Biol. Pharm. Bull.* 20(1):110-112 (1997).

Miyazaki et al., "α-Aminoadipate aminotransferase from an extremely thermophilic bacterium, *Thermus thermophilus*," *Microbiology* 150:2327-2334 (2004).

Mizobata et al., "Purification and characterization of a thermostable class II fumarase from Thermus thermophilus," *Arch. Biochem. Biophys.* 355(1):49-55 (1998).

Mizugaki et al. "Studies on the metabolism of unsaturated fatty acids. IV. Stereochemical studies of the reaction catalyzed by trans-2-enoyl-Coenzyme A reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Momany et al., "Crystallization of diaminopimelate decarboxylase from *Escherichia coli*, a stereo specific D-amino-acid decarboxylase," *Acta. Crystallogr. D. Biol. Crystallogr.* 58(Pt 3):549-552 (2002).

Momany et al., "Crystallographic Structure of PLP-Dependent Ornithine Decarboxylase from Lactobacillus 30a to 3.0 Å Resolution," *J. Mol. Biol.* 252:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moon et al., "Metabolic engineering of *Escherichia coli* for the production of malic acid," *Biochem. Eng. J.* 40(2):312-320 (2008).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris and Jinks-Robertson, "Nucleotide sequence of the LYS2 gene of *Saccharomyces cerevisiae*: homology to *Bacillus brevis* tyrocidine synthetase 1," *Gene* 98:141-145 (1991).

Morsomme et al., "Single point mutations in various domains of a plant plasma membrane $H^+$-ATPase expressed in *Saccharomyces cerevisiae* increase $H^+$-pumping and permit yeast growth at low pH," *Embo. J.* 15(20):5513-5526 (1996).

Morton et al., "Cloning, sequencing, and expressions of genes encoding enzymes of the autotrophic acetyl-CoA pathway in the acetogen Clostridium thermoaceticum," In M. Sebald (ed.), *Genetics and molecular biology of anaerobic bacteria*, Springer Verlag, New York, 389-406 (1992).

Morton et al., "The primary structure of the subunits of carbon monoxide dehydrogenase/acetyl-CoA synthase from Clostridium thermoaceticum," *J. Biol. Chem.* 266(35):23824-23828 (1991).

Moskowitz et al., "Metabolism of poly-β-hydroxybutyrate. II. Enzymatic synthesis of D-(-)-β-hydroxybutyryl Coenzyme A by an enoyl hydrase from *Rhodospirillum rubrum*," *Biochemistry* 8:2748-2755 (1969).

Moszer, "The complete genome of *Bacillus subtilis*: from sequence annotation to data management and analysis," *FEBS Lett.* 430:28-36 (1998).

Mouttaki et al., "Cyclohexane Carboxylate and Benzoate Formation from Crotonate in Syntrophus aciditrophicus," *Appl. Environl. Microbiol.* 73(3):930-938 (2007).

Müh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta.* 1475(3):191-206 (2000).

Muller and Buckel, "Activation of (R)-2-hydroxyglutaryl-CoA dehydratase from Acidaminococcus fermentans," *Eur. J. Biochem.* 230(2):698-704 (1995).

Muller et al., "Nucleotide exchange and excisiion technology (NExT) DNA shuffling; a robust method for DNA fragmentation and directed evolution," *Nucleic Acids Res.* 33:e117 (2005).

Muller, "Energy Conservation in Acetogenic Bacteria," *Appl. Environ. Microbiol.* 69:6345-6353 (2003).

Murakami et al., "Purification and characterization of two muconate cycloisomerase isozymes from aniline-assimilating Frateuria species ANA-18," *Biosci. Biotechnol. Biochem.* 62:1129-1133 (1998).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schonheit, "Novel type of ADP-forming acetyl Coenzyme a synthetase in hyperthermophilic archaea: heterologous expression and characterization of isoenzymes from the sulfate reducer Archaeoglobus fulgidus and the methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Nagasawa et al., "Cloning and Nucleotide Sequence of the Alcohol Acetyltransferase II gene (*ATF2*) from *Saccharomyces cerevisiae* Kyokai No. 7," *Biosci. Biotechnol. Biochem.* 62:1852-1857 (1998).

Nagata et al., "Gene cloning, purification, and characterization of thermostable and halophilic leucine dehydrogenase from a halophilic thermophile, *Bacillus licheniformis* TSN9," *Appl. Microbiol. Biotechnol.* 44:432-438 (1995).

Naggert et al., "Cloning, sequencing, and characterization of *Escherichia coli* thioesterase Ii," *J. Biol. Chem.* 266(17):11044-11050 (1991).

Nahvi et al., "Genetic Control by a Metabolite Binding mRNA," *Chem. Biol.* 9:1043-1049 (2002).

Naidu and Ragsdale, "Characterization of a three-component vanillate O-demethylase from Moorella thermoacetica," *J. Bacteriol.* 183(11):3276-3281 (2001).

Najafpour and Younesi, "Ethanol and acetate synthesis from waste gas using batch culture of *Clostridium ljungdahlii*," *Enzyme Microb. Technol.* 38:223-228 (2006).

Najmudin et al., "Purification, crystallization and preliminary X-ray crystallographic studies on acetolactate decarboxylase," *Acta. Crystallogr. D. Biol. Crystallogr.* 59(Pt 6):1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

Nakazawa et al., "Studies on monooxygenases. V. Manifestation of amino acid oxidase activity by L-lysine monooxygenase," *J. Biol. Chem.* 247:3439-3444 (1972).

Namba et al., "Coenzyme A- and Nicotinamide Adenine Dinucleotide-dependent Branched Chain α-Keto Acid Dehydrogenase," *J. Biol. Chem.* 244(16):4437-4447.

Neidhart et al., "Mandelate racemase and muconate lactonizing enzyme are mechanistically distinct and structurally homologous," *Nature* 347:692-694 (1990).

Ness et al., "Synthetic shuffling expands functional protein diversity by allowing amino acids to recombine independently," *Nat. Biotechnol.* 20:1251-1255 (2002).

Nicolaou et al., "The Diels-Alder Reaction in Total Synthesis," *Angew Chemie Int Ed.* 41:1668-1698 (2002).

Niegemann et al., "Molecular organization of the *Escherichia coli* gab cluster: nucleotide sequence of the structural genes gabD and gabP and expression of the GABA permease gene," *Arch.Microbiol* 160:454-460 (1993).

Nimmo, "Kinetic mechanism of *Escherichia coli* isocitrate dehydrogenase and its inhibition by glyoxylate and oxaloacetate," *Biochem. J.* 234(2):317-323 (1986).

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).

Nishizawa et al., "Gene expression and characterization of two 2-oxoacid:ferredoxin oxidoreductases from Aeropyrum pernix K1," *FEBS Lett.* 579:2319-2322 (2005).

Nissen et al., "Expression of a cytoplasmic transhydrogenase in *Saccharomyces cerevisiae* results in formation of 2-oxoglutarate due to depletion of the NADPH pool," *Yeast* 18:19-32 (2001).

Nogales et al., "Characterization of the last step of the aerobic phenylacetic acid degradation pathway," *Microbiology* 153(Pt 2):357-365 (2007).

Noichinda et al., "Subcellular Localization of Alcohol Acetyltransferase in Strawberry Fruit," *Food Sci. Technol. Res.* 5(3):239-242 (1999).

Nölling et al., "Genome sequence and comparative analysis of the solvent-producing bacterium *Clostridium acetobutylicum*," *J. Bacteriol.* 183(16):4823-4838 (2001).

Norton, "The Diels-Alder Diene Synthesis," *Chem. Rev.* 31:319-523 (1942).

Nowicki et al., "Recombinant tyrosine aminotransferase from *Trypanosoma cruzi*: structural characterization and site directed mutagenesis of a broad substrate specificity enzyme," *Biochim. Biophysica Acta* 1546:268-281 (2001).

O'Brien and Gennis, "Studies of the Thiamin Pyrophosphate Binding Site of *Escherichia coli* Pyruvate Oxidase," *J. Biol. Chem.* 255(8):3302-3307 (1980).

O'Brien et al., "Regulation by Lipids of Cofactor Binding to a Peripheral Membrane Enzyme: Binding of Thiamin Pyrophosphate to Pyruvate Oxidase," *Biochemistry* 16(14):3105-3109 (1977).

O'Brien et al., "Chemical, physical and enzymatic comparisons of formyltetrahydrofolate synthetases from thermo- and mesophilic clostridia," *Experientia. Suppl.* 26:249-262 (1976).

O'Brien et al., "Insight into the Mechanism of the $B_{12}$-Independent Glycerol Dehydratase from *Clostridium butyricum*: Preliminary Biochemical and Structural Characterization," *Biochemistry* 43:4635-4645 (2004).

Ofman et al., "2-Methyl-3-hydroxybutyryl-CoA dehydrogenase deficiency is caused by mutations in the HADH2 gene," *Am. J. Hum. Genet.* 72:1300-1307 (2003).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by *Pseudomonas*. Purification and Properties of a Deacetylase-Thiolesterrease Utilizing 4-Acetamidobutyryl CoA and Related Compounds," *J. Biol. Chem.* 256(14):7642-7651 (1981).

Okino et al., "An efficient succinic acid production process in a metabolically engineered *Corynebacterium glutamicum* strain," *Appl. Microbiol. Biotechnol.* 81(3):459-464 (2008).

Oku and Kaneda, "Biosynthesis of branched-chain fatty acids in *Bacillus subtilis*. A decarboxylase is essental for branched-chain fatty acid synthetase," *J. Biol. Chem.* 263(34):18386-18396 (1988).

Okuno et al., "2-Aminoadipate-2-oxoglutarate aminotransferase isoenzymes in human liver: a plausible physiological role in lysine and tryptophan metabolism," *Enzyme Protein* 47:136-148 (1993).

Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757.

O'Reilly and Devine, "Sequence and analysis of the citrulline biosynthetic operon argC-F from *Bacillus subtilis*," *Microbiology* 140:1023-1025 (1994).

Orencio-Trejo et al., "Metabolic reglulation analysis of an ethanologenic *Escherichia coli* strain based on RT-PCR and enzymatic activities," *Biotechnol. Biofuels* 1:8 (2008). (provided electronically by publisher as pp. 1-13).

Ostermeier et al., "A Combinatorial approach to hybrid enzymes independent of DNA homology," *Nat. Biotechnol.* 17:1205-1209 (1999).

Ostermeier et al., "Combinatorial protein engineering by incremental truncation," *Proc. Natl. Acad. Sci. U.S.A.* 96:3562-3567 (1999).

O'Sullivan et al., "Purification and characterisation of acetolactate decarboxylase from *Leuconostoc lactis* NCW1," *FEMS Microbiol. Lett* 194(2):245-249 (2001).

Otten and Quax, "Directed evolution:selecting today's biocatalysts," *Biomol. Eng.* 22:1-9 (2005).

Overkamp et al., "Functional analysis of structural genes for $NAD^+$-dependent formate dehydrogenase in *Saccharomyces cerevisiae*," *Yeast* 19:509-520 (2002).

Overkamp et al., "In vivo analysis of the mechanism for oxidation of cytosolic NADH by *Saccharomyces cerevisiae* mitochondria," *J. Bacteriol.* 182:2823-2830 (2000).

Padovani and Banerjee, "Assembly and protection of the radical enzyme, methylmalonyl-CoA mutase, by its chaperone," *Biochem.* 45(30):9300-9306 (2006).

Paik and Kim, "Enzymic syntehsis of ε-N-Acetyl-L-Lysine," *Arch. Biochem. Biophys.* 108:221-229 (1964).

Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).

Parales and Harwood, "Characterization of the Genes Encoding β-Ketoadipate: Succinyl-Coenzyme A Transferase in *Pseudomonas putida*," *J. Bacteriol.* 174(14):4657-4666 (1992).

Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in *fadB* mutant *Escherichia coli*," *Biotechnol. Bioeng.* 86(6):681-686 (2004).

Park et al., "Metabolic engineering of *Escherichia coli* for the production of L-valine based on transcriptome analysis and in silico gene knockout simulation," *Proc. Natl. Acad. Sci. U.S.A.* 104(19):7797-7802 (2007).

Park et al., "Regulation of succinate dehydrogenase (*sdhCDAB*) operon expression in *Escherichia coli* in response to carbon supply and anaerobiosis: role of ArcA and Fnr," *Mol. Microbiol.* 15(3):473-482 (1995).

Park et al., "Utilization of Electrically Reduced Neutral Red by *Actinobacillus succinogenes*: Physiological Function of Neutral Red in Membrane-Driven Fumarate Reduction and Energy Conservation," *J. Bacteriol* 181(8):2403-2410 (1999).

Parkin et al., "Rapid and efficient electrocatalytic $CO_2/CO$ interconversions by Carboxydothermus hydrogenoformans CO dehydrogenase I on an electrode," *J. Am. Chem. Soc.* 129(34):10328-10329 (2007).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283.

Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).

Patel et al., "β-ketoadipate enol-lactone hydrolases I and II from *Acinetobacter calcoaceticus*," *J. Biol. Chem.* 250:6567-6577 (1975).

Patil et al., "Use of genome-scale microbial models for metabolic engineering," *Curr. Opin. Biotechnol.* 15(1):64-69 (2004).

Patnaik et al., "Genome shuffling of *Lactobacillus* for improved acid tolerance," *Nat. Biotechnol.* 20:707-712 (2002).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylglutamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier and Harwood, "2-Ketocyclohexanecarboxyl Coenzyme A Hydrolase, the Ring cleavage Enzyme Required for Anaerobic Benzoate Degradation of *Rhodopseudomonas palustris*," *J. Bacteriol.* 180(9):2330-2336 (1998).

Peoples and Sinskey, "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino acid sequence of alcohol dehydrogenase from the thermophilic bacterium Thermoanaerobium brockii," *Biochemistry* 28(16):6549-6555.

Peretz et al., "Molecular cloning, nucleotide sequencing, and expression of genes encoding alcohol dehydrogenases from the thermophile Thermoanaerobacter brockii and the mesophile *Clostridium beijerinckii*," *Anaerobe.* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70:420-426 (2005).

Petersen and Bennett, "Purification of acetoacetate decarboxylase from clostridium acetobutylicum ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta* 421(2):334-347 (1976).

Pfanner and Geissler, "Versatility of the mitochondrial protein import machinery," *Nat. Rev. Mol. Cell. Biol.* 2(5):339-349 (2001).

Pfluger et al., "Lysine-2,3-Aminomutase and β-Lysine Acetyltransferase Genes of Methanogenic Archaea Are Salt Induced and Are Essential for the Biosynthesis of $N^\epsilon$-Acetyl-β-Lysine and Growth at High Salinity," *Appl. Environ. Microbiol.* 69(10):6047-6055 (2003).

Phalip et al., "Purification and properties of the α-acetolactate decarboxylase from *Lactococcus lactis* subsp. *lactis* NCDO 2118," *FEBS Lett.* 351(1):95-99 (1994).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400, 402, 404, 406, 408 (2000).

Pierce et al., "The Complete Genome Sequence of Moorella thermoacetia (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of Desulfovibrio africanus, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in *Bacillus sphericus*," *Biochem. J.* 287:685-690 (1992).

Ploux et al., "The NADPH-linked acetoacetyl-CoA reductase from Zoogloea ramigera, Characterization and mechanistic studies of the cloned enzyme overproduced in *Escherichia coli*," *Eur. J. Biochem.* 174:177-182 (1988).

Pohl et al., "Remarkably broad Sustrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Pollard et al., "Purification, characterisation and reaction mechanisms of monofunctional 2-hydroxypentadienoic acid hydratase from *Escherichia coli*," *Eur. J. Biochem. FEBS* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Pronk et al., "Pyruvate metabolism in *Saccharomyces cerevisiae*," *Yeast* 12:1607-1633 (1996).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant Nad(H)-dependent glutamate dehydrogenase activity in transgenic tobacco via alteration of β subunit levels," *Planta* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4):651-662 (2009).

Qiu et al., "Metabolic engineering of *Aeromonas hydrophila* for the enhanced production of poly(3-hydroxybutyrate-co-3-hydroxyhexanoate)," *Appl. Microbiol. Biotechnol.* 69(5):537-542 (2006).

Qu et al., "Inhibition of human ornthine decarboxylase activity by enantiomers of difluoromethylornithine," *Biochem. J.* 375:465-470 (2003).

Quail and Guest, "Purification, characterization and mode of action of pdhR, the transcriptional repressor of the PdhR-aceEF-Ipd operon of *Escherichia coli*," *Mol. Microbiol.* 15(3):519-529 (1995).

Rado and Hoch, "Phosphotransacetylase from *Bacillus subtilis*: purification and physiological studies," *Biochim. Biophys. Acta* 321:114-125 (1973).

Ragsdale et al., "Acetogenesis and the Wood-Ljungdahl pathway of $CO_2$ fixation," *Biochimica. Biophysica. Acta* 1784(12):1873-1898 (2008).

Ragsdale, "Enzymology of the wood—Ljungdahl pathway of acetogenesis," *Ann. NY Acad Sci.* 1125:129-136 (2008).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Rajpal et al., "A general method for greatly improving the affinity of antibodies by using combinatorial libraries," *Proc. Natl. Acad. Sci. U.S.A.* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J. Biochem.* 149:401-404 (1985).

Rangarajan et al., "Structure of [NiFe] hydrogenase maturation protein HypE from *Escherichia coli* and its interaction with HypF," *J. Bacteriol.* 190(4):1447-1458.

Rasmussen, L.J., et al. "Carbon Metabolism Regulates Expression of the *pfl* (Pyruvate-Formate-Lyase) Gene in *Escherichia coli*," *J. Bacteriol.* 173(20):6390-6397 (1991).

Rathinasabapathi, "Propionate, a source of β-alanine, is an inhibitor of β-alanine methylation in Limonium latifoilium Plunbaginaces," *J. Plant Physiol.* 159:671-674 (2002).

Ratnatilleke et al., "Cloning and sequencing of the Coenzyme $B_{12}$-binding domain of isobutyryl-CoA mutase from Streptomyces cinnamonensis, reconstitution of mutase activity, and characterization of the recombinant enzyme produced in *Escherichia coli*," *J. Biol. Chem.* 274(44):31679-31685 (1999).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin $B_{12}$) biosynthetic genes: functional studies in *S. typhimurium* and *Escherichia coli*," *J. Bacteriol.* 178(3):753-767 (1996).

Ravagnani et al., "Spo0A directly controls the switch from acid to solvent production in solvent-forming clostridia," *Mol. Microbiol.* 37(5):1172-1185 (2000).

Raybuck et al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27(20):7698-7702.

Raynaud et al., "Molecular characterization of the 1,3-propanediol (1,3-PD) operon of clostridium butyricum," *Proc. Natl. Acad. Sci. U.S.A.* 100:5010-5015 (2003).

Rea et al., "Structure and Mechanism of HpcH: A Metal Ion Dependent Class II Aldolase from the Homoprotocatechuate Degradation Pathway of *Escherichia coli*," *J. Mol. Biol.* 373:866-876 (2007).

Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).

Reda et al., "Reversible interconversion of carbon dioxide and formate by an electroactive enzyme," *Proc. Natl. Acad. Sci. U.S.A.* 105:10654-10658 (2008).

Reetz and Carballeira, "Iterative saturation mutagenesis (ISM) for rapid directed evolution of functional enzymes," *Nat. Protoc.* 2:891-903 (2007).

Reetz et al., "Creation of Enantioselective Biocatalysts for Organic Chemistry by in Vitro Evolution," *Angew. Chem. Int. Ed. Engl.* 36:2830-2832 (1997).

Reetz et al., "Directed Evolution of an Enantioselective Enzyme through Combinatorial Multiple-Cassette Mutagenesis, " *Angew. Chem. Int. Ed. Engl.* 40:3589-3591 (2001).

Reetz et al., "Expanding the Range of Substrate Acceptance of Enzymes: Combinatorial Active-site saturation test," *Agnew. Chem. Int. Ed. Engl.* 117:4264-4268 (2005).

Reetz et al., "Iterative saturation mutagenesis on the basis of B factors as a strategy for incresing protein thermostability," *Angew. Chem. Int. Ed.* 45:7745-7751 (2006).

Regev-Rudzki et al., "Yeast Aconitase in Two Locations and Two Metabolic Pathways: Seeing Small Amounts Is Believing," *Mol. Biol. Cell* 16:4163-4171 (2005).

Reidhaar-Olson and Sauer, "Combinatorial cassette mutagenesis as a probe of the informational content of protein sequences," *Science* 241:53-57 (1988).

Reidhaar-Olson et al., "Random mutagenesis of protein sequences using oligonucleotide cassettes," *Methods Enzymmol.* 208:564-586 (1991).

Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).

Reitzer et al., "Crystallization and preliminary X-ray analysis of recombinant glutamate mutase and of the isolated component S from Clostridium cochlearium," *Acta. Crystallogr. D. Biol. Crystallogr.* 54(Pt 5):1039-1042 (1998).

Repetto and Tzagoloff, "Structure and Regulation of KGD1, the Structural Gene for Yeast α-Ketoglutarate Dehydrogenase," *Mol. Cell. Biol.* 9(6):2695-2705 (1989).

Reshetnikov, et al., "Characterization of the ectoine biosynthesis genes of haloalkalotolerant obligate methanotroph 'Methylomicrobium alcaliphilum 20Z'," *Arch. Microbiol.* 184:286-297 (2006).

Resnekov et al., "Organization and regulation of the *Bacillus subtilis* odhAB operon, which encodes two of the subenzymes of the 2-oxoglutarate dehydrogenase complex," *Mol. Gen. Genet.* 234:285-296 (1992).

Rhodes et al., "Production of fumaric acid by *Rhizopus arrhuzus*," *Appl. Microbiol.* 7:74-80 (1959).

Rhodes et al., "Production of Fumaric Acid in 20-Liter Fermentors," *Appl. Microbiol.* 10(1)9-15 (1962).

Rigden et al., "A cofactor-dependent phosphoglycerate mutase homolog from *Bacillus stearothermophilus* is actually a broad specificity phosphatase," *Protein Sci.* 10:1835-1846 (2001).

Ringer et al., "Monoterpene double-bond reductases of the (−)-menthol biosynthetic pathway: isolation and characterization of cDNAs encoding (−)-isopiperitenone reductase and (+)-pulegone reductase of peppermint," *Arch. Biochem. Biophys.* 418(1):80-92 (2003).

Ringquist et al., "Translation initiation in *Escherichia coli*: sequences within the ribosome-binding site," *Mol. Microbiol.* 6(9):1219-1229 (1992).

Riondet et al., "Measurement of the intracellular pH in *Escherichia coli* with the internally conjugated fluorescent probe 5- (and 6-)carboxyfluorescein succinimidyl ester," *Biotechnol. Tech.* 11(10):735-738 (1997).

Rioux et al., "Two outer membrane transport systems for vitamin $B_{12}$ in *Salmonella typhimurium*," *J. Bacteriol.* 171:2986-2993 (1989).

Rioux et al., "Vitamin $B_{12}$ transport in *Escherichia coli* K12 does not require the btuE gene of the *btuCED* operon," *Mol. Gen. Genet.* 217:301-308 (1989).

Riviere et al., "Acetyl:succinate CoA-transferase in procyclic *Trypanosoma brucei*. Gene identification and role in carbohydrate metabolism," *J. Biol. Chem.* 279(44):45337-45346 (2004).

Roa Engel et al., "Fumaric acid production by fermentation," *Appl. Microbiol. Biotechnol.* 78(3):379-389 (2008).

Roberts et al, "The Role of Enoyl-CoA Hydratase in the Metabolism of Isoleucine by *Pseudomonas putida*," *Arch. Microbiol.* 117:99-108 (1978).

Roberts et al., "Acetyl-Coenzyme A synthesis from methyltetrahydrofolate, CO, and Coenzyme A by enzymes purified from *Clostridium thermoaceticum*: attainment of in vivo rates and identification of rate-limiting steps," *J. Bacteriol.* 174(14):4667-4676.

Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86(1):32-36 (1989).

Robinson et al., "Studies on Rat Brain Acyl-Coenzyme A Hydrolase (Short Chain)," *Biochem. Biophys. Res. Commun.* 71(4):959-965 (1976).

Roca et al., "Metabolic engineering of ammonium assimilation in xylose-fermenting *Saccharomyces cerevisiae* improves ethanol production," *Appl. Environ. Microbiol.* 69:4732-4736 (2003).

Rodriguez et al., "Characterization of the *p*-Coumaric Acid Decarboxylase from *Lactobacillus plantarium* CECT 748$^T$," *J. Agric. Food Chem.* 56:3068-3072 (2008).

Roffia et al., "Byproduct Identification in the Terephtalic Acid Production Process and Possible Mechanisms of their Formation," *Ind. Eng. Chem. Prod. Res. Dev.* 23:629-634 (1984).

Rohdich et al., "Enoate reductases of Clostridia. Cloning, sequencing, and expression," *J. Biol. Chem.* 276(8):5779-5787 (2001).

Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).

Romero et al., "Partial purification and characterization and nitrogen regulation of the lysine ε-aminotransferase of Streptomyces clavuligers," *J. Ind. Microbiol. Biotechnol.* 18:241-246 (1997).

Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51.

Rose and Weaver, "The role of the allosteric B site in the fumarase reaction," *Proc. Natl. Acad. Sci. U.S.A.* 101(10):3393-3397 (2004).

Rose et al., "Enzymatic phosphorylation of acetate," *J. Biol. Chem.* 211(2):737-756.

Rosenberg, "A Comparison of Lipid Patterns in Photosynthesizing and Nonphotosynthesizing Cells of *Euglena* Gracilis," *Biochem.* 2:1148-1154 (1963).

Roszak et al., "The Structure and Mechanism of the Type II Dehydroquinase from *Streptomyces coelicolor*," *Structure* 10:493-503 (2002).

Roth et al., "Characterization of the cobalamin (vitamin $B_{12}$) biosynthetic genes of *Salmonella typhimurium*," *J. Bacteriol.* 175:3303-3316 (1993).

Rother and Metcalf, "Anaerobic growth of Methanosarcina acetivorans C2A on carbon monoxide: an unusual way of life for a methanogenic archaeon," *Proc. Natl. Acad. Sci. U.S.A.* 101(48):16929-16934 (2004).

Rother et al., "Genetic and proteomic analyses of CO utilization by *Methanosarcina acetivorans*," *Arch. Microbiol.* 188(5):463-472 (2007).

Rous, "On the occurrence of enzymes of ketone-body metabolism in human adipose tissue," *Biochem. Biophys. Res. Commun.* 69(1):74-78 (1976).

Roux and Walsh, "p-aminobenzoate synthesis in *Escherichia coli*: kinetic and mechanistic characterization of the amidotransferase PabA," *Biochemistry* 31:6904-6910 (1992).

Roux and Walsh, "p-Aminobenzoate synthesis in *Escherichia coli*: mutational analysis of three conserved amino acid residues of the amidotransferase PabA," *Biochemistry* 32:3763-3768 (1993).

Roy and Dawes, "Cloning and Characterization of the gene Encoding Lipoamide Dehydrogenase in *Saccharomyces cerevisiae*," *J. Gen. Microbiol.* 133:925-933 (1987).

Roymoulik et al., "Rearrangement of L-2-hydroxyglutarate to L-threo-3-methylmalate catalyzed by adenosylcobalamin-dependent glutamate mutase," *Biochem.* 39(33):10340-10346 (2000).

Rozell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).

Rudman and Meister, "Transamination in *Escherichia coli*," *J. Biol. Chem.* 200(2):591-604 (1953).

Ruldeekulthamrong et al., "Molecular characterization of lysine 6-dehydrogenase from Achromobacter denitrificans," *BMB Reports* 41(11):790-795 (2008).

Sabo et al., "Purification and physical properties of inducible *Escherichia coli* Lysine Decarboxylase," *Biochemistry* 13(4):662-670 (1974).

Sadowski, "The Flp recombinase of the 2-μm plasmid of *Saccharomyces cerevisiae*," *Prog. Nucleic Acid Res. Mol. Biol.* 51:53-91 (1995).

Saegesser et al., "Stability of broad host range cloning vectors in the phototrophic bacterium *Rhodospirillum rubrum*," *FEMS Microbiol. Lett.* 95:7-11 (1992).

Saito and Doi, "Microbial synthesis and properties of poly(3-hydroxybutyrate-co-4-hydroxybutyrate) in Comamonas acidovorans," *Int. J Biol Macromol.* 16:99-104.

Sakai et al, "Acetate and Ethanol Production from $H_2$ and $CO_2$ by *Morrella* sp. Using a Repeated Batch Culture," *J. Biosci. Bioeng.* 99:252-258 (2005).

Sakanyan et al., "A re-examination of the pathway for ornithine biosynthesis in a thermophilic and two mesophilic *Bacillus* species," *J. Gen. Microbiol.* 138:125-130.

Sakurada et al., "Acetylpolyamine Amidohydrolase from Mycoplana ramosa: Gene Cloning and Characterization of the Metal-Substituted Enzyme," *J. Bacteriol.* 178(19):5781-5786 (1996).

Salmon et al., "Global gene expression profiling in *Escherichia coli* K12. Effects of oxygen availability and ArcA," *J. Biol. Chem.* 280(15):15084-15096 (2005).

Saltzgaber-Muller et al., "Nuclear genes coding the yeast mitochondrial adenosine triphosphatase complex. Isolation of ATP2 coding the $F_1$-ATPase β subunit," *J. Bio. Chem.* 258(19):11465-11470 (1983).

Samanta and Harwood, "Use of *Rhodopseudomonas palustris* genome sequence to identify a single amino acid that contributes to the activity of Coenzyme A ligase with chlorinated substrates," *Mol. Microbiol.* 55(4):1151-1159 (2005).

Samsonova et al., "Molecular cloning and characterization of *Escherichia coli* K12 ygjG gene," *BMC Microbiol.* 3:2 (2003).

Samuelov et al., "Whey fermentation by anaerobiospirillum succiniciproducens for production of a succinate-based animal feed additive," *Appl. Environ. Microbiol.* 65(5):2260-2263 (1999).

San et al., "Metabolic Engineering through Cofactor Manipulation and its Effects on Metabolic Flux Redistribution in *Escherichia coli*," *Metab Eng.* 4(2):182-192 (2002).

Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).

Sanchez et al., "Novel pathway engineering design of the anaerobic central metabolic pathway in *Escherichia coli* to increase succinate yield and productivity," *Metab. Eng.* 7(3): 229-239 (2005).

Sanchez et al., "Batch culture characterization and metabolic flux analysis of succinate-producing *Escherichia coli* strains," *Metab Eng.* 8(3):209-226 (2006).

Sanchez et al., "Effect of different levels of NADH availability on metabolic fluxes of *Escherichia coli* chemostat cultures in defined medium," *J. Biotechnol.* 117(4):395-405 (2005).

Sankaranarayanan et al., "Preliminary x-ray crystallographic analysis of ornithine acetyltransferase (Rv1653) from *Mycobacterium tuberculosis*," *Acta. Crystallogr. Sect. F. Struct. Biol. Cryst. Commun.* 65(Pt 2):173-176 (2009).

Sanyal et al., "Biosyntehsis of pimeloyl-CoA, a biotin precursor in *Escherichia coli*, follows a modified fatty acid synthesis pathway: $^{13}$C-labeling studies," *J. Am. Chem. Soc.* 116:2637-2638 (1994).

Sariaslani, "Development of a Combined biological and Chemical Process for Production of Industrial aromatics from Renewable Resources," *Annu. Rev. Microbiol.* 61:51-69 (2007).

Sass et al., "Folding of fumarase during mitochondrial import determines its dual targeting in yeast," *J. Biol. Chem.* 278(46):45109-45116 (2003).

Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).

Sauer and Thauer, "Methanol:Coenzyme M methyltransferase from Methanosarcina barkeri. Identification of the active-site histidine in the corrinoid-harboring subunit MtaC by site-directed mutagenesis," *Eur. J. Biochem.* 253(3):698-705 (1998).

Sauer et al., "Methanol:Coenzyme M methyltransferase from Methanosarcina barkeri. Purification, properties and encoding genes of the corrinoid protein MT1," *Eur. J. Biochem.* 243(3):670-677 (1997).

Sauer, "Diels-Alder Reactions II: The Reaction Mechanism," *Angew. Chem. Int. Ed.* 6:16-33 (1967).

Sauvageot et al., "Characterisation of the diol dehydratase pdu operon of Lactobacillus collinoides," *FEMS Microbiol. Lett.* 209:69-74 (2002).
Sawers and Boxer, "Purification and properties of membrane-bound hydrogenase isoenzyme 1 from anaerobically grown *Escherichia coli* K12," *Eur. J. Biochem.* 156(2):265-275 (1986).
Sawers et al., "Characterization and physiological roles of membrane-bound hydrogenase isoenzymes from *Salmonella typhimurium*," *J. Bacteriol.* 168(1):398-404 (1986).
Sawers et al., "Differential expression of hydrogenase isoenzymes in *Escherichia coli* K-12: evidence for a third isoenzyme," *J. Bacteriol.* 164(3):1324-1331 (1985).
Sawers, "The hydrogenases and formate dehydrogenases of *Escherichia coli*," *Antonie Van Leeuwenhoek* 66(1-3):57-88 (1994).
Saz and Weil, "The mechanism of the formation of a-methylbutyrate from carbohydrate by Ascaris lumbricoides muscle," *J. Biol. Chem.* 235:914-918 (1960).
Schadt et al., "2-Amino-2-deoxyisochorismate is a key intermediate in *Bacillus subtilis* p-aminobenzoic acid biosynthesis," *J. Am. Chem. Soc.* 131:3481-3483.
Scher and Jakoby, "Maleate isomerase," *J. Biol. Chem.* 244:1878-1882 (1969).
Scherf and Buckel, "Purification and properties of 4-hydroxybutyrate Coenzyme A transferase from *Clostridium aminobutyricum*," *Appl. Environ. Microbiol.* 57(9):2699-2702 (1991).
Scherf and Buckel, "Purification and properties of an iron-sulfur and FAD-containing 4-hydroxybutyryl-CoA dehydratase/vinylacetyl-CoA $\Delta^3$-$\Delta^2$-isomerase from *Clostridium aminobutyricum*," *Eur. J. Biochem.* 215:421-429 (1993).
Scherf et al, "Succinate-ethanol fermentation in *Clostridium kluyveri*: purification and characterisation of 4-hydroxybutyryl-CoA dehydratase/vinylacetyl-CoA $\Delta^3$-$\Delta^2$-isomerase," *Arch. Microbiol.* 161(3):239-245 (1994).
Schilling et al., "Genome-Scale Metabolic Model of Helicobacter pylori 26695," *J. Bacteriol.* 184:4582-4593 (2002).
Schilling et al., "Combining Pathway Analysis with Flux Balance Analysis for the Comprehensive Study of Metabolic Systems," *Biotechnol. Bioeng.* 71(4):286-306 (2000/2001).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schilling et al., "Toward Metabolic Phenomics: Analysis of Genomic Data Using Flux Balances," *Biotechnol. Prog.* 15(3):288-295 (1999).
Schmid et al., "Plasmid-mediated uptake and metabolism of sucrose by *Escherichia coli* K-12," *J. Bacteriol.* 151(1):68-76 (1982).
Schmitzberger et al., "Structural constraints on protein self-processing in L-aspartate-α-decarboxylase," *EMBO J.* 22:6193-6204 (2003).
Schneider and Betz, "Waxmonoester Fermentation in Euglena-Gracilis T Factors Favoring the Synthesis of Odd-Numbered Fatty-Acids and Alcohols," *Planta.* 166:67-73 (1985).
Schneider et al., "The *Escherichia coli* gabDTPC operon: specific γ-aminobutyrate catabolism and nonspecific induction," *J. Bacteriol.* 184:6976-6986 (2002).
Schnell et al., "Anaerobic degradation of aniline and dihydroxybenzenes by newly isolated sulfate-reducing bacteria and description of *Desulfobacterium anilini*," *Arch. Microbiol.* 152:556-563 (1989).
Schousboe et al., "Purification and Characterization of the 4-Aminobutyrate-2-Ketoglurate Transaminase from Mouse Brain," *Biochem.* 2(15):2868-2873 (1973).
Schrock et al., "Preparation and Reactivity of Several Alkylidene Complexes of the Type W(CHR')(N-2, 6-$C_6H_3$-i-$Pr_2$)($OR)_2$ and Related Tungstacyclobutane complexes. Controlling Metathesis Activity through the Choice of Alkoxide Ligand," *J. Am. Chem. Soc.* 110:1423-1435 (1988).
Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).
Schurmann and Sprenger, "Fructose-6-phosphate aldolase is a novel class I aldolase from *Escherichia coli* and is related to a novel group of bacterial transaldolases," *J. Biol. Chem.* 276(14): p. 11055-11061 (2001).
Schwarzer et al., "Nonribosomal peptides: from genes to products," *Nat. Prod. Rep.* 20:275-287 (2003).
Schweiger and Buckel, "On the dehydration of (R)-lactate in the fermentation of alanine to propionat by Clostridium propionicum," *FEBS Lett.* 171:79-84 (1984).
Schweiger et al., "Purification of 2-hydroxyglutaryl-CoA dehydratase from Acidaminococcus fermentans. An iron-sulfur protein," *Eur. J. Biochem.* 169(2):441-448 (1987).
Scott and Jakoby, "Soluble γ-Aminobutyric-Glutamic Transaminase from *Pseudomonas fluorescens*," *J. Biol. Chem.* 234:932-936 (1959).
Scott, A.I., "Discovering nature's diverse pathways to vitamin $B_{12}$: a 35-year odyssey," *J. Org. Chem.* 68:2529-2539 (2003).
Seedorf et al., "The genome of *Clostridium kluyveri*, a strict anaerobe with unique metabolic features," *Proc. Natl. Acad. Sci. U.S.A.* 105(6):2128-2133 (2008).
Seffernick et al., "Melamine deaminase and Atrazine chlorohydrolase: 98 percent identical but functionally different," *J. Bacteriol.* 183 (8):2405-2410 (2001).
Segre et al., "Analysis of optimality in natural and perturbed metabolic networks," *Proc. Natl. Acad. Sci. U.S.A.* 99:15112-15117 (2002).
Seibert et al., "Characterization of a gene cluster encoding the maleylacetate reductase from *Ralstonia eutropha* 335T, and enzyme recruited for growth with 4-fluorobenzoate," *Microbiology* 150:463-472 (2004).
Seibert et al., "Characterization of the maleylacteate reductase MacA of Rhodococcus opacus 1CP and evidence for the presence of an isofunctional enzyme," *J. Bacteriol.* 180:3503-3508 (1998).
Seibert et al., "Purification and characterization of maleylacetate reductase from Alcaligenes eutrophys JMP134(pJP4)," *J. Bacteriol.* 175:6745-6754 (1993).
Selifonova et al., "Rapid evolution of novel traits in microorganisms," *Appl Environ Microbiol.* 67:3645-3649 (2001).
Selmer et al., "Propionate CoA-transferase from *Clostridium propionicum*. Cloning of gene identification of glutamate 324 at the active site," *Eur. J. Biochem.* 269:372-380 (2002).
Seltzer, "Purification and properties of maleylacetone cis-trans isomerase from *Vibrio* 01," *J. Biol. Chem.* 248:215-222 (1973).
Sen et al., "Developments in directed evolution for improving enzyme functions," *Appl. Biochem. Biotechnol.* 143:212-223 (2007).
Sennett et al., "Transmembrane transport of cobalamin in prokaryotic and eukaryotic cells," *Ann. Rev. Biochem.* 50:1053-1086 (1981).
Seravalli et al., "Evidence that NiNi acetyl-CoA synthase is active and that the CuNi enzyme is not," *Biochemistry* 43(13):3944-3955 (2004).
Seravalli et al., "Mechanism of transfer of the methyl group from (6S)-methyltetrahydrofolate to the corrinoid/iron-sulfur protein catalyzed by the methyltransferase from clostridium thermoaceticum: a key step in the Wood-Ljungdahl pathway of acetyl-CoA synthesis," *Biochemistry* 38(18):5728-5735 (1999).
Seyfried et al., "Cloning, Sequencing, and Overexpression of the Genes Encoding Coenzyme $B_{12}$-Dependent Glycerol Dehydratase of *Citrobacter freundii*," *J. Bacteriol.* 178(19):5793-5796 (1996).
Shafiani et al., "Cloning and characterization of aspartate-β-semialdehyde dehydrogenase from *Mycobacterium tuberculosis* H37 Rv," *J. Appl. Microbiol.* 98:832-838 (2005).
Shalel-Levanon et al., "Effect of ArcA and FNR on the expression of genes related to the oxygen regulation and the glycolysis pathway in *Eschericiha coli* under microaerobic growth conditions," *Biotechnol. Bioeng.* 92(2):147-159 (2005).
Shames et al., "Interaction of Aspartate and Aspartate-derived Antimetabolites with the Enzymes of the Threonine Biosynthetic Pathway of *Escherichia coli*," *J. Biol. Chem.* 259(24):15331-15339 (1984).
Shanley et al., "Cloning and expression of *Acinetobacter calcoaceticus* catBCDE genes in *Pseudomonas putida* and *Escherichia coli*," *J. Bacteriol.* 165:557-563.
Shao et al., "Random-priming in vitro recombination: an effective tool for directed evolution," *Nucleic Acids Res.* 26:681-683 (1998).

Sharma et al., "Menaquinone (Vitamin K$_2$) Biosynthesis: Nucleotide Sequence and Expression of themenB Gene from *Escherichia coli*," *J. Bacteriol.* 174(15): 5057-5062 (1992).

Sheppard et al., "Purification and Properties of NADH-Dependent 5,10-Methylenetetrahydrofolate Reductase (MetF) from *Escherichia coli*," *J. Bacteriol.* 181(3):718-725 (1999).

Shi et al., "The Structure of I-Aspartate Ammonia-Lyase from *Escherichia coli*," *Biochemistry* 36:9136-9144 (1997).

Shiba et al., "Engineering of the pyruate dehydrogenase bypass in *Saccharomyces cerevisiae* for high-level production of isoprenoids," *Metab. Eng.* 9:160-168 (2007).

Shibata et al., "Purification, characterization, and immunological properties of fumarase from *Euglena gracilis* var. bacillaris," *J. Bacteriol.* 164(2):762-768 (1985).

Shigeoka and Nakano, "Characterization and molecular properties of 2-oxoglutarate decarboxylase from *Euglena gracilis*," *Arch. Biochem. Biophys.* 288:22-28 (1991).

Shigeoka and Nakano, "The effect of thiamin on the activation of thiamin pyrophosphate-dependent 2-oxoglutarate decarboxylase in Euglena gracilis," *Biochem. J.* 292 (Pt 2):463-467 (1993).

Shigeoka et al., "Effect of L-glutamate on 2-oxoglutarate decarboxylase in *Euglena gracilis*," *Biochem. J.* 282 (Pt 2):319-323 (1992).

Shimaoka et al, "Effects of edd and pgi Disruptions on Inosine Accumulation in *Escherichia coli*," *Biosci. Boitechnol. Biochem.* 69(7):1248-1255 (2005).

Shimoda et al., "Asymmetric Transformation of Enones with Synechococcus sp. PCC 7943," *Bulletin of the Chemical Society of Japan* 77(12):2269-2272 (2204).

Shimomura et al., "3-hydroxyisobutyryl-CoA hydrolase," *Methods Enzymol.* 324:229-240 (2000).

Shimomura et al., "Purification and partial characterization of 3-hydroxyisobutyryl-Coenzyme A hydrolase of rat liver," *J. Biol. Chem.* 269(19):14248-14253 (1994).

Shimoyama et al., "MmcBC in Pelotomaculum thermopropionicum represents a novel group of prokaryotic fumarases," *FEMS Microbiol Lett.* 270(2):207-213 (2007).

Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).

Shlomi et al., "Regulatory on/off minimization of metabolic flux changes after genetic perturbations," *Proc. Natl. Acad. Sci. U.S.A.* 102:7695-7700 (2005).

Shukla et al., "Production of D(-)-lactate from sucrose and molasses," *Biotechnol. Lett.* 26(9):689-693 (2004).

Shuler and Kargi, Operating Considerations for Bioreactors for Suspension and Immobilized Cultures, in *Bioprocess Engineering: Basic Concepts*, Prentice Hall, Inc., Upper Saddle River, NJ., p. 245-247 (2002).

Sibilli et al., "Two regions of the bifunctional protein aspartokinase I-homoserine dehydrogenase I are connected by a short hinge," *J. Biol. Chem.* 256 (20):10228-10230 (1981).

Sieber et al., "Libraries of hybrid proteins from distantly related sequences," *Nat. Biotechnol.* 19:456-460 (2001).

Siegert et al., "Exchanging the substrate specificities of pyruvate decarboxylase from *Zymomonas mobilis* and benzoylformate decarboxylase from *Pseudomonas putida*," *Protein. Eng. Des. Sel.* 18:345-357 (2005).

Siew et al., "Localization and characteristics of rat liver mitochondrial aldehyde dehydrogenases," *Arch. Biochem. Biophys.* 176(2):638-649 (1976).

Sikorski and Heiter, "A system of shuttle vectors and yeast host strains designed for efficient manipulation of DNA in *Saccharomyces cerevisiae*," *Genetics* 122(1):19-27 (1989).

Simanshu et al., "Structure and function of enzymes involved in the anaerobic degradation of L-threonine to propionate," *J. Biosci.* 32(6):1195-1206 (2007).

Siminov et al., "Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Simon et al., "Chiral Compounds Synthesized by Biocatalytic Reductions," *Angew. Chem. Int. Ed. Engl.* 24:539-553 (1985).

Sinclair et al., "Purification and characterization of the branched chain α-ketoacid dehydrogenase complex from *Saccharomyces cerevisiae*," *Biochem. Mol. Biol. Int.* 31(5):911-922 (1993).

Sipma et al., "Microbial CO conversions with applications in synthesis gas purification and bio-desulfurization," *Crit. Rev. Biotechnol.* 26:41-65 (2006).

Sivaraman et al., "Codon choice in genes depends on flanking sequence information—implications for theoretical reverse translation," *Nucleic Acids Res.* 36(3):e16 (2008).

Sjöström et al., "Purification and characterisation of a plasminogen-binding protein from *Haemophilus influenzae*. Sequence determination reveals identity with aspartase," *Biochim. Biophys. Acta* 1324(2):182-190 (1997).

Skarstedt and Silverstein, "*Escherichia coli* acetate kinase mechanism studied by net initial rate, equilibrium, and independent isotopic exchange kinetics," *J. Biol. Chem.* 251:6775-6783 (1976).

Slater et al., "Multiple β-ketothiolases mediate poly(β-hydroxyalkanoate) copolymer synthesis in *Ralstonia eutropha*," *J. Bacteriol.* 180(8):1979-1987 (1998).

Sloane et al., "Studies on the metabolism of p-aminobenzoic acid by *Mycobacterium smegmatis*," *J Biol. Chem.* 193:453-458 (1951).

Slock et al., "An apparent *Bacillus subtilis* folic acid biosynthetic operon containing pab, an amphibolic *trpG* gene, a third gene required for synthesis of para-aminobenzoic acid, and the dihydropteroate synthase gene," *J. Bacteriol.* 172:7211-7226 (1990).

Smit et al., "Identification, cloning and characterization of *Lactococcus lactis* branched-chain α-keto acid decarboxylase involved in flavor formation," *Appl. Environ. Microbiol.* 71:303-311 (2005).

Smith and Gray, "Catalysis of the oxidation of 1,4-cyclohexadiene to benzene by electroactive binuclear rhodium complexes," *Catalysis Lett.* 6:195-199 (1990).

Smith and Kaplan, "Purification, properties and kinetic mechanism of Coenzyme A-linked aldehyde dehydrogenase from *Clostridium kluyveri*," *Arch. Biochem. Biophys.* 203:663-675 (1980).

Smith et al., "Purification and characteristics of a γ-glutamyl kinase involved in *Escherichia coli* proline biosynthesis," *J. Bacteriol.* 157:545-551 (1984).

Smith et al., "Fumarate metabolism and the microaerophily of Campylobacter species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Actin polymerization induced by calspectin, a calmodulin-binding spectrin-like protein," *FEBS Lett* 148(2):221-225 (1982).

Soda and Misono,"L-Lysine:α-ketoglutarate aminotransferase. II. Purification, crystallization, and properties," *Biochemistry* 7:4110-4119 (1968).

Söhling and Gottschalk, "Molecular analysis of the anaerobic succinate degradation pathway in *Clostridium kluyveri*," *J. Bacteriol.* 178:871-880 (1996).

Söhling and Gottschalk, "Purification and characterization of a Coenzyme-A-dependent succinate-semialdehyde dehydrogenase from *Clostridium kluyveri*," *Eur. J. Biochem.* 212:121-127 (1993).

Soini et al., "High cell density media for *Escherichia coli* are generally designed for aerobic cultivations—consequences for large-scale bioprocesses and shake flask cultures," *Microb. Cell. Fact.* 7:26 (2008).

Sokatch et al., "Purification of a Branched-Chain Keto Acid Dehydrogenase from *Pseudomonas putida*," *J. Bacteriol.* 148(2):647-652 (1981).

Somerville, "The Billion-Ton Biofuels Vision," *Science* 312(5778):1277 (2006).

Sone et al., "Nucleotide sequence and expression of the *Enterobacter aerogenes* aacetolactate decarboxylase gene in brewers yeast," *Appl. Environ. Microbiol.* 54:38-42 (1988).

Song et al, "Effects of dissolved CO$_2$ levels on the growth of *Mannheimia succinicproducens* and succinic acid production," *Biotechnol. Bioeng.* 98(6):1296-1304 (2007).

Song et al., "Construction of recombinant *Escherichia coli* strains producing poly (4-hydroxybutyric acid) homopolyester from glucose," *Wei Sheng Wu Xue.Bao*. 45:382-386 (2005). (In Chinses, includes English Abstract).

Song et al., "Ultrasound-mediated DNA transfer for bacteria," *Nucl. Acids Res*. 35:e129 (2007).

Song et al., "Recovery of succinic acid produced by fermentation of a metabolically engineered Mannheimia succiniciproducens strain," *J. Biotechnol*. 132:445-452.

Song et al., "Structure, function, and mechanism of the phenylacetate pathway hot dog-fold thioesterase PeaI," *J. Biol. Chem*. 281(16):11028-11038 (2006).

Soucaille et al., "Butanol tolerance and autobacteriocin production by *Clostridium acetobutylicum*," *Curr. Microbiol*. 14:295-299 (1987).

Sovik, "Mitochondrial 2-methylacetoacetyl-CoA thiolase deficiency: an inborn error of isoleucine and ketone body metabolism," *J. Inherit. Metab. Dis*. 16:46-54 (1993).

Sramek and Frerman, "Purification and properties of *Escherichia coli* Coenzyme A-transferase," *Arch. Biochem. Biophys*. 171(1):14-26 (1975).

St. Maurice et al., "Flavodoxin:quinone reductase (FgrB): a redox partner of pyruvate:ferredoxin oxidoreductase that reversibly couples pyruvate oxidation to NADPH production in *Helicobacter pylori* and *Campylobacter jejuni*," *J. Bacteriol*. 189:4764-4773 (2007).

Stadtman, "The enzyme synthesis of β-alanyl Coenzyme A," *J. Am. Chem. Soc*. 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of *Salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem*. 280(28):26200-26205 (2005).

Starnes et al., "Threonine-sensitive aspartokinase-homoserine dehydrogenase complex, amino acid composition, molecular weight, and subunit composition of the complex," *Biochemistry* 11:677-687 (1973).

Steen et al., "Metabolic engineering of *Saccharomyces cerevisiae* for the production of n-butanol," *Microb. Cell Fact*. 7:36 (provided electronically by publisher as pp. 1-8) (2008).

Steffan and McAlister-Henn, "Isolation and characterization of the yeast gene encoding the MDH3 isozyme of malate dehydrogenase," *J. Biol. Chem*. 267:24708- 24715 (1992).

Steinbacher et al., "Enoate reductase family," in Flavins and Flavoproteins, Proceedings of the Fourteenth International Symposium, St. John's College, University of Cambridge, UK, Jul. 14-18 2002, Chapman et al., pp. 941-949, Rudolf Weber, Agency for Scientific Publications Berlin.

Steinbüchel and Schlegel, "Nad-linked L(+)-lactate dehydrogenase from the strict aerobe alcaligenes eutrophus. 2. Kinetic properties and inhibition by oxaloacetate," *Eur. J. Biochem*. 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem*. 141:555-564 (1984).

Steiner and Sauer, "Long-term continuous evolution of acetate resistant *Acetobacter aceti*," *Biotechnol. Bioeng*. 84:40-44 (2003).

Stemmer, "DNA shuffling by random fragmentation and reassembly: in vitro recombination for molecular evolution," *Proc. Natl. Acad. Sci. U.S.A*. 91:10747- 10751 (1994).

Stemmer, "Rapid evolution of a protein in vitro by DNA shuffling," *Nature* 370:389- 391 (1994).

Stim-Herndon et al., "Characterization of an acetyl-CoA C-acetyltransferase (thiolase) gene from *Clostridium acetobutylicum* ATCC 824," *Gene* 154(1):81-85 (1995).

Stirling and Perry, "Purification and Properties of a Nicotinamide Adenine Dinucleotide-Linked Cyclohexanol Dehydrogenase from a cocardia Species," *Curr. Microbiol*. 4:37-40 (1980).

Stokell et al., "Probing the roles of key residues in the unique regulatory NADH binding site of type II citrate synthase of *Escherichia coli*," *J. Biol. Chem*. 278:35435- 35443 (2003).

Stols and Donnelly, "Production of succinic acid through overexpression of $NAD^+$-dependent malic enzyme in an *Escherichia coli* mutant," *Appl. Environ. Microbiol*. 63(7):2695-2701 (1997).

Stols et al., "Expression of Ascaris suum malic enzyme in a mutant *Escherichia coli* allows production of succinic acid from glucose," *Appl. Biochem. Biotechnol*. 63-65: 153-158 (1997).

Stols et al., "New vectors for co-expression of proteins: Structure of *Bacillus subtilis* ScoAB obtained by High-throughput protocols," *Protein Expr. Purif*. 53:396-403 (2007).

Stoyan et al., "Cloning, sequencing and overexpression of the leucine dehydrogenase gene from *Bacillus cereus*," *J. Biotechnol*. 54:77-80 (1997).

Straathof et al., "Feasibility of acrylic acid production by fermentation," *Appl. Microbiol. Biotechnol*. 67:727-734 (2005).

Strauss and Fuchs, "Enzymes of a novel autotrophic $CO_2$ fixation pathway in the phototrophic bacterium *Chloroflexus auruntiacus*, the 3-hydroxypropionate cycle," *Eur. J. Biochem*. 215:633-643 (1993).

Streit and Entcheva, "Biotin in microbes, the genes involved in its biosynthesis, its biochemical role and perspectives for biotechnological production," *Appl. Microbiol. Biotechnol*. 61:21-31 (2003).

Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," *Gene* 166:73-76 (1995).

Stryer, *Biochemistry*. 3rd Ed. New York: W.H. Freeman and Company, pp. 374-376 (1988).

Suarez de Mata et al., "Propionyl-CoA condensing enzyme from *Ascaris muscle* mitochondria. I. Isolation and characterization of multiple forms," *Arch. Biochem. Biophys*. 285(1):158-165 (1991).

Suarez de Mata et al., "Propionyl-CoA condensing enzyme from *Ascaris muscle* mitochondria. II. Coenzyme A modulation," *Arch. Biochem. Biophys*. 285:166-171 (1991).

Suda et al., "Purification and properties of α-ketoadipate reductase, a newly discovered enzyme from human placenta," *Arch. Biochem. Biophys*. 176(2):610-620 (1976).

Suda et al., "Subcellular localization and tissue distribution of α-ketoadipate reduction and oxidation in the rat," *Biochem. Biophys. Res. Commun*. 77(2):586-591 (1977).

Suematsu et al., "Molecular cloning and functional expression of rat liver cytosolic acetyl-CoA hydrolase," *Eur. J. Biochem*. 268(9):2700-2709 (2001).

Sulzenbacher et al., "Crystal structure of *E.coli* alcohol dehydrogenase YqhD: evidence of a covalently modified NADP Coenzyme," *J. Mol. Biol*. 342(2):489-502 (2004).

Suthers et al., "Metabolic flux elucidation for large-scale models using $^{13}C$ labeled isotopes," *Metab. Eng*. 9:387-405 (2007).

Suzuki et al., "Acetylputrescine deacetylase from *Micrococcus luteus* K-11," *Biochim. Biophys. Acta* 882:140-142 (1986).

Suzuki et al., "GriC and GriD Constitute a carboxylic acid reductase involved in grixazone biosynthesis in *Streptomyces griseus*," *J. Antibiot*. 60(6):380-387 (2007).

Suzuki et al., "Properties and metabolic role of mesaconate hydratase of an aerobic bacterium," *J. Biochem*. 81:1917-1925 (1977).

Suzuki, "Phospotransacetylase of *Escherichia coli* B., activation by pyruvate and inhibition by NADH and certain nucleotides," *Biochem. Biophys. Acta* 191:559-569 (1969).

Svensson et al., "Characterization and isolation of enzymes that hydrolyze short-chain acyl-CoA in rat-liver mitochondria," *Eur. J. Biochem*. 238(2):526-531 (1996).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A*. 101(2):446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol*. 183(17):5134-5144 (2001).

Switzer, "Glutamate mutase," In Dolphin, D. ed., *Vitamin $B_{12}$* (vol. 2: *Biochemistry and Medicine*), Wiley-Interscience: New York, p. 289-305 (1982).
Tae-Kang et al., "Purification and characterization of a cyclohexanol dehydrogenase from *Rhodococcus* sp. TK6," *J. Microbiol. Biotechnol.* 12:39-45 (2002).
Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).
Takacs et al., "Formate hydrogenlyase in the hyperthermophilic archaeon, *Thermococcus litoralis*," *BMC Microbiol.* 8:88 (2008).
Takagi et al, "Purification, crystallization, and molecular properties of aspartase from *Pseudomonas fluorescens*," *J. Biochem.* 96(2):545-552 (1984).
Takagi et al., "Isolation of a versatile *Serratia marcescens* mutant as a host and molecular cloning of the aspartase gene," *J. Bacteriol.* 161:1-6 (1985).
Takagi et al., "Cloning and nucleotide sequence of the aspartase gene of *Pseudomonas fluorescens*," *J. Biochem.* 100(3):697-705 (1986).
Takahashi and Yamada, "Metabolic pathways for cytoxic and end product formation from glutamate- and aspartate-containing peptides by *Porphyromonas gingivalis*," *J. Bacteriol.* 182:4704-4710 (2000).
Takahashi-Abbe et al., "Biochemical and functional properties of a pyruvate formate-lyase (PFL)-activating system in *Streptococcus mutans*," *Oral Microbiol. Immunol.* 18:293-297 (2003).
Takanashi et al., "Characterization of a novel 3-hydroxybutyrate dehydrogenase from *Ralstonia pickettii* T1," *Antonie van Leeuwnhoek* 95(3):249-262 (2009).
Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).
Takatsuka et al., "Identification of the amino acid residues conferring substrate specificity upon *Selenomonas ruminantium* lysine decarboxylase," *Biosci. Biotechnol. Biochem.* 63(10):1843-1846 (1999).
Takeo, "Existence and Properties of Two Malic Enzymes in *Escherichia coli* Especially of NAD-linked Enzyme," *J. Biochem.* 66:379-387 (1969).
Takigawa et al., "Probabilistic path ranking based on adjacent pairwise coexpression for metabolic transcripts analysis," *Bioinform.* 24(2):250-257 (2008).
Tallant and Krzycki, "Coenzyme M methylase activity of the 480-kilodalton corrinoid protein from *Methanosarcina barkeri*," *J. Bacteriol.* 178(5):1295-1301 (1996).
Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).
Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).
Tamaki et al., "Purification, properties, and sequencing of aminoisobutyrate aminotransferases from rat liver," *Methods Enzymol.* 324:376-389 (2000).
Tanaka et al., "Cloning and characterization of a human orthologue of testis-specific succinyl CoA: 3-oxo acid CoA transferase (Scot-t) cDNA," *Mol. Hum. Reprod.* 8:16-23 (2002).
Tanaka et al., "Lysine decarboxylase of *Vibrio parahaemolyticus*: kinetics of transcription and role in acid resistance," *J. Appl. Microbiol.* 104:1283-1293 (2008).
Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).
Tani et al., "Thermostable $NADP^+$-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).
Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).
Tardif et al., "Electrotransformation studies in *Clostridium cellulolyticum*," *J. Ind. Microbiol. Biotechnol.* 27(5):271-274 (2001).
Taylor and Fotheringham, "Nucleotide sequence of the *Bacillus licheniformis* ATCC 10716 dat gene and comparison of the predicted amino acid sequence with those of other bacterial species," *Biochim. Biophys. Acta* 1350(1):38-40 (1997).
Tebbe et al., "Titanium-Catalyzed Olefin Metathesis," *J. Am. Chem. Soc.* 101(17):5074-5075 (1979).
Teipel et al., "The substrate specificity of fumarase," *J. Biol. Chem.* 243:5684-5694 (1968).
ter Schure et al., "Pyruvate decarboxylase catalyzes decarboxylation of branched-chain 2-Oxo acids but is not essential for fusel alcohol production by *Saccharomyces cerevisiae*," *Appl. Environ. Microbiol.* 64(4):1303-1307 (1998).
Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).
Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).
Thauer, "Microbiology. A Fifth Pathway of Carbon Fixation," *Science* 318:1732-1733 (2007).
Thomas et al., "Bimetallic nanocatalysts for the conversion of muconic acid to adipic acid," *Chem. Commun.* 21:1126-1127 (2003).
Thornton et al., "Primary structure of the monomer of the 12S subunit of transcarboxylase as deduced from DNA and characterizatio nof the product expressed in *Escherichia coli*," *J. Bacteriol.* 175:5301-5308 (1993).
Thykaer et al., "Metabolic network analysis of an adipoyl-7-ADCA-producing strain of *Penicillium chrysogenum*: elucidation of adipate degradation," *Metab. Eng.* 4(2):151-158 (2002).
Tian et al., "Variant tricarboxylic acid cycle in *Mycobacterium tuberculosis*: identification of α-ketoglutarate decarboxylase," *Proc. Natl. Acad. Sci. U.S.A.* 102:10670-10675 (2005).
Tischer et al., "Purification and Some Properties of a Hitherto-Unknown Enzyme Reducing the Carbon-Carbon Double Bond of α,β-Unsaturated Carboxylate Anions," *Eur. J. Biochem.* 97(1):103-112 (1979).
Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1744-1777 (1998).
Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).
Tobin et al., "Localization of the Lysine ε-Aminotransferase (lat) and δ-Aminoadipyl)-L-Cysteinyl-D-Valine Synthetase (pcbAB) Genes from *Streptomyces clavuligerus* and Production of Lysine E-Aminotransferase Activity in *Escherichia coli*," *J. Bacteriol.* 173(19):6223-6229 (1991).
Tolentino et al., "A pH-regulated promoter for the expression of recombinant proteins in *Escherichia coli*," *Biotechnol. Lett.* 14:157-162. (1992).
Tomas et al., "Overexpression of groESL in *Clostridium acetobutylicum* Results in Increased Solvent Production and Tolerance, Prolonged Metabolism, and Changes in the Cell's Transcriptional Program," *Appl. Environ. Microbiol.* 69:4951-4965 (2003).
Toraya et al., "Substrate Specificity of Coenzyme $B_{12}$-Dependent Diol Dehydrase: Glycerol as Both a Good Substrate and a Potent Inactivator," *Biochem. Biophys. Res. Commun.* 69:475-480 (1976).
Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).
Tretter and Adam-Vizi, "Alpha-ketoglutarate dehydrogenase: a target and generator of oxidative stress," *Phil. Trans. R. Soc. Lond. B. Biol. Sci.* 360(1464):2335-2345 (2005).
Trower et al., "Isolation and Characterization of a Cyclohexane-Metabolizing Xanthobacter sp.," *Appl. Environ. Microbiol.* 49(5):1282-1289 (1985).
Truscott et al., "Mechanisms of protein import into mitochondria," *Curr. Biol.* 13(8):R326-R337 (2003).
Tsao et al., "Production of multifunctional organic acids from renewable resources," *Adv. Biochem. Eng. Biotechnol.* 65:243-280 (1999).
Tseng et al., "Metabolic Engineering of *Escherichia coli* for Enhanced Production of (R)- and (S)-3-Hydroxybutyrate," *App. Environ. Microbiol.* 75(10):3137-3145 (2009).
Tseng et al., "Oxygen- and growth rate-dependent regulation of *Escherichia coli* fumarase (FumA, FumB, and FumC) activity," *J. Bacteriol.* 183(2):461-467 (2001).
Tsujimoto et al., "L-Lysine biosynthetic pathway of *Methylophilus methylotrophus* and construction of an L-Lysine producer," *J. Biotechnol.* 124:327-337 (2006).
Tucci and Martin, "A novel prokaryotic trans-2-enoyl-CoA reductase from the spirochete *Treponema denticola*," *Febs Lett.* 581(8):1561-1566 (2007).
Tutino et al., "Expression of *Sulfolobus solfataricus trpE* and *trpG* genes in *E. coli*," *Biochem. Biophys. Res. Commun.* 230:306-310 (1997).
Twarog and Wolfe, "Role of butyryl phosphate in the energy metabolism of *Clostridium tetanomorphum*," *J. Bacteriol.* 86:112-117 (1963).
Tyurin et al., "Electrotransformation of *Clostridum acetobutylicum* ATCC 824 using high-voltage radio frequency modulated square pulses," *J. Appl. Microbiol.* 88(2):220-227 (2000).
Tyurin et al., "Electrotransformation of *Clostridium thermocellum*," *Appl. Environ. Microbiol.* 70(2):883-890 (2004).
Tzagoloff and Dieckmann, "PET genes of *Saccharomyces cerevisiae*," *Microbiol. Rev.* 54(3):211-225 (1990).
Uchiyama et al., "Identification of the 4-Hydroxycinnamate Decarboxylase (PAD) Gene of *Klebsiella oxytoca*," *Biosci. Biotechnol. Biochem.* 72: 116-123 (2008).
Ulaganathan et al., "Structure of *Staphylococcus aureus* 1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).
Umbarger and Brown, "Threonine deamination in *Escherichia coli*. II. Evidence fro two L-threonine deaminases," *J. Bacteriol.* 73(1):105-112 (1957).
Underwood et al., "Genetic Changes To Optimize Carbon Partitioning between Ethanol and Biosynthesis in Ethanologenic *Escherichia coli*," *App. Environ. Microbiol.* 68(12):6263-6272 (2002).
Urbance et al., "Evaluation of succinic acid continuous and repeat-batch biofilm fermentation by *Actinobacillus succinogenes* using plastic composite support bioreactors," *Appl. Microbiol. Biotechnol.* 65(6):664-670 (2004).
Uttaro and Opperdoes, "Purification and characterisation of a novel isopropanol dehydrogenase from *Phytomonas* sp.," *Mol. Biochem. Parasitol.* 85:213-219 (1997).
Vadali et al., "Enhanced Isoamyl Acetate Production upon Manipulation of the Acetyl-CoA node in *Escherichia coli*," *Biotech. Prog.* 20:692-697 (2004).
Vadali et al., "Production of isoamyl acetate in ackA-pta and/or ldh mutants of *E. coli.* with overexpression of yeast ATF2," *Appl. Microbiol. Biotechnol.* 63:698-704 (2004).
Vadali et al., "Cofactor engineering of intercellular CoA/acetyl-CoA and its effect on metabolic flux redistribution in *Escherichia coli*," *Metab Eng.* 6(2): 133-139 (2004).
Valdes-Hevia and Gancedo, "Isolation and characterization of the gene encoding phosphoenolpyruvate carboxykinase from *Saccharomyces cerevisiae*," *FEBS Lett.* 258:313-316 (1989).
Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227(1-2):43-60 (1995).

Valentine and Wolfe, "Purification and role of phosphotransbutyrylase," *J. Biol. Chem.* 235:1948-1952 (1960).
Vamecq et al., "The microsomal dicarboxylyl-CoA synthetase," *Biochem. J.* 230(3):683-693 (1985).
Van Beilen et al., "Cloning of Baeyer-Villiger monooxygenases from comamonas, *Xantherobacter* and *Rhodococcus* using polymerase chain reaction with highly degenerate primers," *Environ. Microbiol.* 5(3):174-182 (2003).
van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).
Van Der Westhuizen, et al., "Autolytic Activity and Butanol tolerance of *Clostridium acetobutylicum*," *Appl. Environ. Microbiol.* 44:1277-1281 (1982).
van Grinsven et al., "Acetate:succinate CoA-transferase in the hydrogenosomes of *Trichomonas vaginalis*: identification and characterization," *J. Biol. Chem.* 2833(3):1411-1418 (2008).
van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).
van Maris et al., "Directed evolution of pyruvate decarboxylase-negative *Saccharomyces cerevisiae*, yielding a $C_2$-independent, glucose-tolerant, and pyruvate-hyperproducing yeast," *Appl. Environ. Microbiol.* 7:159-166 (2004).
Van Mullem et al., "Construction of a set of *Saccharomyces cerevisiae* vectors designed for recombinational cloning," *Yeast* 20(8):739-746 (2003).
Vanderwinkel et al., "Growth of *Escherichia coli* on fatty acids: requirement for Coenzyme A transferase activity," *Biochem. Biophys. Res. Commun.* 33(6):902-908 (1968).
Vanrolleghem et al., "Validation of a Metabolic Network for *Saccharomyces cerevisiae* Using Mixed Substrate Studies," *Biotechnol. Prog.* 12(4):434-448 (1996).
Varadarajan and Miller, "Catalytic Upgrading of Fermentation-Derived Organic Acids," *Biotechnol. Prog.* 15:845-854 (1999).
Vardar-Schara et al., "Metabolically engineered bacteria for producing hydrogen via fermentation," *Microbio. Biotechnol.* 1:107-125 (2008).
Varma and Palsson, "Stoichiometric Flux Balance Models Quantitatively Predict Growth and Metabolic By-Product Secretion in Wild-Type *Escherichia coli* W3110," *Appl Env. Microbiol.* 60(10):3724-3731 (1994).
Varma and Palsson, "Metabolic Flux Balancing: Basic Concepts, Scientific and Practical Use," *Biotechnology* 12:994-998 (1994).
Varma et al., "Biochemical Production Capabilities of *Escherichia coli*," *Biotechnol. Bioeng.* 42:59-73 (1993).
Varma et al., "Stoichiometric Interpretation of *Escherichia coli* Glucose Catabolism under Various Oxygenation Rates," *Appl. Environ. Microbiol.* 59:2465-2473 (1993).
Vazquez et al., "Phosphtransbutyrylase expression in *Bacillus megaterium*," *Curr. Microbiol.* 42:345-349 (2001).
Vega et al., "The Biological Production of Ethanol from Synthesis Gas," *Appl. Biochem. Biotechnol.* 20/21:781-797 (1989).
Vellanki et al., "Expression of hepatitis B surface antigen in *Saccharomyces cerevisiae* utilizing glyceraldehyde-3-phosphate dehydrogenase promoter of *Pichia pastoris*," *Biotechnol. Lett.* 29(2):313-318 (2007).
Vemuri et al. "Succinate production in dual-phase *Escherichia coli* fermentations depends on the time of transition from aerobic to anaerobic conditions," *J. Ind. Microbiol. Biotechnol.* 28:325-332 (2002).
Vemuri et al., "Effects of growth mode and pyruvate carboxylase on succinic acid production by metabolically engineered strains of *Escherichia coli*," *Appl. Environ. Microbiol.* 68(4):1715-1727 (2002).
Venkitasubramanian et al. *Biocatalysis in the Pharmaceutical and Biotechnology Industires*, ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Verhaert et al., "Enzyme kinetics in reversed micelles. 2. Behaviour of enoate reductase," *Eur. J. Biochem.* 187:73-79 (1990).

Vernal et al., "Cloning and heterologous expression of a broad specificity aminotransferase of *Leishmania mexicana* promastigotes," *FEMS Microbiol. Lett.* 229:217-222 (2003).

Vernal et al., "Isolation partial characterization of a broad specificity aminotransferase from *Leishmania mexicana* promastigotes," *Mol. Biochem. Parasitol.* 96:83-92 (1998).

Vey et al., "Structural basis for glycyl radical formation by pyruvate formate-lyase activating enzyme," *Proc. Natl. Acad. Sci. U.S.A.* 105:16137-16141 (2008).

Vijay et al., "Diels-Alder reactions between cyclic five-membered dienes and acetylene," *J. Mol. Struc.* 589-590:291-299 (2002).

Viola, "L-Aspartase: New Tricks From an Old Enzyme," *Adv. Enzymol. Relat. Areas. Mol. Biol.* 74:295-341 (2000).

Voellmy and Leisinger, "Role of 4-Aminobutyrate Aminotransferase in the Arginine Metabolism of *Pseudomonas aeruginosa*," *J. Bacteriol.* 128(3):722-729 (1976).

Voets et al., "Reduced intracellular ionic strength as the initial trigger for activation of endothelial volume-regulated anion channels," *Proc. Natl. Acad. Sci. U.S.A.* 96:5298-5303 (1999).

Volkert, et al., "The $\Delta(argF\text{-}lacZ)205$(U169) Deletion Greatly Enhances Resistance to Hydrogen Peroxide in Stationary-Phase *Escherichia coli*," *J. Bact.* 176(3):1297-1302 (1994).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27:e18 (1999).

Vrijbloed et al., "Insertional inactivation of methylmalonyl Coenzyme A (CoA) mutase and isobutyryl-CoA mutase genes in *Streptomyces cinnamonensis*: influence on polyketide antibiotic biosynthesis," *J. Bacteriol.* 181(18):5600-5605 (1999).

Wakil et al., "Studies on the fatty acid oxidizing system of animal tissues. VI. β-Hydroxyacyl Coenzyme A dehydrogenase," *J. Biol. Chem.* 207(2):631-638 (1954).

Walker et al., "Yeast pyruvate carboxylase: identification of two genes encoding isoenzymes," *Biochem. Biophys. Res. Commun.* 176:1210-1217 (2007).

Walter et al., "Molecular characterization of two *Clostridium acetobutylicum* ATCC 824 butanol dehydrogenase isozyme genes," *J. Bacteriol.* 174(22):7149-7158.

Walter et al., "Sequence and arrangement of two genes of the butyrate-synthesis pathway of *Clostridium acetobutylicum* ATCC 824," *Gene* 134(1):107-111 (1993).

Wang and Barker, "Purification and Properties of L-citramalate hydrolase," *J. Biol. Chem.* 244(10):2516-2526 (1969).

Wang and Seah, "Determination of the metal ion dependence and substrate specificty of a hydratase involve din the degradation pathway of biphenyl/chlorobiphenyl," *FEBS J.* 272: 966-974 (2005).

Wang et al, "Molecular cloning and functional identification of a novel phenylacetyl-CoA ligase gene from *Penicillium chrysogenum*," *Biochem. Biopyhs. Res. Commun.* 360(2):453-458 (2007).

Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).

Wang et al., "Bioconversion of fumaric acid to succinic acid by recombinant *E. coli*," *App. Biochem. Biotechnol.* 70-72: 919-928 (1998).

Wang et al., "Cloning, Sequencing, and Expression of the Pyruvate Carboxylase Gene in *Lactococcus lactis* subsp. *lactis* C2," *App. Environ. Microbiol.* 66(3):1223-1227 (2000).

Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).

Wang et al., "Genome-scale in silico aided metabolic analysis and flux comparisons of *Escherichia coli* to improve succinate production," *Appl. Microbiol. Biotechnol.* 73(4):887-894 (2006).

Wang et al., "Screening microorganisms for utilization of furfural and possible intermediates in its degradative pathway," *Biotechnol. Lett.* 16(9):977-982 (1994).

Wang et al., "Site-directed mutagenesis of the phosphorylatable serine (Ser$^8$) in $C_4$ phosphoenolpyruvate carboxylase from sorghum. The effect of negative charge at position 8," *J. Biol. Chem.* 267:16759-16762. (1992).

Wanner and Tressl, "Purification and characterization of two enone reductases from *Saccharomyces cerevisia*," *Eur. J. Biochem.* 255(1):271-278 (1998).

Ward et al., "Molecular analysis of the rele of two aromatic aminotransferases and a broad-specificity aminotransferase in the aromatic amino acid metabolism of *Pyococcus furiosus*," *Archaea* 1:133-141 (2002).

Weaver, "Structure of free fumarase C from *Escherichia coli*," *Acta. Crystallogr. D. Biol. Crystallogr.* 61(Pt 10):1395-1401 (2005).

Weber and Falbe, "Oxo Synthesis Technology," *Ind. Eng. Chem. Res.* 62:33-37 (1970).

Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).

Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).

Wengrovius et al., "Tungsten-Oxo Alkylidene Complexes as Olefin Metathesis Catalysts and the Crystal Structure of W(O)(CHCMe$_3$)(PEt$_3$)CI$_2$$^{1}$" *J. Am. Chem. Soc.* 102:4515-4516 (1980).

Westin et al., "The identification of a succinyl-CoA thioesterase suggests a novel pathway for succinate production in peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbiol.* 7(12):1917-1926 (2005).

Whalen and Berg, "Analysis of an avtA::Mu d1(Ap lac) Mutant: Metabolic Role of Transaminase C," *J. Bacteriol.* 150(2):739-746 (1982).

Whalen and Berg, "Gratuitous repression of avtA in *Escherichia coli* and *Salmonella typhimurium*," *J. Bacteriol.* 158(2):571-574 (1984).

Whelan et al., "Nylon 6 (PA6)," *Kunststof en Rubber*, Wyt en Zonen Uitgevers. Rotterdam, NL. 39(3):38-39 (1986).

Whisstock et al., "Prediction of protein function from protein sequence and structure," *Q. Rev. Biophysics.* 36(3):307-340 (2003).

White et al., "Long-chain alcohol production by yeasts," *7th Int. Symp. Yeasts* S465-S470 (1989).

White et al., "The structural biology of type II fatty acid biosynthesis," *Ann. Rev. Biochem.* 74:791-831 (2005).

Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacteriol.* 167:205-209 (1986).

Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme $C_1$-Tetrahydrofolate Synthase from *Saccharomyces cerevisiae*," *J. Bacteriol.* 170(7):3255-3261 (1988).

Wiesenborn et al., "Coenzyme A Transferase from *Clostridium acetobutylicum* ATCC 824 and Its Role in the Uptake of Acids," *Appl. Environ. Microbiol.* 55(2):323-329 (1989).

Wiesenborn et al., "Phosphotransbutyrylase from *Clostridium acetobutylicum* ATCC 824 and its role in acidogenesis," *Appl. Environ. Microbiol.* 55:317-322 (1989).

Wilkie and Warren, "Recombinant expression, purification, and characterization of three isoenzymes of aspartate aminotransferase from *Arabidopsis thaliana*," *Protein Expr. Purif.* 12:381-389 (1998).

Wilks et al., "A specific, Highly Active Malate Dehydrogenase by Redesign of a Lactate Dehydrogenase Framework," *Science* 242:1541-1544 (1988).

Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).
Wilks et al., "Designs for a Broad Substrate Specificity Keto Acid Dehydrogenase," *Biochemistry* 29:8587-8591 (1990).
Willke and Vorlop, "Biotechnological production of itaconic acid," *Appl. Microbiol. Biotechnol.* 56(3-4):289-295 (2001).
Willke and Vorlop, "Industrial bioconversion of renewable resources as an alternative to conventional chemistry," *Appl. Microbiol. Biotechnol.* 66(2):131-142 (2004).
Winkler et al., "A new type of a multifunctional β-oxidation enzyme in euglena," *Plant. Physiol.* 131(2):753-762 (2003).
Winzeler et al., "Functional Characterization of *S. cerevisiae* Genome by Gene Deletion and Parallel Analysis," *Science* 285:901-906 (1999).
Winzer et al., "Differential regulation of two thiolase genes from *Clostridium acetobutylicum* DSM 792," *J. Mol. Microbiol. Biotechnol.* 2(4):531-541 (2000).
Witkowski et al., "Conversion of β-ketoacyl synthase to a Malonyl Decarboxylase by replacement of the active cysteine with glutamine," *Biochemistry* 38:11643-11650 (1999).
Wittich and Walter, "Putrescine N-acetyltransferase in *Onchocerca volvulus* and *Ascaris suum*, an enzyme which is involved in polyamine degradation and release of N-acetylputrescine," *Mol. Biochem. Parasitol.* 38:13-17 (1990).
Wolff and Kenealy, "Purification and characterization of the oxygen-sensitive 4-hydroxybutanoate dehydrogenase from *Clostridium kluyveri*," *Protein Expr. Purif.* 6:206-212 (1995).
Wong et al., "Molecular Properties of Pyruvate Formate-Lyase Activating Enzyme," *Biochemistry* 32:14102-14110 (1993).
Wong et al., "Sequence saturation mutagenesis (SeSaM): a novel method for directed evolution," *Nucleic Acids Res* 32:e26 (2004).
Wong et al., "Sequence saturation mutagenesis with tunable mutation frequencies," *Anal. Biochem.* 341:187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).
Wood, "Life with CO or $CO_2$ and $H_2$ as a source of carbon and energy," *Fed. Amer. Societies Experi. Biol. J.* 5:156-163 (1991).
Woods, "Two biochemically distinct classes of fumarase in *Escherichia coli*," *Biochim. Biophys. Acta* 954(1):14-26 (1988).
Wu and Woodard, "New insights into the evolutionary links relating to the 3-deoxy-D-arabino-heptulosonate 7-phosphate synthase subfamilies," *J. Biol. Chem.* 281:4042-4048 (2006).
Wu et al., "Microbial synthesis of cis-cis-muconic acid by *Sphingobacterium* sp. GcG generated from effluent of a styrene monomer (SM) production plant," *Enzyme Microbial Tech.* 35:598-604 (2004).
Wu et al., "Thermotoga maritima 3-deoxy-D-arabino-heptulosonate 7-phosphate (DAHP) synthase: the ancestral eubacterial DAHP synthase?" *J. Biol. Chem.* 278:27525-27531 (2003).
Wu et al., "Life in hot carbon monoxide: the complete genome sequence of *Carboxydothermus hydrogenoformans* Z-2901," *PLoS Genet.* 1(5):e65 (2005).
Wylie et al., "Nematode.net: a tool for navigating sequences from parasitic and free-living nematodes," *Nucleic Acids Res.* 32:D423-D426 (2004).
Wynn et al., "Chaperonins GroEL and GroES promote assembly of heterotetramers ($\alpha_2\beta_2$) of mammalian mitochondrial branched-chain α-keto acid decarboxylase in *Escherichia coli*," *J. Biol. Chem.* 267:12400-12403 (1992).
Wynn et al., "Cloning and expression in *Escherichia coli* of mature E1β subunit of bovine mitochondrial branched-chain α-keto acid dehydrogenase complex. Mapping of the E1 β-binding region on E2," *J. Biol. Chem.* 267:1881-1887 (1992).
Yabutani et al., "Analysis of β-ketothiolase and acetoacetyl-CoA reductase genes of a methylotrophic bacterium, *Paracoccus denitrificans*, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from *Hydrogenobacter thermophilus*," *Extremophiles* 14:79-85 (2010).
Yamamoto et al., "Purification and Properties of NADP-dependent Formate Dehydrogenase from *Clostridium thermoaceticum*, a tungsten-Selenium-Iron Protein," *J. Biol. Chem.* 258(3):1826-1832 (1983).
Yamano et al., "Construction of a brewers yeast having α-acetolactate decarboxylase gene from *Acetobacter aceti* ssp. xylinum integrated in the genome," *J. Biotechnol.* 32:173-178 (1994).
Yan and Chen, "Coenzyme A-acylating aldehyde dehydrogenase from *Clostridium beijerinckii* NRRL B592," *Appl. Environ. Microbiol.* 56:2591-2599 (1990).
Yang et al., "Aspartate Dehydrogenase, a Novel Enzyme Identified from Structural and Functional Studies of TM1643," *J. Biol. Chem.* 278(10):8804-8808 (2003).
Yang et al., "Effect of inactivation of *nuo* and *ackA-pta* on redistribution of metabolic fluxes in *Escherichia coli*," *Biotechnol Bioeng.* 65(3):291-297 (1999).
Yang et al., "Effect of Variation of *Klebsiella pneumoniae* Acetolactate Synthase Expression on Metabolic Flux Redistribution in *Escherichia coli*," *Biotechnol. Bioeng.* 69(2):150-159 (2000).
Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990). With correction in *J. Biol. Chem.* 266(24):16255 (1991).
Yang et al., "Nucleotide sequence of the *fadA* gene. Primary structure of 3-ketoacyl-Coenzyme A thiolase from *Escherichia coli* and the structural organization of the *fadAB* operon," *J. Biol. Chem.* 266(24):16255 (1991).
Yang et al., "Nucleotide sequence of the promoter and fadB gene of the fad BA operon and primary structure of the multifunctional fatty acid oxidation protein from *Escherichia coli*," *Biochemistry* 30(27):6788-6795 (1991).
Yang et al., "Redistribution of Metabolic Fluxes in *Escherichia coli* with Fermentative Lactate Dehydrogenase Overexpression and Deletion," *Metab. Eng.* 1:141-152 (1999).
Yang et al., "The effects of feed and intracellular pyruvate levels on the redistribution of metabolic fluxes in *Escherichia coli*," *Metab Eng.* 3(2):115-123 (2001).
Yang, "Location of the fadBA operon on the physical map of *Escherichia coli*," *J. Bacteriol.* 173(23):7405-7406 (1991).
Yanisch-Perron et al., "Improved M13 phage cloning vectors and host strains: nucleotide sequences of the M13mp18 and pUC19 vectors," *Gene* 33:103-119 (1985).
Yano et al., "Directed evolution of an aspartate aminotransferase with new substrate specificities," *Proc. Natl. Acad. Sci U.S.A.* 95:5511-5515 (1998).
Yarlett et al., "*Trichomonas vaginalis*: characterization of ornithine decarboxylase," *Biochem. J.* 293(Pt2):487-493 (1993).
Yeh and Ornston, Evolutionarily Homologous $\alpha_2\beta_2$ Oligomeric Structures in β-Ketoadipate Succinyl-CoA Transferases from *Acinetobacter calcoaceticus* and *Pseudomonas putida*, *J. Biol. Chem.* 256(4):1565-1569 (1981).
Ylianttila et al., "Crystal Structure of Yeast Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of *Candida tropicalis* (3R)-hydroxyacyl-CoA dehydrogenase," *Biochem. Biophys. Res. Commun.* 324:25-30 (2004).

Yoshida et al., "The Structures of L-Rhamnose Isomerase from *Pseudomonas stutzeri* in Complexes with L-Rhamnose and D-Allose Provide Insights into Broad Substrate Specificity," *J. Mol. Biol.* 365:1505-1516 (2007).

Yoshimoto, et al., "Isolation and Characterization of the *ATF2* Gene Encoding Alcohol Acetyltransferase II in the Bottom Fermenting Yeast *Saccharomyces pastorianus*," *Yeast* 15:409-417 (1999).

Yoshioka and Hashimoto, "Ester formation by Alcohol Acetyltransferase from Brewers' Yeast," *Agric. Biol. Chem.* 45:2183-2190 (1981).

Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).

Yun et al., "The genes for anabolic 2-oxoglutarate: ferredoxin oxidoreductse from *Hydrogenobacter thermophilus* TK-6," *Biochem. Biophys. Res. Commun.* 282(2):589-594 (2001).

Yun et al., "ω-Amino acid:pyruvate transaminase from *Alcaligenes denitrificans* Y2k-2: a new catalyst for kinetic resolution of β-amino acids and amines," *Appl. Environ. Microbiol.* 70(4):2529-2534 (2004).

Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zeikus et al., "Biotechnology of succinic acid production and markets for derived industrial products," *Appl. Microbiol. Biotechnol.* 51:545-552 (1999).

Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the Coenzyme $B_{12}$-dependent isobutyryl-CoA mutase from *Streptomyces cinnamonensis*," *J. Biol. Chem.* 273(11):6508-6517 (1998).

Zhang et al., "2-Oxoacid:Ferredoxin Oxidoreductase from the thermoacidophilic Archaeon, sulfolobus sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. U.S.A.* 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fayy acids and marcrolide antibiotic production," *Microbiol.* 145 (Pt 9):2323-2334 (1999).

Zhang et al., "Isolation and properties of a levo-lactonase from *Fusarium proliferatum* ECU2002: a robust biocatalyst for production of chiral lactones," *Appl. Microbiol. Biotechnol.* 75:1087-1094 (2007).

Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by *Rhizopus oryzae* using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by *Rhizopus oryzae* ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*," *Acta. Crystallogr. Sect. F. Struct. Biol. Cryst. Commun.* 61(Pt 5):537-540 (2005).

Zhu and Sadowski, "Cleavage-dependent ligation by the FLP recombinase. Characterization of a mutant FLP protein with an alteration in a catalytic amino acid," *J. Biol. Chem.* 270(39):23044-23054 (1995).

Zhuang et al., "The YbgC protein encoded by the *ybgC* gene of the *tol-pal* gene cluster of *Haemophilus influenzae* catalyzes acyl-coenzyme A thioester hydrolysis," *FEBS Lett.* 516:161-163 (2002).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/~FwAsma:1:BASIC (printed Feb. 17, 2010).

Two pages from URL: web.archive.org/web/20080302001450/http://www.verenium.com/Pages/Technology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

Ferreira-Torres et al., "Microscale process evaluation of recombinant biocatalyst libraries: application to Baeyer-Villiger monooxygenase catalysed lactone synthesis," *Bioprocess Biosyst. Eng.* 28(2):83-93 (2005).

Locher et al., "Crystal structure of the Acidaminococcus fermentans 2hydroxyglutaryl-CoA dehydratase component A," *J. Mol. Biol.* 307(1):297-308 (2001).

Niu et al., "Benzene-free synthesis of adipic acid," *Biotechnol. Prog.* 18:201-211 (2002).

Reed et al., "An expanded genome-scale model of *Escherichia coli* K-12 (iJR904 GSM/GPR)," *Genome. Biol.* 4(9):R54 (2003).

Database Reaxys [Online] Elsevier Properties SA; RX-ID Nos. 715357 and 5957085; Volmar: Comptes Rendus Hebdomadaires Des Seances De L'Academie Des Sciences, vol. 181; (1925); p. 467 (document printed Apr. 11, 2011).

Tsuji et al., "Purification and Properties of 4-Aminobenzoate Hydroxylase, a New Monooxygenase from *Agaricus bisporus*," *J. Biol. Chem.* 261(28):13203-13209 (1986).

Nichols et al., "*para*-Aminobenzoate Synthesis from Chorismate Occurs in Two Steps," *J. Biol. Chem.* 264(15):8597-8601 (1989).

Dosselaere et al., "A Metabolic Node in Action: Chorismate-Utilizing Enzymes in Microorganisms," *Crit. Rev. Microbiol.* 27(2):75-131 (2001).

Nicolaou et al., "Total Synthesis of Abyssomicin C, Atrop-abyssomicin C, and Abyssomicin D: Implications for Natural Origins of Atrop-abyssomicin C," *J. Am. Chem. Soc.* 129(2):429-440 (2007).

Bister et al., "Abyssomicin C-A polycyclic antibiotic from a marine Verrucosispora strain as an inhibitor of the p-aminobenzoic acid/tetrahydrofolate biosynthesis pathway," *Angew Chem. Int. Ed. Engl.* 43(19):2574-2576 (2004).

Feist et al., "Modeling methanogenesis with a genome-scale metabolic reconstruction of *Methanosarcina barkeri*," *Mol. Syst. Biol.* 2:2006.0004 (2006).

One page from URL: <www.dtu.dk/English/Service/Phonebook.aspx?Ig=showcommon&id=193466> Containing 182 page document: Patil, Ph.D. Thesis, "Systems Biology of Metabolic Networks: Uncovering Regulatory and stoichiometric Principles," 2006. (Printed from the Internet Jun. 8, 2011).

Tweedy et al., "Metabolism of 3-(p-bromophenyl)-1-methoxy-1-methylurea (metobromuron) by selected soil microorganisms," *J. Agric. Food Chem.* 18(5):851-853 (1970).

Peres et al., "Biodegradation of nitrobenzene by its simultaneous reduction into aniline and mineralization of the aniline formed," *Appl. Microbiol. Biotechnol.* 49(3):343-349 (1998).
White, "Biosynthesis of methanopterin," Biochemistry 35(11):3447-3456 (1996).
Genbank Accession No. YP_001211907.1 Gl:147677692 (Nov. 22, 2010).
Genbank Accession No. P32614.1 Gl:418423 (Nov. 30, 2010).
Genbank Accession No. NP_012585.1 Gl:6322511 (Aug. 17, 2010).
Genbank Accession No. NP_418578.1 Gl:16131979 (Oct. 14, 2010).
Genbank Accession No. NP_418577.1 Gl:16131978 (Oct. 14, 2010).
Genbank Accession No. NP_418576.1 Gl:16131977 (Oct. 14, 2010).
Genbank Accession No. NP_418475.1 Gl:16131877 (Oct. 14, 2010).
Genbank Accession No. NP_014785.1 Gl:6324716 (Aug. 17, 2010).
Genbank Accession No. NP_011760.1 Gl:6321683 (Aug. 17, 2010).
Genbank Accession No. NP_415256.1 Gl:16128703 (Oct. 14, 2010).
Genbank Accession No. AAC73823.1 GI:1786949 (Oct. 7, 2010).
Genbank Accession No. BAB21494.1 Gl:12583691 (Apr. 21, 2001).
Genbank Accession No. BAB21495.1 Gl:12583692 (Apr. 21, 2001).
Genbank Accession No. BAB62132.1 Gl:14970994 (Jul. 24, 2001).
Genbank Accession No. BAB62133.1 Gl:14970995 (Jul. 24, 2001).
Genbank Accession No. BAB62134.1 Gl:14970996 (Jul. 24, 2001).
Genbank Accession No. BAB62135.1 Gl:14970997 (Jul. 24, 2001).
Genbank Accession No. BAB62136.1 Gl:14970998 (Jul. 24, 2001).
Genbank Accession No. ACD89303.1 Gl:189339900 (Jun. 4, 2008).
Genbank Accession No. ACD89302.1 Gl:189339899 (Jun. 4, 2008).
Genbank Accession No. ACD90192.1 Gl:189340789 (Jun. 4, 2008).
Genbank Accession No. ACD90193.1 Gl:189340790 (Jun. 4, 2008).
Genbank Accession No. YP_430825.1 GI:83590816 (Nov. 22, 2010).
Genbank Accession No. YP_430826.1 GI:83590817 (Nov. 22, 2010).
Genbank Accession No. YP_428917.1 Gl:83588908 (Nov. 22, 2010).
Genbank Accession No. NP_378302.1 Gl:15922633 (Jun. 9, 2010).
Genbank Accession No. BAA80470.1 Gl:5105156 (May 19, 2007).
Genbank Accession No. BAA80471.2 Gl:116062794 (May 19, 2007).
Genbank Accession No. AAC38210.1 Gl:2935178 (Mar. 6, 1998).
Genbank Accession No. AAC38211.1 Gl:2935179 (Mar. 6, 1998).
Genbank Accession No. AAC38212.1 Gl:2935180 (Mar. 6, 1998).
Genbank Accession No. AAC38213.1 Gl:2935181 (Mar. 6, 1998).
Genbank Accession No. NP_661069.1 Gl:21673004 (Mar. 30, 2010).
Genbank Accession No. NP_661068.1 Gl:21673003 (Mar. 30, 2010).
Genbank Accession No. CAA12243.2 Gl:19571179 (Apr. 15, 2005).
Genbank Accession No. CAD27440.1 Gl:19571178 (Apr. 15, 2005).
Genbank Accession No. YP_427805.1 GI:83594053 (Apr. 1, 2010).
Genbank Accession No. YP_427806.1 GI:83594054 (Apr. 1, 2010).
Genbank Accession No. AC184720.1 GI:209772816 (Jun. 8, 2009).
Genbank Accession No. AAA34703.1 GI:171749 (Apr. 27, 1993).
Genbank Accession No. BAC00856.1 GI:21396513 (Jun. 13, 2002).
Genbank Accession No. AAM71597.1 GI:21646271 (Mar. 12, 2010).
Genbank Accession No. NP_952516.1 GI:39996565 (Oct. 14, 2010).
Genbank Accession No. YP_393560.1 GI:78777245 (Apr. 27, 2010).
Genbank Accession No. BAF34932.1 GI:116234991 (Jun. 9, 2007).
Genbank Accession No. BAF34931.1 GI:116234990 (Jun. 9, 2007).
Genbank Accession No. BAD02487.1 GI:38602676 (Jun. 9, 2007).
Genbank Accession No. YP_315314.1 GI:74317574 (Mar. 12, 2010).
Genbank Accession No. YP_315313.1 GI:74317573 (Apr. 1, 2010).
Genbank Accession No. YP_314612.1 GI:74316872 (Apr. 1, 2010).
Genbank Accession No. YP_003473030.1 GI:289548042 (Feb. 24, 2010).
Genbank Accession No. YP_003473029.1 GI:289548041 (Feb. 24, 2010).
Genbank Accession No. YP_003473406.1 GI:289548418 (Feb. 24, 2010).
Genbank Accession No. AAC74358.1 GI:1787531 (Oct. 25, 2010).
Genbank Accession No. AAC73229.1 GI:2367097 (Oct. 25, 2010).
Genbank Accession No. NP_460671.1 GI:16765056 (Dec. 14, 2010).
Genbank Accession No. NP_459163.1 GI:16763548 (Dec. 14, 2010).
Genbank Accession No. AAA34389.1 GI:170982 (Apr. 27, 1993).
Genbank Accession No. CAA70873.1 GI:1770208 (Sep. 26, 1997).
Genbank Accession No. YP_012236.1 GI:46581428 (Aug. 26, 2010).
Genbank Accession No. ABB40031.1 GI:78220682 (Dec. 3, 2010).
Genbank Accession No. YP_002478891.1 GI:220903579 (Apr. 15, 2010).
Genbank Accession No. YP_428946.1 GI:83588937 (Nov. 22, 2010).
Genbank Accession No. NP_415896.1 GI:16129339 (Oct. 14, 2010).
Genbank Accession No. NP_662511.1 GI:21674446 (Mar. 4, 2010).
Genbank Accession No. YP_179630.1 GI:57238499 (Mar. 4, 2010).
Genbank Accession No. ADE85473.1 GI:294476085 (Jun. 24, 2010).
Genbank Accession No. BAA95603.1 GI:7768912 (Dec. 10, 2005).
Genbank Accession No. BAA95604.1 GI:7768913 (Dec. 10, 2005).
Genbank Accession No. BAA95605.1 GI:7768914 (Dec. 10, 2005).
Genbank Accession No. BAA95606.1 GI:7768915 (Dec. 10, 2005).
Genbank Accession No. BAA95607.1 GI:7768916 (Dec. 10, 2005).
Genbank Accession No. YP_001482096.1 GI:157414840 (Apr. 27, 2010).
Genbank Accession No. NP_207955.1 GI:15645778 (Mar. 29, 2010).
Genbank Accession No. EDK33306.1 GI:146346770 (Feb. 21, 2008).
Genbank Accession No. EDK33307.1 GI:146346771 (Feb. 21, 2008).
Genbank Accession No. EDK33308.1 GI:146346772 (Feb. 21, 2008).
Genbank Accession No. EDK33309.1 GI:146346773 (Feb. 21, 2008).
Genbank Accession No. EDK33310.1 GI:146346774 (Feb. 21, 2008).
Genbank Accession No. EDK33311.1 GI:146346775 (Feb. 21, 2008).
Genbank Accession No. NP_207955.1 GI:15645778 (Mar. 29, 2010).
Genbank Accession No. AAW35824.1 GI:57167045 (Mar. 10, 2010).
Genbank Accession No. P28861.4 GI:399486 (Nov. 30, 2010).
Genbank Accession No. AAC75595.1 GI:1788892 (Oct. 7, 2010).
Genbank Accession No. NP_001149023.1 GI:226497434 (Apr. 10, 2009).
Genbank Accession No. ZP_05392639.1 GI:255525707 (Nov. 10, 2010).
Genbank Accession No. ZP_05392638.1 GI:255525706 (Nov. 10, 2010).
Genbank Accession No. ZP_05392636.1 GI:255525704 (Nov. 10, 2010).
Genbank Accession No. ZP_05395060.1 GI:255528241 (Nov. 10, 2010).
Genbank Accession No. ZP_05392450.1 GI:255525514 (Nov. 10, 2010).
Genbank Accession No. ZP_05391084.1 GI:255524124 (Nov. 10, 2010).
Genbank Accession No. BAE02673.1 GI:68163284 (Jun. 24, 2005).
Genbank Accession No. AAA83524.1 GI:144806 (Dec. 15, 1995).
Genbank Accession No. AAY79867.1 GI:68566938 (Mar. 10, 2010).
Genbank Accession No. AAC75578.1 GI:1788874 (Oct. 25, 2010).
Genbank Accession No. AAD07340.1 GI:2313367 (Mar. 5, 2010).
Genbank Accession No. CAL34484.1 GI:112359698 (May 13, 2009).

Genbank Accession No. ABC18400.1 GI:83571848 (Mar. 11, 2010).
Genbank Accession No. ABC19514.1 GI:83572962 (Mar. 11, 2010).
Genbank Accession No. ABC20188.1 GI:83573636 (Mar. 11, 2010).
Genbank Accession No. ABC20404.1 GI:83573852 (Mar. 11, 2010).
Genbank Accession No. ZP_05394383.1 GI:255527515 (Nov. 10, 2010).
Genbank Accession No. ZP_05392958.1 GI:255526034 (Nov. 10, 2010).
Genbank Accession No. ZP_05392281.1 GI:255525342 (Nov. 10, 2010).
Genbank Accession No. ZP_05395295.1 GI:255528511 (Nov. 10, 2010).
Genbank Accession No. ZP_05391615.1 GI:255524662 (Nov. 10, 2010).
Genbank Accession No. ZP_05391304.1 GI:255524347 (Nov. 10, 2010).
Genbank Accession No. ABC23064.1 GI:83576513 (Mar. 11, 2010).
Genbank Accession No. ABC22716.1 GI:83576165 (Mar. 11, 2010).
Genbank Accession No. ABC22826.1 GI:83576275 (Mar. 11, 2010).
Genbank Accession No. P38946.1 GI:729048 (Aug. 10, 2010).
Genbank Accession No. XP_001330176.1 GI:123975034 (Nov. 1, 2008).
Genbank Accession No. XP_828352.1 GI:71754875 (May 16, 2008).
Genbank Accession No. AAN69545.1 GI:24985644 (Mar. 5, 2010).
Genbank Accession No. NP_746082.1 GI:26990657 (Jun. 29, 2010).
Genbank Accession No. ACD85596.1 GI:189233555 (Jun. 2, 2008).
Genbank Accession No. YP_627417.1 GI:108563101 (Dec. 17, 2010).
Genbank Accession No. YP_627418.1 GI:108563102 (Dec. 17, 2010).
Genbank Accession No. NP_391778.1 GI:16080950 (Mar. 31, 2010).
Genbank Accession No. NP_391777.1 GI:16080949 (Mar. 31, 2010).
Genbank Accession No. NP_000427.1 GI:4557817 (Dec. 27, 2010).
Genbank Accession No. NP_071403.1 GI:11545841 (Dec. 30, 2010).
Genbank Accession No. NP_416726.1 GI:16130159 (Oct. 14, 2010).
Genbank Accession No. NP_416725.1 GI:16130158 (Oct. 14, 2010).
Genbank Accession No. NP_149326.1 GI:15004866 (Apr. 26, 2009).
Genbank Accession No. NP_149327.1 GI:15004867 (Apr. 26, 2009).
Genbank Accession No. AAP42564.1 GI:31075384 (Dec. 2, 2010).
Genbank Accession No. AAP42565.1 GI:31075385 (Dec. 2, 2010).
Genbank Accession No. AAF89840.1 GI:9622535 (Aug. 1, 2000).
Genbank Accession No. AAF89841.1 GI:9622536 (Aug. 1, 2000).
Genbank Accession No. AAU45405.1 GI:52421824 (Sep. 27, 2004).
Genbank Accession No. AAU45406.1 GI:52421825 (Sep. 27, 2004).
Genbank Accession No. YP_158075.1 GI:56476486 (May 24, 2010).
Genbank Accession No. YP_158074.1 GI:56476485 (May 24, 2010).
Genbank Accession No. YP_384480.1 GI:78222733 (Aug. 27, 2010).
Genbank Accession No. YP_384481.1 GI:78222734 (Aug. 27, 2010).
Genbank Accession No. NP_417395.1 GI:16130821 (Oct. 14, 2010).
Genbank Accession No. ZP_03838384.1 GI:227334728 (May 1, 2009).
Genbank Accession No. YP_001573497.1 GI:161506385 (Dec. 11, 2010).
Genbank Accession No. ZP_04635364.1 GI:238791727 (Nov. 9, 2010).
Genbank Accession No. NP_603179.1 GI:19703617 (Jul. 28, 2010).
Genbank Accession No. NP_603180.1 GI:19703618 (Jul. 28, 2010).
Genbank Accession No. NP_602657.1 GI:19705162 (Jul. 28, 2010).
Genbank Accession No. NP_602656.1 GI:19705161 (Jul. 28, 2010).
Genbank Accession No. NP_905281.1 GI:34540802 (Jun. 29, 2010).
Genbank Accession No. NP_905290.1 GI:34540811 (Jun. 29, 2010).
Genbank Accession No. NP_622378.1 GI:20807207 (May 14, 2010).
Genbank Accession No. NP_622379.1 GI:20807208 (May 14, 2010).
Genbank Accession No. AAC73716.1 GI:1786832 (Oct. 25, 2010).
Genbank Accession No. AAC73717.2 GI:87081764 (Oct. 25, 2010).
Genbank Accession No. AAC73718.1 GI:1786834 (Oct. 25, 2010).
Genbank Accession No. AAC73719.2 GI:87081765 (Oct. 25, 2010).
Genbank Accession No. AAC73714.1 GI:1786830 (Oct. 25, 2010).
Genbank Accession No. AAC73715.1 GI:1786831 (Oct. 25, 2010).
Genbank Accession No. CAA71633.1 GI:2842397 (Nov. 30, 2006).
Genbank Accession No. CAA71632.1 GI:2842396 (Nov. 30, 2006).
Genbank Accession No. CAA71635.1 GI:2842395 (Nov. 30, 2006).
Genbank Accession No. CAA71636.1 GI:3413797 (Nov. 30, 2006).
Genbank Accession No. CAA71634.1 GI:2842398 (Nov. 30, 2006).
Genbank Accession No. NP_459613.1 GI:16763998 (Dec. 14, 2010).
Genbank Accession No. AAL19573.1 GI:16419133 (Feb. 23, 2009).
Genbank Accession No. NP_459064.1 GI:16763449 (Dec. 14, 2010).
Genbank Accession No. NP_459616.1 GI:16764001 (Dec. 14, 2010).
Genbank Accession No. NP_459611.1 GI:16763996 (Dec. 14, 2010).
Genbank Accession No. NP_459612.1 GI:16763997 (Dec. 14, 2010).
Genbank Accession No. CAA56217.1 GI:565619 (Jun. 12, 2006).
Genbank Accession No. CAA56216.1 GI:565618 (Jun. 12, 2006).
Genbank Accession No. CAA56215.1 GI:565617 (Jun. 12, 2006).
Genbank Accession No. BAH66541.1 GI:238774045 (Jun. 2, 2009).
Genbank Accession No. CAA56218.1 GI:565620 (Jun. 12, 2006).
Genbank Accession No. AAL60463.1 GI:18140907 (Apr. 12, 2002).
Genbank Accession No. NP_416799.1 GI:16130231 (Oct. 14, 2010).
Genbank Accession No. AAB18301.1 GI:1491790 (Nov. 5, 1996).
Genbank Accession No. AAA72042.1 GI:349834 (Oct. 11, 2005).
Genbank Accession No. AAC74919.1 GI:1788155 (Oct. 25, 2010).
Genbank Accession No. NP_349675.1 GI:15896326 (Dec. 14, 2010).
Genbank Accession No. Q97111.1 GI:20137415 (Oct. 5, 2010).
Genbank Accession No. NP_416800.1 GI:16130232 (Oct. 14, 2010).
Genbank Accession No. P39646.3 GI:730415 (Nov. 30, 2010).
Genbank Accession No. EDK33432.1 GI:146346896 (Feb. 21, 2008).
Genbank Accession No. Q9X0L4.1 GI:6685776 (Nov. 30, 2010).
Genbank Accession No. NP_349676.1 GI:15896327 (Dec. 14, 2010).
Genbank Accession No. AAR19757.1 GI:38425288 (Mar. 18, 2004).
Genbank Accession No. CAC07932.1 GI:10046659 (Jun. 9, 2001).
Genbank Accession No. AAC77039.1 GI:1790505 (Oct. 25, 2010).
Genbank Accession No. AAA21945.1 GI:141890 (Apr. 24, 1993).
Genbank Accession No. ABC87079.1 GI:86169671 (Feb. 4, 2006).
Genbank Accession No. AAL23099.1 GI:16422835 (Feb. 23, 2009).
Genbank Accession No. Q01574.2 GI:257050994 (Nov. 30, 2010).
Genbank Accession No. NP_070039.1 GI:11498810 (May 5, 2010).
Genbank Accession No. NP_070807.1 GI:11499565 (May 5, 2010).
Genbank Accession No. YP_135572.1 GI:55377722 (Jun. 8, 2010).
Genbank Accession No. NP_560604.1 GI:18313937 (Jun. 15, 2010).
Genbank Accession No. AAC24333.2 GI:22711873 (Feb. 2, 2005).
Genbank Accession No. YP_431142.2 GI:148283121 (Nov. 22, 2010).
Genbank Accession No. YP_431144.1 GI:83591135 (Nov. 22, 2010).
Genbank Accession No. YP_846816.1 GI:116750129 (Apr. 10, 2010).
Genbank Accession No. YP_846817.1 GI:116750130 (Apr. 10, 2010).

Genbank Accession No. YP_846818.1 GI:116750131 (Apr. 10, 2010).
Genbank Accession No. YP_846819.1 GI:116750132 (Apr. 10, 2010).
Genbank Accession No. YP_359585.1 GI:78044572 (Mar. 31, 2010).
Genbank Accession No. YP_359586.1 GI:78044500 (Mar. 31, 2010).
Genbank Accession No. YP_359587.1 GI:78044647 (Mar. 31, 2010).
Genbank Accession No. ZP_05390901.1 GI:255523938 (Nov. 10, 2010).
Genbank Accession No. ZP_05394380.1 GI:255527512 (Nov. 10, 2010).
Genbank Accession No. YP_428991.1 GI:83588982 (Nov. 22, 2010).
Genbank Accession No. YP_361182.1 GI:78045024 (Mar. 31, 2010).
Genbank Accession No. P13419.1 GI:120562 (Aug. 10, 2010).
Genbank Accession No. ZP_05391913.1 GI:255524966 (Nov. 10, 2010).
Genbank Accession No. ZP_05392946.1 GI:255526022 (Nov. 10, 2010).
Genbank Accession No. ACL18622.1 GI:219536883 (Jan. 5, 2009).
Genbank Accession No. YP_001393842.1 GI:153953077 (May 6, 2010).
Genbank Accession No. YP_003781893.1 GI:300856909 (Sep. 30, 2010).
Genbank Accession No. YP_430368.1 GI:83590359 (Nov. 22, 2010).
Genbank Accession No. NP_415062.1 GI:16128513 (Oct. 14, 2010).
Genbank Accession No. YP_360698.1 GI:78044829 (Mar. 31, 2010).
Genbank Accession No. ZP_05392948.1 GI:255526024 (Nov. 10, 2010).
Genbank Accession No. ADK16789.1 GI:300437022 (Jul. 27, 2010).
Genbank Accession No. NP_951919.1 GI:39995968 (Oct. 14, 2010).
Genbank Accession No. YP_725874.1 GI:113867385 (Apr. 12, 2010).
Genbank Accession No. YP_696506.1 GI:110800457 (Mar. 30, 2010).
Genbank Accession No. YP_430048.1 GI:83590039 (Nov. 22, 2010).
Genbank Accession No. NP_418376.1 GI:16131779 (Oct. 14, 2010).
Genbank Accession No. YP_360071.1 GI:78044792 (Mar. 31, 2010).
Genbank Accession No. YP_003781889.1 GI:300856905 (Sep. 30, 2010).
Genbank Accession No. ZP_07335241.1 GI:303248996 (Nov. 10, 2010).
Genbank Accession No. ZP_05392950.1 GI:255526026 (Nov. 10, 2010).
Genbank Accession No. ZP_07633513.1 GI:307691067 (Dec. 10, 2010).
Genbank Accession No. YP_001560205.1 GI:160881237 (Apr. 27, 2010).
Genbank Accession No. YP_430054.1 GI:83590045 (Nov. 22, 2010).
Genbank Accession No. YP_430055.1 GI:83590046 (Nov. 22, 2010).
Genbank Accession No. YP_430056.1 GI:83590047 (Nov. 22, 2010).
Genbank Accession No. YP_430057.1 GI:83590048 (Nov. 22, 2010).
Genbank Accession No. YP_430058.1 GI:83590049 (Nov. 22, 2010).
Genbank Accession No. YP_430059.1 GI:83590050 (Nov. 22, 2010).
Genbank Accession No. YP_430060.1 GI:83590051 (Nov. 22, 2010).
Genbank Accession No. YP_430061.1 GI:83590052 (Nov. 22, 2010).
Genbank Accession No. YP_360065.1 GI:78044202 (Mar. 31, 2010).
Genbank Accession No. YP_360064.1 GI:78042962 (Mar. 31, 2010).
Genbank Accession No. YP_360063.1 GI:78044060 (Mar. 31, 2010).
Genbank Accession No. YP_360062.1 GI:78044449 (Mar. 31, 2010).
Genbank Accession No. YP_360061.1 GI:78043584 (Mar. 31, 2010).
Genbank Accession No. YP_360060.1 GI:78042742 (Mar. 31, 2010).
Genbank Accession No. YP_360059.1 GI:78044249 (Mar. 31, 2010).
Genbank Accession No. ZP_05392944.1 GI:255526020 (Nov. 10, 2010).
Genbank Accession No. ZP_05392945.1 GI:255526021 (Nov. 10, 2010).
Genbank Accession No. ZP_05392952.1 GI:255526028 (Nov. 10, 2010).
Genbank Accession No. ZP_05392953.1 GI:255526029 (Nov. 10, 2010).
Genbank Accession No. ZP_05392954.1 GI:255526030 (Nov. 10, 2010).
Genbank Accession No. ZP_05392955.1 GI:255526031 (Nov. 10, 2010).
Genbank Accession No. ZP_05392956.1 GI:255526032 (Nov. 10, 2010).
Genbank Accession No. NP_618736.1 GI:20092661 (Jun. 29, 2010).
Genbank Accession No. NP_618735.1 GI:20092660 (Jun. 29, 2010).
Genbank Accession No. NP_618734.1 GI:20092659 (Jun. 29, 2010).
Genbank Accession No. NP_618733.1 GI:20092658 (Jun. 29, 2010).
Genbank Accession No. NP_618732.1 GI:20092657 (Jun. 29, 2010).
Genbank Accession No. NP_618731.1 GI:20092656 (Jun. 29, 2010).
Genbank Accession No. NP_615961.1 GI:20089886 (Jun. 29, 2010).
Genbank Accession No. NP_615962.1 GI:20089887 (Jun. 29, 2010).
Genbank Accession No. NP_615963.1 GI:20089888 (Jun. 29, 2010).
Genbank Accession No. NP_615964.1 GI:20089889 (Jun. 29, 2010).
Genbank Accession No. NP_615965.1 GI:20089890 (Jun. 29, 2010).
Genbank Accession No. NP_615966.1 GI:20089891 (Jun. 29, 2010).
Genbank Accession No. YP_304299.1 GI:73668284 (Jun. 18, 2010).
Genbank Accession No. YP_304298.1 GI:73668283 (Jun. 18, 2010).
Genbank Accession No. YP_307082.1 GI:73671067 (Jun. 18, 2010).
Genbank Accession No. YP_307081.1 GI:73671066 (Jun. 18, 2010).
Genbank Accession No. YP_304612.1 GI:73668597 (Jun. 18, 2010).
Genbank Accession No. YP_304611.1 GI:73668596 (Jun. 18, 2010).
Genbank Accession No. NP_615421.1 GI:20089346 (Jun. 29, 2010).
Genbank Accession No. NP_615422.1 GI:20089347 (Jun. 29, 2010).
Genbank Accession No. NP_619254.1 GI:20093179 (Jun. 29, 2010).

Genbank Accession No. NP_619253.1 GI:20093178 (Jun. 29, 2010).
Genbank Accession No. NP_616549.1 GI:20090474 (Jun. 29, 2010).
Genbank Accession No. NP_616550.1 GI:20090475 (Jun. 29, 2010).
Genbank Accession No. YP_430066.1 GI:83590057 (Nov. 22, 2010).
Genbank Accession No. YP_430065.1 GI:83590056 (Nov. 22, 2010).
Genbank Accession No. YP_304602.1 GI:73668587 (Jun. 18, 2010).
Genbank Accession No. NP_619241.1 GI:20093166 (Jun. 29, 2010).
Genbank Accession No. NP_616548.1 GI:20090473 (Jun. 29, 2010).
Genbank Accession No. YP_430937.1 GI:83590928 (Nov. 22, 2010).
Genbank Accession No. YP_431175.1 GI:83591166 (Nov. 22, 2010).
Genbank Accession No. YP_430935.1 GI:83590926 (Nov. 22, 2010).
Genbank Accession No. YP_430813.1 GI:83590804 (Nov. 22, 2010).
Genbank Accession No. YP_358957.1 GI:78044574 (Mar. 31, 2010).
Genbank Accession No. YP_358958.1 GI:78045112 (Mar. 31, 2010).
Genbank Accession No. ZP_05390164.1 GI:255523193 (Nov. 10, 2010).
Genbank Accession No. ZP_05390341.1 GI:255523371 (Nov. 10, 2010).
Genbank Accession No. ZP_05391756.1 GI:255524806 (Nov. 10, 2010).
Genbank Accession No. YP_384856.1 GI:78223109 (Aug. 27, 2010).
Genbank Accession No. YP_910642.1 GI:119355998 (Apr. 1, 2010).
Genbank Accession No. YP_910643.1 GI:119355999 (Apr. 1, 2010).
Genbank Accession No. YP_002504800.1 GI:220927891 (May 29, 2010).
Genbank Accession No. YP_002478973.1 GI:220903661 (Apr. 15, 2010).
Genbank Accession No. YP_002478972.1 GI:220903660 (Apr. 15, 2010).
Genbank Accession No. YP_355490.1 GI:77917675 (May 27, 2010).
Genbank Accession No. YP_355491.1 GI:77917676 (May 27, 2010).
Genbank Accession No. YP_355492.1 GI:77917677 (May 27, 2010).
Genbank Accession No. YP_001407343.1 GI:154175407 (Apr. 12, 2010).
Genbank Accession No. YP_360644.1 GI:78043418 (Mar. 31, 2010).
Genbank Accession No. YP_360645.1 GI:78044791 (Mar. 31, 2010).
Genbank Accession No. YP_360646.1 GI:78044340 (Mar. 31, 2010).
Genbank Accession No. YP_360647.1 GI:78043871 (Mar. 31, 2010).
Genbank Accession No. YP_360648.1 GI:78044023 (Mar. 31, 2010).
Genbank Accession No. YP_360649.1 GI:78043124 (Mar. 31, 2010).
Genbank Accession No. YP_360650.1 GI:78043938 (Mar. 31, 2010).
Genbank Accession No. YP_360651.1 GI:78044700 (Mar. 31, 2010).
Genbank Accession No. YP_360652.1 GI:78043942 (Mar. 31, 2010).
Genbank Accession No. YP_360654.1 GI:78043296 (Mar. 31, 2010).
Genbank Accession No. YP_360655.1 GI:78044021 (Mar. 31, 2010).
Genbank Accession No. AAC45118.1 GI:1515468 (Apr. 5, 2002).
Genbank Accession No. AAC45119.1 GI:1515469 (Apr. 5, 2002).
Genbank Accession No. AAC45120.1 GI:1515470 (Apr. 5, 2002).
Genbank Accession No. AAC45121.1 GI:1498746 (Apr. 5, 2002).
Genbank Accession No. AAC45122.1 GI:1498747 (Apr. 5, 2002).
Genbank Accession No. AAC45123.1 GI:1498748 (Apr. 5, 2002).
Genbank Accession No. AAC45124.1 GI:1498749 (Apr. 5, 2002).
Genbank Accession No. AAC45125.1 GI:1498750 (Apr. 5, 2002).
Genbank Accession No. AAC45126.1 GI:1498751 (Apr. 5, 2002).
Genbank Accession No. AAC74057.1 GI:1787206 (Oct. 25, 2010).
Genbank Accession No. AAC74058.1 GI:1787207 (Oct. 25, 2010).
Genbank Accession No. AAC74059.1 GI:1787208 (Oct. 25, 2010).
Genbank Accession No. AAC74060.1 GI:1787209 (Oct. 25, 2010).
Genbank Accession No. AAC74061.1 GI:1787210 (Oct. 25, 2010).
Genbank Accession No. AAC74062.1 GI:1787211 (Oct. 25, 2010).
Genbank Accession No. AAC76033.1 GI:1789371 (Oct. 25, 2010).
Genbank Accession No. AAC76032.1 GI:1789370 (Oct. 25, 2010).
Genbank Accession No. AAC76031.1 GI:2367183 (Oct. 25, 2010).
Genbank Accession No. AAC76030.1 GI:1789368 (Oct. 25, 2010).
Genbank Accession No. AAC76029.1 GI:1789367 (Oct. 25, 2010).
Genbank Accession No. AAC76028.1 GI:1789366 (Oct. 25, 2010).
Genbank Accession No. AAC76027.1 GI:1789365 (Oct. 25, 2010).
Genbank Accession No. AAC76026.1 GI:1789364 (Oct. 25, 2010).
Genbank Accession No. NP_417205.1 GI:16130632 (Oct. 14, 2010).
Genbank Accession No. NP_417204.1 GI:16130631 (Oct. 14, 2010).
Genbank Accession No. NP_417203.1 GI:16130630 (Oct. 14, 2010).
Genbank Accession No. NP_417202.1 GI:16130629 (Oct. 14, 2010).
Genbank Accession No. NP_417201.1 GI:16130628 (Oct. 14, 2010).
Genbank Accession No. NP_417200.1 GI:16130627 (Oct. 14, 2010).
Genbank Accession No. NP_417199.1 GI:16130626 (Oct. 14, 2010).
Genbank Accession No. NP_417198.1 GI:16130625 (Oct. 14, 2010).
Genbank Accession No. NP_417197.1 GI:16130624 (Oct. 14, 2010).
Genbank Accession No. NP_416976.4 GI:90111444 (Oct. 14, 2010).
Genbank Accession No. NP_416977.1 GI:16130407 (Oct. 14, 2010).
Genbank Accession No. NP_416978.4 GI:90111445 (Oct. 14, 2010).
Genbank Accession No. NP_416979.1 GI:16130409 (Oct. 14, 2010).
Genbank Accession No. NP_416980.1 GI:16130411 (Oct. 14, 2010).
Genbank Accession No. NP_416981.1 GI:16130411 (Oct. 14, 2010).
Genbank Accession No. NP_416982.1 GI:16130412 (Oct. 14, 2010).
Genbank Accession No. NP_416983.1 GI:16130413 (Oct. 14, 2010).
Genbank Accession No. NP_416984.1 GI:16130414 (Oct. 14, 2010).
Genbank Accession No. NP_416985.4 GI:90111446 (Oct. 14, 2010).
Genbank Accession No. NP_416986.4 GI:90111447 (Oct. 14, 2010).
Genbank Accession No. NP_417206.1 GI:16130633 (Oct. 14, 2010).
Genbank Accession No. NP_417207.1 GI:16130634 (Oct. 14, 2010).
Genbank Accession No. NP_417208.1 GI:16130635 (Oct. 14, 2010).

Genbank Accession No. NP_417209.1 GI:16130636 (Oct. 14, 2010).
Genbank Accession No. NP_417210.2 GI:226524740 (Oct. 14, 2010).
Genbank Accession No. NP_417192.1 GI:16130619 (Oct. 14, 2010).
Genbank Accession No. YP_431007.1 GI:83590998 (Nov. 22, 2010).
Genbank Accession No. YP_431008.1 GI:83590999 (Nov. 22, 2010).
Genbank Accession No. YP_431009.1 GI:83591000 (Nov. 22, 2010).
Genbank Accession No. YP_431010.1 GI:83591001 (Nov. 22, 2010).
Genbank Accession No. YP_431011.1 GI:83591002 (Nov. 22, 2010).
Genbank Accession No. YP_431012.1 GI:83591003 (Nov. 22, 2010).
Genbank Accession No. YP_431013.1 GI:83591004 (Nov. 22, 2010).
Genbank Accession No. YP_431014.1 GI:83591005 (Nov. 22, 2010).
Genbank Accession No. YP_431015.1 GI:83591006 (Nov. 22, 2010).
Genbank Accession No. YP_431016.1 GI:83591007 (Nov. 22, 2010).
Genbank Accession No. YP_431017.1 GI:83591008 (Nov. 22, 2010).
Genbank Accession No. YP_431018.1 GI:83591009 (Nov. 22, 2010).
Genbank Accession No. YP_431019.1 GI:83591010 (Nov. 22, 2010).
Genbank Accession No. YP_431020.1 GI:83591011 (Nov. 22, 2010).
Genbank Accession No. YP_431021.1 GI:83591012 (Nov. 22, 2010).
Genbank Accession No. YP_431022.1 GI:83591013 (Nov. 22, 2010).
Genbank Accession No. YP_431023.1 GI:83591014 (Nov. 22, 2010).
Genbank Accession No. YP_431024.1 GI:83591015 (Nov. 22, 2010).
Genbank Accession No. YP_429313.1 GI:83589304 (Nov. 22, 2010).
Genbank Accession No. YP_429314.1 GI:83589305 (Nov. 22, 2010).
Genbank Accession No. YP_429315.1 GI:83589306 (Nov. 22, 2010).
Genbank Accession No. YP_429316.1 GI:83589307 (Nov. 22, 2010).
Genbank Accession No. YP_429670.1 GI:83589661 (Nov. 22, 2010).
Genbank Accession No. YP_429671.1 GI:83589662 (Nov. 22, 2010).
Genbank Accession No. YP_429672.1 GI:83589663 (Apr. 4, 2006).
Genbank Accession No. YP_429673.1 GI:83589664 (Jul. 22, 2008).
Genbank Accession No. YP_429674.1 GI:83589665 (Nov. 22, 2010).
Genbank Accession No. YP_429675.1 GI:83589666 (Nov. 22, 2010).
Genbank Accession No. YP_429676.1 GI:83589667 (Nov. 22, 2010).
Genbank Accession No. YP_430050.1 GI:83590041 (Nov. 22, 2010).
Genbank Accession No. YP_430051.1 GI:83590042 (Nov. 22, 2010).
Genbank Accession No. YP_430052.1 GI:83590043 (Nov. 22, 2010).
Genbank Accession No. YP_430053.1 GI:83590044 (Nov. 22, 2010).
Genbank Accession No. YP_430562.1 GI:83590553 (Nov. 22, 2010).
Genbank Accession No. YP_430563.1 GI:83590554 (Nov. 22, 2010).
Genbank Accession No. YP_430564.1 GI:83590555 (Nov. 22, 2010).
Genbank Accession No. YP_430726.1 GI:83590717 (Nov. 22, 2010).
Genbank Accession No. YP_430727.1 GI:83590718 (Nov. 22, 2010).
Genbank Accession No. YP_430728.1 GI:83590719 (Nov. 22, 2010).
Genbank Accession No. YP_430729.1 GI:83590720 (Nov. 22, 2010).
Genbank Accession No. YP_430730.1 GI:83590721 (Nov. 22, 2010).
Genbank Accession No. YP_430731.1 GI:83590722 (Nov. 22, 2010).
Genbank Accession No. YP_430305.1 GI:83590296 (Nov. 22, 2010).
Genbank Accession No. YP_430306.1 GI:83590297 (Nov. 22, 2010).
Genbank Accession No. YP_430307.1 GI:83590298 (Nov. 22, 2010).
Genbank Accession No. NP_942727.1 GI:38637753 (Mar. 16, 2010).
Genbank Accession No. NP_942728.1 GI:38637754 (Mar. 16, 2010).
Genbank Accession No. NP_942729.1 GI:38637755 (Mar. 16, 2010).
Genbank Accession No. NP_942730.1 GI:38637756 (Mar. 16, 2010).
Genbank Accession No. NP_942731.1 GI:38637757 (Mar. 16, 2010).
Genbank Accession No. NP_942732.1 GI:38637758 (Mar. 16, 2010).
Genbank Accession No. NP_953767.1 GI:39997816 (Oct. 14, 2010).
Genbank Accession No. NP_953766.1 GI:39997815 (Oct. 14, 2010).
Genbank Accession No. NP_953765.1 GI:39997814 (Oct. 14, 2010).
Genbank Accession No. NP_953764.1 GI:39997813 (Oct. 14, 2010).
Genbank Accession No. NP_953763.1 GI:39997812 (Oct. 14, 2010).
Genbank Accession No. NP_953762.1 GI:39997811 (Oct. 14, 2010).
Genbank Accession No. NP_441418.1 GI:16330690 (Aug. 26, 2010).
Genbank Accession No. NP_441417.1 GI:16330689 (Aug. 26, 2010).
Genbank Accession No. NP_441416.1 GI:16330688 (Aug. 26, 2010).
Genbank Accession No. NP_441415.1 GI:16330687 (Aug. 26, 2010).
Genbank Accession No. NP_441414.1 GI:16330686 (Aug. 26, 2010).
Genbank Accession No. NP_441413.1 GI:16330685 (Aug. 26, 2010).
Genbank Accession No. NP_441412.1 GI:16330684 (Aug. 26, 2010).
Genbank Accession No. NP_441411.1 GI:16330683 (Aug. 26, 2010).
Genbank Accession No. NP_484737.1 GI:17228189 (Mar. 31, 2010).
Genbank Accession No. NP_484738.1 GI:17228190 (Mar. 30, 2010).
Genbank Accession No. NP_484739.1 GI:17228191 (Mar. 30, 2010).
Genbank Accession No. NP_484740.1 GI:17228192 (Mar. 30, 2010).
Genbank Accession No. NP_484741.1 GI:17228193 (Mar. 30, 2010).

Genbank Accession No. NP_484742.1 GI:17228194 (Mar. 30, 2010).
Genbank Accession No. NP_484743.1 GI:17228195 (Mar. 30, 2010).
Genbank Accession No. AAP50519.1 GI:37787351 (Dec. 9, 2009).
Genbank Accession No. AAP50520.1 GI:37787352 (Dec. 9, 2009).
Genbank Accession No. AAP50521.1 GI:37787353 (Dec. 9, 2009).
Genbank Accession No. AAP50522.1 GI:37787354 (Dec. 9, 2009).
Genbank Accession No. AAP50523.1 GI:37787355 (Dec. 9, 2009).
Genbank Accession No. NP_418391.1 GI:16131794 (Oct. 14, 2010).
Genbank Accession No. AAB58883.2 GI:28572162 (Feb. 27, 2003).
Genbank Accession No. ABB53270.1 GI:80973080 (Jun. 29, 2007).
Genbank Accession No. NP_013023.1 GI:6322950 (Jun. 3, 2010).
Genbank Accession No. NP_417862.1 GI:16131280 (Oct. 14, 2010).
Genbank Accession No. YP_089485.1 GI:52426348 (May 24, 2010).
Genbank Accession No. O09460.1 GI:3122621 (Nov. 30, 2010).
Genbank Accession No. Q6W6X5 GI:75440571 (Oct. 31, 2006).
Genbank Accession No. P43923.1 GI:1172573 (Nov. 30, 2010).
Genbank Accession No. NP_011453.1 GI:6321376 (Jun. 3, 2010).
Genbank Accession No. NP_009777.1 GI:6319695 (Jun. 3, 2010).
Genbank Accession No. YP_890857.1 GI:118470447 (Mar. 31, 2010).
Genbank Accession No. NP_415996.2 GI:90111281 (Oct. 14, 2010).
Genbank Accession No. NP_416958.1 GI:16130388 (Oct. 14, 2010).
Genbank Accession No. P27443.1 GI:126732 (Nov. 30, 2010).
Genbank Accession No. NP_416728.1 GI:16130161 (Oct. 14, 2010).
Genbank Accession No. NP_349476.1 GI:15896127 (Dec. 14, 2010).
Genbank Accession No. NP_149242.1 GI:15004782 (Apr. 26, 2009).
Genbank Accession No. NP_015297.1 GI:6325229 (Aug. 17, 2010).
Genbank Accession No. P21177.2 GI:119811 (Nov. 2, 2010).
Genbank Accession No. P77399.1 GI:3334437 (Nov. 30, 2010).
Genbank Accession No. EDK34807.1 GI:146348271 (Feb. 21, 2008).
Genbank Accession No. EDK32512.1 GI:146345976 (Feb. 21, 2008).
Genbank Accession No. P52041.2 GI:18266893 (Nov. 30, 2010).
Genbank Accession No. 002691.3 GI:3183024 (Nov. 30, 2010).
Genbank Accession No. P23238.1 GI:130017 (Aug. 10, 2010).
Genbank Accession No. YP_353825.1 GI:77464321 (May 25, 2010).
Genbank Accession No. NP_349314.1 GI:15895965 (Dec. 14, 2010).
Genbank Accession No. AAM14586.1 GI:20162442 (Apr. 17, 2002).
Genbank Accession No. YP_001191505.1 GI:146304189 (Aug. 10, 2010).
Genbank Accession No. YP_001190500.1 GI:146303184 (Aug. 10, 2010).
Genbank Accession No. YP_001190490.1 GI:146303174 (Aug. 10, 2010).
Genbank Accession No. YP_001192057.1 GI:146304741 (Aug. 10, 2010).
Genbank Accession No. YP_047869.1 GI:50086359 (May 24, 2010).
Genbank Accession No. AAC45217.1 GI:1684886 (Dec. 20, 2007).
Genbank Accession No. BAB85476.1 GI:18857901 (Mar. 18, 2005).
Genbank Accession No. P38947.1 GI:730847 (Feb. 5, 2008).
Genbank Accession No. NP_904963.1 GI:34540484 (Jun. 29, 2010).
Genbank Accession No. BAA03892.1 GI:425213 (Feb. 16, 2008).
Genbank Accession No. AAV66076.1 GI:55818563 (Jun. 8, 2005).
Genbank Accession No. AAP42563.1 GI:31075383 (Dec. 2, 2010).
Genbank Accession No. YP_001190808.1 GI:146303492 (Aug. 10, 2010).
Genbank Accession No. NP_378167.1 GI:15922498 (Jun. 9, 2010).
Genbank Accession No. NP_343563.1 GI:15898958 (Jun. 9, 2010).
Genbank Accession No. YP_256941.1 GI:70608071 (Aug. 9, 2010).
Genbank Accession No. AAT66436.1 GI:49473535 (Apr. 26, 2006).
Genbank Accession No. AAA80209.1 GI:687645 (Oct. 27, 1995).
Genbank Accession No. P77445.1 GI:2498347 (Nov. 30, 2010).
Genbank Accession No. YP_726053.1 GI:113867564 (Apr. 12, 2010).
Genbank Accession No. L21902.1 GI:1228100 (Mar. 15, 1996).
Genbank Accession No. Q94B07 GI:75249805 (Oct. 31, 2006).
Genbank Accession No. AAR91477.1 GI:40795502 (May 27, 2008).
Genbank Accession No. P84067 GI:75345323 (Oct. 31, 2006).
Genbank Accession No. P28811.1 GI:127211 (Nov. 30, 2010).
Genbank Accession No. Q59477.1 GI:2842618 (Oct. 5, 2010).
Genbank Accession No. P31937.2 GI:12643395 (Nov. 30, 2010).
Genbank Accession No. P32185.1 GI:416872 (Oct. 5, 2010).
Genbank Accession No. BAB12273.1 GI:9967138 (Mar. 18, 2005).
Genbank Accession No. NP_014032.1 GI:6323961 (Jun. 3, 2010).
Genbank Accession No. NP_417484.1 GI:16130909 (Oct. 14, 2010).
Genbank Accession No. NP_349892.1 GI:15896543 (Dec. 14, 2010).
Genbank Accession No. NP_349891.1 GI:15896542 (Dec. 14, 2010).
Genbank Accession No. YP_162971.1 GI:56552132 (Aug. 13, 2010)
Genbank Accession No. NP_415757.1 GI:16129202 (Oct. 14, 2010).
Genbank Accession No. AAK09379.1 GI:12958626 (Jan. 17, 2002).
Genbank Accession No. YP_001433009.1 GI:156742880 (Nov. 2, 2010).
Genbank Accession No. ZP_01039179.1 GI:85708113 (Nov. 9, 2010).
Genbank Accession No. ZP_01626393.1 GI:119504313 (Nov. 9, 2010).
Genbank Accession No. AAC76268.1 GI:1789632 (Oct. 25, 2010).
Genbank Accession No. NP_415898.1 GI:16129341 (Oct. 14, 2010).
Genbank Accession No. YP_725182.1 GI:113866693 (Apr. 12, 2010).
Genbank Accession No. AAA58352.1 GI:177198 (Dec. 31, 1994).
Genbank Accession No. AAA23199.2 GI:60592974 (Mar. 9, 2005).
Genbank Accession No. P14941.1 GI:113443 (Nov. 30, 2010).
Genbank Accession No. CAD36475.1 GI:21615553 (Apr. 15, 2005).
Genbank Accession No. AAC25556.1 GI:3288810 (Jul. 20, 2004).
Genbank Accession No. P76459.1 GI:2492994 (Nov. 30, 2010).
Genbank Accession No. P76458.1 GI:2492990 (Nov. 30, 2010).
Genbank Accession No. NP_570103.1 GI:18543355 (Nov. 10, 2010).
Genbank Accession No. CAA57200.1 GI:559393 (Mar. 22, 1995).
Genbank Accession No. NP_009538.1 GI:6319456 (Jun. 3, 2010).
Genbank Accession No. CAA15502.1 GI:3191970 (Jan. 13, 2009).
Genbank Accession No. NP_414986.1 GI:16128437 (Oct. 14, 2010).
Genbank Accession No. NP_570112.2 GI:51036669 (Dec. 26, 2010).
Genbank Accession No. NP_415027.1 GI:16128478 (Oct. 14, 2010).
Genbank Accession No. NP_415264.1 GI:16128711 (Oct. 14, 2010).
Genbank Accession No. NP_415914.1 GI:16129357 (Oct. 14, 2010).
Genbank Accession No. NP_415129.1 GI:16128580 (Oct. 147, 2010).
Genbank Accession No. Q5XIE6.2 GI:146324906 (Nov. 30, 2010).
Genbank Accession No. Q6NVY1.2 GI:146324905 (Nov. 30, 2010).
Genbank Accession No. P28817.2 GI:2506374 (Nov. 30, 2010).
Genbank Accession No. AAP09256.1 GI:29895975 (Mar. 11, 2010).
Genbank Accession No. NP_414777.1 GI:16128228 (Oct. 14, 2010).
Genbank Accession No. CAJ15517.1 GI:77019264 (Nov. 14, 2006).
Genbank Accession No. ABS19624.1 GI:152002983 (Jul. 21, 2007).
Genbank Accession No. NP_390902.2 GI:50812281 (Apr. 25, 2009).

Genbank Accession No. NP_084486.1 GI:21313520 (Dec. 29, 2010).
Genbank Accession No. NP_076417.2 GI:31982927 (Dec. 27, 2010).
Genbank Accession No. YP_001191504.1 Ii:146304188 (Aug. 10, 2010).
Genbank Accession No. AAR91681.1 GI:40796035 (Mar. 9, 2004).
Genbank Accession No. AB183656.1 GI:114848891 (Jan. 3, 2007).
Genbank Accession No. YP_978699.1 GI:121638475 (Dec. 14, 2010).
Genbank Accession No. YP_978898.1 GI:121638674 (Dec. 14, 2010).
Genbank Accession No. YP_118225.1 GI:54023983 (May 12, 2010).
Genbank Accession No. YP_120266.1 GI:54026024 (May 12, 2010).
Genbank Accession No. YP_001828302.1 GI:182440583 (Apr. 14, 2010).
Genbank Accession No. YP_001822177.1 GI:182434458 (Apr. 14, 2010).
Genbank Accession No. YP_887275.1 GI:118473501 (Mar. 31, 2010).
Genbank Accession No. YP_889972.1 GI:118469671 (Mar. 31, 2010).
Genbank Accession No. YP_886985.1 GI:118471293 (Mar. 31, 2010).
Genbank Accession No. NP_959974.1 GI:41407138 (May 12, 2010).
Genbank Accession No. NP_961833.1 GI:41408997 (May 12, 2010).
Genbank Accession No. YP_001850422.1 GI:183982131 (May 12, 2010).
Genbank Accession No. YP_001851230.1 GI:183982939 (May 12, 2010).
Genbank Accession No. YP_001850220.1 GI:183981929 (May 12, 2010).
Genbank Accession No. ZP_04027864.1 GI:227980601 (Apr. 28, 2009).
Genbank Accession No. ZP_04026660.1 GI:227979396 (Apr. 28, 2009).
Genbank Accession No. ZP_05045132.1 Gl:254431429 (Jun. 8, 2010).
Genbank Accession No. XP_636931.1 GI:66806417 (Jan. 29, 2010).
Genbank Accession No. YP_001825755.1 GI:182438036 (Apr. 14, 2010).
Genbank Accession No. YP_001825756.1 GI:182438037 (Apr. 14, 2010).
Genbank Accession No. AAA34747.1 Gl:171867 (Feb. 12, 2001).
Genbank Accession No. P50113.1 Gl:1708896 (Nov. 30, 2010).
Genbank Accession No. AAC02241.1 Gl:2853226 (Jan. 30, 2001).
Genbank Accession No. AAO26020.1 Gl:28136195 (Jul. 30, 2003).
Genbank Accession No. P40976.3 Gl:13124791 (Nov. 30, 2010).
Genbank Accession No. Q10474.1 Gl:1723561 (Nov. 30, 2010).
Genbank Accession No. CAA74300.1 Gl:3282044 (Nov. 14, 2006).
Genbank Accession No. NP_437676.1 Gl:16264884 (Apr. 1, 2010).
Genbank Accession No. BAD86668.1 Gl:57506672 (Jan. 7, 2008).
Genbank Accession No. BAE72684.1 Gl:84570594 (Mar. 25, 2008).
Genbank Accession No. BAE72685.1 Gl:84570596 (Mar. 25, 2008).
Genbank Accession No. BAF91602.1 Gl:158937170 (Mar. 12, 2010).
Genbank Accession No. AAP09256.1 Gl:29895975 (Mar. 11, 2010).
Genbank Accession No. NP_149328.1 Gl:15004868 (Apr. 26, 2009).
Genbank Accession No. AAP42566.1 GI:31075386 (Dec. 2, 2010).
Genbank Accession No. YP_001310906.1 Gl:150018652 (Apr. 1, 2010).
Genbank Accession No. YP_299391.1 Gl:73539024 (Mar. 31, 2010).
Genbank Accession No. AAP39869.1 Gl:31322946 (Apr. 29, 2004).
Genbank Accession No. NP_349318.1 Gl:15895969 (Dec. 14, 2010).
Genbank Accession No. NP_745427.1 Gl:26990002 (Jun. 29, 2010).
Genbank Accession No. NP_745426.1 Gl:26990001 (Jun. 29, 2010).
Genbank Accession No. ABF82233.1 Gl:106636093 (Aug. 2, 2007).
Genbank Accession No. ABF82234.1 Gl:106636094 (Aug. 2, 2007).
Genbank Accession No. NP_415905.1 Gl:16129348 (Oct. 14, 2010).
Genbank Accession No. NP_415911.1 Gl:16129354 (Oct. 14, 2010).
Genbank Accession No. NP_415912.1 Gl:16129355 (Oct. 14, 2010).
Genbank Accession No. CAB60035.2 Gl:70910046 (May 13, 2008).
Genbank Accession No. YP_001396399.1 Gl:153955634 (May 6, 2010).
Genbank Accession No. YP_001191403.1 Gl:146304087 (Aug. 10, 2010).
Genbank Accession No. YP_001191305.1 Gl:146303989 (Aug. 10, 2010).
Genbank Accession No. AAS20429.1 GI:42561982 (Feb. 22, 2004).
Genbank Accession No. P38947.2 GI:172046062 (Nov. 30, 2010).
Genbank Accession No. YP_256941.1 Gl:70608071 (Aug. 9, 2010).
Genbank Accession No. NP_904964.1 Gl:34540485 (Jun. 29, 2010).
Genbank Accession No. NP_906037.1 Gl:34541558 (Jun. 29, 2010).
Genbank Accession No. ZP_05391757.1 Gl:255524807 (Nov. 10, 2010).
Genbank Accession No. ZP_05391758.1 Gl:255524808 (Nov. 10, 2010).
Genbank Accession No. NP_462380.1 Gl:16766765 (Dec. 14, 2010).
Genbank Accession No. NP_460970.1 Gl:16765355 (Dec. 14, 2010).
Genbank Accession No. NP_460969.1 Gl:16765354 (Dec. 14, 2010).
Genbank Accession No. NP_460972.1 Gl:16765357 (Dec. 14, 2010).
Genbank Accession No. NP_460974.1 Gl:16765359 (Dec. 14, 2010).
Genbank Accession No. NP_460973.1 Gl:16765358 (Dec. 14, 2010).
Genbank Accession No. NP_460977.1 Gl:16765362 (Dec. 14, 2010).
Genbank Accession No. NP_460971.1 Gl:16765356 (Dec. 14, 2010).
Genbank Accession No. NP_460976.1 Gl:16765361 (Dec. 14, 2010).
Genbank Accession No. NP_460975.1 Gl:16765360 (Dec. 14, 2010).
Genbank Accession No. NP_460978.1 Gl:16765363 (Dec. 14, 2010).
Genbank Accession No. NP_460980.1 Gl:16765365 (Dec. 14, 2010).
Genbank Accession No. NP_459679.1 Gl:16764064 (Dec. 14, 2010).
Genbank Accession No. P31570.1 Gl:399274 (Nov. 30, 2010).
Genbank Accession No. AAA27268.1 Gl:154436 (Jul. 23, 1993).
Genbank Accession No. Q05600.1 Gl:543942 (Aug. 10, 2010).
Genbank Accession No. NP_460963.1 Gl:16765348 (Dec. 14, 2010).
Genbank Accession No. NP_460961.1 Gl:16765346 (Dec. 14, 2010).
Genbank Accession No. AAA27270.1 Gl:154438 (Jul. 23, 1993).
Genbank Accession No. NP_459635.1 Gl:16764020 (Dec. 14, 2010).
Genbank Accession No. NP_416495.1 Gl:16129932 (Oct. 14, 2010).
Genbank Accession No. NP_416496.1 Gl:16129933 (Oct. 14, 2010).
Genbank Accession No. NP_416497.1 Gl:16129934 (Oct. 14, 2010).

Genbank Accession No. NP_417827.1 GI:16131246 (Oct. 14, 2010).
Genbank Accession No. NP_012995.1 GI:6322922 (Jun. 3, 2010).
Genbank Accession No. NP_009772.1 GI:6319690 (Aug. 17, 2010).
Genbank Accession No. NP_418401.1 GI:16131804 (Oct. 14, 2010).
Genbank Accession No. NP_416226.1 GI:16129667 (Oct. 14, 2010).
Genbank Accession No. NP_416224.1 GI:16129665 (Oct. 14, 2010).
Genbank Accession No. NP_414700.1 GI:16128151 (Oct. 14, 2010).
Genbank Accession No. NP_415768.1 GI:16129213 (Oct. 14, 2010).
Genbank Accession No. NP_417479.1 GI:16130904 (Oct. 14, 2010).
Genbank Accession No. NP_417478.1 GI:16130903 (Oct. 14, 2010).
Genbank Accession No. AAA27031.1 GI:153891 (Apr. 26, 1993).
Genbank Accession No. NP_460306.1 GI:16764691 (Dec. 14, 2010).
Genbank Accession No. NP_460308.1 GI:16764693 (Dec. 14, 2010).
Genbank Accession No. AAL20266.1 GI:16419860 (Feb. 23, 2009).

* cited by examiner

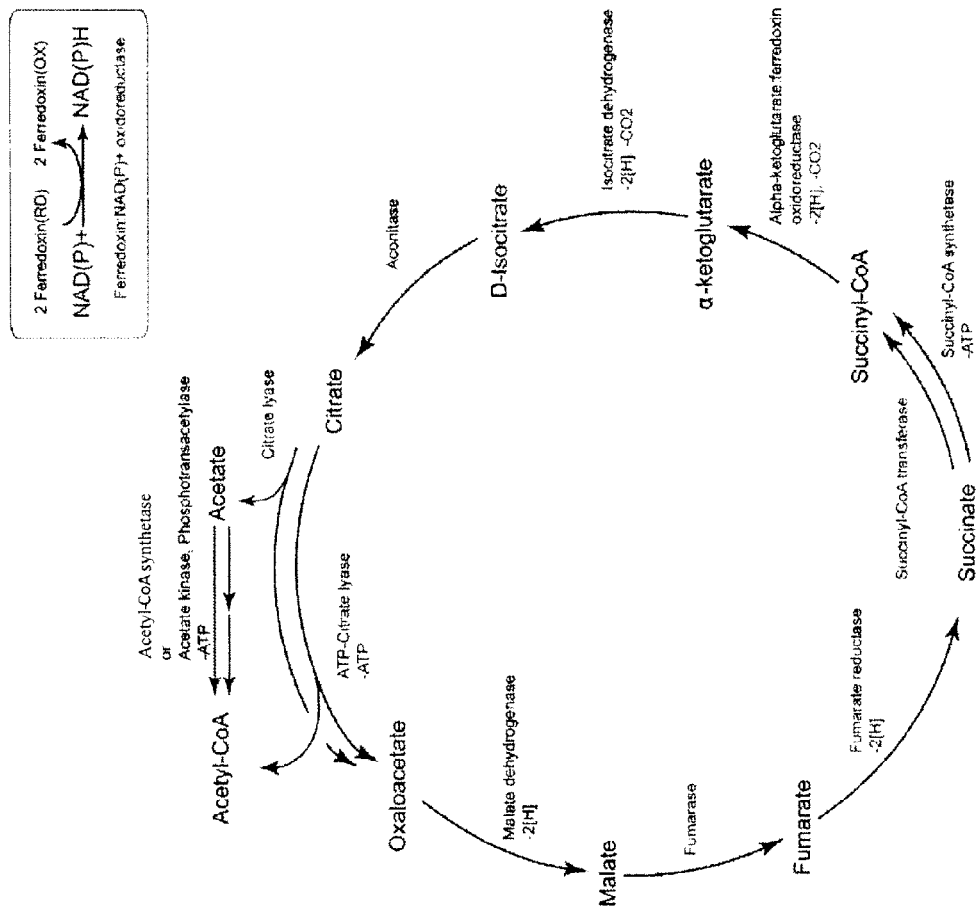
Figure 2A (updated)

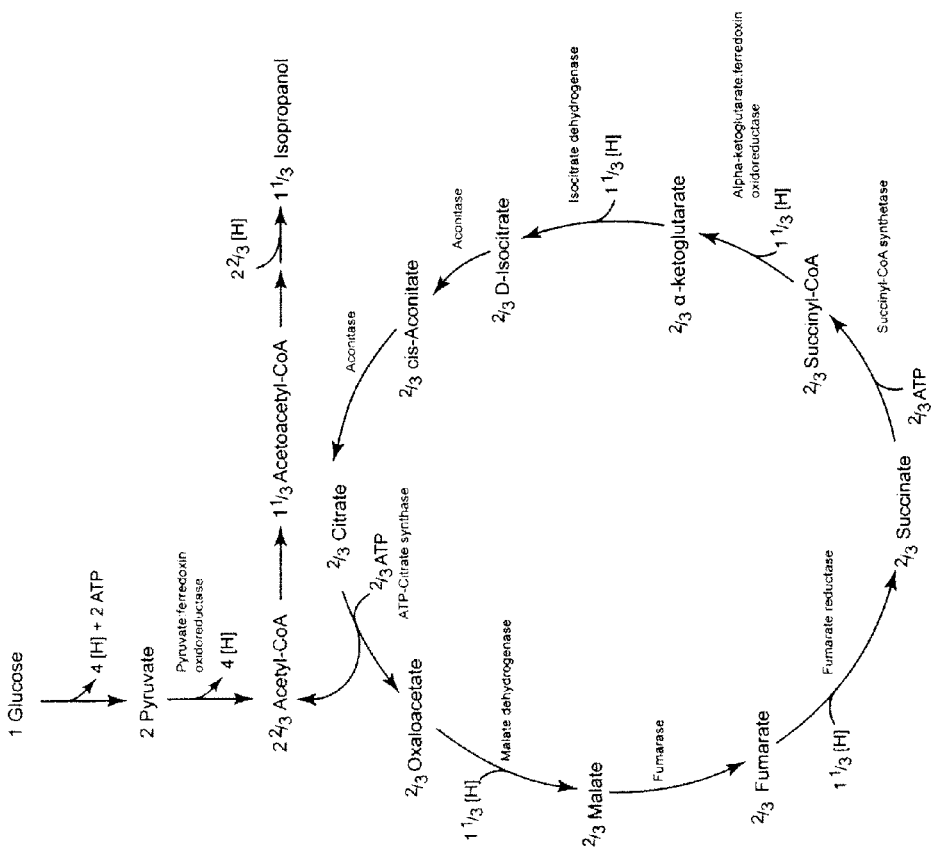
Figure 2B (updated)

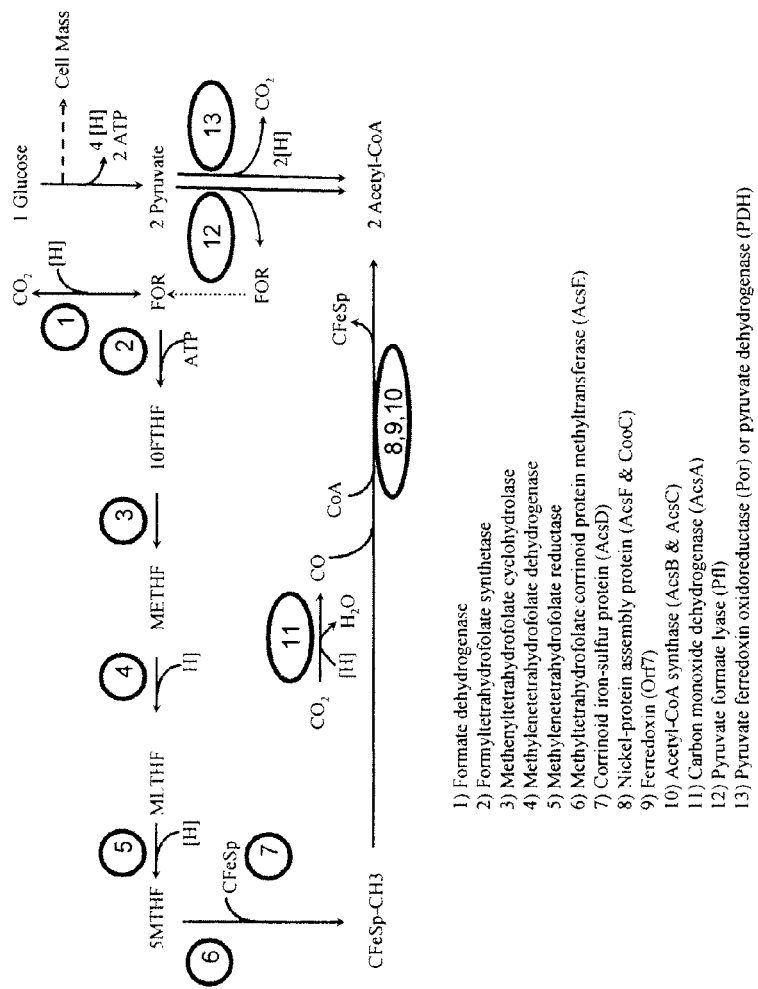
Figure 4A (updated)

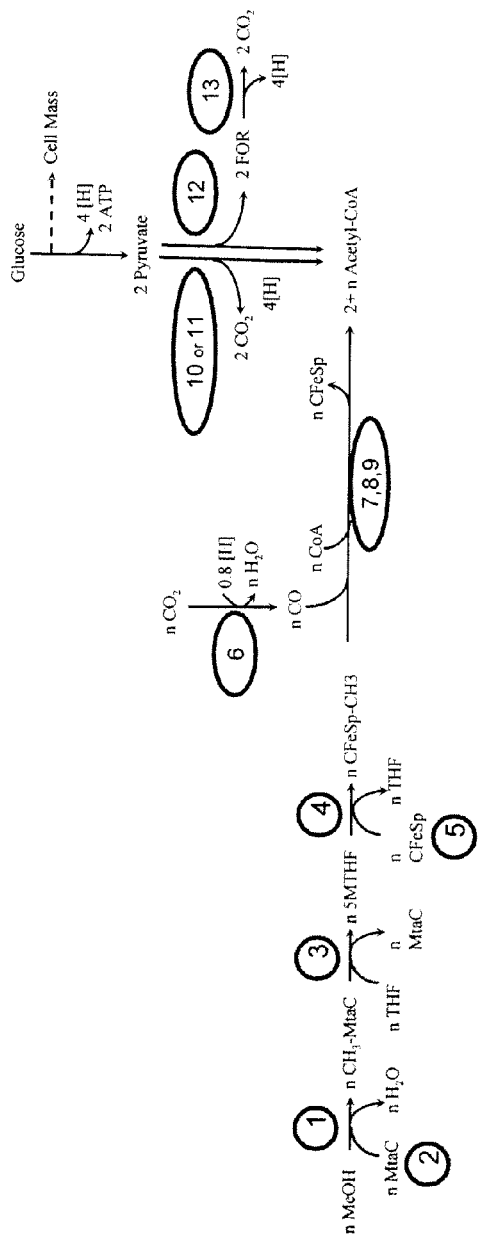
Figure 4B (updated)

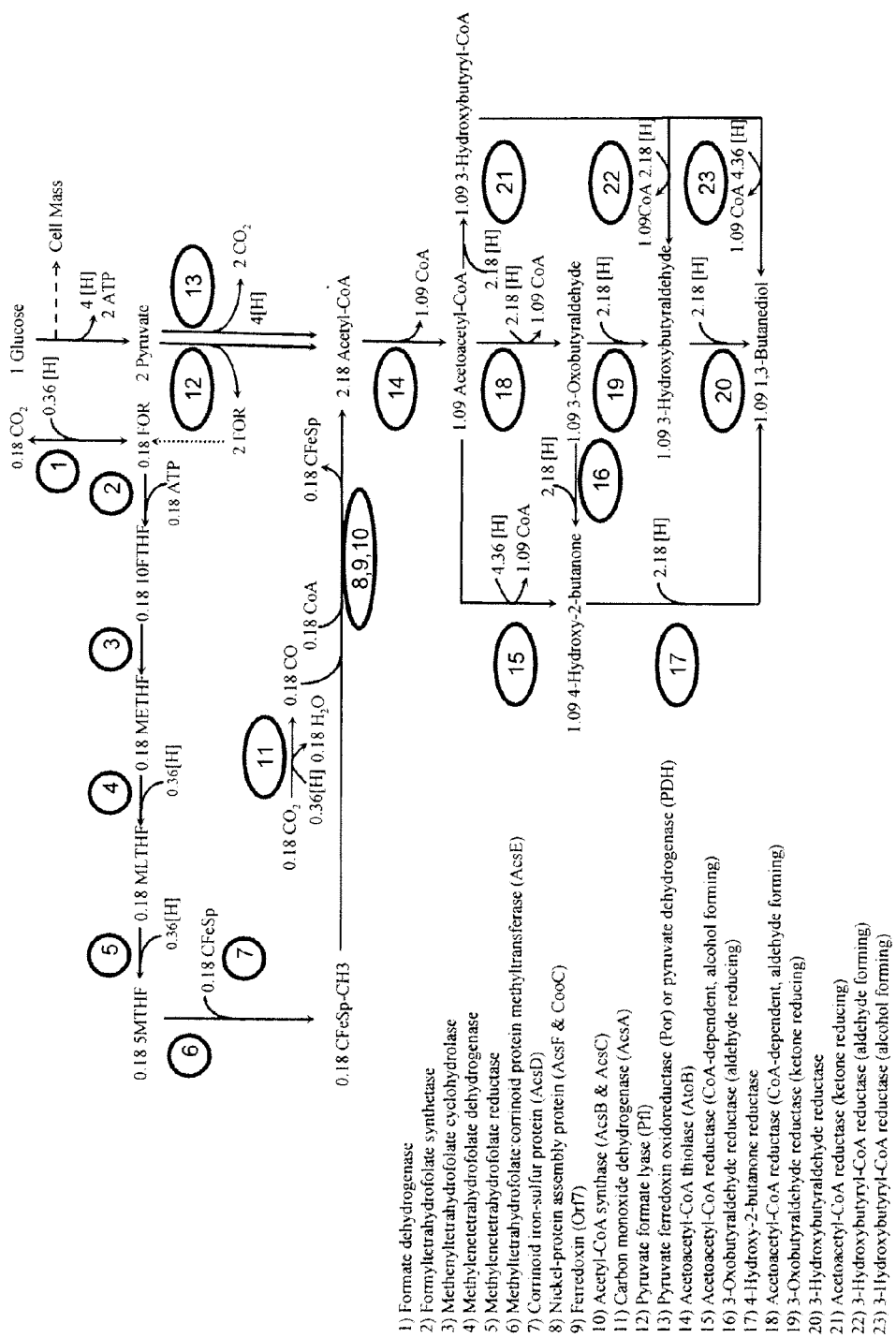
Figure 5A (updated)

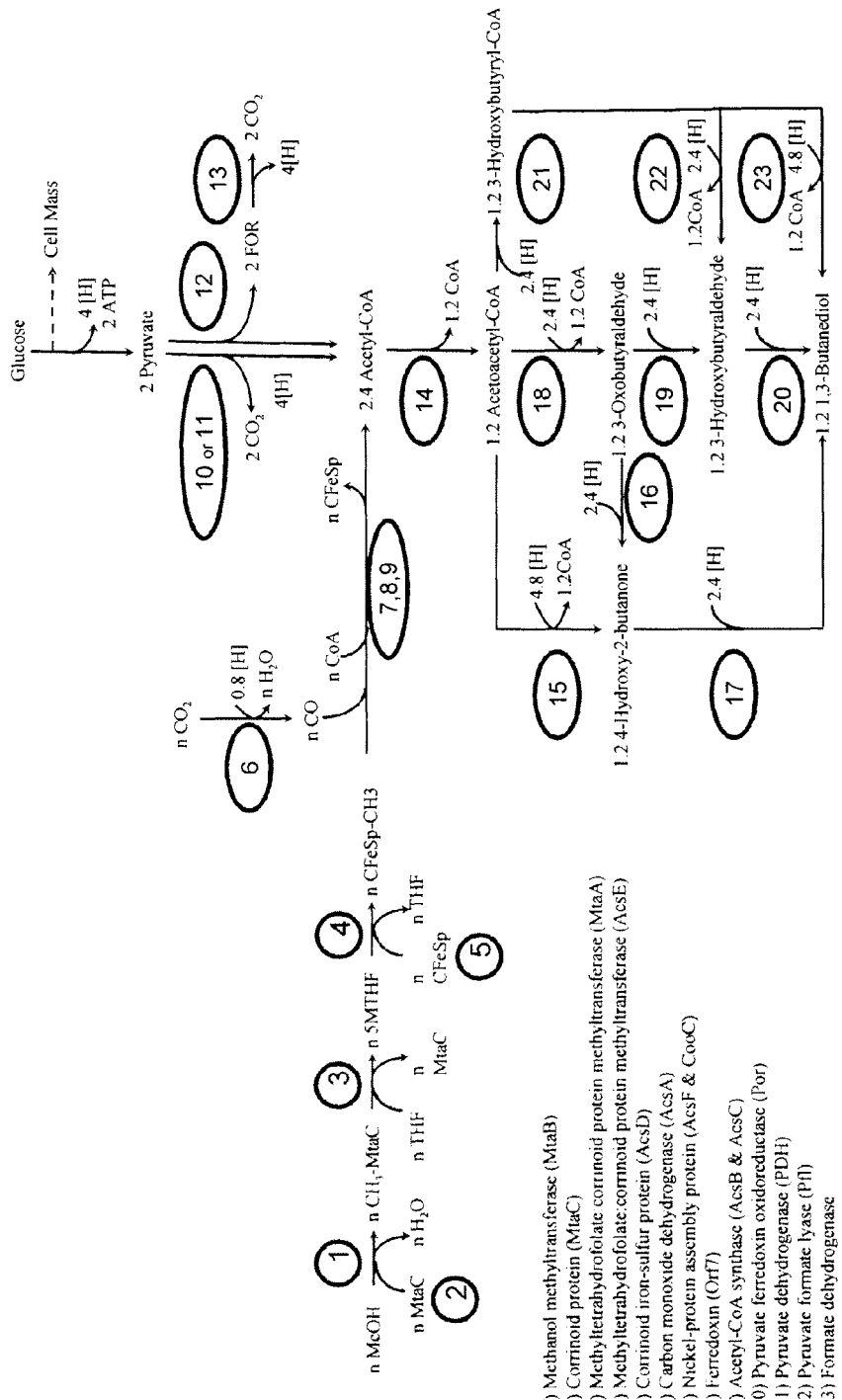
Figure 5B (updated)

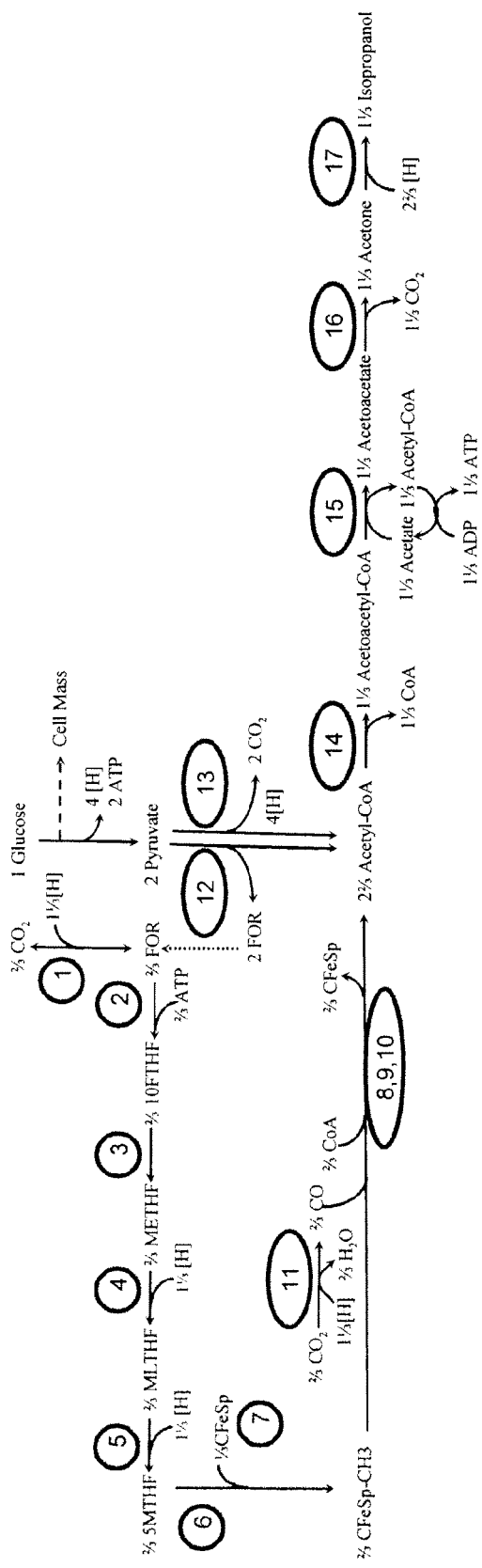

Figure 6A (updated)

1) Formate dehydrogenase
2) Formyltetrahydrofolate synthetase
3) Methenyltetrahydrofolate cyclohydrolase
4) Methylenetetrahydrofolate dehydrogenase
5) Methylenetetrahydrofolate reductase
6) Methyltetrahydrofolate corrinoid protein methyltransferase (AcsE)
7) Corrinoid iron-sulfur protein (AcsD)
8) Nickel-protein assembly protein (AcsF & CooC)
9) Ferredoxin (Orf7)
10) Acetyl-CoA synthase (AcsB & AcsC)
11) Carbon monoxide dehydrogenase (AcsA)
12) Pyruvate formate lyase (Pfl)
13) Pyruvate ferredoxin oxidoreductase (Por) or pyruvate dehydrogenase (PDH)
14) Acetoacetyl-CoA thiolase (AtoB)
15) Acetoacetyl-CoA:acetate:CoA transferase (AtoAD)
16) Acetoacetate decarboxylase (Adc)
17) Isopropanol dehydrogenase (Adh)

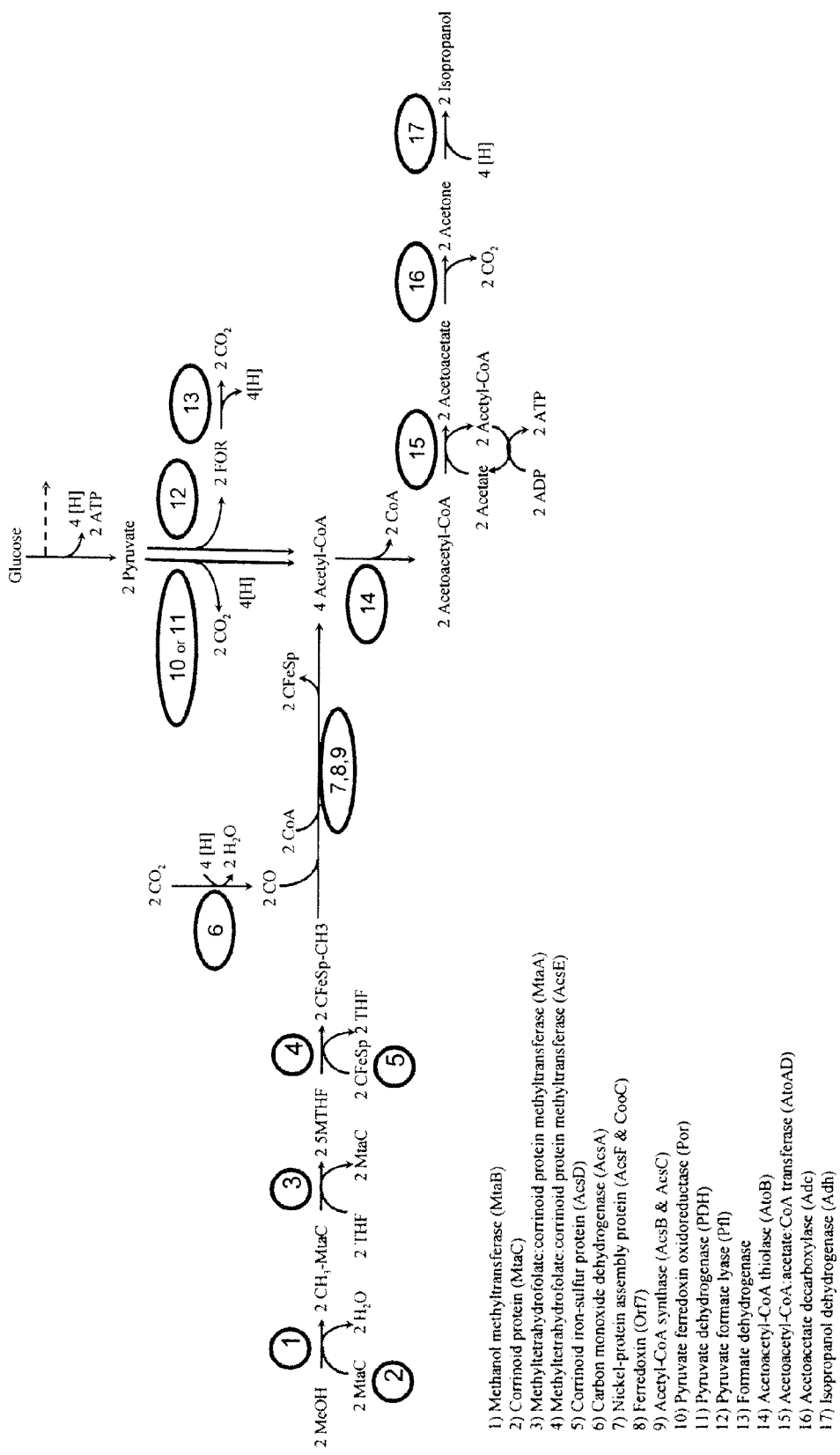
Figure 6B (updated)

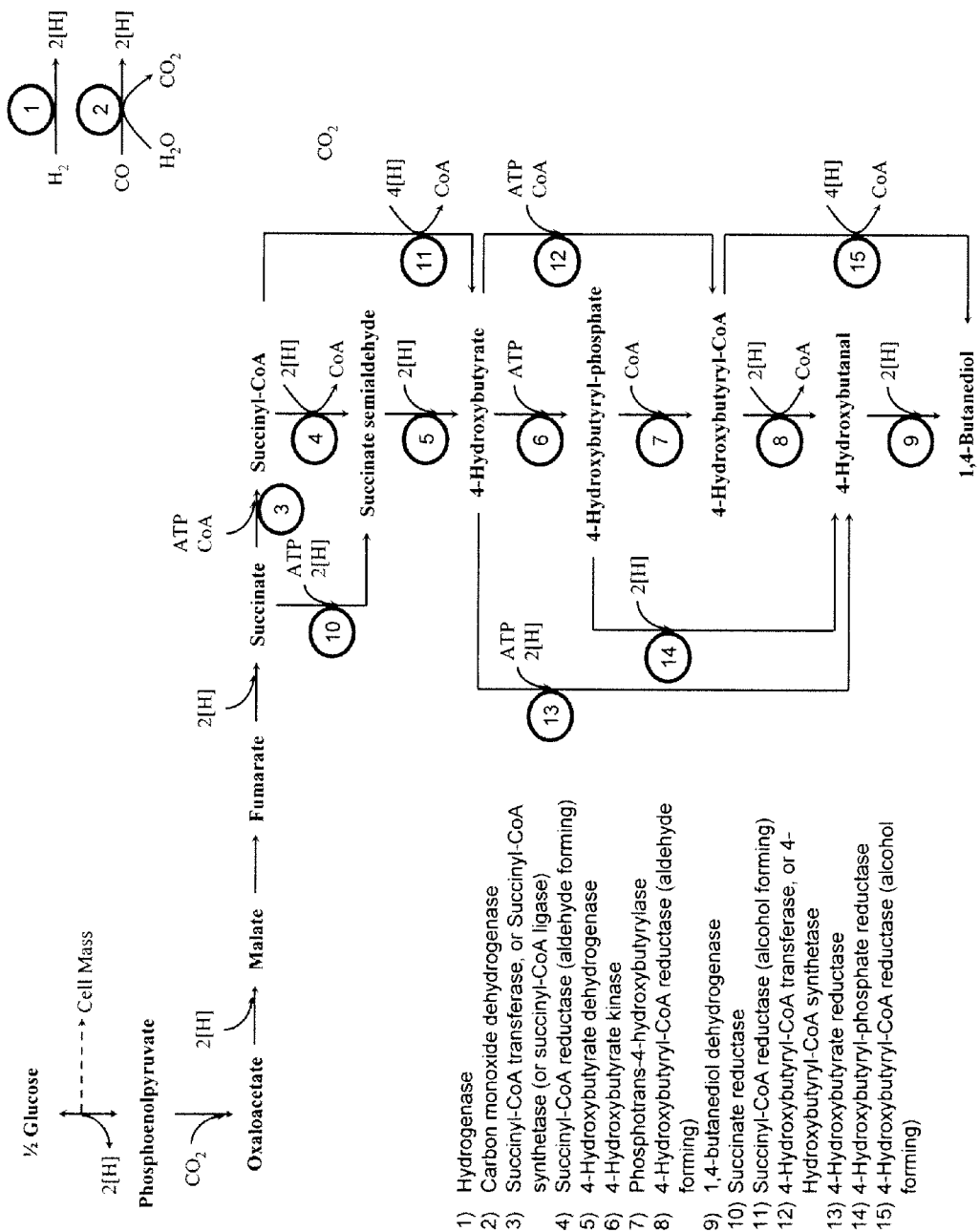
Figure 7A (updated)

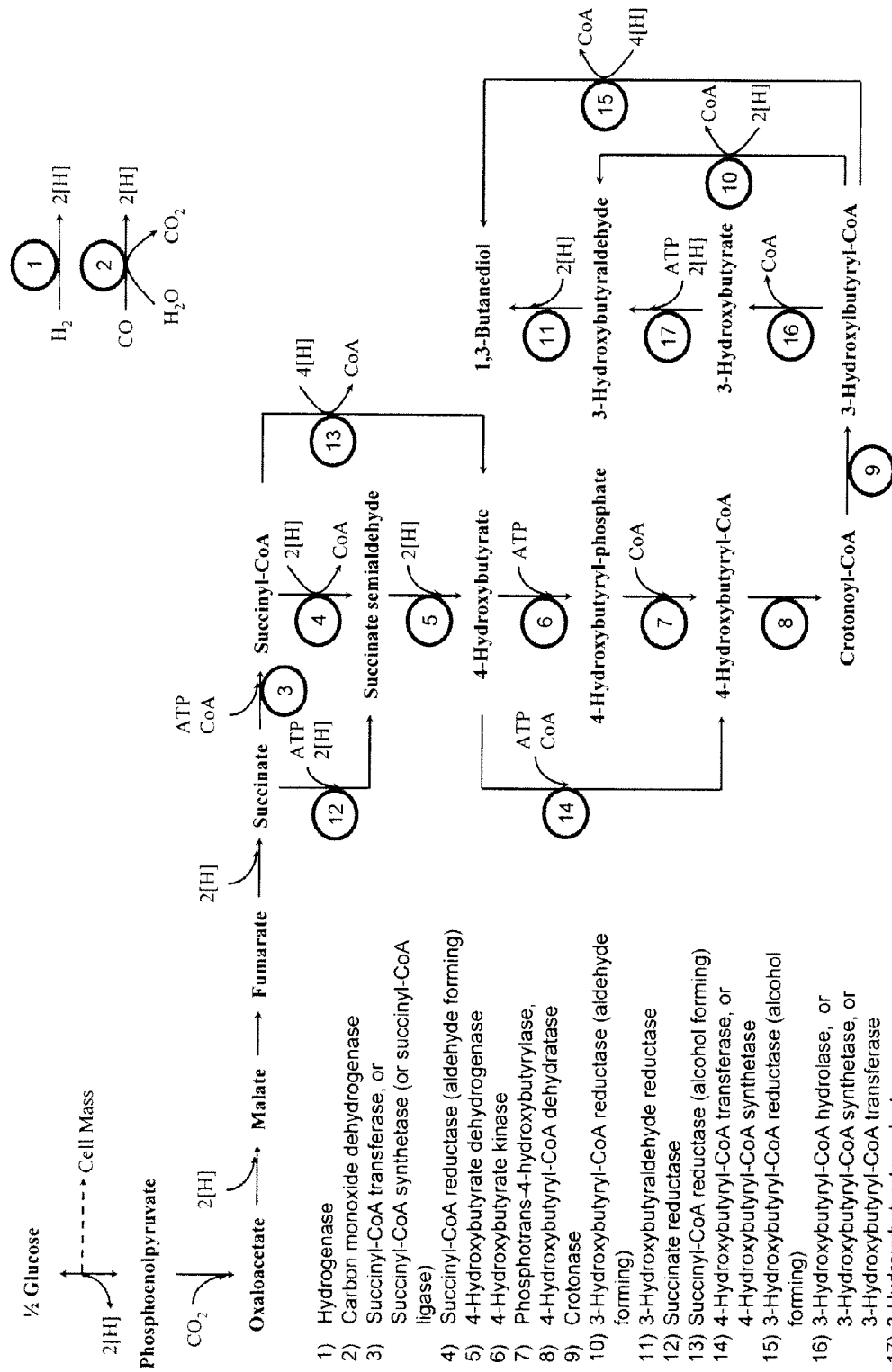
Figure 7B (updated)

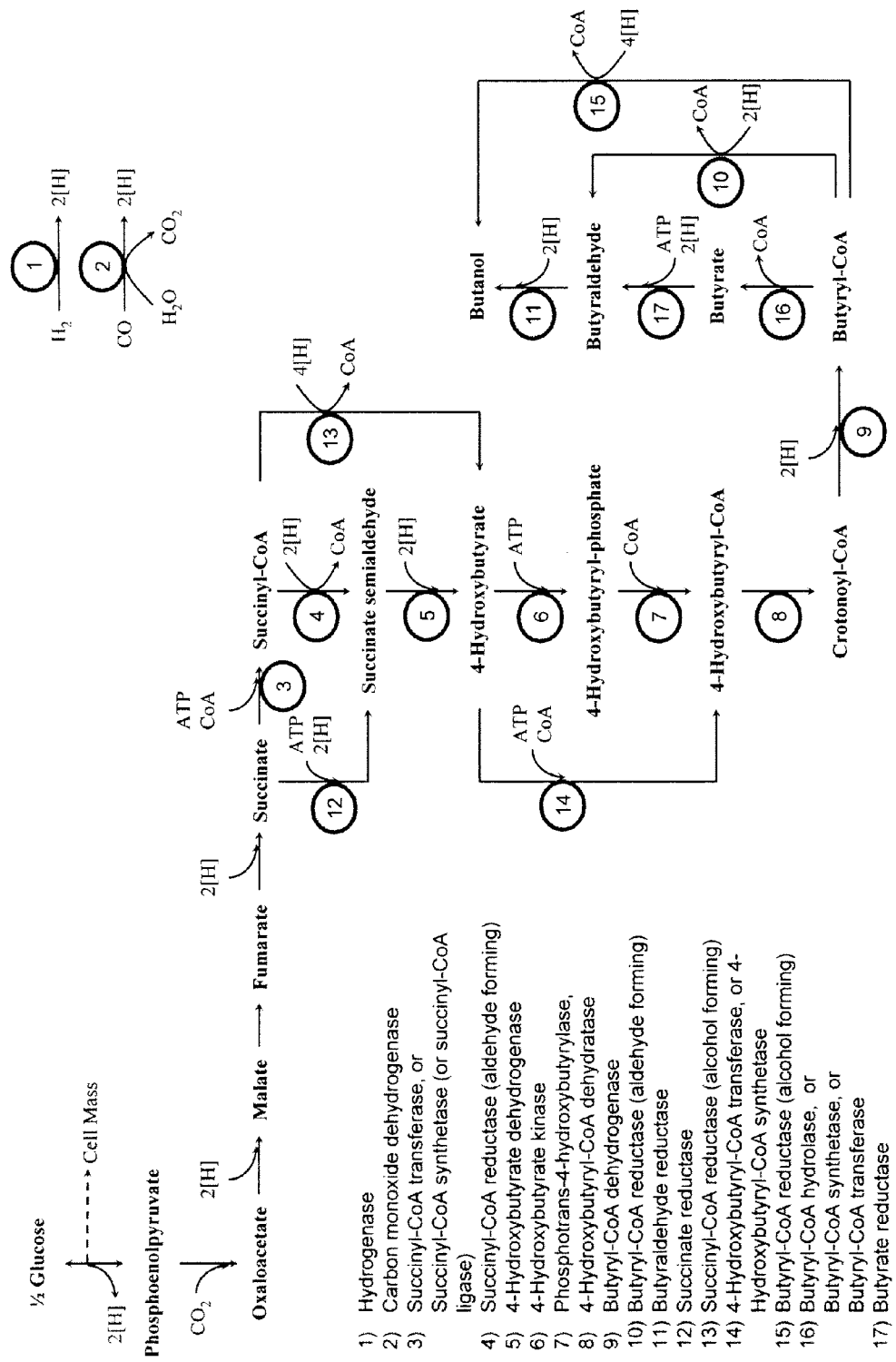
Figure 7C (updated)

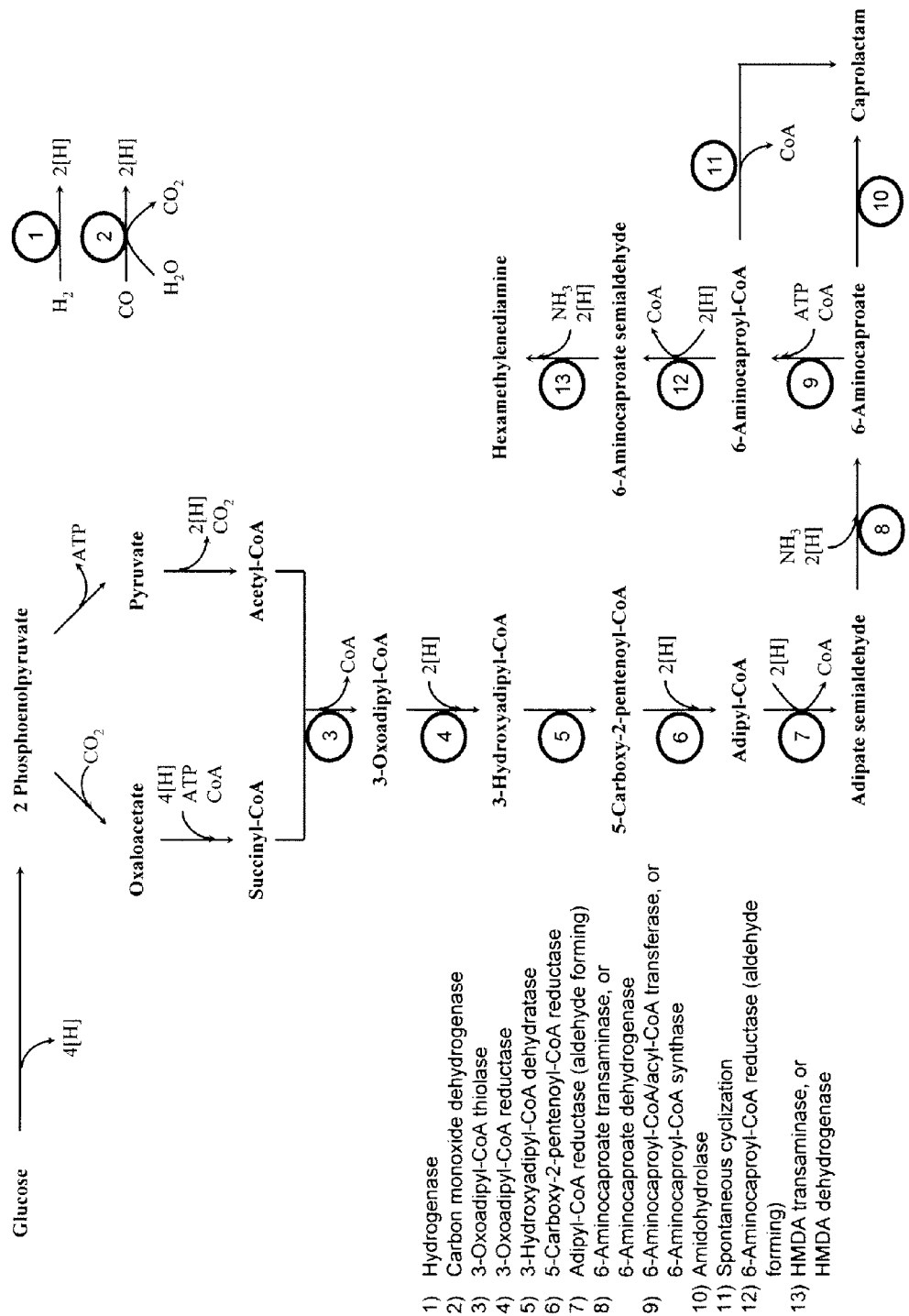
Figure 7D (updated)

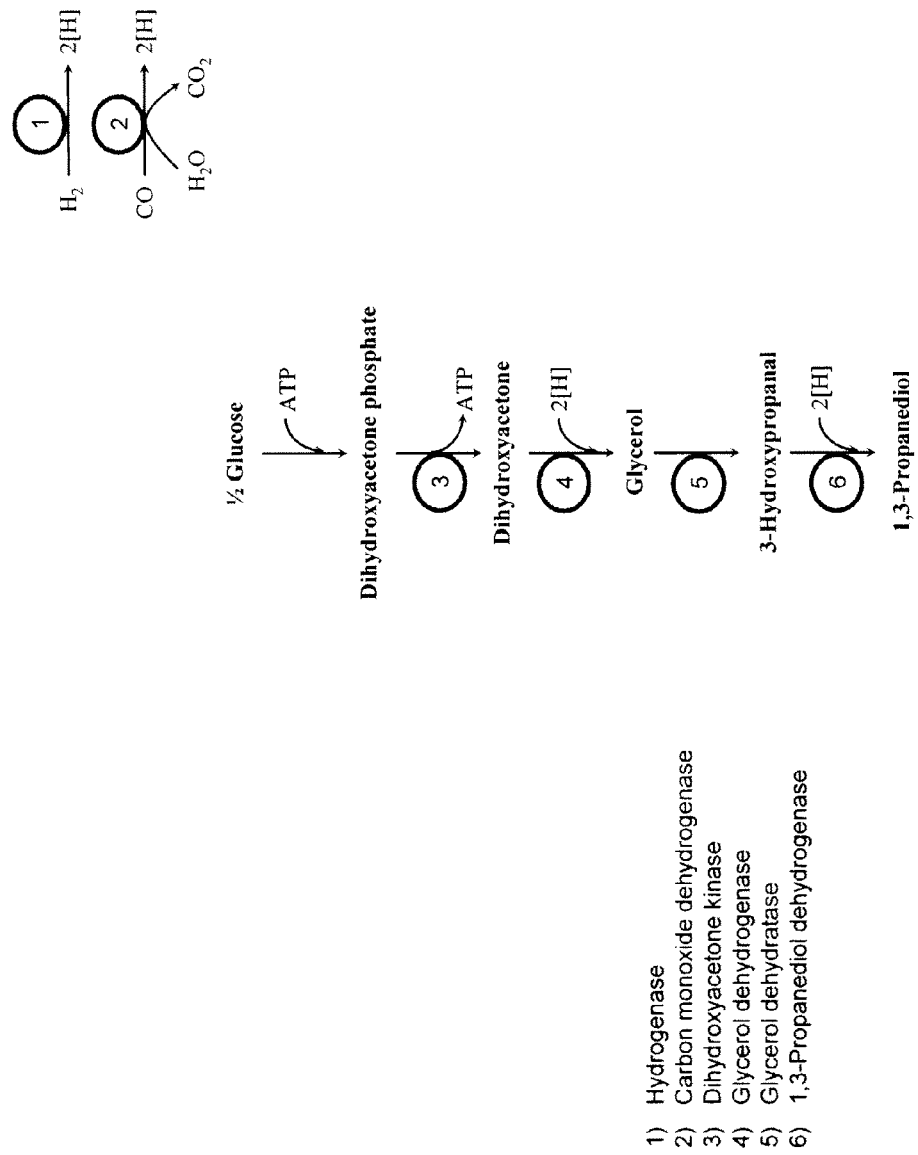
Figure 7E (updated)

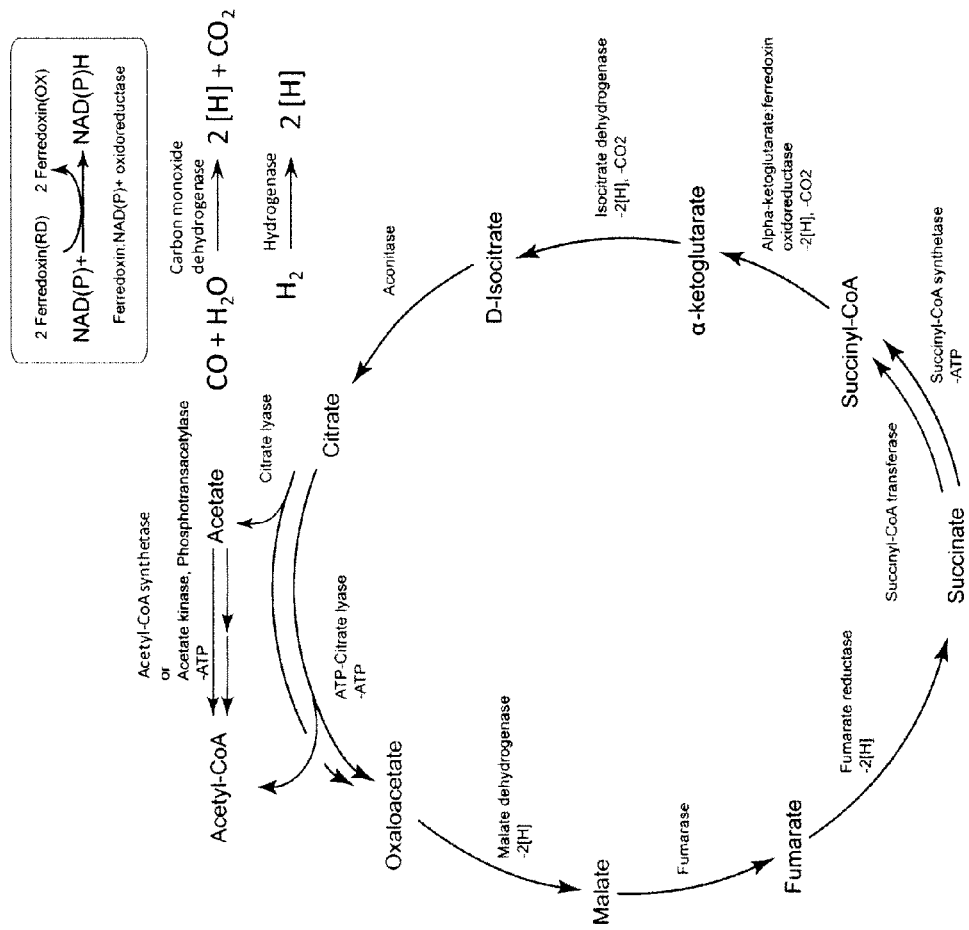
Figure 8 (updated)

US 8,048,661 B2

MICROBIAL ORGANISMS COMPRISING EXOGENOUS NUCLEIC ACIDS ENCODING REDUCTIVE TCA PATHWAY ENZYMES

This application claims the benefit of priority under 35 U.S.C §119(e) to U.S. Provisional Application 61/307,437, filed Feb. 23, 2010 and U.S. Provisional Application 61/314,570, filed Mar. 16, 2010, each of which is incorporated herein by reference in its entirety.

BACKGROUND OF THE INVENTION

This invention relates generally to biosynthetic processes and, more specifically to organisms having enhanced carbon fixation capabilities.

1,3-butanediol (1,3-BDO) is a four carbon diol traditionally produced from acetylene via its hydration. The resulting acetaldehyde is then converted to 3-hydroxybutyraldehdye which is subsequently reduced to form 1,3-BDO. More recently, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycemic agent. Optically active 1,3-BDO is a useful starting material for the synthesis of biologically active compounds and liquid crystals. Another use of 1,3-butanediol is that its dehydration affords 1,3-butadiene (Ichikawa et al. *Journal of Molecular Catalysis A-Chemical* 256:106-112 (2006); Ichikawa et al. *Journal of Molecular Catalysis A-Chemical* 231:181-189 (2005), which is useful in the manufacture synthetic rubbers (e.g., tires), latex, and resins. The reliance on petroleum based feedstocks for either acetylene or ethylene warrants the development of a renewable feedstock based route to 1,3-butanediol and to butadiene.

Isopropanol (IPA) is a colorless, flammable liquid that mixes completely with most solvents, including water. The largest use for IPA is as a solvent, including its well known yet small use as "rubbing alcohol," which is a mixture of IPA and water. As a solvent, IPA is found in many everyday products such as paints, lacquers, thinners, inks, adhesives, general-purpose cleaners, disinfectants, cosmetics, toiletries, de-icers, and pharmaceuticals. Low-grade IPA is also used in motor oils. IPA is also used as a chemical intermediate for the production of isopropylamines (Ag products), isopropy-lethers, and isopropyl esters. Isopropanol is manufactured by two petrochemical routes. The predominant process entails the hydration of propylene either with or without sulfuric acid catalysis. Secondarily, IPA is produced via hydrogenation of acetone, which is a by-product formed in the production of phenol and propylene oxide.

4-hydroxybutanoic acid (4-hydroxybutanoate, 4-hydroxybutyrate, 4-HB) is a 4-carbon carboxylic acid that is used as a building block for various commodity and specialty chemicals. In particular, 4-HB can serve as an entry point into the 1,4-butanediol family of chemicals, which includes solvents, resins, polymer precursors, and specialty chemicals.

1,4-butanediol (BDO) is a valuable chemical for the production of high performance polymers, solvents, and fine chemicals. It is the basis for producing other high value chemicals such as tetrahydrofuran (THF) and gamma-buty-rolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA® fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production.

BDO is produced by two main petrochemical routes with a few additional routes also in commercial operation. One route involves reacting acetylene with formaldehyde, followed by hydrogenation. More recently BDO processes involving butane or butadiene oxidation to maleic anhydride, followed by hydrogenation have been introduced. BDO is used almost exclusively as an intermediate to synthesize other chemicals and polymers.

Thus, there exists a need for the development of methods for effectively producing commercial quantities of compounds such as 1,4-butanediol, 4-hydroxybutyrate, 1,3-butanediol, or isopropanol. The present invention satisfies this need and provides related advantages as well. Additional product molecules that can be produced by the teachings of this invention include but are not limited to ethanol, butanol, isobutanol, isopropanol, succinic acid, fumaric acid, malic acid, 3-hydroxypropionic acid, lactic acid, adipic acid, 6-aminocaproic acid, hexamethylenediamine, caprolactam, 3-hydroxyisobutyric acid, 2-hydroxyisobutyric acid, methacrylic acid, acrylic acid, 1,3-propanediol, glycerol, and long chain hydrocarbons, alcohols, acids, and esters.

SUMMARY OF THE INVENTION

In some aspects, embodiments disclosed herein relate to a non-naturally occurring microbial organism that includes a microbial organism having a reductive TCA pathway which includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, and an alpha-ketoglutarate:ferredoxin oxidoreductase. In some aspects, embodiments disclosed herein relate to a method for enhancing carbon flux through acetyl-CoA that includes culturing this non-naturally occurring microbial organism under conditions and for a sufficient period of time to produce a product having acetyl-CoA as a building block.

In some aspects, embodiments disclosed herein relate to a non-naturally occurring microbial organism that includes a microbial organism having a Wood-Ljungdahl pathway which includes at least one exogenous nucleic acid encoding a Wood-Ljungdahl pathway enzyme expressed in a sufficient amount to enhance carbon flux through acetyl-CoA. The at least one exogenous nucleic acid is selected from a) Formate dehydrogenase, b) Formyltetrahydrofolate synthetase, c) Methenyltetrahydrofolate cyclohydrolase, d) Methylenetetrahydrofolate dehydrogenase, e) Methylenetetrahydrofolate reductase, f) Methyltetrahydrofolate:corrinoid protein methyltransferase (AcsE), g) Corrinoid iron-sulfer protein (AcsD), h) Nickel-protein assembly protein (AcsF & CooC), i) Ferredoxin (Orf7), j) Acetyl-CoA synthase (AcsB & AcsC), k) Carbon monoxide dehydrogenase (AcsA), and l) Pyruvate ferredoxin oxidoreductase or pyruvate dehydrogenase, and m) pyruvate formate lyase. In some aspects, embodiments disclosed herein relate to a method for enhancing carbon flux through acetyl-CoA that includes culturing this non-naturally occurring microbial organism under conditions and for a sufficient period of time to produce a product having acetyl-CoA as a building block.

In some aspects, embodiments disclosed herein relate to a non-naturally occurring microbial organism that includes a microbial organism having a methanol Wood-Ljungdahl pathway which includes at least one exogenous nucleic acid encoding a methanol Wood-Ljungdahl pathway enzyme expressed in a sufficient amount to enhance carbon flux through acetyl-CoA. The at least one exogenous nucleic acid is selected from a) Methanol methyltransferase (MtaB), b) Corrinoid protein (MtaC), c) Methyltetrahydrofolate:corrinoid protein methyltransferase (MtaA), d) Methyltetrahydrofolate:corrinoid protein methyltransferase (AcsE), e) Corrinoid iron-sulfer protein (AcsD), f) Nickel-protein assembly protein (AcsF & CooC), g) Ferredoxin (Orf7), h) Acetyl-CoA synthase (AcsB & AcsC), i) Carbon monoxide dehydrogenase (AcsA), j) Pyruvate ferredoxin oxidoreductase or pyruvate dehydrogenase, k) pyruvate formate lyase, and l) NAD(P)H:ferredoxin oxidoreductase. In some aspects, embodiments disclosed herein relate to a method for enhancing carbon flux through acetyl-CoA, comprising culturing this non-naturally occurring microbial organism under conditions and for a sufficient period of time to produce a product having acetyl-CoA as a building block.

In some aspects, embodiments disclosed herein relate to a non-naturally occurring microbial organism that includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some aspects, embodiments disclosed herein relate to a method for enhancing the availability of reducing equivalents in the presence of carbon monoxide or hydrogen thereby increasing the yield of redox-limited products via carbohydrate-based carbon feedstock, the method includes culturing this non-naturally occurring microbial organism under conditions and for a sufficient period of time to produce a product.

In some aspects, embodiments disclosed herein relate to a non-naturally occurring microbial organism that includes a microbial organism having a reductive TCA pathway which includes at least one exogenous nucleic acid encoding a reductive TCA pathway enzyme. the at least one exogenous nucleic acid is selected from an ATP-citrate lyase, citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$.

In some aspects, embodiments disclosed herein relate to a method that includes culturing a non-naturally occurring microbial organism that includes a microbial organism having a reductive TCA pathway comprising at least one exogenous nucleic acid encoding a reductive TCA pathway enzyme. The at least one exogenous nucleic acid is selected from an ATP-citrate lyase, citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$ to produce a product.

BRIEF DESCRIPTION OF THE DRAWINGS

FIG. 2a shows the reverse TCA cycle for fixation of $CO_2$ on carbohydrates as substrates. The enzymatic transformations are carried out by the enzymes as shown.

FIG. 2b shows the flux distribution showing an enhanced maximum theoretical yield of isopropanol on glucose when carbon is routed via the reductive TCA cycle

FIG. 4a shows a pathway for enabling carbon fixation from syngas into acetyl CoA. The reducing equivalents are derived from carbohydrates such as glucose. The enzymatic transformations are carried out by the following enzymes: 1) Formate dehydrogenase, 2) Formyltetrahydrofolate synthetase, 3) Methenyltetrahydrofolate cyclohydrolase, 4) Methylenetetrahydrofolate dehydrogenase, 5) Methylenetetrahydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH).

FIG. 4b shows a pathway for enabling carbon fixation from methanol into acetyl CoA. The reducing equivalents are derived from carbohydrates such as glucose. "n" depicts the number of moles of methanol that are provided. The enzymatic transformations are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase FIG. 5a shows the flux distribution with an enhanced maximum theoretical yield of 1,3-butanediol on glucose when carbon fixation via the Wood-Ljungdahl pathway is employed in the absence of methanol; the enzymatic transformations shown are carried out by the following enzymes: 1) Formate dehydrogenase, 2) Formyltetrahydrofolate synthetase, 3) Methenyltetra-hydrofolate cyclohydrolase, 4) Methylenetetrahydrofolate dehydrogenase, 5) Methylenetetra-hydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH), 14) Acetoacetyl-CoA thiolase (AtoB), 15) Acetoacetyl-CoA reductase (CoA-dependent, alcohol forming), 16) 3-Oxobutyraldehyde reductase (aldehyde reducing), 17) 4-Hydroxy-2-butanone reductase, 18) Acetoacetyl-CoA reductase (CoA-dependent, aldehyde forming), 19) 3-Oxobutyraldehyde reductase (ketone reducing), 20) 3-Hydroxybutyraldehyde reductase, 21) Acetoacetyl-CoA reductase (ketone reducing), 22) 3-Hydroxybutyryl-CoA reductase (aldehyde forming), 23) 3-Hydroxybutyryl-CoA reductase (alcohol forming); when glucose is fed in the presence of the Wood-Ljungdahl pathway, a yield increase from 1 mol 1,3-butanediol/mol glucose to 1.09 mol 1,3-butanediol/mol glucose is realized.

FIG. 5b shows the flux distribution with an enhanced maximum theoretical yield of 1,3-butanediol from glucose when carbon fixation via the methanol Wood-Ljungdahl pathway is employed using both syngas and methanol; the enzymatic transformations shown are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase, 14) Acetoacetyl-CoA thiolase (AtoB), 15) Acetoacetyl-CoA reductase (CoA-dependent, alcohol forming), 16) 3-Oxobutyraldehyde reductase (aldehyde reducing), 17) 4-Hydroxy-2-butanone reductase, 18) Acetoacetyl-CoA reductase (CoA-dependent, aldehyde forming), 19) 3-Oxobutyraldehyde reductase (ketone reducing), 20) 3-Hydroxybutyraldehyde reductase, 21) Acetoacetyl-CoA reductase (ketone reducing), 22) 3-Hydroxybutyryl-CoA reductase (aldehyde forming), 23) 3-Hydroxybutyryl-CoA reductase (alcohol forming); when glucose and methanol are fed in 1.0:0.4 ratio, it affords an increase from 1 mol 1,3-butanediol/mol glucose to 1.2 mol 1,3-butanediol/mol glucose.

FIG. 6a shows the flux distribution with an enhanced maximum theoretical yield of isopropanol from glucose when carbon fixation via the Wood-Ljungdahl pathway is employed in the absence of methanol; the enzymatic transformations shown are carried out by the following enzymes: 1) Formate dehydrogenase, 2) Formyltetrahydrofolate synthetase, 3) Methenyltetra-hydrofolate cyclohydrolase, 4) Methylenetetrahydrofolate dehydrogenase, 5) Methylenetetrahydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH), 14) Acetoacetyl-CoA thiolase (AtoB), 15) Acetoacetyl-CoA:acetate:CoA transferase (AtoAD), 16) Acetoacetate decarboxylase (Adc), and 17) Isopropanol dehydrogenase (Adh).

FIG. 6b shows the flux distribution with an enhanced maximum theoretical yield of isopropanol from glucose when carbon fixation via the methanol Wood-Ljungdahl pathway is employed using both syngas and methanol; the enzymatic transformations shown are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase, 14) Acetoacetyl-CoA thiolase (AtoB), 15) Acetoacetyl-CoA:acetate:CoA transferase (AtoAD), 16) Acetoacetate decarboxylase (Adc), and 17) Isopropanol dehydrogenase (Adh); when glucose and methanol are fed in 1.2 ratio, it provides an increase from 1 mol isopropanol/mol glucose to 2 mol isopropanol/mol glucose.

FIG. 7a shows flux distribution for improvement in 1,4-BDO yields from carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, Succinyl-CoA hydrolase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA reductase (aldehyde forming), 9) 1,4-butanediol dehydrogenase, 10) Succinate reductase, 11) Succinyl-CoA reductase (alcohol forming), 12) 4-Hydroxybutyryl-CoA transferase, 4-Hydroxybutyryl-CoA hydrolase, or 4-Hydroxybutyryl-CoA synthetase, 13) 4-Hydroxybutyrate reductase, 14) 4-Hydroxybutyryl-phosphate reductase, and 15) 4-Hydroxybutyryl-CoA reductase (alcohol forming).

FIG. 7b shows flux distribution for improvement in 1,3-BDO yields from carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) crotonase, 10) 3-Hydroxybutyryl-CoA reductase (aldehyde forming), 11) 3-Hydroxybutyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) 3-Hydroxybutyryl-CoA reductase (alcohol forming), 16) 3-Hydroxybutyryl-CoA hydrolase, or 3-Hydroxybutyryl-CoA synthetase, or 3-Hydroxybutyryl-CoA transferase, and 17) 3-Hydroxybutyrate reductase.

FIG. 7c shows flux distribution for improvement in butanol yields on carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) butyryl-CoA dehydrogenase, 10) Butyryl-CoA reductase (aldehyde forming), 11) Butyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) Butyryl-CoA reductase (alcohol forming), 16) Butyryl-CoA hydrolase, or Butyryl-CoA synthetase, or Butyryl-CoA transferase, and 17) Butyrate reductase.

FIG. 7d shows flux distribution for improvement in yields of 6-aminocaproic acid and hexamethylene diamine on carbohydrates when reducing equivalents from syngas components are available; the enzymatic transformations shown are carried out by the following enzymes: 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) Amidohydrolase, 11) Spontaneous cyclization, 12) 6-Aminocaproyl-CoA reductase (aldehyde forming), and 13) HMDA transaminase, or HMDA dehydrogenase.

FIG. 7e shows flux distribution for improvement in yields of glycerol and 1,3-propanediol on carbohydrates when reducing equivalents from syngas components are available; the enzymatic transformations shown are carried out by the following enzymes: 1) Hydrogenase, 2) Carbon monoxide dehydrogenase, 3) Dihydroxyacetone kinase, 4) Glycerol dehydrogenase, 5) Glycerol dehydratase, 6) 1,3-Propanediol dehydrogenase.

FIG. 8 shows the pathway for the reverse TCA cycle coupled with carbon monoxide dehydrogenase and hydrogenase for the conversion of syngas to acetyl-CoA.

DETAILED DESCRIPTION OF THE INVENTION

Figure 1A:
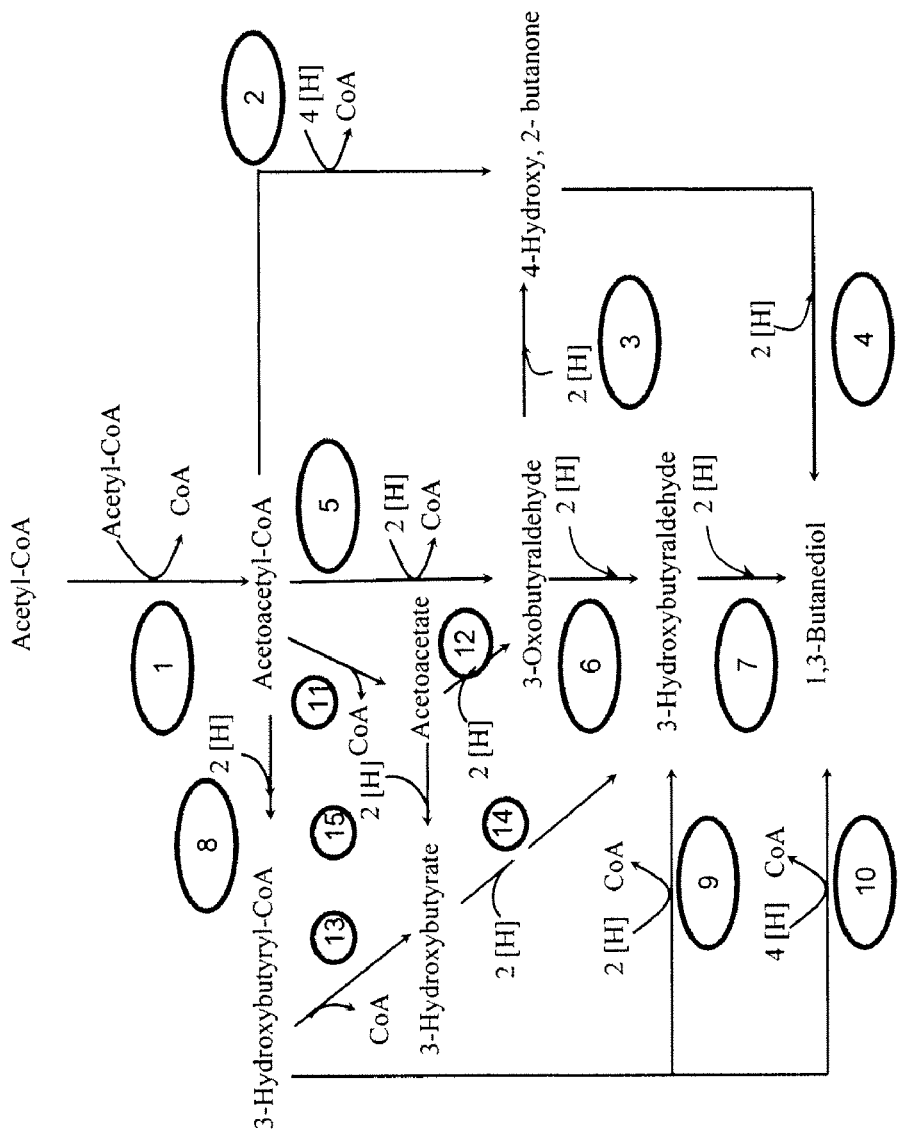
FIG. 1a shows the pathways for the biosynthesis of 1,3-butanediol from acetyl-CoA; the enzymatic transformations shown are carried out by the following enzymes: 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

This invention is directed, in part to engineered biosynthetic pathways to improve carbon flux through the central metabolism intermediate, acetyl-CoA, en route to product molecules. Exemplary product molecules include, without limitation, 1,3-butanediol, isopropanol, 4-hydroxybutyrate, and 1,4-butanediol, although given the teachings and guidance provided herein, it will be recognized by one skilled in the art that any product molecule that has acetyl-CoA as a building block can exhibit enhanced production through increased carbon flux through acetyl-CoA. The present invention provides non-naturally occurring microbial organisms having one or more exogenous genes encoding enzymes that can catalyze various enzymatic transformations en route to acetyl-CoA. In some embodiments, these enzymatic transformations are part of the reductive tricarboxylic acid (RTCA) cycle and are used to improve product yields from carbohydrate-based carbon feedstock.

This invention is also directed, in part, to improving product yields based on enzymatic transformations of the Wood-Ljungdahl pathway. In some embodiments, syngas components, such as CO and $H_2$, can serve as source of reducing equivalents. Such reducing equivalents can improve product yields from carbohydrate-based carbon feedstock as described herein below.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of products by (i) enhancing carbon fixation via the Wood-Ljungdahl pathway and/or the reductive TCA cycle, and (ii) accessing additional reducing equivalents from gaseous syngas components such as CO, $CO_2$, and/or $H_2$. Products that can be produced by non-naturally occurring organisms and methods described herein include, without limitation, ethanol, butanol, isobutanol, 1,3-butanediol, isopropanol, 4-hydroxybutyrate, 1,4-butanediol, succinic acid, fumaric acid, malic acid, 3-hydroxypropionic acid, lactic acid, adipic acid, 6-aminocaproic acid, hexamethylenediamine, caprolactam, 3-hydroxyisobutyric acid, 2-hydroxyisobutyric acid, methacrylic acid, acrylic acid, 1,3-propanediol, glycerol, and long chain hydrocarbons, alcohols, acids, and esters.

The $CO_2$-fixing reductive tricarboxylic acid (RTCA) cycle is an endergenic anabolic pathway of $CO_2$ assimilation which uses NAD(P)H and ATP (FIG. 2a). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol. Note that the pathways for the exemplary product molecules described herein all proceed through acetyl-CoA. For example, the fixation of $CO_2$ provides 2.67 molecules of acetyl-CoA from every molecule of glucose, thus improving the maximum product yields as follows:

1,3-Butanediol: $C_6H_{12}O_6 \rightarrow 1.091 C_4H_{10}O_2 + 1.636 CO_2 + 0.545 H_2O$ Isopropanol: $C_6H_{12}O_6 \rightarrow 1.333 C_3H_8O + 2CO_2 + 0.667 H_2O$ 4-Hydroxybutyate: $C_6H_{12}O_6 \rightarrow 1.333 C_4H_8O_3 + 0.667 CO_2 + 0.667 H_2O$ 1,4-Butanediol: $C_6H_{12}O_6 \rightarrow 1.091 C_4H_{10}O_2 + 1.636 CO_2 + 0.545 H_2O$ FIG. 2b provides an exemplary flux distribution showing how the maximum theoretical isopropanol yield increases from 1 mole/mole glucose to 1.33 moles per mole glucose. The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al. *J. Bacteriol.* 187:3020-3027 (2005); Hugler et al. *Environ. Microbiol.* 9:81-92 (2007)). In some cases, reductive and oxidative (Krebs) TCA cycles are present in the same organism (Hugler et al. supra (2007); Siebers et al. *J. Bacteriol.* 186:2179-2194 (2004). Some methanogens and obligate anaerobes possess incomplete oxidative or reductive TCA cycles that can function to synthesize biosynthetic intermediates (Ekiel et al. *J. Bacteriol.* 162:905-908 (1985); Wood et al. *FEMS Microbiol.* 28: 335-352 (2004).

Many of the enzymes in the TCA cycle are reversible and can catalyze reactions in the reductive and oxidative directions. Several reactions are irreversible and utilize different enzymes to catalyze the forward and reverse directions. These reactions include: 1) conversion of citrate to oxaloacetate and acetyl-CoA, 2) conversion of fumarate to succinate, 3) conversion of succinyl-CoA to 2-oxoglutarate. In the catabolic TCA cycle, citrate is formed from the condensation of oxaloacetate and acetyl-CoA. The reverse reaction, cleavage of citrate to oxaloacetate and acetyl-CoA, is ATP-dependent and catalyzed by ATP citrate lyase or citryl-CoA synthetase and citryl-CoA lyase. The conversion of succinate to fumarate is catalyzed by succinate dehydrogenase while the reverse reaction is catalyzed by fumarate reductase. In the catabolic TCA cycle, succinyl-CoA is formed from the NAD(P)$^+$ dependent decarboxylation of 2-oxoglutarate by the AKGDH complex. The reverse reaction is catalyzed by alpha-ketoglutarate:ferredoxin oxidoreductase. In some embodiments, the invention provides non-naturally occurring organisms that enhance carbon flux through acetyl-CoA by engineering one or more enzymes that are part of the reverse TCA cycle.

In some embodiments, the invention provides enhanced product yields via carbohydrate-based carbon feedstock by fixing carbon dioxide and/or methanol via the Wood-Ljungdahl pathway or components thereof. Synthesis gas (syngas) is a mixture of $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and this source represents an inexpensive and flexible feedstock for the biological production of renewable chemicals and fuels.

There are known pathways in organisms such as *Clostridia* that utilize syngas effectively. Specifically, acetogens, such as *Moorella thermoacetica*, *C. ljungdahlii* and *C. carboxidivorans*, can grow on a number of carbon sources ranging from hexose sugars to carbon monoxide. Hexoses, such as glucose, are metabolized first via Embden-Meyerhof-Parnas (EMP) glycolysis to pyruvate, which is then converted to acetyl-CoA via pyruvate:ferredoxin oxidoreductase (PFOR). Acetyl-CoA can be used to build biomass precursors or can be converted to acetate which produces energy via acetate kinase and phosphotransacetylase. The overall conversion of glucose to acetate, energy, and reducing equivalents is $C_6H_{12}O_6 + 4ADP + 4Pi \rightarrow 2CH_3COOH + 2CO_2 + 4ATP + 8[H]$ Acetogens extract even more energy out of the glucose to acetate conversion while also maintaining redox balance by further converting the released $CO_2$ to acetate via the Wood-Ljungdahl pathway:

$2CO_2 + 4H_2 + nADP + nPi \rightarrow CH_3COOH + 2H_2O + nATP$

The coefficient "n" in the above equation signifies that this conversion is an energy generating endeavor, as many acetogens can grow in the presence of $CO_2$ via the Wood-Ljungdahl pathway even in the absence of glucose as long as hydrogen is present to supply reducing equivalents.

$2CO_2 + 4H_2 + nADP + nPi \rightarrow CH_3COOH + 2H_2O + nATP$

Figure 3A:
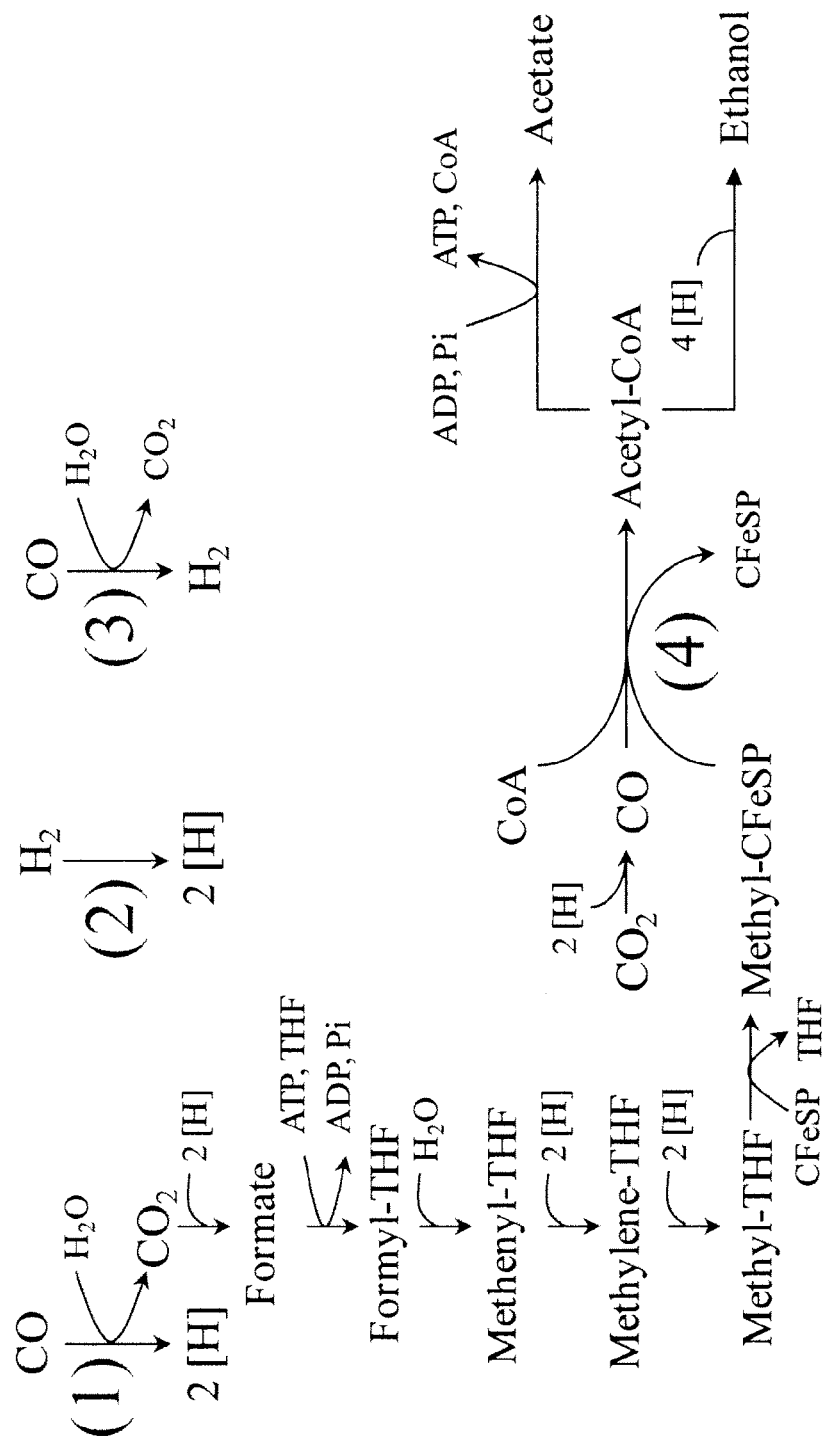
FIG. 3a shows a flow diagram depicting the Wood-Ljungdahl pathway and formation routes for acetate and ethanol; the transformations that are carried out in organisms capable of growth on synthesis gas are 1) CO dehydrogenase, 2) hydrogenase, 3) energy-conserving hydrogenase (ECH), and 4) bi-functional CO dehydrogenase/acetyl-CoA synthase.

The Wood-Ljungdahl pathway, illustrated in FIG. 3A, is coupled to the creation of Na$^+$ or H$^+$ ion gradients that can generate ATP via an Na$^+$ or H$^+$-dependant ATP synthase, respectively (Muller, V., *Appl. Environ. Microbiol.* 69:6345-6353 (2003)). Based on these known transformations, acetogens also have the capacity to utilize CO as the sole carbon and energy source. Specifically, CO can be oxidized to produce reducing equivalents and $CO_2$, or directly assimilated into acetyl-CoA which is subsequently converted to either biomass or acetate.

$4CO + 2H_2O \rightarrow CH_3COOH + 2CO_2$

Even higher acetate yields, however, can be attained when enough hydrogen is present to satisfy the requirement for reducing equivalents.

$2CO + 2H_2 \rightarrow CH_3COOH$

Following from FIG. 3A, the production of acetate via acetyl-CoA generates one ATP molecule.

Figure 3B:
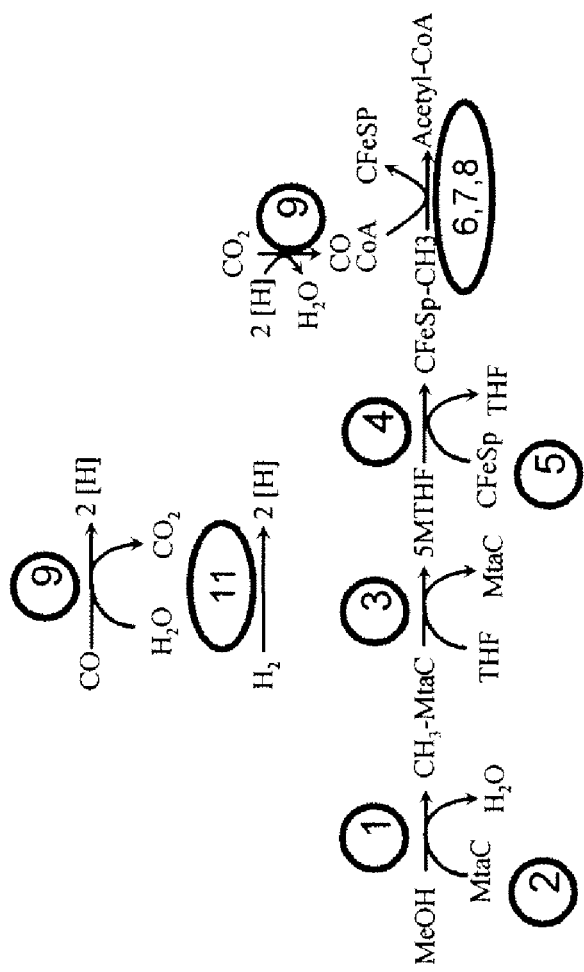
FIG. 3b shows a pathway for the utilization of methanol for the formation of acetyl-CoA; the enzymatic transformations shown are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Nickel-protein assembly protein (AcsF & CooC), 7) Ferredoxin (Orf7), 8) Acetyl-CoA synthase (AcsB & AcsC), and 9) Carbon monoxide dehydrogenase (AcsA).

Methanol is a relatively inexpensive organic feedstock that can be derived from synthesis gas components, CO and $H_2$, via catalysis. A non-naturally occurring microbial organism of the invention capable of utilizing methanol can also utilize gases including, for example, CO, $CO_2$, and/or $H_2$ for conversion to acetyl-CoA, cell mass, and products. Specifically, acetogens such as *Moorella thermoacetica* (formerly, *Clostridium thermoaceticum*) use syngas via the Wood-Ljungdahl pathway. This pathway includes two branches: the Eastern (or methyl) branch converts $CO_2$ to methyltetrahydrofolate (Me-THF) and the Western (or carbonyl) branch that converts methyl-THF, CO, and Coenzyme-A into acetyl-CoA (FIG. 3B). Any non-naturally occurring microorganism of the invention expressing genes encoding enzymes that catalyze the carbonyl-branch of the Wood-Ljungdahl pathway in conjunction with a MtaABC-type methyltransferase system is capable of 'fixing' carbon from exogenous CO and/or $CO_2$ and methanol to synthesize acetyl-CoA, cell mass, and products.

Implementing the pathway to form acetyl-CoA from methanol and syngas, heretofor referred to as the "methanol Wood-Ljungdahl pathway," is energetically favorable compared to utilizing the full Wood-Ljungdahl pathway. For example, the direct conversion of synthesis gas to acetate is an energetically neutral process (see FIG. 3B). Specifically, one ATP molecule is consumed during the formation of formyl-THF by formyl-THF synthase and one ATP molecule is produced during the production of acetate via acetate kinase. ATP consumption can be circumvented by ensuring that the methyl group on the methyl branch product, methyl-THF, is obtained from methanol rather than $CO_2$. The result is that acetate formation has a positive ATP yield that can help support cell growth and maintenance. A non-naturally occurring microbial organism of the present invention, engineered with these capabilities, that also naturally possesses the capability for anapleurosis (e.g., *E. coli*) can grow on the methanol and syngas-generated acetyl-CoA in the presence of a suitable external electron acceptor such as nitrate. This electron acceptor is used to accept electrons from the reduced quinone formed via succinate dehydrogenase. A further use of adding an external electron acceptor is that additional energy for cell growth, maintenance, and product formation can be generated from respiration of acetyl-CoA. In some embodiments, engineering a pyruvate ferredoxin oxidoreductase (PFOR) enzyme into a non-naturally occurring microbial organism allows the synthesis of biomass precursors in the absence of an external electron acceptor.

Carbon from syngas and/or methanol can be fixed via the Wood-Ljungdahl pathway and portions thereof when using carbohydrate-based carbon feedstock for the formation of molecules such as 1,3-butanediol, isopropanol, 4-hydroxybutyrate, and 1,4-butanediol using the pathways described herein. Specifically, the combination of certain syngas-utilization pathway components with the acetyl-CoA to 1,3-butanediol, isopropanol, 4-hydroxybutyrate, or 1,4-butanediol pathways results in high yields of these products from carbohydrates by providing an efficient mechanism for fixing the carbon present in carbon dioxide, fed exogenously or produced endogenously, into acetyl-CoA as shown below. Exemplary carbohydrates include but are not limited to glucose, sucrose, xylose, arabinose and glycerol. The enzymatic transformations for carbon fixation are shown in FIGS. 4A and 4B respectively.

1,3-Butanediol: $C_6H_{12}O_6 \rightarrow 1.091 C_4H_{10}O_2 + 1.636 CO_2 + 0.545 H_2O$ Isopropanol: $C_6H_{12}O_6 \rightarrow 1.333 C_3H_8O + 2 CO_2 + 0.667 H_2O$ 4-Hydroxybutyate: $C_6H_{12}O_6 \rightarrow 1.333 C_4H_8O_3 + 0.667 CO_2 + 0.667 H_2O$ 1,4-Butanediol: $C_6H_{12}O_6 \rightarrow 1.091 C_4H_{10}O_2 + 1.636 CO_2 + 0.545 H_2O$ The maximum theoretical yields of isopropanol, 4-hydroxybutyrate, and 1,4-butanediol from synthesis gases or carbohydrates can be further enhanced by the addition of methanol in different ratios of methanol to glucose. This is shown in the equations below:

1,3-Butanediol: $CH_4O + C_6H_{12}O_6 \rightarrow 1.364 C_4H_{10}O_2 + 1.545 CO_2 + 1.182 H_2O$ Isopropanol: $CH_4O + C_6H_{12}O_6 \rightarrow 1.667 C_3H_8O + 2 CO_2 + 1.333 H_2O$ 4-Hydroxybutyate: $CH_4O + C_6H_{12}O_6 \rightarrow 1.667 C_4H_8O_3 + 0.333 CO_2 + 1.333 H_2O$ 1,4-Butanediol: $CH_4O + C_6H_{12}O_6 \rightarrow 1.364 C_4H_{10}O_2 + 1.545 CO_2 + 1.182 H_2O$ 1,3-Butanediol: $2 CH_4O + C_6H_{12}O_6 \rightarrow 1.636 C_4H_{10}O_2 + 1.455 CO_2 + 1.818 H_2O$ Isopropanol: $2 CH_4O + C_6H_{12}O_6 \rightarrow 2 C_3H_8O + 2 CO_2 + 2 H_2O$ 4-Hydroxybutyate: $2 CH_4O + C_6H_{12}O_6 \rightarrow 2 C_4H_8O_3 + 2 H_2O$ 1,4-Butanediol: $2 CH_4O + C_6H_{12}O_6 \rightarrow 1.636 C_4H_{10}O_2 + 1.455 CO_2 + 1.818 H_2O$ Exemplary flux distributions showing improvements in yields of 1,3-butanediol and isopropanol via carbohydrate-based carbon feedstock when carbon can be fixed via the Wood-Ljungdahl pathway using syngas components with and without methanol are shown in FIGS. 5 and 6, respectively.

Thus, the non-naturally occurring microbial organisms and conversion routes described herein provide an efficient means of converting carbohydrates to products such as isopropanol, 4-hydroxybutyrate, or 1,4-butanediol. Additional product molecules that can be produced by the teachings of this invention include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, caprolactam, 3-hydroxyisobutyric acid, 2-hydroxyisobutyric acid, methacrylic acid, acrylic acid, glycerol, 1,3-propanediol, and long chain hydrocarbons, alcohols, acids, and esters.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a 1,4-butanediol, 4-hydroxybutyrate, 1,3-butanediol, isopropanol, 6-aminocaproic acid, hexamethylene diamine, caprolactam, glycerol, or 1,3-propanediol biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 1,4-butanediol, 4-hydroxybutyrate, 1,3-butanediol, isopropanol, 6-aminocaproic acid, hexamethylene diamine, caprolactam, glycerol, or 1,3-propanediol biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the present invention provides a non-naturally occurring microbial organism that includes a microbial organism having a reductive TCA pathway in which at least one exogenous nucleic acid encoding a reductive TCA pathway enzyme is expressed in a sufficient amount to enhance carbon flux through acetyl-CoA. At least one exogenous nucleic acid is selected from an ATP-citrate lyase, citrate lyase, a fumarate reductase, and an alpha-ketoglutarate:ferredoxin oxidoreductase.

In some embodiments, the non-naturally occurring microbial organism includes two exogenous nucleic acids each encoding a reductive TCA pathway enzyme.

In some embodiments, the non-naturally occurring microbial organism includes three exogenous nucleic acids each encoding a reductive TCA pathway enzyme.

In some embodiments, the non-naturally occurring microbial organism includes three exogenous nucleic acids encoding an ATP-citrate lyase, a fumarate reductase, and an alpha-ketoglutarate:ferredoxin oxidoreductase.

In some embodiments, the non-naturally occurring microbial organism includes three exogenous nucleic acids encoding a citrate lyase, a fumarate reductase, and an alpha-ketoglutarate:ferredoxin oxidoreductase.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism further induces an isopropanol pathway, the isopropanol pathway converting acetyl-CoA to isopropanol, wherein the isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway which is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway; said 1,3-butanediol pathway converting acetyl-CoA to 1,3-butanediol, wherein said 1,3-butanediol pathway comprises at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway which is encoded by an exogenous nucleic acid.

In some embodiments, the non-naturally occurring microbial organism includes at least two enzymes of the 1,3-butanediol pathway are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol, wherein the 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway which is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of said 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate, wherein the 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway which is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, the non-naturally occurring microbial organism further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism utilizes a carbon feedstock selected from CO, $CO_2$, $CO_2$ and $H_2$, synthesis gas comprising CO and $H_2$, and synthesis gas comprising CO, $CO_2$, and $H_2$.

In some embodiments, a non-naturally occurring microbial organism includes a microbial organism having a Wood-Ljungdahl pathway that includes at least one exogenous nucleic acid encoding a Wood-Ljungdahl pathway enzyme expressed in a sufficient amount to enhance carbon flux through acetyl-CoA. The at least one exogenous nucleic acid is selected from a) Formate dehydrogenase, b) Formyltetrahydrofolate synthetase, c) Methenyltetrahydrofolate cyclohydrolase, d) Methylenetetrahydrofolate dehydrogenase, e) Methylenetetrahydrofolate reductase, f) Methyltetrahydrofolate:corrinoid protein methyltransferase (AcsE), g) Corrinoid iron-sulfur protein (AcsD), h) Nickel-protein assembly protein (AcsF & CooC), i) Ferredoxin (Orf7), j) Acetyl-CoA synthase (AcsB & AcsC), k) Carbon monoxide dehydrogenase (AcsA), l) Pyruvate ferredoxin oxidoreductase or pyruvate dehydrogenase, m) Pyruvate formate lyase In some embodiments, the non-naturally occurring microbial organism includes two exogenous nucleic acids each encoding a Wood-Ljungdahl pathway enzyme.

In some embodiments, the non-naturally occurring microbial organism includes three exogenous nucleic acids each encoding a Wood-Ljungdahl pathway enzyme.

In some embodiments, the non-naturally occurring microbial organism includes four exogenous nucleic acids each encoding a Wood-Ljungdahl pathway enzyme.

In some embodiments, the non-naturally occurring microbial organism includes five exogenous nucleic acids each encoding a Wood-Ljungdahl pathway enzyme.

In some embodiments, the non-naturally occurring microbial organism includes six exogenous nucleic acids each encoding a Wood-Ljungdahl pathway enzyme.

In some embodiments, the non-naturally occurring microbial organism includes seven exogenous nucleic acids each encoding a Wood-Ljungdahl pathway enzyme.

In some embodiments, the non-naturally occurring microbial organism includes eight exogenous nucleic acids each encoding a Wood-Ljungdahl pathway enzyme.

In some embodiments, the non-naturally occurring microbial organism includes nine exogenous nucleic acids each encoding a Wood-Ljungdahl pathway enzyme.

In some embodiments, the non-naturally occurring microbial organism includes ten exogenous nucleic acids each encoding a Wood-Ljungdahl pathway enzyme.

In some embodiments, the non-naturally occurring microbial organism includes eleven exogenous nucleic acids each encoding a Wood-Ljungdahl pathway enzyme.

In some embodiments, the non-naturally occurring microbial organism includes twelve exogenous nucleic acids each encoding a Wood-Ljungdahl pathway enzyme.

In some embodiments, the non-naturally occurring microbial organism includes at least one exogenous nucleic acid that is a heterologous nucleic acid.

In some embodiments, the non-naturally occurring microbial organism includes is in a substantially anaerobic culture medium.

In some embodiments, the non-naturally occurring microbial organism further includes an isopropanol pathway, the isopropanol pathway converting acetyl-CoA to isopropanol. The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes the four enzymes of the isopropanol pathway which are encoded by exogenous nucleic acids.

In some embodiments, the non-naturally occurring microbial organism further includes a 1,3-butanediol pathway; the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, a non-naturally occurring microbial organism includes a microbial organism having a methanol Wood-Ljungdahl pathway that includes at least one exogenous nucleic acid encoding a Wood-Ljungdahl pathway enzyme expressed in a sufficient amount to enhance carbon flux through acetyl-CoA. The at least one exogenous nucleic acid is selected from a) Methanol methyltransferase (MtaB), b) Corrinoid protein (MtaC), c) Methyltetrahydrofolate:corrinoid protein methyltransferase (MtaA), d) Methyltetrahydrofolate:corrinoid protein methyltransferase (AcsE), e) Corrinoid iron-sulfur protein (AcsD), f) Nickel-protein assembly protein (AcsF & CooC), g) Ferredoxin (Orf7), h) Acetyl-CoA synthase (AcsB & AcsC), i) Carbon monoxide dehydrogenase (AcsA), j) Pyruvate ferredoxin oxidoreductase, k) NAD(P)H:ferredoxin oxidoreductase, l) Pyruvate dehydrogenase, m) Pyruvate formate lyase, n) Formate dehydrogenase.

In some embodiments, the non-naturally occurring microbial organism includes two exogenous nucleic acids each encoding a methanol Wood-Ljungdahl pathway enzyme.

In some embodiments, the non-naturally occurring microbial organism includes three exogenous nucleic acids each encoding a methanol Wood-Ljungdahl pathway enzyme.

In some embodiments, the non-naturally occurring microbial organism includes four exogenous nucleic acids each encoding a methanol Wood-Ljungdahl pathway enzyme.

In some embodiments, the non-naturally occurring microbial organism includes five exogenous nucleic acids each encoding a methanol Wood-Ljungdahl pathway enzyme.

In some embodiments, the non-naturally occurring microbial organism includes six exogenous nucleic acids each encoding a methanol Wood-Ljungdahl pathway enzyme.

In some embodiments, the non-naturally occurring microbial organism includes seven exogenous nucleic acids each encoding a methanol Wood-Ljungdahl pathway enzyme.

In some embodiments, the non-naturally occurring microbial organism includes eight exogenous nucleic acids each encoding a methanol Wood-Ljungdahl pathway enzyme.

In some embodiments, the non-naturally occurring microbial organism includes nine exogenous nucleic acids each encoding a methanol Wood-Ljungdahl pathway enzyme.

In some embodiments, the non-naturally occurring microbial organism includes ten exogenous nucleic acids each encoding a methanol Wood-Ljungdahl pathway enzyme.

In some embodiments, the non-naturally occurring microbial organism includes eleven exogenous nucleic acids each encoding a methanol Wood-Ljungdahl pathway enzyme.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes an isopropanol pathway, the isopropanol pathway converting acetyl-CoA to isopropanol. The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway, the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, the present invention provides a non-naturally occurring microbial organism that includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin.

In some embodiments, the non-naturally occurring microbial organism includes two exogenous nucleic acids.

In some embodiments, the non-naturally occurring microbial organism includes three exogenous nucleic acids.

In some embodiments, the non-naturally occurring microbial organism includes four exogenous nucleic acids.

In some embodiments, the non-naturally occurring microbial organism includes four exogenous nucleic acids encoding a carbon monoxide dehydrogenase, a hydrogenase, an NAD(P)H:ferredoxin oxidoreductase, and a ferredoxin.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism includes a 1,4-butanediol pathway that includes at least one exogenous nucleic acid encoding an enzyme selected from 1) Hydrogenase, 2) Carbon monoxide dehydrogenase, 3) Succinyl-CoA transferase, Succinyl-CoA hydrolase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA reductase (aldehyde forming), 9) 1,4-butanediol dehydrogenase, 10) Succinate reductase, 11) Succinyl-CoA reductase (alcohol forming), 12) 4-Hydroxybutyryl-CoA transferase, 4-Hydroxybutyryl-CoA hydrolase, or 4-Hydroxybutyryl-CoA synthetase, 13) 4-Hydroxybutyrate reductase, 14) 4-Hydroxybutyryl-phosphate reductase, and 15) 4-Hydroxybutyryl-CoA reductase (alcohol forming).

In some embodiments, the non-naturally occurring microbial organism further includes a 1,3-butanediol pathway comprising at least one exogenous nucleic acid encoding an enzyme selected from: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) Crotonase, 10) 3-Hydroxybutyryl-CoA reductase (aldehyde forming), 11) 3-Hydroxybutyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) 3-Hydroxybutyryl-CoA reductase (alcohol forming), 16) 3-Hydroxybutyryl-CoA hydrolase, or 3-Hydroxybutyryl-CoA synthetase, or 3-Hydroxybutyryl-CoA transferase, 17) 3-Hydroxybutyrate reductase In some embodiments, the non-naturally occurring microbial organism includes a butanol pathway that includes at least one exogenous nucleic acid encoding an enzyme selected from 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) butyryl-CoA dehydrogenase, 10) Butyryl-CoA reductase (aldehyde forming), 11) Butyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) Butyryl-CoA reductase (alcohol forming), 16) Butyryl-CoA hydrolase, or Butyryl-CoA synthetase, or Butyryl-CoA transferase, 17) Butyrate reductase.

In some embodiments, the non-naturally occurring microbial organism further includes a 6-aminocaproic acid pathway that includes at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), and 8) 6-Aminocaproate transaminase, or 6-Aminocaproate dehydrogenase.

In some embodiments, the non-naturally occurring microbial organism further includes a hexamethylenediamine pathway comprising at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) 6-Aminocaproyl-CoA reductase (aldehyde forming), and 11) HMDA transaminase, or HMDA dehydrogenase.

In some embodiments, the non-naturally occurring microbial organism includes an adipic acid pathway.

In some embodiments, the non-naturally occurring microbial organism further includes a caprolactam pathway that includes at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) amidohydrolase, and 11) Spontaneous cyclization.

In some embodiments, the non-naturally occurring microbial organism further includes a glycerol pathway that includes at least one exogenous nucleic acid encoding an enzyme selected from 1) Hydrogenase, 2) Carbon monoxide dehydrogenase, 3) Dihydroxyacetone kinase, and 4) Glycerol dehydrogenase.

In some embodiments, the non-naturally occurring microbial organism includes a 1,3-propanediol pathway that at least one exogenous nucleic acid encoding an enzyme selected from 1) Hydrogenase, 2) Carbon monoxide dehydrogenase, 3) Dihydroxyacetone kinase, 4) Glycerol dehydrogenase, 5) Glycerol dehydratase, and 6) 1,3-Propanediol dehydrogenase.

In some embodiments, the non-naturally occurring microbial organism includes a microbial organism having: a reductive TCA pathway that includes at least one exogenous nucleic acid encoding a reductive TCA pathway enzyme; the at least one exogenous nucleic acid is selected from an ATP-citrate lyase, a citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$.

In some embodiments, the non-naturally occurring microbial organism further includes at least one exogenous nucleic acid encoding a citrate lyase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

In some embodiments, the non-naturally occurring microbial organism further includes an isopropanol pathway, the isopropanol pathway converting acetyl-CoA to isopropanol, The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway, the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

Enzymes of the reductive TCA cycle useful in the non-naturally occurring microbial organisms of the present invention include one or more of ATP-citrate lyase and three CO2-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each of these steps are shown below.

ATP citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha(4) beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. The *Chlorobium tepidum* a recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum*, *Sulfurihydrogenibium subterraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000), *Aspergillus nidulans* and *Yarrowia lipolytica* (Hynes and Murray, *Eukaryotic Cell, July:* 1039-1048, (2010), and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | *Chlorobium limicola* |
| adB | BAB21375.1 | 12407235 | *Chlorobium limicola* |
| aclA | AAM72321.1 | 21647054 | *Chlorobium tepidum* |
| adB | AAM72322.1 | 21647055 | *Chlorobium tepidum* |
| aclA | ABI50076.1 | 114054981 | *Balnearium lithotrophicum* |
| adB | ABI50075.1 | 114054980 | *Balnearium lithotrophicum* |
| aclA | ABI50085.1 | 114055040 | *Sulfurihydrogenibium subterraneum* |
| adB | ABI50084.1 | 114055039 | *Sulfurihydrogenibium subterraneum* |
| aclA | AAX76834.1 | 62199504 | *Sulfurimonas denitrificans* |
| adB | AAX76835.1 | 62199506 | *Sulfurimonas denitrificans* |
| acl1 | XP_504787.1 | 50554757 | *Yarrowia lipolytica* |
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| adB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002).

| Protein | GenBank ID | GI Number | Organism |
|---|---|---|---|
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |

| Protein | GenBank ID | GI Number | Organism |
|---|---|---|---|
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278: 25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278: 45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from Pelotomaculum thermopropionicum is another class of fumarase with two subunits (Shimoyama et al., *FEMS Microbiol. Lett.* 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352:175-181 (1998)), which localize to the cytosol and promitochondrion, respectively, and are used for anaerobic growth on glucose (Arikawa et al., *FEMS Microbiol. Lett.* 165:111-116 (1998)).

| Protein | GenBank ID | GI Number | Organism |
|---|---|---|---|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., *Biochemistry* 24:6245-6252 (1985)). These proteins are identified below:

| Protein | GenBank ID | GI Number | Organism |
|---|---|---|---|
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from $CO_2$ and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., Archaea. *Adv. Protein Chem.* 48:101-180 (1996)). Enzymes in this class are reversible and function in the carboxylation direction in organisms that fix carbon by the RTCA cycle such as *Hydrogenobacter thermophilus*, *Desulfobacter hydrogenophilus* and *Chlorobium* species (Shiba et al. 1985; Evans et al., *Proc. Natl. Acad. ScI. U.S.A.* 55:92934 (1966); Buchanan, 1971). The two-subunit enzyme from *H. thermophilus* enzyme, encoded by korAB, has been cloned and expressed in *E. coli* (Yun et al., *Biochem. Biophys. Res. Commun.* 282:589-594 (2001)). A five subunit OFOR from the same organism with strict substrate specificity for succinyl-CoA, encoded by forDABGE, was recently identified and expressed in *E. coli* (Yun et al. 2002). The kinetics of $CO_2$ fixation of both *H. thermophilus* OFOR enzymes have been characterized (Yamamoto et al., *Extremophiles* 14:79-85 (2010)). A $CO_2$-fixing OFOR from *Chlorobium thiosulfatophilum* has been purified and characterized but the genes encoding this enzyme have not been identified to date. Enzyme candidates in *Chlorobium* species can be inferred by sequence similarity to the *H. thermophilus* genes. For example, the *Chlorobium limicola* genome encodes two similar proteins. Acetogenic bacteria such as *Moorella thermoacetica* are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon *Sulfolobus* sp. strain 7, encoded by ST2300, has been extensively studied (Zhang et al. 1996. A plasmid-based expression system has been developed for efficiently expressing this protein in *E. coli* (Fukuda et al., *Eur. J. Biochem.* 268:5639-5646 (2001)) and residues involved in substrate specificity were determined (Fukuda and Wakagi, *Biochim. Biophys. Acta* 1597:74-80 (2002)). The OFOR encoded by Ape1472/Ape1473 from *Aeropyrum pernix* str. K1 was recently cloned into *E. coli*, characterized, and found to react with 2-oxoglutarate and a broad range of 2-oxoacids (Nishizawa et al., *FEBS Lett.* 579:2319-2322 (2005)). Another exemplary OFOR is encoded by oorDABC in *Helicobacter pylori* (Hughes et al. 1998). An enzyme very specific to alpha-ketoglutarate has been reported in *Thauera aromatics* (Dorner and Boll, *J, Bacteriol.* 184 (14), 3975-83 (2002). A similar enzyme can be found in *Rhodospirillum rubrum* by sequence homology. A two subunit enzyme has also been identified in *Chlorobium tepidum* (Eisen et al., *PNAS* 99(14): 9509-14 (2002)).

| Protein | GenBank ID | GI Number | Organism |
|---|---|---|---|
| korA | BAB21494 | 12583691 | *Hydrogenobacter thermophilus* |
| korB | BAB21495 | 12583692 | *Hydrogenobacter thermophilus* |
| forD | BAB62132.1 | 14970994 | *Hydrogenobacter thermophilus* |

-continued

| Protein | GenBank ID | GI Number | Organism |
|---|---|---|---|
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |
| Ape1473 | BAA80471.2 | 116062794 | Aeropyrum pernix |
| oorD | AAC38210.1 | 2935178 | Helicobacter pylori |
| oorA | AAC38211.1 | 2935179 | Helicobacter pylori |
| oorB | AAC38212.1 | 2935180 | Helicobacter pylori |
| oorC | AAC38213.1 | 2935181 | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatica |
| korB | CAD27440.1 | 19571178 | Thauera aromatica |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of NAD(P)$^+$. IDH enzymes in Saccharomyces cerevisiae and Escherichia coli are encoded by IDP1 and icd, respectively (Haselbeck and McAlister-Henn, J. Biol. Chem. 266:2339-2345 (1991); Nimmo, H. G., Biochem. J. 234:317-2332 (1986)). The reverse reaction in the reductive TCA cycle, the reductive carboxylation of 2-oxoglutarate to isocitrate, is favored by the NADPH-dependent $CO_2$-fixing IDH from Chlorobium limicola and was functionally expressed in E. coli (Kanao et al., Eur. J. Biochem. 269:1926-1931 (2002)). A similar enzyme with 95% sequence identity is found in the C. tepidum genome in addition to some other candidates listed below.

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In H. thermophilus the reductive carboxylation of 2-oxoglutarate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, Mol. Microbiol. 62:748-759 (2006)). This enzyme is a large complex composed of two subunits. Biotinylation of the large (A) subunit is required for enzyme function (Aoshima et al., Mol. Microbiol. 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in H. thermophilus. The kinetic parameters of this enzyme indicate that the enzyme only operates in the reductive carboxylation direction in vivo, in contrast to isocitrate dehydrogenase enzymes in other organisms (Aoshima and Igarashi, J. Bacteriol. 190:2050-2055 (2008)). Based on sequence homology, gene candidates have also been found in Thiobacillus denitrificans and Thermocrinis albus.

| Protein | GenBank ID | GI Number | Organism |
|---|---|---|---|
| cfiA | BAF34932.1 | 116234991 | Hydrogenobacter thermophilus |
| cifB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and isocitrate via the intermediate cis-aconitate. Two aconitase enzymes are encoded in the E. coli genome by acnA and acnB. AcnB is the main catabolic enzyme, while AcnA is more stable and appears to be active under conditions of oxidative or acid stress (Cunningham et al., Microbiology 143 (Pt 12):3795-3805 (1997)). Two isozymes of aconitase in Salmonella typhimurium are encoded by acnA and acnB (Horswill and Escalante-Semerena, Biochemistry 40:4703-4713 (2001)). The S. cerevisiae aconitase, encoded by ACO1, is localized to the mitochondria where it participates in the TCA cycle (Gangloff et al., Mol. Cell. Biol. 10:3551-3561 (1990)) and the cytosol where it participates in the glyoxylate shunt (Regev-Rudzki et al., Mol. Biol. Cell. 16:4163-4171 (2005)).

| Protein | GenBank ID | GI Number | Organism |
|---|---|---|---|
| acnA | AAC7438.1 | 1787531 | Escherichia coli |
| acnB | AAC73229.1 | 2367097 | Escherichia coli |
| acnA | NP_460671.1 | 16765056 | Salmonella typhimurium |
| acnB | NP_459163.1 | 16763548 | Salmonella typhimurium |
| ACO1 | AAA34389.1 | 170982 | Saccharomyces cerevisiae |

Pyruvate ferredoxin oxidoreductase (PFOR) catalyzes the oxidation of pyruvate to form acetyl-CoA. The PFOR from Desulfovibrio africanus has been cloned and expressed in E. coli resulting in an active recombinant enzyme that was stable for several days in the presence of oxygen (Pieulle et al., J. Bacteriol. 179:5684-5692 (1997)). Oxygen stability is relatively uncommon in PFORs and is believed to be conferred by a 60 residue extension in the polypeptide chain of the D. africanus enzyme. Two cysteine residues in this enzyme form a disulfide bond that protects it against inactivation in the form of oxygen. This disulfide bond and the stability in the presence of oxygen has been found in other Desulfovibrio species also (Vita et al., Biochemistry, 47: 957-64 (2008)). The M. thermoacetica PFOR is also well characterized (Menon and Ragsdale, Biochemistry 36:8484-8494 (1997)) and was shown to have high activity in the direction of pyruvate synthesis during autotrophic growth (Furdui and Ragsdale, J. Biol. Chem. 275:28494-28499 (2000)). Further, E. coli possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including, *Rhodobacter capsulatas* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. The protein sequences of these exemplary PFOR enzymes can be identified by the following GenBank accession numbers. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189: 4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

(Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the *E. coli* PDH, the *B. subtilis* complex is active and required for growth under anaerobic conditions (Nakano et al., J. Bacteriol. 179:6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter vinelandii* are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol. 27:477-

| Protein | GenBank ID | GI Number | Organism |
|---|---|---|---|
| Por | CAA70873.1 | 1770208 | *Desulfovibrio africanus* |
| por | YP_012236.1 | 46581428 | *Desulfovibrio vulgaris* str. Hildenborough |
| Dde_3237 | ABB40031.1 | 78220682 | *DesulfoVibrio desulfuricans* G20 |
| Ddes_0298 | YP_002478891.1 | 220903579 | *Desulfovibrio desulfuricans* subsp. *desulfuricans* str. ATCC 27774 |
| Por | YP_428946.1 | 83588937 | *Moorella thermoacetica* |
| YdbK | NP_415896.1 | 16129339 | *Escherichia coli* |
| nifJ (CT1628) | NP_662511.1 | 21674446 | *Chlorobium tepidum* |
| CJE1649 | YP_179630.1 | 57238499 | *Campylobacter jejuni* |
| nifJ | ADE85473.1 | 294476085 | *Rhodobacter capsulatus* |
| porE | BAA95603.1 | 7768912 | *Hydrogenobacter thermophilus* |
| porD | BAA95604.1 | 7768913 | *Hydrogenobacter thermophilus* |
| porA | BAA95605.1 | 7768914 | *Hydrogenobacter thermophilus* |
| porB | BAA95606.1 | 776891 | *Hydrogenobacter thermophilus* |
| porG | BAA95607.1 | 7768916 | *Hydrogenobacter thermophilus* |
| FqrB | YP_001482096.1 | 157414840 | *Campylobacter jejuni* |
| HP1164 | NP_207955.1 | 15645778 | *Helicobacter pylori* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., J. Biol. Chem. 256:815-82 (1981); Bremer, J., Eur. J. Biochem. 8:535-540 (1969); Gong et al., J. Biol. Chem. 275:13645-13653 (2000)). Enzyme engineering efforts have improved the *E. coli* PDH enzyme activity under anaerobic conditions 492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that pflA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., J. Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase.

Acetyl-CoA synthetase is a native enzyme in several other organisms including *E. coli* (Kumari et al., J. Bacteriol. 177: 2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several *Clostridia* and *Methanosarcina thermophile*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:$NADP^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:$NADP^+$ oxidoreductase enzyme is encoded in the *E. coli* genome by fpr (Bianchi et al. 1993). Ferredoxin:$NAD^+$ oxidoreductase utilizes reduced ferredoxin to generate NADH from $NAD^+$. In several organisms, including *E. coli*, this enzyme is a component of multifunctional dioxygenase enzyme complexes. The ferredoxin:$NAD^+$ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., *J. Bacteriol.* 190:784-791 (2008)) provide a means to generate NADH or NADPH from reduced ferredoxin. Additional ferredoxin:$NAD(P)+$ oxidoreductases have been annotated in *Clostridium carboxydivorans* P7.

| Protein | GenBank ID | GI Number | Organism |
| --- | --- | --- | --- |
| HP1164 | NP_207955.1 | 15645778 | *Helicobacter pylori* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |

Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica*, *Clostridium carboxidivorans* P7 and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA: acetyl-CoA transferase activity (Sohling and Gottschalk, J. Bacteriol. 178:871-880 (1996)). In addition, the activity is present in *Trichomonas vaginalis* (van Grinsven et al. 2008) and *Trypanosoma brucei* (Riviere et al. 2004). The succinyl-CoA: acetate CoA-transferase from *Acetobacter aceti*, encoded by aarC, replaces succinyl-CoA synthetase in a variant TCA cycle (Mullins et al. 2008). Similar succinyl-CoA transferase activities are also present in *Trichomonas vaginalis*(van Grinsven et al. 2008), *Trypanosoma brucei* (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

| Protein | GenBank ID | GI Number | Organism |
|---|---|---|---|
| cat1 | P38946.1 | 729048 | *Clostridium kluyveri* |
| TVAG_395550 | XP_001330176 | 123975034 | *Trichomonas vaginalis* G3 |

-continued

| Protein | GenBank ID | GI Number | Organism |
|---|---|---|---|
| Tb11.02.0290 | XP_828352 | 71754875 | *Trypanosoma brucei* |
| pcaI | AAN69545.1 | 24985644 | *Pseudomonas putida* |
| pcaJ | NP_746082.1 | 26990657 | *Pseudomonas putida* |
| aarC | ACD85596.1 | 189233555 | *Acetobacter aceti* |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanaka et al. 2002). The aforementioned proteins are identified below.

| Protein | GenBank ID | GI Number | Organism |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Converting succinate to succinyl-CoA by succinyl-CoA:3: ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA:acetate:CoA transferase. Acetoacetyl-CoA:acetate:CoA transferase converts acetoacetyl-CoA and acetate to acetoacetate and acetyl-CoA, or vice versa. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., *Biosci. Biotechnol Biochem.* 71:58-68 (2007)) are shown below.

| Protein | GenBank ID | GI Number | Organism |
| --- | --- | --- | --- |
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatics* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
| --- | --- | --- | --- |
| bbsE | AAF89840 | 9622535 | *Thauera aromatic* |
| Bbsf | AAF89841 | 9622536 | *Thauera aromatic* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

| Protein | GenBank ID | GI Number | Organism |
| --- | --- | --- | --- |
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

Finally, although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bacteriol.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional genes from *Porphyrmonas gingivalis* and *Thermoanaerobacter tengcongensis* can be identified in a similar fashion (Kreimeyer, et al., *J. Biol. Chem.* 282 (10) 7191-7197 (2007)). The aforementioned proteins are identified below.

| Protein | GenBank ID | GI Number | Organism |
| --- | --- | --- | --- |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88 (1997); Bott and Dimroth, *Mol. Microbiol.* 14:347-356 (1994)). The aforementioned proteins are tabulated below.

| Protein | GenBank ID | GI Number | Organism |
|---|---|---|---|
| citF | AAC73716.1 | 1786832 | Escherichia coli |
| citE | AAC73717.2 | 87081764 | Escherichia coli |
| citD | AAC73718.1 | 1786834 | Escherichia coli |
| citC | AAC73719.2 | 87081765 | Escherichia coli |
| citG | AAC73714.1 | 1786830 | |
| citX | AAC73715.1 | 1786831 | |
| citF | CAA71633.1 | 2842397 | Leuconostoc mesenteroides |
| citE | CAA71632.1 | 2842396 | Leuconostoc mesenteroides |
| citD | CAA71635.1 | 2842395 | Leuconostoc mesenteroides |
| citC | CAA71636.1 | 3413797 | Leuconostoc mesenteroides |
| citG | CAA71634.1 | 2842398 | Leuconostoc mesenteroides |
| citX | CAA71634.1 | 2842398 | Leuconostoc mesenteroides |
| citF | NP_459613.1 | 16763998 | Salmonella typhimurium |
| citE | AAL19573.1 | 16419133 | Salmonella typhimurium |
| citD | NP_459064.1 | 16763449 | Salmonella typhimurium |
| citC | NP_459616.1 | 16764001 | Salmonella typhimurium |
| citG | NP_459611.1 | 16763996 | Salmonella typhimurium |
| citX | NP_459612.1 | 16763997 | Salmonella typhimurium |
| citF | CAA56217.1 | 565619 | Klebsiella pneumoniae |
| citE | CAA56216.1 | 565618 | Klebsiella pneumoniae |
| citD | CAA56215.1 | 565617 | Klebsiella pneumoniae |
| citC | BAH66541.1 | 238774045 | Klebsiella pneumoniae |
| citG | CAA56218.1 | 565620 | Klebsiella pneumoniae |
| citX | AAL60463.1 | 18140907 | Klebsiella pneumoniae |

Acetate kinase (EC 2.7.2.1) catalyzes the reversible ATP-dependent phosphorylation of acetate to acetylphosphate. Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
|---|---|---|---|
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
|---|---|---|---|
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |

| Protein | GenBank ID | GI Number | Organism |
| --- | --- | --- | --- |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

Formate dehydrogenase is a two subunit selenocysteine-containing protein that catalyzes the incorporation of $CO_2$ into formate in *Moorella thermoacetica* (Andreesen and Ljungdahl, *J. Bacteriol.* 116:867-873 (1973); Li et al., *J. Bacteriol.* 92:4-50412 (1966); Yamamoto et al., *J. Biol. Chem.* 258:1826-1832 (1983)). The loci, Moth_2312 and Moth_2313 are actually one gene that is responsible for encoding the alpha subunit of formate dehydrogenase while the beta subunit is encoded by Moth_2314 (Pierce et al., *Environ. Microbiol.* 10:2550-2573 (2008)). Another set of genes encoding formate dehydrogenase activity with a propensity for $CO_2$ reduction is encoded by Sfum_2703 through Sfum_2706 in *Syntrophobacter fumaroxidans* (Reda et al., *Proc. Natl. Acad. Sci. U.S.A.* 105:10654-10658 (2008); de Bok et al., *Eur. J. Biochem.* 270:2476-2485 (2003). Similar to their *M. thermoacetica* counterparts, Sfum_2705 and Sfum_2706 are actually one gene. A similar set of genes that have been indicated to carry out the same function are encoded by CHY_0731, CHY_0732, and CHY_0733 in *C. hydrogenoformans* (Wu et al., *PLoS Genet.* 1:e65 (2005)). Homologs are also found in *C. carboxidivorans* P7.

| Protein | GenBank ID | GI Number | Organism |
| --- | --- | --- | --- |
| Moth_2312 | YP_431142 | 148283121 | Moorella thermoacetica |
| Moth_2314 | YP_431144 | 83591135 | Moorella thermoacetica |
| Sfum_2703 | YP_846816.1 | 116750129 | Syntrophobacter fumaroxidans |
| Sfum_2704 | YP_846817.1 | 116750130 | Syntrophobacter fumaroxidans |
| Sfum_2705 | YP_846818.1 | 116750131 | Syntrophobacter fumaroxidans |
| Sfum_2706 | YP_846819.1 | 116750132 | Syntrophobacter fumaroxidans |
| CHY_0731 | YP_359585.1 | 78044572 | Carboxydothermus hydrogenoformans |
| CHY_0732 | YP_359586.1 | 78044500 | Carboxydothermus hydrogenoformans |
| CHY_0733 | YP_359587.1 | 78044647 | Carboxydothermus hydrogenoformans |
| CcarbDRAFT_0901 | ZP_05390901.1 | 255523938 | Clostridium carboxidivorans P7 |
| CcarbDRAFT_4380 | ZP_05394380.1 | 255527512 | Clostridium carboxidivorans P7 |

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
| --- | --- | --- | --- |
| Moth_0109 | YP_428991.1 | 83588982 | Moorella thermoacetica |
| CHY_2385 | YP_361182.1 | 78045024 | Carboxydothermus hydrogenoformans |
| FHS | P13419.1 | 120562 | Clostridium acidurici |
| CcarbDRAFT_1913 | ZP_05391913.1 | 255524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| fhs | YP_001393842.1 | 153953077 | Clostridium kluyveri DSM 555 |
| fhs | YP_003781893.1 | 300856909 | Clostridium ljungdahlii DSM 13528 |

In *M. thermoacetica, E. coli*, and *C. hydrogenoformans*, methenyltetrahydrofolate cyclohydrolase and methylenetetrahydrofolate dehydrogenase are carried out by the bi-functional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
| --- | --- | --- | --- |
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonia eutropha* H16 |
| folD | NP_348702.1 | 15895353 | *Clostridium acetobutylicum* ATCC 824 |
| folD | YP_696506.1 | 110800457 | *Clostridium perfringens* |

The final step of the methyl branch of the Wood-Ljungdahl pathway is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below.

| Protein | GenBank ID | GI number | Organism |
| --- | --- | --- | --- |
| Moth_1191 | YP_430048.1 | 83590039 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoid-iron-sulfur-protein is methylated by methyltetrahydrofolate via a methyltransferase. Expression of ACS/CODH in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/acetyl-CoA synthase activity typically reside in a limited region of the native genome that can be an extended operon (Ragsdale, S. W., *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989). Each of the genes in this operon from the acetogen, *M. thermoacetica*, has already been cloned and expressed actively in *E. coli* (Morton et al. supra; Roberts et al. supra; Lu et al., *J. Biol. Chem.* 268:5605-5614 (1993). The protein sequences of these genes can be identified by the following GenBank accession numbers.

| Protein | GenBank ID | GI number | Organism |
| --- | --- | --- | --- |
| AcsE | YP_430054 | 83590045 | *Moorella thermoacetica* |
| AcsD | YP_430055 | 83590046 | *Moorella thermoacetica* |
| AcsF | YP_430056 | 83590047 | *Moorella thermoacetica* |
| Orf7 | YP_430057 | 83590048 | *Moorella thermoacetica* |
| AcsC | YP_430058 | 83590049 | *Moorella thermoacetica* |
| AcsB | YP_430059 | 83590050 | *Moorella thermoacetica* |
| AcsA | YP_430060 | 83590051 | *Moorella thermoacetica* |
| CooC | YP_430061 | 83590052 | *Moorella thermoacetica* |

The hydrogenic bacterium, *Carboxydothermus hydrogenoformans*, can utilize carbon monoxide as a growth substrate by means of acetyl-CoA synthase (Wu et al., *PLoS*

Genet. 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., Proc. Natl. Acad. Sci. U.S.A. 101:446-451 (2004)). The protein sequences of the C. hydrogenoformans genes from strain Z-2901 can be identified by the following GenBank accession numbers.

| Protein | GenBank ID | GI number | Organism |
|---|---|---|---|
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of *Clostridium carboxidivorans* P7.

| Protein | GenBank ID | GI Number | Organism |
|---|---|---|---|
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. U.S.A.* 103:17921-17926 (2006)). This organism contains two sets of genes that encode ACS/CODH activity (Rother and Metcalf, *Proc. Natl. Acad. Sci. U.S.A.* 101: 16929-16934 (2004)). The protein sequences of both sets of *M. acetivorans* genes are identified by the following GenBank accession numbers.

| Protein | GenBank ID | GI number | Organism |
|---|---|---|---|
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |

-continued

| Protein | GenBank ID | GI number | Organism |
|---|---|---|---|
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenic bacteria such as *C. hydrogenoformans*. Hypotheses for the existence of two active CODH/ACS operons in *M. acetivorans* include catalytic properties (i.e., $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

Expression of the modified Wood-Ljungdahl (i.e., methanol Wood-Ljungdahl pathway) in a foreign host (see FIG. 3B) requires introducing a set of methyltransferases to utilize the carbon and hydrogen provided by methanol and the carbon provided by CO and/or $CO_2$. A complex of 3-methyltransferase proteins, denoted MtaA, MtaB, and MtaC, perform the desired methanol methyltransferase activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that catalyzes the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri, M. acetivorans*, and *M. thermoaceticum* can be identified by their following GenBank accession numbers.

| Protein | GenBank ID | GI number | Organism |
|---|---|---|---|
| MtaB1 | YP_304299 | 73668284 | Methanosarcina barkeri |
| MtaC1 | YP_304298 | 73668283 | Methanosarcina barkeri |
| MtaB2 | YP_307082 | 73671067 | Methanosarcina barkeri |
| MtaC2 | YP_307081 | 73671066 | Methanosarcina barkeri |
| MtaB3 | YP_304612 | 73668597 | Methanosarcina barkeri |
| MtaC3 | YP_304611 | 73668596 | Methanosarcina barkeri |
| MtaB1 | NP_615421 | 20089346 | Methanosarcina acetivorans |
| MtaB1 | NP_615422 | 20089347 | Methanosarcina acetivorans |
| MtaB2 | NP_619254 | 20093179 | Methanosarcina acetivorans |
| MtaC2 | NP_619253 | 20093178 | Methanosarcina acetivorans |
| MtaB3 | NP_616549 | 20090474 | Methanosarcina acetivorans |
| MtaC3 | NP_616550 | 20090475 | Methanosarcina acetivorans |
| MtaB | YP_430066 | 83590057 | Moorella thermoacetica |
| MtaC | YP_430065 | 83590056 | Moorella thermoacetica |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611, were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from CH$_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). It is also important to note that there are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from CH$_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---|---|---|---|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |

Anaerobic growth on synthesis gas and methanol in the absence of an external electron acceptor is conferred upon the host organism with MTR and ACS/CODH activity by enabling pyruvate synthesis via pyruvate ferredoxin oxidoreductase (PFOR). The gene candidates for PFOR and other methods for converting pyruvate to acetyl-CoA are described herein elsewhere.

The product yields per C-mol of substrate of microbial cells synthesizing reduced fermentation products such as ethanol, butanol, isobutanol, 2-butanol, isopropanol, 1,4-butanediol, succinic acid, fumaric acid, malic acid, 4-hydroxybutyric acid, adipic acid, 6-aminocaproic acid, hexamethylenediamine, caprolactam, 3-hydroxyisobutyric acid, 2-hydroxyisobutyric acid, methacrylic acid, acrylic acid, 1,3-propanediol, glycerol, etc., are limited by insufficient reducing equivalents in the carbohydrate feedstock. Reducing equivalents, or electrons, can be extracted from synthesis gas components such as CO and H$_2$ using carbon monoxide dehydrogenase (CODH) and hydrogenase enzymes, respectively. The reducing equivalents are then passed to acceptors such as oxidized ferredoxins, oxidized quinones, oxidized cytochromes, NADP+, water, or hydrogen peroxide to form reduced ferredoxin, reduced quinones, reduced cytochromes, NAD(P)H, H$_2$, or water, respectively. Reduced ferredoxin and NAD(P)H are particularly useful as they can serve as redox carriers for various Wood-Ljungdahl pathway and reductive TCA cycle enzymes.

Here, we show specific examples of how additional redox availability from CO and/or H$_2$ can improve the yields of reduced products such as 1,4-BDO, 1,3-BDO, butanol, 6-aminocaproic acid, hexamethylene diamine, caprolactam, glycerol and 1,3-propanediol.

Figure 1B:
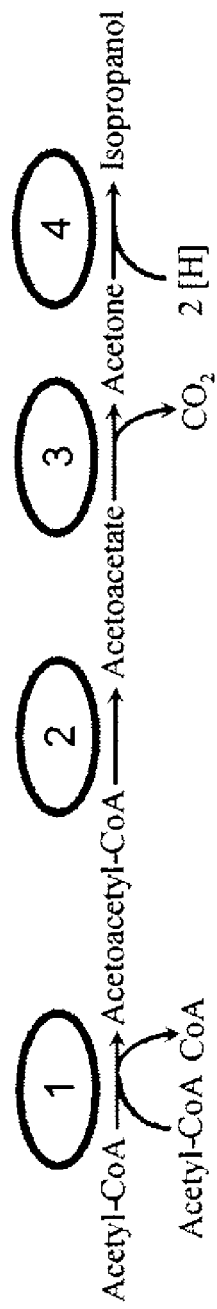
FIG. 1b shows the pathways for the biosynthesis of isopropanol from acetyl-CoA; the enzymatic transformations shown are carried out by the following enzymes: 1) Acetoacetyl-CoA thiolase (AtoB), 2) Acetoacetyl-CoA transferase, acetoacetyl-CoA hydrolase, acetoacetyl-CoA synthetase, or phosphotransacetoacetylase/acetoacetate kinase, 3) Acetoacetate decarboxylase (Adc), and 4) Isopropanol dehydrogenase (Adh)
Figure 1C:
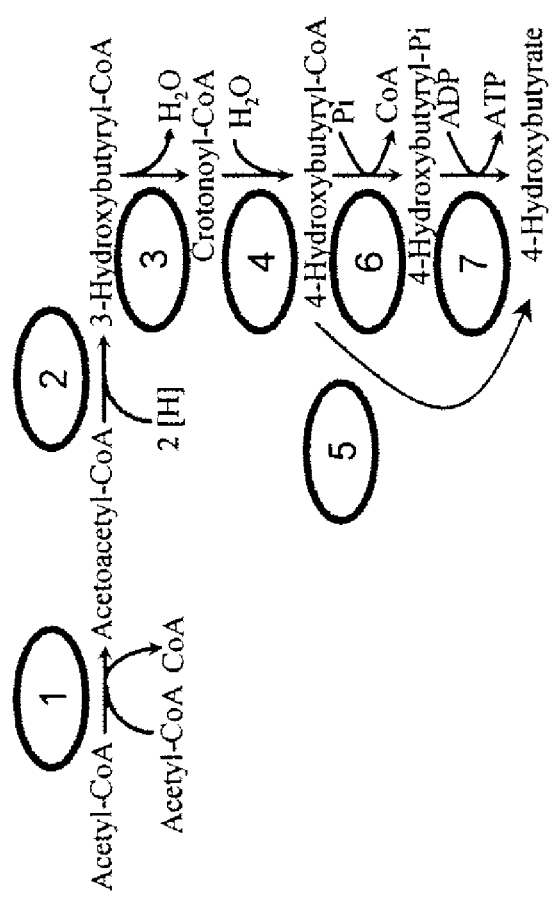
FIG. 1c shows the pathways for the biosynthesis of 4-hydroxybutyrate (4-HB); the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.
Figure 1D:
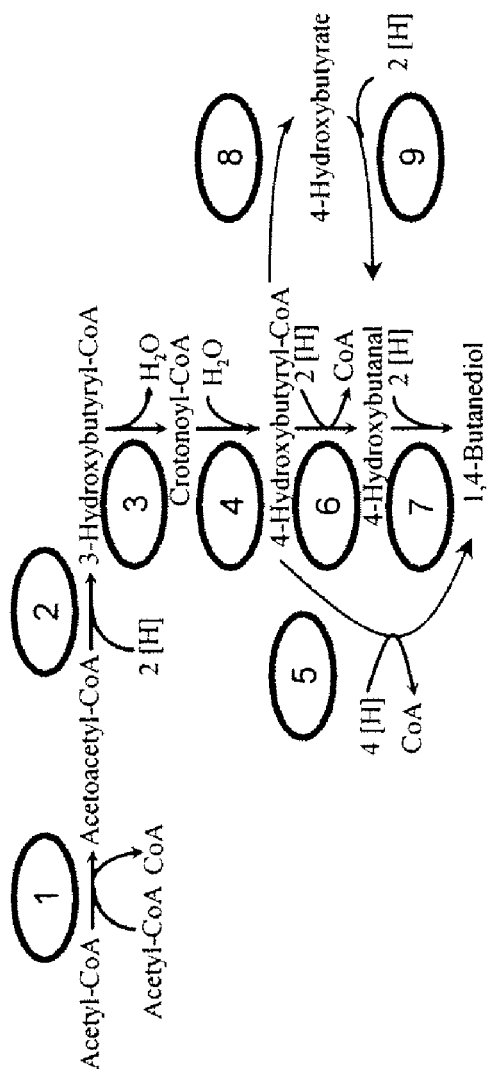
FIG. 1d shows the pathways for the biosynthesis of 1,4-butanediol; the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

The maximum theoretical yield to produce 1,4-BDO from glucose is 1.0 mole 1,4-BDO per mole of glucose under aerobic conditions via the pathways shown in FIG. 1D:

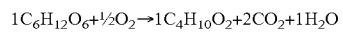

Or 1.09 mol 1,4-BDO per mol of glucose under anaerobic conditions:

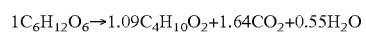

When both feedstocks of sugar and syngas are available, the syngas components CO and H$_2$ can be utilized to generate reducing equivalents by employing the hydrogenase and CO dehydrogenase. The reducing equivalents generated from syngas components will be utilized to power the glucose to BDO production pathways. Theoretically, all carbons in glucose will be conserved, thus resulting in a maximal theoretical yield to produce 1,4-BDO from glucose at 2 mol 1,4-BDO per mol of glucose under either aerobic or anaerobic conditions as shown in FIG. 7A:

$$1C_6H_{12}O_6+2CO+8H_2 \rightarrow 2C_4H_{10}O_2+4H_2O$$

In a similar manner, the maximum theoretical yield of 1,3-butanediol can be improved further to 2 mol/mol glucose. An exemplary flux distribution with the improved yields is shown in FIG. 7B.

$$1C_6H_{12}O_6+2CO+8H_2 \rightarrow 2C_4H_{10}O_2+4H_2O$$

Butanol is yet another example of a reduced product. The production of butanol through fermentation has a theoretical yield of 1 mol butanol per mol of glucose. It is currently manufactured from propylene and usually used close to the point of manufacture. Butanol is largely used as an industrial intermediate, particularly for the manufacture of butyl acrylate, butyl acetate, dibutyl phthalate, dibutyl sebacate and other butyl esters. Other industrial uses include the manufacture of pharmaceuticals, polymers, plastics, and herbicide. It can also be used as a solvent for the extraction of essential oils, antibiotics, hormones, and vitamins, or as a solvent for paints, coatings, natural resins, gums, synthetic resins, dyes, alkaloids, and camphor. Butanol has also been proposed as the next generation biofuel to substitute for diesel fuel and gasoline. It is also used in a wide range of consumer products.

$$1C_6H_{12}O_6 \rightarrow 1C_4H_{10}O+2CO_2+1H_2O$$

When the combined feedstocks strategy is applied to butanol production, the reducing equivalents generated from syngas can increase the butanol theoretical yield from glucose to 2 mol butanol per mol of glucose with the pathways detailed in FIG. 7C.

$$1C_6H_{12}O_6+2CO+10H_2 \rightarrow 2C_4H_{10}O+6H_2O$$

Hexamethylenediamine (HMDA) can be used to produce nylon 6,6, a linear polyamide made by condensing hexamethylenediamine with adipic acid. This is employed for manufacturing different kinds of fibers. In addition to HMDA being used in the production of nylon-6,6, it is also utilized to make hexamethylene diisocyanate, a monomer feedstock used in the production of polyurethane. The diamine also serves as a cross-linking agent in epoxy resins. HMDA is presently produced by the hydrogenation of adiponitrile.

The production of HMDA through fermentation has a theoretical yield of 0.7059 mol HMDA per mol of glucose.

$$17C_6H_{12}O_6+24NH_3 \rightarrow 12C_6H_{16}N_2+CO_2+42H_2O$$

When the combined feedstocks strategy is applied to the HMDA production, the reducing equivalents generated from syngas can increase the HMDA theoretical yield from glucose to 1 mol HMDA per mol of glucose with the pathways detailed in FIG. 7D.

$$1C_6H_{12}O+2NH_3+5H_2 \rightarrow 1C_6H_{16}N_2+6H_2O$$

or $$1C_6H_{12}O_6+2NH_3+5CO \rightarrow 1C_6H_{16}N_2+H_2O+5CO_2$$

or $$1C_6H_{12}O_6+2NH_3+2CO+3H_2 \rightarrow 1C_6H_{16}N_2+4H_2O+2CO_2$$

Caprolactam is an organic compound which is a lactam of 6-aminohexanoic acid (ε-aminohexanoic acid, 6-aminocaproic acid). It can alternatively be considered a cyclic amide of caproic acid. One use of caprolactam is as a monomer in the production of nylon-6. Caprolactam can be synthesized from cyclohexanone via an oximation process using hydroxylammonium sulfate followed by catalytic rearrangement using the Beckmann rearrangement process step. The production of caprolactam through fermentation has a theoretical yield of 0.8 mol caprolactam per mol of glucose.

$$5C_6H_{12}O_6+4NH_3 \rightarrow 4C_6H_{13}NO_2+6CO_2+10H_2O$$

When the combined feedstocks strategy is applied to caprolactam production, the reducing equivalents generated from syngas can increase the caprolactam theoretical yield from glucose to 1 mol caprolactam per mol of glucose with the pathways detailed in FIG. 7D.

$$1C_6H_{12}O_6+1NH_3+3H_2 \rightarrow 1C_6H_{13}NO_2+4H_2O$$

or $$1C_6H_{12}O_6+1NH_3+3CO \rightarrow 1C_6H_{13}NO_2+1H_2O+3CO_2$$

or $$1C_6H_{12}O_6+1NH_3+1CO+2H_2 \rightarrow 1C_6H_{13}NO_2+3H_2O+1CO_2$$

Other exemplary products for which the yields on carbohydrates can be improved by providing additional reducing equivalents are 1,3-propanediol (1,3-PDO) and glycerol. 1,3-PDO is mainly used as a building block in the production of polymers. It can be formulated into a variety of industrial products including composites, adhesives, laminates, coatings, moldings, aliphatic polyesters, copolyesters. It is also a solvent and used as an antifreeze and wood paint.

1,3-PDO can be chemically synthesized via the hydration of acrolein or by the hydroformylation of ethylene oxide to afford 3-hydroxypropionaldehyde. The resultant aldehyde is hydrogenated to give 1,3-PDO. Additionally, 1,3-PDO can be produced biologically. The production of 1,3-PDO through fermentation has a theoretical yield of 1.5 mol 1,3-PDO per mol of glucose.

$$2C_6H_{12}O_6 \rightarrow 3C_3H_8O_2+3CO_2$$

When the combined feedstock strategy is applied to 1,3-PDO production, the reducing equivalents generated from syngas can increase the 1,3-PDO theoretical yield based on glucose to 2 mol 1,3-PDO per mol of glucose by the pathways shown in FIG. 7E.

$$1C_6H_{12}O_6+4H_2 \rightarrow 2C_3H_8O_2+2H_2O$$

or $$1C_6H_{12}O_6+4CO+2H_2 \rightarrow 2C_3H_8O_2+4CO_2$$

or $$1C_6H_{12}O_6+2CO+2H_2 \rightarrow 2C_3H_8O_2+2CO_2$$

Similarly, the production of glycerol through fermentation can be improved by the combined feedstock strategy. The production of glycerol through fermentation has a theoretical yield of 1.71 mol glycerol per mol of glucose.

$$7C_6H_{12}O_6+6H_2O \rightarrow 12C_3H_8O_3+6CO_2$$

When the combined feedstocks strategy is applied to glycerol production, the reducing equivalents generated from syngas can increase the glycerol theoretical yield from glucose to 2 mol glycerol per mol of glucose with the pathways detailed in FIG. 7E.

$$1C_6H_{12}O_6 + 2H_2 \rightarrow 2C_3H_8O_3$$

or $$1C_6H_{12}O_6 + 2CO + 2H_2O \rightarrow 2C_3H_8O_3 + 2CO_2$$

or $$1C_6H_{12}O_6 + 1CO + 1H_2 + 1H_2O \rightarrow 2C_3H_8O_3 + 1CO_2$$

As shown in above three examples, a combined feedstock strategy where syngas is combined with a sugar-based feedstock or other carbon substrate can greatly improve the theoretical yields. In this co-feeding approach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of 1,4-BDO, 1,3-BDO and butanol productions from glucose or sugar, the theoretical yields improve from 1 mol or 1.09 mol products per mol of glucose to 2 mol products per mol of glucose. Such improvements provide environmental and economic benefits and greatly enhance sustainable chemical production.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicotinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
|---|---|---|---|
| CODH (putative) | YP_430813 | 83590804 | *Moorella thermoacetica* |
| CODH-II (CooS-II) | YP_358957 | 78044574 | *Carboxydothermus hydrogenoformans* |
| CooF | YP_358958 | 78045112 | *Carboxydothermus hydrogenoformans* |
| CODH (putative) | ZP_05390164.1 | 255523193 | *Clostridium carboxidivorans* P7 |
|  | ZP_05390341.1 | 255523371 | *Clostridium carboxidivorans* P7 |
|  | ZP_05391756.1 | 255524806 | *Clostridium carboxidivorans* P7 |
|  | ZP_05392944.1 | 255526020 | *Clostridium carboxidivorans* P7 |
| CODH | YP_384856.1 | 78223109 | *Geobacter metallireducens* GS-15 |
| Cpha266_0148 (cytochrome c) | YP_910642.1 | 119355998 | *Chlorobium phaeobacteroides* DSM 266 |
| Cpha266_0149 (CODH) | YP_910643.1 | 119355999 | *Chlorobium phaeobacteroides* DSM 266 |
| Ccel_0438 | YP_002504800.1 | 220927891 | *Clostridium cellulolyticum* H10 |
| Ddes_0382 (CODH) | YP_002478973.1 | 220903661 | *Desulfovibrio desulfuricans* subsp. *desulfuricans* str. ATCC 27774 |
| Ddes_0381 (CooC) | YP_002478972.1 | 220903660 | *Desulfovibrio desulfuricans* subsp. *desulfuricans* str. ATCC 27774 |
| Pcar_0057 (CODH) | YP_355490.1 | 7791767 | *Pelobacter carbinolicus* DSM 2380 |
| Pcar_0058 (CooC) | YP_355491.1 | 7791766 | *Pelobacter carbinolicus* DSM 2380 |
| Pcar_0058 (HypA) | YP_355492.1 | 7791765 | *Pelobacter carbinolicus* DSM 2380 |
| CooS (CODH) | YP_001407343.1 | 154175407 | *Campylobacter curvus* 525.92 |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J. Bacteriol.* 178:6200-6208 (1996)). The CODH-I of *C. hydro-*

*genoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
| --- | --- | --- | --- |
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to *E. coli* and other enteric bacteria are multiple genes encoding up to four hydrogenases (Sawers, G., *Antonie Van Leeuwenhoek* 66:57-88 (1994); Sawers et al., *J. Bacteriol.* 164:1324-1331 (1985); Sawers and Boxer, *Eur. J Biochem.* 156:265-275 (1986); Sawers et al., *J Bacteriol.* 168: 398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., How *E. coli* is equipped to oxidize hydrogen under different redox conditions, *J Biol Chem* published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
| --- | --- | --- | --- |
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |
| HyaF | AAC74062.1 | 1787211 | Escherichia coli |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., *Appl Microbiol Biotechnol* 76(5):1035-42 (2007)). Hydrogenase activity in *E. coli* is also dependent upon the expression of the hyp genes whose corresponding proteins are involved in the assembly of the hydrogenase complexes (Jacobi et al., *Arch. Microbiol* 158:444-451 (1992); Rangarajan et al., *J. Bacteriol.* 190: 1447-1458 (2008)).

| Protein | GenBank ID | GI Number | Organism |
| --- | --- | --- | --- |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The *M. thermoacetica* hydrogenases are suitable for a host that lacks sufficient endogenous hydrogenase activity. *M. thermoacetica* can grow with $CO_2$ as the exclusive carbon source indicating that reducing equivalents are extracted from $H_2$ to enable acetyl-CoA synthesis via the Wood-Ljungdahl pathway (Drake, H. L., *J. Bacteriol.* 150:702-709 (1982); Drake and Daniel, Res. *Microbiol.* 155:869-883 (2004); Kellum and Drake, *J. Bacteriol.* 160:466-469 (1984)) (see FIG. 2A). *M. thermoacetica* has homologs to several hyp, hyc, and hyf genes from *E. coli*. The protein sequences encoded for by these genes are identified by the following GenBank accession numbers.

Proteins in *M. thermoacetica* whose genes are homologous to the *E. coli* hyp genes are shown below.

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

Proteins in *M. thermoacetica* that are homologous to the *E. coli* Hydrogenase 3 and/or 4 proteins are listed in the following table.

| Protein | GenBank ID | GI Number | Organism |
|---|---|---|---|
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |

In addition, several gene clusters encoding hydrogenase functionality are present in *M. thermoacetica* and their corresponding protein sequences are provided below.

| Protein | GenBank ID | GI Number | Organism |
|---|---|---|---|
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |

-continued

| Protein | GenBank ID | GI Number | Organism |
|---|---|---|---|
| Moth_1453 | YP_430306 | 83590297 | *Moorella thermoacetica* |
| Moth_1454 | YP_430307 | 83590298 | *Moorella thermoacetica* |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
|---|---|---|---|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
| --- | --- | --- | --- |
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high NaHCO$_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
| --- | --- | --- | --- |
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
| --- | --- | --- | --- |
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

Malic enzyme can be applied to convert CO$_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and CO$_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

| Protein | GenBank ID | GI Number | Organism |
| --- | --- | --- | --- |
| maeA | NP_415996 | 90111281 | *Escherichia coli* |
| maeB | NP_416958 | 16130388 | *Escherichia coli* |
| NAD-ME | P27443 | 126732 | *Ascaris suum* |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

| Protein | GenBank ID | GI Number | Organism |
| --- | --- | --- | --- |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

Enzymes, genes and methods for engineering pathways from succinyl-CoA to various products into a microorganism are now known in the art. The additional reducing equivalents obtained from CO and H$_2$, as disclosed herein, improve the yields of all these products when utilizing carbohydrate-based feedstock. For example, 1,4-butanediol can be produced from succinyl-CoA via previously disclosed pathways (see for example, Burk et al., WO 2008/115840). Exemplary enzymes for the conversion succinyl-CoA to 1,4-butanediol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA reductase (aldehyde forming), 1,4-butanediol dehydrogenase, succinyl-CoA reductase (alcohol forming), 4-hydroxybutyryl-CoA transferase, 4-hydroxybutyryl-CoA synthetase, 4-hydroxybutyryl-phosphate reductase, 4-hydroxybutyrate reductase, and 4-hydroxybutyryl-CoA reductase (alcohol forming). Succinate reductase can be additionally useful in converting succinate directly to the 1,4-butanediol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

1,3-butanediol can be produced from succinyl-CoA via the pathways have been described. Exemplary enzymes for the conversion succinyl-CoA to 1,3-butanediol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, crotonase, 3-hydroxybutyryl-CoA reductase (aldehyde forming), 3-hydroxybutyraldehyde reductase, succinyl-CoA reductase (alcohol forming), 4-hydroxybutyryl-CoA transferase, 4-hydroxybutyryl-CoA synthetase, 3-hydroxybutyryl-CoA hydrolase, 3-hydroxybutyryl-CoA synthetase, 3-hydroxybutyryl-CoA transferase, 3-hydroxybutyrate reductase, 3-hydroxybutyryl-CoA reductase (alcohol forming). Succinate reductase can be additionally useful by converting succinate directly to the 1,3-butanediol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

n-butanol can be produced from succinyl-CoA via known pathways. Exemplary enzymes for the conversion succinyl-CoA to butanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, butyryl-CoA dehydrogenase, butyryl-CoA hydrolase, butyryl-coA synthetase, butyryl-coA transferase, butyrate reductase, butyryl-CoA reductase (aldehyde forming), butyraldehyde reductase, butyryl-CoA reductase (alcohol forming), succinyl-CoA reductase (alcohol forming), 4-hydroxybutyryl-CoA transferase, 4-hydroxybutyryl-CoA synthetase. Succinate reductase can be additionally useful by converting succinate directly to the butanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

Isobutanol can be produced from succinyl-CoA via known pathways. Exemplary enzymes for the conversion succinyl-CoA to isobutanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, butyryl-CoA dehydrogenase, isobutyryl-CoA mutase, isobutyryl-CoA hydrolase, isobutyryl-coA synthetase, isobutyryl-coA transferase, isobutyrate reductase, isobutyryl-CoA reductase (aldehyde forming), isobutyraldehyde reductase, isobutyryl-CoA reductase (alcohol forming), succinyl-CoA reductase (alcohol forming), 4-hydroxybutyryl-CoA transferase, 4-hydroxybutyryl-CoA synthetase. Succinate reductase can be additionally useful by converting succinate directly to the isobutanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

Isopropanol can be produced from succinyl-CoA via known pathways. Exemplary enzymes for the conversion succinyl-CoA to isopropanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, crotonase, 3-hydroxybutyryl-CoA dehydrogenase, acetoacetyl-CoA synthetase, acetoacetate-CoA transferase, acetoacetyl-CoA hydrolase, acetoacetate decarboxylase, acetone reductase, succinyl-CoA reductase (alcohol forming), 4-hydroxybutyryl-CoA transferase, and 4-hydroxybutyryl-CoA synthetase. Succinate reductase can be additionally useful by converting succinate directly to the isopropanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

n-propanol can be produced from succinyl-CoA via known pathways. Exemplary enzymes for the conversion succinyl-CoA to n-propanol include propionaldehyde dehydrogenase, propanol dehydrogenase, propionyl-CoA:phosphate propanoyltransferase, propionyl-CoA hydrolase, propionyl-CoA transferase, propionyl-CoA synthetase, propionate kinase, propionate reductase, propionyl phosphate reductase, methylmalonyl-CoA mutase, methylmalonyl-CoA epimerase, methylmalonyl-CoA decarboxylase, and methylmalonyl-CoA carboxytransferase.

Adipate can be produced from succinyl-CoA via known pathways (see for example, Burgard et al., (WO/2009/151728A2). Exemplary enzymes for the conversion of succinyl-CoA to adipate include succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, 3-oxoadipyl-CoA transferase, 3-oxoadipate reductase, 3-hydroxyadipate dehydratase, and 2-enoate reductase.

6-aminocaproate can be produced from succinyl-CoA via known pathways. Exemplary enzymes for the conversion of succinyl-CoA to 6-aminocaproate include succinyl-CoA: acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, adipate reductase, adipyl-CoA reductase, CoA-dependent aldehyde dehydrogenase (e.g., adipyl-CoA reductase (aldehyde forming), transaminase (e.g., 6-aminocaproate transaminase), 6-aminocaproate dehydrogenase, 3-oxoadipyl-CoA transferase, 3-oxoadipate reductase, 3-hydroxyadipate dehydratase, and 2-enoate reductase.

Hexamethylenediamine can be produced from succinyl-CoA via known pathways. Exemplary enzymes for the conversion of succinyl-CoA to adipate include succinyl-CoA: acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, adipate reductase, adipyl-CoA reductase, CoA-dependent aldehyde dehydrogenase (e.g., adipyl-CoA reductase (aldehyde forming), transaminase (e.g., 6-aminocaproate transaminase), 6-aminocaproate dehydrogenase, 3-oxoadipyl-CoA transferase, 3-oxoadipate reductase, 3-hydroxyadipate dehydratase, 2-enoate reductase, 6-aminocaproyl-CoA/acyl-CoA transferase, 6-aminocaproyl-CoA synthase, 6-aminocaproyl-CoA reductase (aldehyde forming), hexamethylenediamine transaminase, and hexamethylenediamine dehydrogenase.

Enzymes, genes and methods for engineering pathways from glycolysis intermediates to various products into a microorganism are known in the art. The additional reducing equivalents obtained from CO and $H_2$, as described herein, improve the yields of all these products on carbohydrates. For example, glycerol and 1,3-propanediol can be produced from the glycolysis intermediate, dihydroxyacetone phosphate, via the pathways described in (Nakamura and Whited, Curr. Opin. Biotechnol. 14(5) 454-459 (2003)). Exemplary enzymes for the conversion of dihydroxyacetone phosphate to glycerol include glycerol-3-phosphate dehydrogenase and glycerol-3-phosphate phosphatase. Exemplary enzymes for the conversion of dihydroxyacetone phosphate to 1,3-propanediol include glycerol-3-phosphate dehydrogenase, glycerol-3-phosphate phosphatase, glycerol dehydratase, and 1,3-propanediol oxidoreductase.

In some embodiments, the reductive TCA cycle, coupled with carbon monoxide and hydrogenase enzymes, can be employed to allow syngas utilization by microorganisms. Synthesis gas (syngas) is a mixture of primarily $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels.

The $CO_2$-fixing reductive tricarboxylic acid (RTCA) cycle is an endergenic anabolic pathway of $CO_2$ assimilation, requiring reducing equivalents and ATP. The reductive TCA cycle was first reported in the green sulfur photosynthetic bacterium Chlorobium limicola (Evans et al., Proc. Natl. Acad. Sci. U.S.A. 55:928-934 (1966)). Similar pathways have been characterized in some prokaryotes (proteobacteria, green sulfur bacteria and thermophillic Knallgas bacteria) and sulfur-dependent archaea (Hugler et al., J. Bacteriol. 187:3020-3027 (2005; Hugler et al., Environ. Microbiol. 9:81-92 (2007). In some cases, reductive and oxidative (Krebs) TCA cycles are present in the same organism (Hugler et al., supra (2007); Siebers et al., J. Bacteriol. 186:2179-2194 (2004)). Some methanogens and obligate anaerobes possess incomplete oxidative or reductive TCA cycles that may function to synthesize biosynthetic intermediates (Ekiel et al., J. Bacteriol. 162:905-908 (1985); Wood et al., FEMS Microbiol. Rev. 28:335-352 (2004)).

The components of synthesis gas can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, and reduced flavodoxins. The reducing equivalents, particularly NADH, NADPH, and reduced ferredoxin, can serve as cofactors for the RTCA cycle enzymes (e.g., malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), and isocitrate dehydrogenase). The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: 1. conversion of citrate to oxaloacetate and acetyl-CoA, 2. conversion of fumarate to succinate, 3. conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP citrate lyase or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the $NAD(P)^+$ dependent decarboxylation of oxaloacetate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, NAD(P)H:ferredoxin oxidoreductase, carbon monoxide dehydrogenase, hydrogenase, and ferredoxin (see FIG. 8). Enzyme enzymes and the corresponding genes required for these activities are described herein above.

Carbon from syngas can be fixed via the reverse TCA cycle and components thereof. Specifically, the combination of certain syngas-utilization pathway components with the pathways for formation of isopropanol, butanol, 4-hydroxybutyrate, 1,3-butanediol, or 1,4-butanediol from acetyl-CoA results in high yields of these products by providing an efficient mechanism for fixing the carbon present in carbon dioxide, fed exogenously or produced endogenously from CO, into acetyl-CoA (see below).

Isopropanol: $3CO+6H_2 \rightarrow C_3H_8O+2H_2O$ $9CO+4H_2O \rightarrow C_3H_8O+6CO_2$ $9H_2+3CO_2 \rightarrow C_3H_8O+5H_2O$ Butanol: $4CO+8H_2 \rightarrow C_4H_{10}O+3H_2O$ $12CO+5H_2O \rightarrow C_4H_{10}O+8CO_2$ $12H_2+4CO_2 \rightarrow C_4H_{10}O+5H_2O$ 4-Hydroxybutyrate: $4CO+5H_2 \rightarrow C_4H_8O_3+H_2O$ $9CO+4H_2O \rightarrow C_4H_8O_3+5CO_2$ $9H_2+4CO_2 C_4H_8O_3+5H_2O$ 1,3 or 1,4-butanediol: $4CO+7H_2 \rightarrow C_4H_{10}O_2+2H_2O$ $11CO+5H_2O \rightarrow C_4H_{10}O_2+7CO_2$ $11H_2+4CO_2 \rightarrow C_4H_{10}O_2+6H_2O$ The organisms and conversion routes described herein provide an efficient means of converting synthesis gas and its components to products such as isopropanol, butanol, 4-hydroxybutyrate, 1,3-butanediol or 1,4-butanediol. Additional product molecules that can be produced by the teachings of this invention include but are not limited to ethanol, n-propanol, isobutanol, succinic acid, fumaric acid, malic acid, 3-hydroxypropionic acid, lactic acid, adipic acid, 6-aminocaproic acid, hexamethylenediamine, 3-hydroxyisobutyric acid, 2-hydroxyisobutyric acid, methacrylic acid, acrylic acid, and long chain hydrocarbons, alcohols, acids, and esters.

While generally described herein as a microbial organism that contains a 1,4-butanediol, 4-hydroxybutyrate, 1,3-butanediol, isopropanol pathway, or other product, it is understood that the invention additionally provides a non-naturally occurring microbial organism comprising at least one exogenous nucleic acid encoding a 1,4-butanediol, 4-hydroxybutyrate, 1,3-butanediol, or isopropanol pathway enzyme expressed in a sufficient amount to produce an intermediate of a 1,4-butanediol, 4-hydroxybutyrate, 1,3-butanediol, or isopropanol pathway, or other product intermediate. For example, as disclosed herein, a 1,4-butanediol, 4-hydroxybutyrate, 1,3-butanediol, or isopropanol pathway are exemplified in FIGS. 1-4. Therefore, in addition to a microbial organism containing a 1,4-butanediol, 4-hydroxybutyrate, 1,3-butanediol, or isopropanol pathway that produces 1,4-butanediol, 4-hydroxybutyrate, 1,3-butanediol, or isopropanol, the invention additionally provides a non-naturally occurring microbial organism comprising at least one exogenous nucleic acid encoding a 1,4-butanediol, 4-hydroxybutyrate, 1,3-butanediol, or isopropanol pathway enzyme, where the microbial organism produces a 1,4-butanediol, 4-hydroxybutyrate, 1,3-butanediol, or isopropanol pathway intermediate.

It is understood that any of the pathways disclosed herein, as described in the Examples and exemplified in the Figures, including the pathways of FIGS. 1-8, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 1,4-butanediol, 4-hydroxybutyrate, 1,3-butanediol, or isopropanol pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more 1,4-butanediol, 4-hydroxybutyrate, 1,3-butanediol, or isopropanol biosynthetic pathways. Depending on the host microbial organism chosen for biosynthesis, nucleic acids for some or all of a particular 1,4-butanediol, 4-hydroxybutyrate, 1,3-butanediol, or isopropanol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 1,4-butanediol, 4-hydroxybutyrate, 1,3-butanediol, or isopropanol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 1,4-butanediol, 4-hydroxybutyrate, 1,3-butanediol, or isopropanol.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizo-* bus oryzae, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the 1,4-butanediol, 4-hydroxybutyrate, 1,3-butanediol, or isopropanol biosynthetic pathway constituents of a selected host microbial organism, the non-naturally occurring microbial organisms of the invention will include at least one exogenously expressed 1,4-butanediol, 4-hydroxybutyrate, 1,3-butanediol, or isopropanol pathway-encoding nucleic acid and up to all encoding nucleic acids for one or more 1,4-butanediol, 4-hydroxybutyrate, 1,3-butanediol, or isopropanol biosynthetic pathways. For example, 1,4-butanediol, 4-hydroxybutyrate, 1,3-butanediol, or isopropanol biosynthesis can be established in a host deficient in a pathway enzyme or protein through exogenous expression of the corresponding encoding nucleic acid. In a host deficient in all enzymes or proteins of a 1,4-butanediol, 4-hydroxybutyrate, 1,3-butanediol, or isopropanol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 1,4-butanediol, 4-hydroxybutyrate, 1,3-butanediol, or isopropanol can be included.

Given the teachings and guidance provided herein, those skilled in the art will understand that the number of encoding nucleic acids to introduce in an expressible form will, at least, parallel the 1,4-butanediol, 4-hydroxybutyrate, 1,3-butanediol, or isopropanol pathway deficiencies of the selected host microbial organism. Therefore, a non-naturally occurring microbial organism of the invention can have one, two, three, four, five, six, seven, eight, or up to all nucleic acids encoding the enzymes or proteins constituting a 1,4-butanediol, 4-hydroxybutyrate, 1,3-butanediol, or isopropanol biosynthetic pathway disclosed herein. In some embodiments, the non-naturally occurring microbial organisms also can include other genetic modifications that facilitate or optimize 1,4-butanediol, 4-hydroxybutyrate, 1,3-butanediol, or isopropanol biosynthesis or that confer other useful functions onto the host microbial organism. One such other functionality can include, for example, augmentation of the synthesis of one or more of the 1,4-butanediol, 4-hydroxybutyrate, 1,3-butanediol, or isopropanol pathway precursors.

Generally, a host microbial organism is selected such that it produces the precursor of a 1,4-butanediol, 4-hydroxybutyrate, 1,3-butanediol, or isopropanol pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a 1,4-butanediol, 4-hydroxybutyrate, 1,3-butanediol, or isopropanol pathway.

In some embodiments, a non-naturally occurring microbial organism of the invention is generated from a host that contains the enzymatic capability to synthesize 1,4-butanediol, 4-hydroxybutyrate, 1,3-butanediol, or isopropanol. In this specific embodiment it can be useful to increase the synthesis or accumulation of a 1,4-butanediol, 4-hydroxybutyrate, 1,3-butanediol, or isopropanol pathway product to, for example, drive 1,4-butanediol, 4-hydroxybutyrate, 1,3-butanediol, or isopropanol pathway reactions toward 1,4-butanediol, 4-hydroxybutyrate, 1,3-butanediol, or isopropanol production. Increased synthesis or accumulation can be accomplished by, for example, overexpression of nucleic acids encoding one or more of the above-described 1,4-butanediol, 4-hydroxybutyrate, 1,3-butanediol, or isopropanol pathway enzymes or proteins. Over expression the enzyme or enzymes and/or protein or proteins of the 1,4-butanediol, 4-hydroxybutyrate, 1,3-butanediol, or isopropanol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 1,4-butanediol, 4-hydroxybutyrate, 1,3-butanediol, or isopropanol, through overexpression of one, two, three, four, five, six, seven, eight, up to all nucleic acids encoding 1,4-butanediol, 4-hydroxybutyrate, 1,3-butanediol, or isopropanol biosynthetic pathway enzymes or proteins. In addition, a non-naturally occurring organism can be generated by mutagenesis of an endogenous gene that results in an increase in activity of an enzyme in the 1,4-butanediol, 4-hydroxybutyrate, 1,3-butanediol, or isopropanol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a 1,4-butanediol, 4-hydroxybutyrate, 1,3-butanediol, or isopropanol biosynthetic pathway onto the microbial organism. Alternatively, encoding nucleic acids can be introduced to produce an intermediate microbial organism having the biosynthetic capability to catalyze some of the required reactions to confer 1,4-butanediol, 4-hydroxybutyrate, 1,3-butanediol, or isopropanol biosynthetic capability. For example, a non-naturally occurring microbial organism having a 1,4-butanediol, 4-hydroxybutyrate, 1,3-butanediol, or isopropanol biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, as desired, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of 1,4-butanediol, 4-hydroxybutyrate, 1,3-butanediol, or isopropanol as described herein, the non-naturally occurring microbial organisms and methods of the invention also can be utilized in various combinations with each other and with other microbial organisms and methods well known in the art to achieve product biosynthesis by other routes. For example, one alternative to produce 1,4-butanediol, 4-hydroxybutyrate, 1,3-butanediol, or isopropanol other than use of the 1,4-butanediol, 4-hydroxybutyrate, 1,3-butanediol, or isopropanol producers is through addition of another microbial organism capable of converting a 1,4-butanediol, 4-hydroxybutyrate, 1,3-butanediol, or isopropanol pathway intermediate to 1,4-butanediol, 4-hydroxybutyrate, 1,3-butanediol, or isopropanol. One such procedure includes, for example, the fermentation of a microbial organism that produces a 1,4-butanediol, 4-hydroxybutyrate, 1,3-butanediol, or isopropanol pathway intermediate. The 1,4-butanediol, 4-hydroxybutyrate, 1,3-butanediol, or isopropanol pathway intermediate can then be used as a substrate for a second microbial organism that converts the 1,4-butanediol, 4-hydroxybutyrate, 1,3-butanediol, or isopropanol pathway intermediate to 1,4-butanediol, 4-hydroxybutyrate, 1,3-butanediol, or isopropanol. The 1,4-butanediol, 4-hydroxybutyrate, 1,3-butanediol, or isopropanol pathway intermediate can be added directly to another culture of the second organism or the original culture of the 1,4-butanediol, 4-hydroxybutyrate, 1,3-butanediol, or isopropanol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 1,4-butanediol, 4-hydroxybutyrate, 1,3-butanediol, or isopropanol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 1,4-butanediol, 4-hydroxybutyrate, 1,3-butanediol, or isopropanol can be accomplished by constructing a microbial organism that contains biosynthetic pathways for conversion of one pathway intermediate to another pathway intermediate or the product. Alternatively, 1,4-butanediol, 4-hydroxybutyrate, 1,3-butanediol, or isopropanol also can be biosynthetically produced from microbial organisms through co-culture or co-fermentation using two organisms in the same vessel, where the first microbial organism produces a 1,4-butanediol, 4-hydroxybutyrate, 1,3-butanediol, or isopropanol intermediate and the second microbial organism converts the intermediate to 1,4-butanediol, 4-hydroxybutyrate, 1,3-butanediol, or isopropanol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 1,4-butanediol, 4-hydroxybutyrate, 1,3-butanediol, or isopropanol.

Sources of encoding nucleic acids for a 1,4-butanediol, 4-hydroxybutyrate, 1,3-butanediol, or isopropanol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *S. cerevisiae*, *B. subtilis*, *Candida boidinii*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 1,4-butanediol, 4-hydroxybutyrate, 1,3-butanediol, or isopropanol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 1,4-butanediol, 4-hydroxybutyrate, 1,3-butanediol, or isopropanol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 1,4-butanediol, 4-hydroxybutyrate, 1,3-butanediol, or isopropanol biosynthetic pathway exists in an unrelated species, 1,4-butanediol, 4-hydroxybutyrate, 1,3-butanediol, or isopropanol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 1,4-butanediol, 4-hydroxybutyrate, 1,3-butanediol, or isopropanol.

Methods for constructing and testing the expression levels of a non-naturally occurring 1,4-butanediol, 4-hydroxybutyrate, 1,3-butanediol, or isopropanol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of 1,4-butanediol, 4-hydroxybutyrate, 1,3-butanediol, or isopropanol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 1,4-butanediol, 4-hydroxybutyrate, 1,3-butanediol, or isopropanol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for enhancing carbon flux through acetyl-CoA that includes culturing the aforementioned non-naturally occurring microbial organisms under conditions and for a sufficient period of time to produce a product having acetyl-CoA as a building block. Such culturing can be in a substantially anaerobic culture medium and can include organisms having any number of exogenous nucleic acids as described herein above.

As described above, these cultured organisms can have an isopropanol pathway, a 1,3-butanediol pathway; a 1,4-butanediol pathway, a 4-hydroxybutrate pathway, or any other functional pathway that utilizes acetyl-CoA. The culturing of these microbial organism can be performed with a carbon feedstock selected from CO, $CO_2$, and $H_2$, synthesis gas comprising CO and $H_2$, and synthesis gas comprising CO, $CO_2$, and $H_2$.

Suitable purification and/or assays to test for the production of 1,4-butanediol, 4-hydroxybutyrate, 1,3-butanediol, or isopropanol can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The 1,4-butanediol, 4-hydroxybutyrate, 1,3-butanediol, or isopropanol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 1,4-butanediol, 4-hydroxybutyrate, 1,3-butanediol, or isopropanol producers can be cultured for the biosynthetic production of 1,4-butanediol, 4-hydroxybutyrate, 1,3-butanediol, or isopropanol.

For the production of 1,4-butanediol, 4-hydroxybutyrate, 1,3-butanediol, or isopropanol, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 1,4-butanediol, 4-hydroxybutyrate, 1,3-butanediol, or isopropanol.

In addition to renewable feedstocks such as those exemplified above, the 1,4-butanediol, 4-hydroxybutyrate, 1,3-butanediol, or isopropanol microbial organisms of the invention also can be modified for growth on syngas as its source of carbon. In this specific embodiment, one or more proteins or enzymes are expressed in the 1,4-butanediol, 4-hydroxybutyrate, 1,3-butanediol, or isopropanol producing organisms to provide a metabolic pathway for utilization of syngas or other gaseous carbon source.

Given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 1,4-butanediol, 4-hydroxybutyrate, 1,3-butanediol, or isopropanol and any of the intermediate metabolites in the 1,4-butanediol, 4-hydroxybutyrate, 1,3-butanediol, or isopropanol pathway. All that is required is to engineer in one or more of the required enzyme or protein activities to achieve biosynthesis of the desired compound or intermediate including, for example, inclusion of some or all of the 1,4-butanediol, 4-hydroxybutyrate, 1,3-butanediol, or isopropanol biosynthetic pathways. Accordingly, the invention provides a non-naturally occurring microbial organism that produces and/or secretes 1,4-butanediol, 4-hydroxybutyrate, 1,3-butanediol, or isopropanol when grown on a carbohydrate or other carbon source and produces and/or secretes any of the intermediate metabolites shown in the 1,4-butanediol, 4-hydroxybutyrate, 1,3-butanediol, or isopropanol pathway when grown on a carbohydrate or other carbon source. The 1,4-butanediol, 4-hydroxybutyrate, 1,3-butanediol, or isopropanol producing microbial organisms of the invention can initiate synthesis from an intermediate.

The non-naturally occurring microbial organisms of the invention are constructed using methods well known in the art as exemplified herein to exogenously express at least one nucleic acid encoding a 1,4-butanediol, 4-hydroxybutyrate, 1,3-butanediol, or isopropanol pathway enzyme or protein in sufficient amounts to produce 1,4-butanediol, 4-hydroxybutyrate, 1,3-butanediol, or isopropanol. It is understood that the microbial organisms of the invention are cultured under conditions sufficient to produce 1,4-butanediol, 4-hydroxybutyrate, 1,3-butanediol, or isopropanol. Following the teachings and guidance provided herein, the non-naturally occurring microbial organisms of the invention can achieve biosynthesis of 1,4-butanediol, 4-hydroxybutyrate, 1,3-butanediol, or isopropanol resulting in intracellular concentrations between about 0.1-200 mM or more. Generally, the intracellular concentration of 1,4-butanediol, 4-hydroxybutyrate, 1,3-butanediol, or isopropanol is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 1,4-butanediol, 4-hydroxybutyrate, 1,3-butanediol, or isopropanol producers can synthesize 1,4-butanediol, 4-hydroxybutyrate, 1,3-butanediol, or isopropanol at intracellular concentrations of 5-10 mM or more as well as all other concentrations exemplified herein. It is understood that, even though the above description refers to intracellular concentrations, 1,4-butanediol, 4-hydroxybutyrate, 1,3-butanediol, or isopropanol producing microbial organisms can produce 1,4-butanediol, 4-hydroxybutyrate, 1,3-butanediol, or isopropanol intracellularly and/or secrete the product into the culture medium.

In addition to the culturing and fermentation conditions disclosed herein, growth condition for achieving biosynthesis of 1,4-butanediol, 4-hydroxybutyrate, 1,3-butanediol, or isopropanol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonio-acetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 1,4-butanediol, 4-hydroxybutyrate, 1,3-butanediol, or isopropanol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 1,4-butanediol, 4-hydroxybutyrate, 1,3-butanediol, or isopropanol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 1,4-butanediol, 4-hydroxybutyrate, 1,3-butanediol, or isopropanol. Generally, and as with non-continuous culture procedures, the continuous and/or near-continuous production of 1,4-butanediol, 4-hydroxybutyrate, 1,3-butanediol, or isopropanol will include culturing a non-naturally occurring 1,4-butanediol, 4-hydroxybutyrate, 1,3-butanediol, or isopropanol producing organism of the invention in sufficient nutrients and medium to sustain and/or nearly sustain growth in an exponential phase. Continuous culture under such conditions can be included, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 1,4-butanediol, 4-hydroxybutyrate, 1,3-butanediol, or isopropanol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 1,4-butanediol, 4-hydroxybutyrate, 1,3-butanediol, or isopropanol producers of the invention for continuous production of substantial quantities of 1,4-butanediol, 4-hydroxybutyrate, 1,3-butanediol, or isopropanol, the 1,4-butanediol, 4-hydroxybutyrate, 1,3-butanediol, or isopropanol producers also can be, for example, simultaneously subjected to chemical synthesis procedures to convert the product to other compounds or the product can be separated from the fermentation culture and sequentially subjected to chemical conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,4-butanediol, 4-hydroxybutyrate, 1,3-butanediol, or isopropanol.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a 1,4-butanediol, 4-hydroxybutyrate, 1,3-butanediol, or isopropanol pathway can be introduced into a host organism. In some cases, it can be desirable to modify an activity of a 1,4-butanediol, 4-hydroxybutyrate, 1,3-butanediol, or isopropanol pathway enzyme or protein to increase production of 1,4-butanediol, 4-hydroxybutyrate, 1,3-butanediol, or isopropanol. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 1,4-butanediol, 4-hydroxybutyrate, 1,3-butanediol, or isopropanol pathway enzyme or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or Endo V to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res.* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng.* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

EXAMPLES

Non-Naturally Occurring Organism to Produce 1,3-Butanediol, Isopropanol, 4-Hydroxybutyrate or 1,4-Butanediol From Acetyl-CoA In the following Examples, pathways for formation of 1,3-BDO (FIG. 1A), isopropanol (FIG. 1B), 4-HB (FIG. 1C), and 1,4-BDO (FIG. 1D) are described from the intermediate, acetyl-CoA. The maximum theoretical yield of each of these product molecules from glucose is 1 mole per mole using only the metabolic pathways proceeding from acetyl-CoA as described herein. Specifically, 2 moles of acetyl-CoA are derived per mole of glucose via glycolysis and 2 moles of acetyl-CoA are used per mole of 1,3-butanediol, isopropanol, 4-hydroxybutyrate, or 1,4-butanediol. The net conversions are described by the following stoichiometric equations:

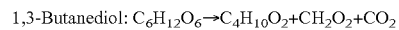

1,3-Butanediol: $C_6H_{12}O_6 \rightarrow C_4H_{10}O_2 + CH_2O_2 + CO_2$

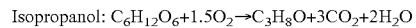

Isopropanol: $C_6H_{12}O_6 + 1.5O_2 \rightarrow C_3H_8O + 3CO_2 + 2H_2O$

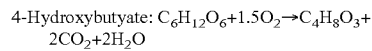

4-Hydroxybutyate: $C_6H_{12}O_6 + 1.5O_2 \rightarrow C_4H_8O_3 + 2CO_2 + 2H_2O$

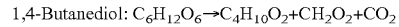

1,4-Butanediol: $C_6H_{12}O_6 \rightarrow C_4H_{10}O_2 + CH_2O_2 + CO_2$

Example I 1,3-Butanediol Synthesis Pathway 1,3-butanediol production can be achieved in recombinant *E. coli* by alternative pathways as described in FIG. 1A. All pathways first convert two molecules of acetyl-CoA into one molecule of acetoacetyl-CoA employing a thiolase.

Acetoacetyl-CoA thiolase converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol.* 21:796-802 (2003), thlA and thlB from *C. acetobutylicum* (Hanai et al., *Appl. Environ. Microbiol.* 73:7814-7818 (2007); Winzer et al., *J. Mol. Microbiol. Biotechnol.* 2:531-541 (2000), and ERG10 from *S. cerevisiae* (Hiser et al., *J. Biol. Chem.* 269:31383-31389 (1994).

| Protein | GenBank ID | GI number | Organism |
|---|---|---|---|
| AtoB | NP_416728 | 16130161 | *Escherichia coli* |
| ThlA | NP_349476.1 | 15896127 | *Clostridium acetobutylicum* |
| ThlB | NP_149242.1 | 15004782 | *Clostridium acetobutylicum* |
| ERG10 | NP_015297 | 6325229 | *Saccharomyces cerevisiae* |

Acetoacetyl-CoA can first be reduced to 3-hydroxybutyryl-CoA by acetoacetyl-CoA reductase (ketone reducing). This can subsequently be converted to 3-hydroxybutyraldehyde via a CoA-dependent aldehyde reductase called 3-hydroxybutyryl-CoA reductase. 3-hydroxybutyraldehyde can eventually be reduced to the product 1,3-BDO by 3-hydroxybutyraldehyde reductase. Alternatively, 3-hydroxybutyryl-CoA can be reduced directly to 1,3-BDO by an alcohol-forming CoA-dependent 3-hydroxybutyryl-CoA reductase. The gene candidates for each of the steps in the pathway are described below.

Acetoacetyl-CoA reductase catalyzing the reduction of acetoacetyl-CoA to 3-hydroxybutyryl-CoA participates in the acetyl-CoA fermentation pathway to butyrate in several species of *Clostridia* and has been studied in detail (Jones and Woods, *Microbiol. Rev.* 50:484-524 (1986)). The enzyme from *Clostridium acetobutylicum*, encoded by hbd, has been cloned and functionally expressed in *E. coli* (Youngleson et al., *J. Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock and Schulz, *Methods Enzymol.* 71 Pt C:403-411 (1981)). Yet other gene candidates demonstrated to reduce acetoacetyl-CoA to 3-hydroxybutyryl-CoA are phbB from *Zoogloea ramigera* (Ploux et al., *Eur. J. Biochem.* 174:177-182 (1988)) and phaB from *Rhodobacter sphaeroides* (Alber et al., *Mol. Microbiol.* 61:297-309 (2006)). The former gene candidate is NADPH-dependent, its nucleotide sequence has been determined (Peoples and Sinskey, *Mol. Microbiol.* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., *Eur. J. Biochem.* 174:177-182 (1988)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J. Biol. Chem.* 207:631-638 (1954)).

| Protein | Genbank ID | GI number | Organism |
|---|---|---|---|
| fadB | P21177.2 | 119811 | *Escherichia coli* |
| fadJ | P77399.1 | 3334437 | *Escherichia coli* |
| Hbd2 | EDK34807.1 | 146348271 | *Clostridium kluyveri* |
| Hbd1 | EDK32512.1 | 146345976 | *Clostridium kluyveri* |
| hbd | P52041.2 | | *Clostridium acetobutylicum* |
| HSD17B10 | O02691.3 | 3183024 | *Bos Taurus* |
| phbB | P23238.1 | 130017 | *Zoogloea ramigera* |
| phaB | YP_353825.1 | 77464321 | *Rhodobacter sphaeroides* |

A number of similar enzymes have been found in other species of *Clostridia* and in *Metallosphaera sedula* (Berg et al., *Science* 318:1782-1786 (2007).

| Protein | GenBank ID | GI number | Organism |
|---|---|---|---|
| hbd | NP_349314.1 | NP_349314.1 | *Clostridium acetobutylicum* |
| hbd | AAM14586.1 | AAM14586.1 | *Clostridium beijerinckii* |
| Msed_1423 | YP_001191505 | YP_001191505 | *Metallosphaera sedula* |
| Msed_0399 | YP_001190500 | YP_001190500 | *Metallosphaera sedula* |
| Msed_0389 | YP_001190490 | YP_001190490 | *Metallosphaera sedula* |
| Msed_1993 | YP_001192057 | YP_001192057 | *Metallosphaera sedula* |

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *J. Bacteriol.* 179:2969-2975 (1997), the *Acinetobacter* sp. M-1 fatty acyl-CoA reductase (Ishige et al., *Appl. Environ. Microbiol.* 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 1778:871-880 (1996)). SucD of *P. gingivalis* is another succinate semialdehyde dehydrogenase (Takahashi et al., *J. Bacteriol.* 182:4704-4710 (2000). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:45-55 (1972); Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.* 71:58-68 (2007)).

| Protein | GenBank ID | GI number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al., *J. Bacteriol.* 188: 8551-8559 (2006); Hugler et al., *J. Bacteriol.* 184:2404-2410 (2002)). The enzyme is encoded by Msed_0709 in *Metal-* losphaera sedula (Alber et al., supra (2006); Berg et al., Science 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WO 2007/141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl. Environ. Microbiol.* 65:4973-4980 (1999). This enzyme has been reported to reduce acetyl-CoA and butyryl-CoA to their corresponding aldehydes. This gene is very similar to cutE that encodes acetaldehyde dehydrogenase of *Salmonella typhimurium* and *E. coli* (Toth et al., supra).

| Protein | GenBank ID | GI number | Organism |
| --- | --- | --- | --- |
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 9473535 | *Clostridium beijerinckii* |
| eutE | AAA80209 | 687645 | *Salmonella typhimurium* |
| eutE | P77445 | 2498347 | *Escherichia coli* |

Enzymes exhibiting 3-hydroxybutyraldehyde reductase activity (EC 1.1.1.61) have been characterized in *Ralstonia eutropha* (Bravo et al., *J. Forensic Sci.* 49:379-387 (2004)), *Clostridium kluyveri* (Wolff and Kenealy, *Protein Expr. Purif.* 6:206-212 (1995)) and *Arabidopsis thaliana* (Breitkreuz et al., *J. Biol. Chem.* 278:41552-41556 (2003). Yet another gene candidate is the alcohol dehydrogenase adhI from *Geobacillus thermoglucosidasius* (Jeon et al., *J. Biotechnol.* 135:127-133 (2008).

| Protein | GenBank ID | GI number | Organism |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |
| adhI | AAR91477.1 | 40795502 | *Geobacillus thermoglucosidasius* M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.* 352:905-917 (2005)). The reversibility of the human 3-hydroxyisobutyrate dehydrogenase was demonstrated using isotopically-labeled substrate (Manning and Pollitt, *Biochem. J.* 231:481-484 (1985)). Additional genes encoding this enzyme include 3hidh in *Homo sapiens* (Hawes et al., *Methods Enzymol.* 324:218-228 (2000) and *Oryctolagus cuniculus* (Hawes et al., supra; Chowdhury et al., *Biosci. Biotechnol.* 60:2043-2047 (1996), mmsb in *Pseudomonas aeruginosa*, and dhat in *Pseudomonas putida* (Aberhart and Hsu, *J. Chem. Soc. [Perkin 1]* 6:1404-1406 (1979); Chowdhury et al., supra; Chowdhury et al., *Biosci. Biotechnol. Biochem.* 67:438-441 (2003)).

| Protein | GenBank ID | GI number | Organism |
| --- | --- | --- | --- |
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Other exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *App. Environ. Microbiol.* 66:5231-5235 (2000), ADH2 from *Saccharomyces cerevisiae* (Atsumi et al., *Nature* 451:86-89 (2008)), yqhD from *E. coli* which has preference for molecules longer than C3 (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J. Biol. Chem.* 283:7346-7353 (2008)). ADH1 from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol.* 22:249-254 (1985)). The protein sequences for each of these exemplary gene products, if available, can be found using the following GenBank accession numbers:

| Protein | GenBank ID | GI number | Organism |
| --- | --- | --- | --- |
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Exemplary two-step oxidoreductases that convert an acyl-CoA to alcohol include those that transform substrates such as acetyl-CoA to ethanol (e.g., adhE from *E. coli* (Kessler et al., *FEBS Lett.* 281:59-63 (1991)) and butyryl-CoA to butanol (e.g. adhE2 from *C. acetobutylicum* (Fontaine et al., *J. Bacteriol.* 184:821-830 (2002)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)).

| Protein | GenBank ID | GI number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, Eur. J. Biochem. 215:633-643 (1993). This enzyme, with a mass of 300 kDa, is highly substrate-specific and shows little sequence similarity to other known oxidoreductases (Hugler, supra (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI number | Organism |
|---|---|---|---|
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiol.* 122:635-644 (2000)).

| | | | |
|---|---|---|---|
| FAR | AAD38039.1 | 5020215 | *Simmondsia chinensis* |

The reduction of acetoacetyl-CoA into 3-oxobutyraldehyde can be accomplished via the CoA-dependent aldehyde forming acetoacetyl-CoA reductase. 3-oxobutyraldehyde is next reduced to 3-hydroxybutyraldehyde by 3-oxobutyraldehyde reductase (ketone reducing), and eventually, this intermediate is reduced to 1,3-butanediol by a 3-hydroxybutyraldehyde reductase. The candidates for each of these steps are listed below.

The enzymes for acetoacetyl-CoA reductase (CoA-dependent, aldehyde forming) are the same as that for the aldehyde forming 3-hydroxybutyryl-CoA reductase described above.

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel and Schlegel, *Eur. J. Biochem.* 130:329-334 (1983)). Conversion of the oxo functionality to the hydroxyl group can also be catalyzed by 2-keto 1,3-butanediol reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). All of these enzymes are good candidates for 3-oxobutyraldehyde reductase. An additional candidate for these steps is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase that converts acetone to isopropanol as was shown in *C. beijerinckii* (Ismaiel et al., *J. Bacteriol.* 175:5097-5105 (1993) and *T. brockii* (Lamed and Zeikus, *Biochem. J.* 195:183-190 (1981); Peretz and Burstein, *Biochemistry* 28:6549-6555 (1989)). Methyl ethyl ketone (MEK) reductase, or alternatively, 2-butanol dehydrogenase, catalyzes the reduction of MEK to form 2-butanol. Exemplary enzymes can be found in *Rhodococcus ruber* (Kosjek et al., *Biotechnol. Bioeng.* 86:55-62 (2004) and *Pyrococcus furiosus* (van der et al. 2001).

| Protein | GenBank ID | GI number | Organism |
|---|---|---|---|
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* |
| adh | P14941.1 | 113443 | *Thermoanaerobacter brockii* |
| sadh | CAD36475 | 21615553 | *Rhodococcus ruber* |
| adhA | 3288810 | AAC25556 | *Pyrococcus furiosus* |

Acetoacetyl-CoA can also be reduced to 4-hydroxy,2-butanone by the CoA-dependent, alcohol forming acetoacetyl-CoA reductase. This intermediate is then reduced to 1,3-butanediol by 4-hydroxybutanone reductase. 4-hydroxybutanone can also be formed from 3-oxobutyraldehyde by an aldehyde reducing 3-oxobutyraldehyde reductase.

Enzymes for acetoacetyl-CoA reductase (CoA-dependent, alcohol forming) are the same as those for the alcohol-forming 3-hydroxybutyryl-CoA reductase described herein.

The enzymes for 4-hydroxybutanone reductase are the same as those described for 3-oxobutyraldehyde reductase. Additionally, a number of organisms can catalyze the reduction of 4-hydroxy,2-butanone to 1,3-butanediol, including those belonging to the genus *Bacillus*, *Brevibacterium*, *Candida*, and *Klebsiella* among others, as described by Matsuyama et al. (1).

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000), ADH2 from *Saccharomyces cerevisiae* (Atsumi et al., *Nature* 451:86-89 (2008), yqhD from *E. coli* which has preference for molecules longer than C3 (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992). The gene product of yqhD catalyzes the reduction of acetaldehyde, malondialdehyde, propionaldehyde, butyraldehyde, and acrolein using NADPH as the cofactor (Perez et al., J. Biol. Chem. 283:7346-7353 (2008)). ADH1 from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol.* 22:249-254 (1985)).

The protein sequences for each of these exemplary gene products, if available, can be found using the following GenBank accession numbers:

| Protein | GenBank ID | GI number | Organism |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Acetoacetyl-CoA can be converted into acetoacetate by acetoacetyl-CoA transferase, hydrolase, or synthetase. Acetoacetate can next be reduced to 3-hydroxybutyrate by 3-hydroxybutyrate dehydrogenase and that gets further converted into 3-hydroxybutyraldehyde by 3-hydroxybutyrate reductase. Alternatively, acetoacetate can be reduced to 3-oxobutyraldehyde by acetoacetate reductase. 3-hydroxybutyryl-CoA can also be transformed into 3-hydroxybutyrate via 3-hydroxybutyryl-CoA transferase, hydrolase, or synthetase.

The conversion of acetoacetyl-CoA to acetoacetate can be carried out by an acetoacetyl-CoA transferase which conserves the energy stored in the CoA-ester bond. Several exemplary transferase enzymes capable of catalyzing this transformation are provided below. These enzymes either naturally exhibit the desired acetoacetyl-CoA transferase activity or they can be engineered via directed evolution to accept acetetoacetyl-CoA as a substrate with increased efficiency. Such enzymes, either naturally or following directed evolution, are also suitable for catalyzing the conversion of 3-hydroxybutyryl-CoA to 3-hydroxybutyrate via a transferase mechanism.

Acetoacetyl-CoA:acetyl-CoA transferase naturally converts acetoacetyl-CoA and acetate to acetoacetate and acetyl-CoA. This enzyme may also accept 3-hydroxybutyryl-CoA as a substrate or could be engineered to do so. Exemplary enzymes include the gene products of atoAD from *E. coli* (Hanai et al., *Appl Environ Microbiol* 73:7814-7818 (2007)), ctfAB from *C. acetobutylicum* (Jojima et al., *Appl Microbiol Biotechnol* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below.

| Protein | GenBank ID | GI number | Organism |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., Genomics 68:144-151 (2000); Tanaka et al., *Mol. Hum. Reprod.* 8:16-23 (2002)). Information related to these proteins and genes is shown below:

| Protein | GenBank ID | GI number | Organism |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Additional suitable acetoacetyl-CoA and 3-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below:

| Protein | GenBank ID | GI number | Organism |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA can be hydrolyzed to acetoacetate by acetoacetyl-CoA hydrolase. Similarly, 3-hydroxybutyryl-CoA can be hydrolyzed to 3-hydroxybutyate by 3-hydroxybutyryl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding succinyl-CoA:3-ketoacid-CoA transferases and acetoacetyl-CoA:acetyl-CoA transferases can also be used as hydrolases with certain mutations to change their function. The acetyl-CoA hydrolase, ACH1, from *S. cerevisiae* represents another candidate hydrolase (Buu et al., *J. Biol. Chem.* 278:17203-17209 (2003)). Information related to these proteins and genes is shown below:

| Protein | GenBank ID | GI number | Organism |
|---|---|---|---|
| Acot12 | NP_570103.1 | 18543355 | *Rattus norvegicus* |
| GctA | CAA57199 | 559392 | *Acidaminococcus fermentans* |
| GctB | CAA57200 | 559393 | *Acidaminococcus fermentans* |
| ACH1 | NP_009538 | 6319456 | *Saccharomyces cerevisiae* |

Another hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)) including 3-hydroxybutyryl-CoA (Tseng et al., *Appl. Environ. Microbiol.* 75(10):3137-3145 (2009)). A similar enzyme has also been characterized in the rat liver (Deana, *Biochem. Int.* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). Information related to these proteins and genes is shown below:

| Protein | GenBank ID | GI number | Organism |
|---|---|---|---|
| Acot8 | CAA15502 | 3191970 | *Homo sapiens* |
| TesB | NP_414986 | 16128437 | *Escherichia coli* |
| Acot8 | NP_570112 | 51036669 | *Rattus norvegicus* |
| TesA | NP_415027 | 16128478 | *Escherichia coli* |
| YbgC | NP_415264 | 16128711 | *Escherichia coli* |
| PaaI | NP_415914 | 16129357 | *Escherichia coli* |
| YbdB | NP_415129 | 16128580 | *Escherichia coli* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994). Candidate genes by sequence homology include hibch of *Saccharomyces cerevisiae* and BC_2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below:

| Protein | GenBank ID | GI number | Organism |
|---|---|---|---|
| Hibch | Q5XIE6.2 | 146324906 | *Rattus norvegicus* |
| Hibch | Q6NVY1.2 | 146324905 | *Homo sapiens* |
| Hibch | P28817.2 | 2506374 | *Saccharomyces cerevisiae* |
| BC_2292 | AP09256 | 29895975 | *Bacillus cereus* ATCC 14579 |

An alternative method for removing the CoA moiety from acetoacetyl-CoA or 3-hydroxybutyryl-CoA is to apply a pair of enzymes such as a phosphate-transferring acyltransferase and a kinase to impart acetoacetyl-CoA or 3-hydroxybutyryl-CoA synthetase activity. This activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10):3137-3145 (2009)). Specifically, the ptb gene from *C. acetobutylicum* encodes an enzyme that can convert an acyl-CoA into an acyl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186:2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below:

| Protein | GenBank ID | GI number | Organism |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below:

| Protein | GenBank ID | GI number | Organism |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

The hydrolysis of acetoacetyl-CoA or 3-hydroxybutyryl-CoA can alternatively be carried out by a single enzyme or enzyme complex that exhibits acetoacetyl-CoA or 3-hydroxybutyryl-CoA synthetase activity. This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Information related to these proteins and genes is shown below:

| Protein | GenBank ID | GI number | Organism |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318: 1782-1786 (2007)). This function has been tentatively assigned to the Msed_1422 gene. Information related to these proteins and genes is shown below:

| Protein | GenBank ID | GI number | Organism |
|---|---|---|---|
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus*, *H. maris-* mortui and *P. aerophilum* have all been cloned, functionally expressed, and characterized in *E. coli* (Musfeldt et al., supra; Brasen et al., supra (2004)). Information related to these proteins and genes is shown below:

| Protein | GenBank ID | GI number | Organism |
|---------|------------|-----------|----------|
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

The conversion of 3-hydroxybutyrate to 3-hydroxybutyraldehyde can be carried out by a 3-hydroxybutyrate reductase.

Similarly, the conversion of acetoacetate to acetoacetaldehyde can be carried out by an acetoacetate reductase. A suitable enzyme for these transformations is the aryl-aldehyde dehydrogenase, or equivalently a carboxylic acid reductase, from *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)). Information related to these proteins and genes is shown below:

| Protein | GI Number | genbank ID | Organism |
|---------|-----------|------------|----------|
| Car | 40796035 | AAR91681.1 | *Nocardia iowensis* (sp. NRRL 5646) |
| Npt | 114848891 | ABI83656.1 | *Nocardia iowensis* (sp. NRRL 5646) |

Additional car and npt genes can be identified based on sequence homology.

| Protein | GENBANK ID | GI Number | Organism |
|---------|------------|-----------|----------|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial. Information related to these proteins and genes is shown below:

| Protein | GI number | genbank ID | Organism |
|---------|-----------|------------|----------|
| griC | 182438036 | YP_001825755.1 | *Streptomyces griseus* subsp. *griseus* NBRC 13350 |

| Protein | GI number | genbank ID | Organism |
|---------|-----------|------------|----------|
| griD | 182438037 | YP_001825756.1 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in Saccharomyces cerevisiae (Morris et al., Gene 98:141-145 (1991)), Candida albicans (Guo et al., Mol. Genet. Genomics 269:271-279 (2003)), and Schizosaccharomyces pombe (Ford et al., Curr. Genet. 28:131-137 (1995)). The AAR from S. pombe exhibited significant activity when expressed in E. coli (Guo et al., Yeast 21:1279-1288 (2004)). The AAR from Penicillium chrysogenum accepts S-carboxymethyl-L-cysteine as an alternate substrate, but did not react with adipate, L-glutamate or diaminopimelate (Hijarrubia et al., J. Biol. Chem. 278:8250-8256 (2003)). The gene encoding the P. chrysogenum PPTase has not been identified to date. Information related to these proteins and genes is shown below:

| Protein | GI number | genbank ID | Organism |
|---------|-----------|------------|----------|
| LYS2 | 171867 | AAA34747.1 | Saccharomyces cerevisiae |
| LYS5 | 1708896 | P50113.1 | Saccharomyces cerevisiae |
| LYS2 | 2853226 | AAC02241.1 | Candida albicans |
| LYS5 | 28136195 | AAO26020.1 | Candida albicans |
| Lys1p | 13124791 | P40976.3 | Schizosaccharomyces pombe |
| Lys7p | 1723561 | Q10474.1 | Schizosaccharomyces pombe |
| Lys2 | 3282044 | CAA74300.1 | Penicillium chrysogenum |

Any of these CAR or CAR-like enzymes can exhibit 3-hydroxybutyrate or acetoacetate reductase activity or can be engineered to do so.

The requisite 3-hydroxybutyrate dehydrogenase catalyzes the reduction of acetoacetate to form 3-hydroxybutyrate. Exemplary enzymes can be found in Rhodococcus ruber (Kosjek et al., Biotechnol Bioeng. 86:55-62 (2004)) and Pyrococcus furiosus (van der et al., Eur. J. Biochem. 268:3062-3068 (2001)). Additional secondary alcohol dehydrogenase enzymes capable of this transformation include adh from C. beijerinckii (Hanai et al., Appl Environ Microbiol 73:7814-7818 (2007); Jojima et al., Appl Microbiol Biotechnol 77:1219-1224 (2008)) and adh from Thermoanaerobacter brockii (Hanai et al., Appl Environ Microbiol 73:7814-7818 (2007); Peretz et al., Anaerobe 3:259-270 (1997)). The cloning of the bdhA gene from Rhizobium (Sinorhizobium) Meliloti into E. coli conferred the ability to utilize 3-hydroxybutyrate as a carbon source (Aneja and Charles, J. Bacteriol. 181(3):849-857 (1999)). Additional 3-hydroxybutyrate dehydrogenase can be found in Pseudomonas fragi (Ito et al., J. Mol. Biol. 355(4) 722-733 (2006)) and Ralstonia pickettii (Takanashi et al., Antonie van Leeuwenoek, 95(3):249-262 (2009)). Information related to these proteins and genes is shown below:

| Protein | Genbank ID | GI Number | Organism |
|---------|------------|-----------|----------|
| Sadh | CAD36475 | 21615553 | Rhodococcus rubber |
| AdhA | AAC25556 | 3288810 | Pyrococcus furiosus |
| Adh | P14941.1 | 113443 | Thermoanaerobobacter brockii |
| Adh | AAA23199.2 | 60592974 | Clostridium beijerinckii |
| BdhA | NP_437676.1 | 16264884 | Rhizobium (Sinorhizobium) Meliloti |
| PRK13394 | BAD86668.1 | 57506672 | Pseudomonas fragi |
| Bdh1 | BAE72684.1 | 84570594 | Ralstonia pickettii |
| Bdh2 | BAE72685.1 | 84570596 | Ralstonia pickettii |
| Bdh3 | BAF91602.1 | 158937170 | Ralstonia pickettii |

Example II

Isopropanol Synthesis Pathway

This Example shows how isopropanol production was achieved in recombinant E. coli following expression of two heterologous genes from C. acetobutylicum (thl and adc encoding acetoacetyl-CoA thiolase and acetoacetate decarboxylase, respectively) and one from C. beijerinckii (adh encoding a secondary alcohol dehydrogenase), along with the increased expression of the native atoA and atoD genes which encode acetoacetyl-CoA: acetate: CoA transferase activity (Hanai et al., Appl. Environ. Microbiol. 73:7814-7818 (2007)). The acetoacetyl-CoA thiolase (AtoB) enzymes are described herein above.

The conversion of acetoacetyl-CoA to acetoacetate or of 4-hydroxybutyryl-CoA to 4-hydroxybutyrate can be carried out by an acetoacetyl-CoA transferase or 4-hydroxybutyryl-CoA transferase, respectively. These enzymes conserve the energy stored in the CoA-ester bonds of acetoacetyl-CoA and 4-hydroxybutyryl-CoA. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. Acetoacetyl-CoA transferase catalyzes the conversion of acetoacetyl-CoA to acetoacetate while transferring the CoA moiety to a CoA acceptor molecule. Several exemplary transferase enzymes capable of catalyzing this transformation are provided below. These enzymes either naturally exhibit the desired acetoacetyl-CoA transferase activity or they can be engineered via directed evolution to accept acetoacetyl-CoA as a substrate with increased efficiency. Such enzymes, either naturally or following directed evolution, are also suitable for catalyzing the conversion of 4-hydroxybutyryl-CoA to 4-hydroxybutyrate via a transferase mechanism.

In one embodiment an exemplary acetoacetyl-CoA transferase is acetoacetyl-CoA:acetate-CoA transferase. This enzyme naturally converts acetate to acetyl-CoA while converting acetoacetyl-CoA to acetoacetate. In another embodiment, a succinyl-CoA:3-ketoacid CoA transferase (SCOT) catalyzes the conversion of the 3-ketoacyl-CoA, acetoacetyl-CoA, to the 3-ketoacid, acetoacetate.

Acetoacetyl-CoA:acetyl-CoA transferase naturally converts acetoacetyl-CoA and acetate to acetoacetate and acetyl-CoA. This enzyme can also accept 3-hydroxybutyryl-CoA as a substrate or could be engineered to do so. Exemplary enzymes include the gene products of atoAD from E. coli (Hanai et al., Appl Environ Microbiol 73:7814-7818 (2007)), ctfAB from C. acetobutylicum (Jojima et al., Appl Microbiol Biotechnol 77:1219-1224 (2008)), and ctfAB from

*Clostridium saccharoperbutylacetonicum* (Kosaka et al., *Biosci. Biotechnol Biochem.* 71:58-68 (2007)). Information related to these proteins and genes is shown below:

| Protein | GENBANK ID | GI NUMBER | ORGANISM |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics* 68:144-151 (2000); Tanaka et al., *Mol. Hum. Reprod.* 8:16-23 (2002)). Information related to these proteins and genes is shown below:

| Protein | GENBANK ID | GI NUMBER | ORGANISM |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Additional suitable acetoacetyl-CoA and 4-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below:

| Protein | GENBANK ID | GI NUMBER | ORGANISM |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA can be hydrolyzed to acetoacetate by acetoacetyl-CoA hydrolase. Similarly, 4-hydroxybutyryl-CoA can be hydrolyzed to 4-hydroxybutyate by 4-hydroxybutyryl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding acetoacetyl-CoA transferases and 4-hydroxybutyryl-CoA transferases can also be used as hydrolases with certain mutations to change their function. The acetyl-CoA hydrolase, ACH1, from *S. cerevisiae* represents another candidate hydrolase (Buu et al., *J. Biol. Chem.*

278:17203-17209 (2003)). Information related to these proteins and genes is shown below:

| Protein | GENBANK ID | GI NUMBER | ORGANISM |
|---|---|---|---|
| Acot12 | NP_570103.1 | 18543355 | Rattus norvegicus |
| GctA | CAA57199 | 559392 | Acidaminococcus fermentans |
| GctB | CAA57200 | 559393 | Acidaminococcus fermentans |
| ACH1 | NP_009538 | 6319456 | Saccharomyces cerevisiae |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)) including 3-hydroxybutyryl-CoA (Tseng et al., *Appl. Environ. Microbiol.* 75(10):3137-3145 (2009)). A similar enzyme has also been characterized in the rat liver (Deana, *Biochem. Int.* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). Information related to these proteins and genes is shown below:

| Protein | GENBANK ID | GI NUMBER | ORGANISM |
|---|---|---|---|
| Acot8 | CAA15502 | 3191970 | Homo sapiens |
| TesB | NP_414986 | 16128437 | Escherichia coli |
| Acot8 | NP_570112 | 51036669 | Rattus norvegicus |
| TesA | NP_415027 | 16128478 | Escherichia coli |
| YbgC | NP_415264 | 16128711 | Escherichia coli |
| PaaI | NP_415914 | 16129357 | Escherichia coli |
| YbdB | NP_415129 | 16128580 | Escherichia coli |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994). Candidate genes by sequence homology include hibch of *Saccharomyces cerevisiae* and BC_2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below:

| Protein | GENBANK ID | GI NUMBER | ORGANISM |
|---|---|---|---|
| Hibch | Q5XIE6.2 | 146324906 | Rattus norvegicus |
| Hibch | Q6NVY1.2 | 146324905 | Homo sapiens |
| Hibch | P28817.2 | 2506374 | Saccharomyces cerevisiae |
| BC_2292 | AP09256 | 29895975 | Bacillus cereus ATCC 14579 |

The hydrolysis of acetoacetyl-CoA or 4-hydroxybutyryl-CoA can alternatively be carried out by a single enzyme or enzyme complex that exhibits acetoacetyl-CoA or 4-hydroxybutyryl-CoA synthetase activity. This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Information related to these proteins and genes is shown below:

| Protein | GENBANK ID | GI NUMBER | ORGANISM |
|---|---|---|---|
| SucC | NP_415256.1 | 16128703 | Escherichia coli |
| SucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed_1422 gene. Information related to these proteins and genes is shown below:

| Protein | GENBANK ID | GI NUMBER | ORGANISM |
|---|---|---|---|
| Phl | CAJ15517.1 | 77019264 | Penicillium chrysogenum |
| PhlB | ABS19624.1 | 152002983 | Penicillium chrysogenum |
| PaaF | AAC24333.2 | 22711873 | Pseudomonas putida |
| BioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J.*

Bacteriol. 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Information related to these proteins and genes is shown below:

| Protein | GENBANK ID | GI NUMBER | ORGANISM |
| --- | --- | --- | --- |
| AF1211 | NP_070039.1 | 11498810 | *Archaeoglobus fulgidus* DSM 4304 |
| Scs | YP_135572.1 | 55377722 | *Haloarcula marismortui* ATCC 43049 |
| PAE3250 | NP_560604.1 | 18313937 | *Pyrobaculum aerophilum* str. IM2 |

An alternative method for removing the CoA moiety from acetoacetyl-CoA or 4-hydroxybutyryl-CoA is to apply a pair of enzymes such as a phosphate-transferring acyltransferase and a kinase to impart acetoacetyl-CoA or 4-hydroxybutyryl-CoA synthetase activity. Exemplary names for these enzymes include phosphotrans-4-hydroxybutyrylase/4-hydroxybutyrate kinase, which can remove the CoA moiety from 4-hydroxybutyryl-CoA, and phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10):3137-3145 (2009)). Specifically, the ptb gene from *C. acetobutylicum* encodes an enzyme that can convert an acyl-CoA into an acyl-phosphate (Walter et al. Gene 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186:2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below:

| Protein | GENBANK ID | GI NUMBER | ORGANISM |
| --- | --- | --- | --- |
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below:

| Protein | GENBANK ID | GI NUMBER | ORGANISM |
| --- | --- | --- | --- |
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

Acetoacetate decarboxylase converts acetoacetate into carbon dioxide and acetone. Exemplary acetoacetate decarboxylase enzymes are encoded by the gene products of adc from *C. acetobutylicum* (Petersen and Bennett, *Appl. Environ. Microbiol.* 56:3491-3498 (1990) and adc from *Clostridium saccharoperbutylacetonicum* (Kosaka et al., *Biosci. Biotechnol. Biochem.* 71:58-68 (2007)). The enzyme from *C. beijerinkii* can be inferred from sequence similarity.

| Protein | GenBank ID | GI Number | Organism |
| --- | --- | --- | --- |
| Adc | NP_149328.1 | 15004868 | *Clostridium acetobutylicum* |
| Adc | AAP42566.1 | 31075386 | *Clostridium saccharoperbutylacetonicum* |
| Adc | YP_001310906.1 | 150018652 | *Clostridium beijerinckii* |

The final step in the isopropanol synthesis pathway involves the reduction of acetone to isopropanol. Exemplary alcohol dehydrogenase enzymes capable of this transformation include adh from *C. beijerinckii* (Jojima et al., *Appl. Microbiol. Biotechnol.* 77:1219-1224 (2008); Hanai et al., *Appl. Environ. Microbiol.* 73:7814-7818 (2007) and adh from *Thermoanaerobacter brockii* (Hanai et al., supra; Peretz et al., *Anaerobe* 3:259-270 (1997)). Additional characterized enzymes include alcohol dehydrogenases from *Ralstonia eutropha* (formerly *Alcaligenes eutrophus*) (Steinbuchel and Schlegel, *Eur. J. Biochem.* 141:555-564 (1984) and *Phytomonas* species (Uttaro and Opperdoes, *Mol. Biochen. Parasitol.* 85: 213-219 (1997)).

| Protein | GenBank ID | GI Number | Organism |
| --- | --- | --- | --- |
| Adh | P14941.1 | 113443 | *Thermoanaerobobacter brockii* |
| Adh | AAA23199.2 | 60592974 | *Clostridium beijerinckii* |
| Adh | YP_299391.1 | 73539024 | *Ralstonia eutropha* |
| iPDH | AAP39869.1 | 31322946 | *Phtomonas* sp. |

Example III

4-Hydroxybutyrate Synthesis Pathway

This Example shows further enzymes that can be used in a 4-hydroxybutyrate pathway. The genes for the first enzyme, acetoacetyl-CoA thiolase are described herein above.

Exemplary 3-hydroxyacyl dehydrogenases which convert acetoacetyl-CoA to 3-hydroxybutyryl-CoA include hbd from *C. acetobutylicum* (Boynton et al., *J. Bacteriol.* 178:3015-3024 (1996), hbd from *C. beijerinckii* (Colby and Chen, *Appl. Environ. Microbiol.* 58:3297-3302 (1992), and a number of similar enzymes from *Metallosphaera sedula* (Berg et al., *Science* 318:1782-1786 (2007).

| Protein   | GenBank ID   | GI Number | Organism                  |
|-----------|--------------|-----------|---------------------------|
| hbd       | NP_349314.1  | 15895965  | *Clostridium acetobutylicum* |
| hbd       | AAM14586.1   | 20162442  | *Clostridium beijerinckii* |
| Msed_1423 | YP_001191505 | 146304189 | *Metallosphaera sedula*   |
| Msed_0399 | YP_001190500 | 146303184 | *Metallosphaera sedula*   |
| Msed_0389 | YP_001190490 | 146303174 | *Metallosphaera sedula*   |
| Msed_1993 | YP_001192057 | 146304741 | *Metallosphaera sedula*   |

The gene product of crt from *C. acetobutylicum* catalyzes the dehydration of 3-hydroxybutyryl-CoA to crotonyl-CoA (Boynton et al., *J. Bacteriol.* 178:3015-3024 (1996); Atsumi et al., *Metab. Eng.* (2007)). Further, enoyl-CoA hydratases are reversible enzymes and thus suitable candidates for catalyzing the dehydration of 3-hydroxybutyryl-CoA to crotonyl-CoA. The enoyl-CoA hydratases, phaA and phaB, of *P. putida* are believed to carry out the hydroxylation of double bonds during phenylacetate catabolism (Olivera et al., *Proc. Nat. Acad. Sci. U.S.A.* 95:6419-6424 (1998)). The paaA and paaB from *P. fluorescens* catalyze analogous transformations (Olivera et al., supra). Lastly, a number of *Escherichia coli* genes have been shown to demonstrate enoyl-CoA hydratase functionality including maoC, paaF, and paaG (Park and Lee, *J. Bacteriol.* 185:5391-5397 (2003); Park and Lee, *Appl. Biochem. Biotechnol.* 113-116:335-346 (2004); Park and Yup, *Biotechnol. Bioeng.* 86:681-686 (2004); Ismail et al., *J. Bacteriol.* 175:5097-5105 (2003)).

| Protein | GenBank ID   | GI Number | Organism                    |
|---------|--------------|-----------|-----------------------------|
| crt     | NP_349318.1  | 15895969  | *Clostridium acetobutylicum* |
| paaA    | NP_745427.1  | 26990002  | *Pseudomonas putida*        |
| paaB    | NP_745426.1  | 26990001  | *Pseudomonas putida*        |
| phaA    | ABF82233.1   | 106636093 | *Pseudomonas fluorescens*   |
| phaB    | ABF82234.1   | 106636094 | *Pseudomonas fluorescens*   |
| maoC    | NP_415905.1  | 16129348  | *Escherichia coli*          |
| paaF    | NP_415911.1  | 16129354  | *Escherichia coli*          |
| paaG    | NP_415912.1  | 16129355  | *Escherichia coli*          |

Several enzymes that naturally catalyze the reverse reaction (i.e., the dehydration of 4-hydroxybutyryl-CoA to crotonoyl-CoA) in vivo have been identified in numerous species. This transformation is required for 4-aminobutyrate fermentation by *Clostridium aminobutyricum* (Scherf and Buckel, *Eur. J. Biochem.* 215:421-429 (1993) and succinate-ethanol fermentation by *Clostridium kluyveri* (Scherf et al., *Arch. Microbiol.* 161:239-245 (1994)). The transformation is also a key step in Archaea, for example, *Metallosphaera sedula*, as part of the 3-hydroxypropionate/4-hydroxybutyrate autotrophic carbon dioxide assimilation pathway (Berg et al., *Science* 318:1782-1786 (2007)). This pathway requires the hydration of crotonoyl-CoA to form 4-hydroxybutyryl-CoA. The reversibility of 4-hydroxybutyryl-CoA dehydratase is well-documented (Muh et al., *Biochemistry* 35:11710-11718 (1996); Friedrich et al., *Agnew Chem. Int. Ed. Engl.* 47:3254-3257 (2008); Muh et al., *Eur. J. Biochem.* 248:380-384 (1997) and the equilibrium constant has been reported to be about 4 on the side of crotonoyl-CoA (Scherf and Buckel, *Eur. J. Biochem.* 215:421-429 (1993). This implies that the downstream 4-hydroxybutyryl-CoA dehydrogenase must keep the 4-hydroxybutyryl-CoA concentration low so as to not create a thermodynamic bottleneck at crotonyl-CoA. The reverse reaction of 4-hydroxybutyryl-CoA dehydratase is crotonyl-CoA hydratase.

| Protein   | GenBank ID   | GI Number | Organism                    |
|-----------|--------------|-----------|-----------------------------|
| AbfD      | CAB60035     | 70910046  | *Clostridium aminobutyricum* |
| AbfD      | YP_001396399 | 153955634 | *Clostridium kluyveri*      |
| Msed_1321 | YP_001191403 | 146304087 | *Metallosphaera sedula*     |
| Msed_1220 | YP_001191305 | 146303989 | *Metallosphaera sedula*     |

Suitable acetoacetyl-CoA and 4-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FN0272 and FN0273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GENBANK ID | GI NUMBER | ORGANISM |
| --- | --- | --- | --- |
| Cat1 | P38946.1 | 729048 | Clostridium kluyveri |
| Cat2 | P38942.2 | 1705614 | Clostridium kluyveri |
| Cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| FN0272 | NP_603179.1 | 19703617 | Fusobacterium nucleatum |
| FN0273 | NP_603180.1 | 19703618 | Fusobacterium nucleatum |
| FN1857 | NP_602657.1 | 19705162 | Fusobacterium nucleatum |
| FN1856 | NP_602656.1 | 19705161 | Fusobacterium nucleatum |
| PG1066 | NP_905281.1 | 34540802 | Porphyromonas gingivalis W83 |
| PG1075 | NP_905290.1 | 34540811 | Porphyromonas gingivalis W83 |
| TTE0720 | NP_622378.1 | 20807207 | Thermoanaerobacter tengcongensis MB4 |
| TTE0721 | NP_622379.1 | 20807208 | Thermoanaerobacter tengcongensis MB4 |

An alternative method for removing the CoA moiety from acetoacetyl-CoA or 4-hydroxybutyryl-CoA is to apply a pair of enzymes such as a phosphate-transferring acyltransferase and a kinase to impart acetoacetyl-CoA or 4-hydroxybutyryl-CoA synthetase activity. Exemplary names for these enzymes include phosphotrans-4-hydroxybutyrylase/4-hydroxybutyrate kinase, which can remove the CoA moiety from 4-hydroxybutyryl-CoA, and phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from Clostridium acetobutylicum has been successfully applied to remove the CoA group from 3-hydroxybutyryl-CoA when functioning as part of a pathway for 3-hydroxybutyrate synthesis (Tseng et al., Appl. Environ. Microbiol. 75(10):3137-3145 (2009)). Specifically, the ptb gene from C. acetobutylicum encodes an enzyme that can convert an acyl-CoA into an acyl-phosphate (Walter et al. Gene 134(1): p. 107-11 (1993)); Huang et al. J Mol Microbiol Biotechnol 2(1): p. 33-38 (2000). Additional ptb genes can be found in butyrate-producing bacterium L2-50 (Louis et al. J. Bacteriol. 186:2099-2106 (2004)) and Bacillus megaterium (Vazquez et al. Curr. Microbiol 42:345-349 (2001)). Additional exemplary phosphate-transferring acyltransferases include phosphotransacetylase, encoded by pta. The pta gene from E. coli encodes an enzyme that can convert acetyl-CoA into acetyl-phosphate, and vice versa (Suzuki, T. Biochim. Biophys. Acta 191:559-569 (1969)). This enzyme can also utilize propionyl-CoA instead of acetyl-CoA forming propionate in the process (Hesslinger et al. Mol. Microbiol 27:477-492 (1998)). Information related to these proteins and genes is shown below.

| Protein | GENBANK ID | GI NUMBER | ORGANISM |
| --- | --- | --- | --- |
| Pta | NP_416800.1 | 16130232 | Escherichia coli |
| Ptb | NP_349676 | 15896327 | Clostridium acetobutylicum |
| Ptb | AAR19757.1 | 38425288 | butyrate-producing bacterium L2-50 |
| Ptb | CAC07932.1 | 10046659 | Bacillus megaterium |

Exemplary kinases include the E. coli acetate kinase, encoded by ackA (Skarstedt and Silverstein J. Biol. Chem. 251:6775-6783 (1976)), the C. acetobutylicum butyrate kinases, encoded by buk1 and buk2 ((Walter et al. Gene 134(1):107-111 (1993); Huang et al. J Mol Microbiol Biotechnol 2(1):33-38 (2000)), and the E. coli gamma-glutamyl kinase, encoded by proB (Smith et al. J. Bacteriol. 157:545-551 (1984)). These enzymes phosphorylate acetate, butyrate, and glutamate, respectively. The ackA gene product from E. coli also phosphorylates propionate (Hesslinger et al. Mol. Microbiol 27:477-492 (1998)). Information related to these proteins and genes is shown below:

| Protein | GENBANK ID | GI NUMBER | ORGANISM |
| --- | --- | --- | --- |
| AckA | NP_416799.1 | 16130231 | Escherichia coli |
| Buk1 | NP_349675 | 15896326 | Clostridium acetobutylicum |
| Buk2 | Q97II1 | 20137415 | Clostridium acetobutylicum |
| ProB | NP_414777.1 | 16128228 | Escherichia coli |

Example IV 1,4-Butanediol Synthesis Pathway

This Example shows further enzymes that can be used in a 1,4-butanediol pathway. The genes for acetoacetyl-CoA thiolase, 3-Hydroxybutyryl-CoA dehydrogenase (Hbd), Crotonase (Crt), and Crotonyl-CoA hydratase (4-Budh) are described herein above.

Alcohol-forming 4-hydroxybutyryl-CoA reductase enzymes catalyze the 2 reduction steps required to form 1,4-butanediol from 4-hydroxybutyryl-CoA. Exemplary 2-step oxidoreductases that convert an acyl-CoA to alcohol include those that transform substrates such as acetyl-CoA to ethanol (e.g., adhE from E. coli (Kessler et al., FEBS Lett. 281:59-63 (1991)) and butyryl-CoA to butanol (e.g. adhE2 from C. acetobutylicum (Fontaine et al., J. Bacteriol. 184:821-830 (2002)). The adhE2 enzyme from C. acetobutylicum was specifically shown in ref. (WO/2008/115840 (2008)) to produce BDO from 4-hydroxybutyryl-CoA. In addition to reducing acetyl-CoA to ethanol, the enzyme encoded by adhE in Leuconostoc mesenteroides has been shown to oxide the branched chain compound isobutyraldehyde to isobutyryl-CoA (Kazahaya et al., J. Gen. Appl. Microbiol. 18:43-55 (1972; Koo et al., Biotechnol. Lett. 27:505-510 (2005)).

| Protein | GenBank ID | GI Number | Organism |
|---|---|---|---|
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
|---|---|---|---|
| mcr | AAS20429.1 | 42561982 | Chloroflexus aurantiacus |
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

An alternative route to BDO from 4-hydroxybutyryl-CoA involves first reducing this compound to 4-hydroxybutanal. Several acyl-CoA dehydrogenases are capable of reducing an acyl-CoA to its corresponding aldehyde. Exemplary genes that encode such enzymes include the *Acinetobacter calcoaceticus* acyl encoding a fatty acyl-CoA reductase (Reiser and Somerville, *J. Bacteriol.* 179:2969-2975 (1997), the *Acinetobacter* sp. M-1 fatty acyl-CoA reductase (Ishige et al., *Appl. Environ. Microbiol.* 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 178:8710880 (1996)). SucD of *P. gingivalis* is another succinate semialdehyde dehydrogenase (Takahashi et al., *J. Bacteriol.* 182:4704-4710 (2000)). These succinate semialdehyde dehydrogenases were specifically shown in ref. (WO/2008/115840 (2008)) to convert 4-hydroxybutyryl-CoA to 4-hydroxybutanal as part of a pathway to produce 1,4-butanediol. The enzyme acylating acetaldehyde dehydrogenase in *Pseudomonas* sp, encoded by bphG, is yet another capable enzyme as it has been demonstrated to oxidize and acylate acetaldehyde, propionaldehyde, butyraldehyde, isobutyraldehyde and formaldehyde (Powlowski et al., *J. Bacteriol.* 175:377-385 (1993)).

| Protein | GenBank ID | GI Number | Organism |
|---|---|---|---|
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al., *J. Bacteriol.* 188: 8551-8559 (2006); Hugler et al., *J. Bacteriol.* 184:2404-2410 (2002)). The enzyme is encoded by Msed_0709 in *Metallosphaera sedula* (Alber et al. *Mol. Microbiol.* 61:297-309 (2006); Berg et al., *Science* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth, *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999). These proteins are identified below.

| Protein | GenBank ID | GI Number | Organism |
|---|---|---|---|
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | P77445 | 2498347 | Escherichia coli |

4-Hydroxybutyryl-CoA can also be converted to 4-hydroxybutanal in several enzymatic steps, though the intermediate 4-hydroxybutyrate. First, 4-hydroxybutyryl-CoA can be converted to 4-hydroxybutyrate by a CoA transferase, hydrolase or synthetase. Alternately, 4-hydroxybutyryl-CoA can be converted to 4-hydroxybutyrate via a phosphonated intermediate by enzymes with phosphotrans-4-hydroxybutyrylase and 4-hydroxybutyrate kinase. Exemplary candidates for these enzymes are described above.

Subsequent conversion of 4-hydroxybutyrate to 4-hydroxybutanal is catalyzed by an aryl-aldehyde dehydrogenase, or equivalently a carboxylic acid reductase. Such an enzyme is found in *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)) and is capable of catalyzing the conversion of 4-hydroxybutyrate to 4-hydroxybutanal. This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Gene name | GI Number | GenBank ID | Organism |
|---|---|---|---|
| Car | 40796035 | AAR91681.1 | *Nocardia iowensis* (sp. NRRL 5646) |
| Npt | 114848891 | ABI83656.1 | *Nocardia iowensis* (sp. NRRL 5646) |

Additional car and npt genes can be identified based on sequence homology.

griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Gene name | GI Number | GenBank ID | Organism |
|---|---|---|---|
| griC | 182438036 | YP_001825755.1 | *Streptomyces griseus* subsp. *griseus* NBRC 13350 |
| Grid | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137

| Gene name | GI Number | GenBank ID | Organism |
|---|---|---|---|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene name | GI Number | GenBank ID | Organism |
|---|---|---|---|
| LYS2 | 171867 | AAA34747.1 | *Saccharomyces cerevisiae* |
| LYS5 | 1708896 | P50113.1 | *Saccharomyces cerevisiae* |
| LYS2 | 2853226 | AAC02241.1 | *Candida albicans* |
| LYS5 | 28136195 | AAO26020.1 | *Candida albicans* |
| Lys1p | 13124791 | P40976.3 | *Schizosaccharomyces pombe* |
| Lys7p | 1723561 | Q10474.1 | *Schizosaccharomyces pombe* |
| Lys2 | 3282044 | CAA74300.1 | *Penicillium chrysogenum* |

Enzymes exhibiting 1,4-butanediol dehydrogenase activity are capable of forming 1,4-butanediol from 4-hydroxybutanal. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani *Appl. Environ. Micro* et al. 66:5231-5235 (2000), ADH2 from *Saccharomyces cerevisiae* (Aoshima et al., *Mol. Microbiol.* 51:791-798 (2004)), yqhD from *E. coli* which has preference for molecules longer than C(3) (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)).

| Protein | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharymyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Enzymes exhibiting 4-hydroxybutyrate dehydrogenase activity (EC 1.1.1.61) also fall into this category. Such enzymes have been characterized in *Ralstonia eutropha* (Bravo et al., *J. Forensic Sci.* 49:379-387 (2004), *Clostridium kluyveri* (Wolff and Kenealy, *Protein* Expr. Purif. 6:206-212 (1995)) and *Arabidopsis thaliana* (Breitkreuz et al., *J. Biol. Chem.* 278:41552-41556 (2003)).

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Example V

Methods for Handling CO and Anaerobic Cultures

This example describes methods used in handling CO and anaerobic cultures.

A. Handling of CO in small quantities for assays and small cultures. CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in larger quantities fed to large-scale cultures. Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic chamber and conditions. Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic microbiology. Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 µM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Example VI

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as Clostridial (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., *Biochemistry* 43:3944-3955 (2004)). A typical activity of *M. thermoacetica* CODH specific activity is 500 U at 55° C.

or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mL of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude E. coli cell extracts of ACS90 and ACS91 (CODH-ACS operon of M. thermoacetica with and without, respectively, the first cooC). 10 microliters of extract were added at a time, mixed and assayed. Reduced $CH_3$ viologen turns purple. The results of an assay are shown in Table I.

TABLE I

Crude extract CO Oxidation Activities.

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

ACS90 7.7 mg/ml
ACS91 11.8 mg/ml
Mta98 9.8 mg/ml
Mta99 11.2 mg/ml
Averages
ACS90 0.057 U/mg
ACS91 0.045 U/mg
Mta99 0.0018 U/mg Mta98/Mta99 are E. coli MG1655 strains that express methanol methyltransferase genes from M. thermoacetia and, therefore, are negative controls for the ACS90 ACS91 E. coli strains that contain M. thermoacetica CODH operons.

If ~1% of the cellular protein is CODH, then these figures would be approximately 100× less than the 500 U/mg activity of pure M. thermoacetica CODH. Actual estimates based on Western blots are 0.5% of the cellular protein, so the activity is about 50× less than for M. thermoacetica CODH. Nevertheless, this experiment demonstrates CO oxidation activity in recombinant E. coli with a much smaller amount in the negative controls. The small amount of CO oxidation ($CH_3$ viologen reduction) seen in the negative controls indicates that E. coli may have a limited ability to reduce $CH_3$ viologen.

Figure 9:
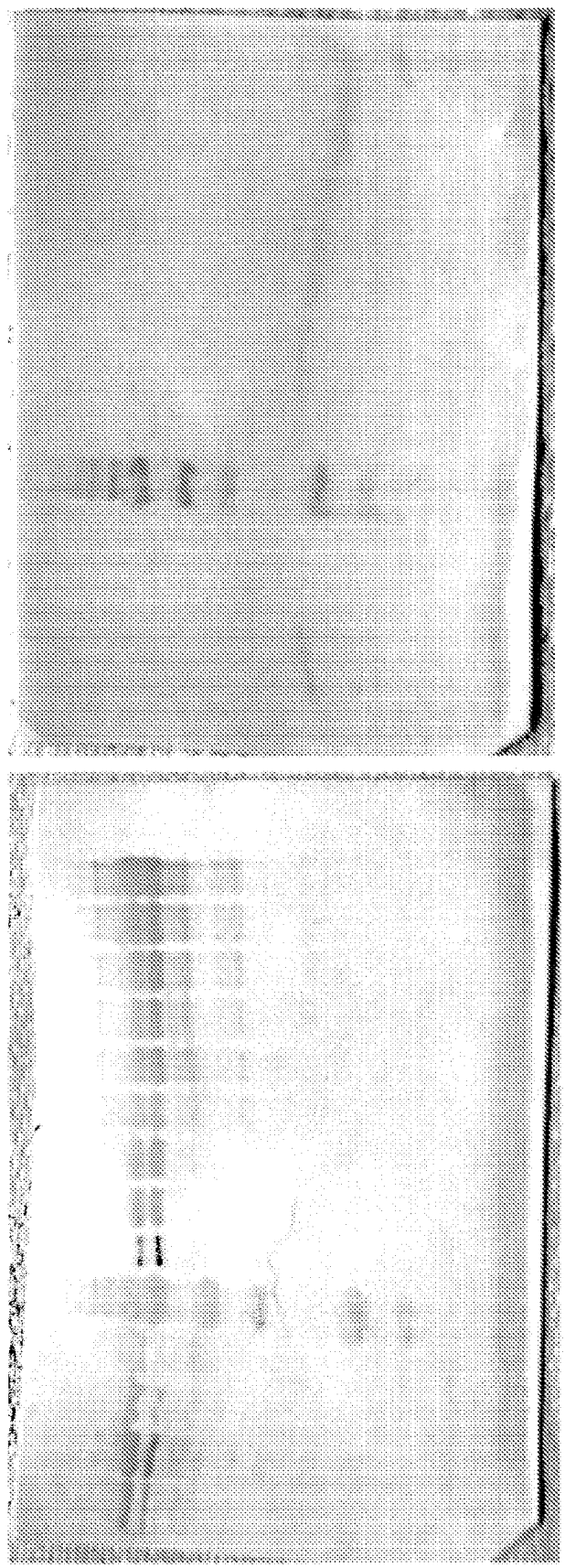
FIG. 9 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified M. thermoacetica CODH-ACS and Mtr proteins and were visualized using an alkaline phosphatase-linked goat-anti-rabbit secondary antibody. The Westerns were performed and results are shown in FIG. 9. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant E. coli cells express multiple components of a 7 gene operon. In addition, both the methyltransferase and corrinoid iron sulfur protein were active in the same recombinant E. coli cells. These proteins are part of the same operon cloned into the same cells.

Figure 10:
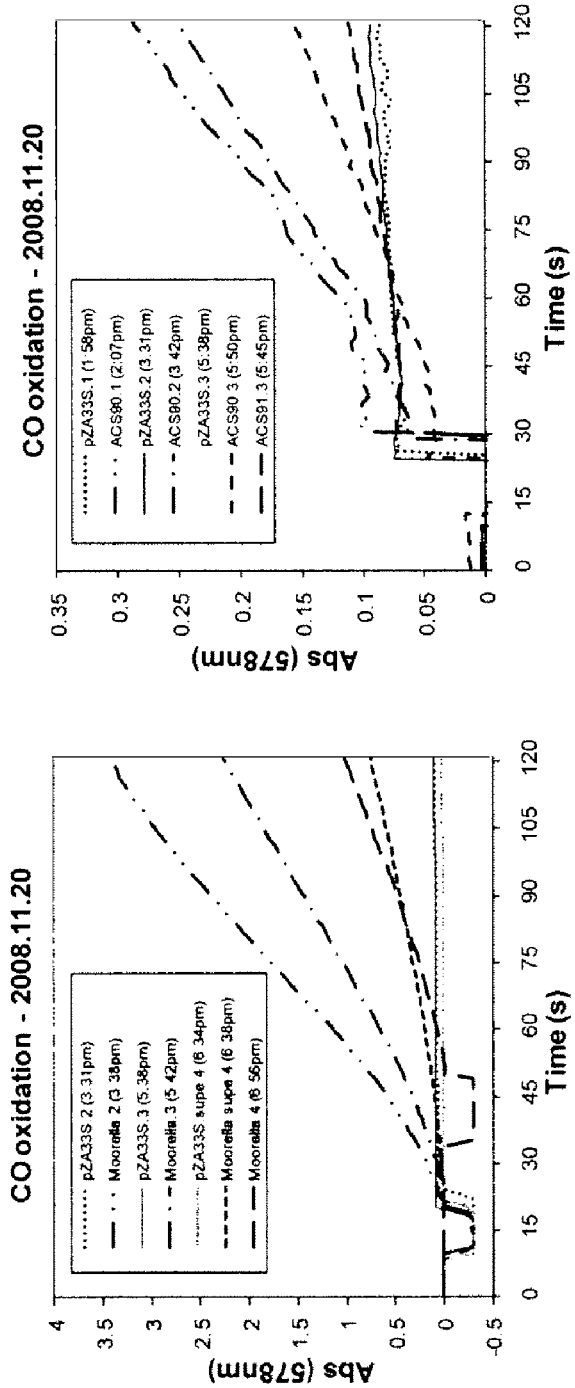
FIG. 10 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of Moorella thermoacetica cells for the positive controls. Though CODH activity in E. coli ACS90 and ACS91 was measurable, it was at about 130-150× lower than the M. thermoacetica control. The results of the assay are shown in FIG. 10. Briefly, cells (M. thermoacetica or E. coli with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant E. coli cells expressed CO oxidation activity as measured by the methyl viologen reduction assay.

Example VII

Acetyl-CoA Synthase (ACS) Activity Assay (CO Exchange Assay)

This Example describes an ACS assay method.

This assay measures the ACS-catalyzed exchange of the carbonyl group of acetyl-CoA with CO (Raybuck et al., Biochemistry 27:7698-7702 (1988)). ACS (as either a purified enzyme or part of a cell extract) is incubated with acetyl-CoA labeled with $^{14}C$ at the carbonyl carbon under a CO atmosphere. In the presence of active ACS, the radioactivity in the liquid phase of the reaction decreases exponentially until it reaches a minimum defined by the equilibrium between the levels of $^{14}C$-labeled acetyl-CoA and $^{14}C$-labeled CO. The same cell extracts of E. coli MG1655 expressing ACS90 and ACS91 employed in the other assays as well as control extracts were assayed by this method.

Briefly in more detail, in small assay vials under normal atmosphere, a solution of 0.2 mM acetyl-CoA, 0.1 mM methyl viologen, and 2 mM Ti(III) citrate in 0.3M MES buffer, pH 6.0, was made. The total reaction volume when all components were added was 500 µl. Vials were sealed with rubber stoppers (Bellco) and crimp aluminum seals (Bellco) to create a gas-tight reaction atmosphere. Each vial was sparged with 100% CO for several minutes, long enough to completely exchange the vials' atmosphere, and brought into an anaerobic chamber. The assay vials were placed in a 55° C. sand bath and allowed to equilibrate to that temperature. A total of 10 scintillation vials with 40 µl of 1M HCl were prepared for each assay vial. A gas-tight Hamilton syringe was used to add ACS to the assay vial and incubated for approximately 2-3 minutes for the reaction to come to equilibrium. A gas-tight Hamilton syringe was used to add 1 µl (0.36 nmoles) $^{14}C$-acetyl-CoA to start the assay (time=0 min). Time points were taken starting immediately. Samples (40 µl) were removed from the assay vials with a gas-tight Hamilton syringe. Each sample was added to the 40 μl of HCl in the prepared scintillation vials to quench the reaction. As the ACS enzyme transfers $^{14}C$ label to CO from acetyl-CoA, the concentration of the isotope decreases exponentially. Therefore, the assay was sampled frequently in the early time points. The precise time for each sample was recorded. The exact pace of the reaction depends on the ACS enzyme, but generally several samples are taken immediately and sampled over the initial 10-15 minutes. Samples are continued to be taken for 1-2 hours.

In a particular exemplary assay, four assay conditions were used: blank (no ACS), 12 μl of purified E. coli strains expressing M. thermoacetica ACS, 4 μl of purified E. coli ACS, and 3.7 μl of M. thermoacetica CODH/ACS. In another exemplary assay, four assay conditions were used: 108 μg CODH/ACS, 1 mg Mta99 cell extract, 1 mg ACS90 cell extract, and 1 mg ACS91 cell extract. The enzymes were added as 100 μl solutions (50 mM KPi, 0.1M NaCl, pH7.6). A more sensitive assay that can be used for most of the CODH-ACS activities is the synthesis assay described below. This example describes the assay conditions for measuring ACS activity.

Example VIII

Acetyl-CoA Synthesis and Methyltransferase Assays

This example describes acetyl-CoA synthesis and methyltransferase assays.

Acetyl-CoA synthesis assay. This assay is an in vitro reaction that synthesizes acetyl-CoA from methyl-tetrahydrofolate, CO, and CoA using CODH/ACS, methyltransferase (MeTr), and corrinoid Fe—S protein (CFeSP) (Raybuck et al., Biochemistry 27:7698-7702 (1988)). By adding or leaving out each of the enzymes involved, this assay can be used for a wide range of experiments, from testing one or more purified enzymes or cell extracts for activity, to determining the kinetics of the reaction under various conditions or with limiting amounts of substrate or enzyme. Samples of the reaction taken at various time points are quenched with 1M HCl, which liberates acetate from the acetyl-CoA end product. After purification with Dowex columns, the acetate can be analyzed by chromatography, mass spectrometry, or by measuring radioactivity. The exact method can be determined by the specific substrates used in the reaction.

A $^{14}C$-labeled methyl-THF was utilized, and the radioactivity of the isolated acetate samples was measured. The primary purpose was to test CFeSP subunits. The assay also included +/−purified methyltransferase enzymes. The following 6 different conditions were assayed: (1) purified CODH/ACS, MeTr, and CFeSP as a positive control; (2) purified CODH/ACS with ACS90 cell extract; (3) purified CODH/ACS with ACS91 cell extract; (4) purified CODH/ACS, MeTr with ACS90 cell extract; (5) purified CODH/ACS, MeTr with ACS91 cell extract; (6) purified CODH/ACS, MeTr with as much ACS91 cell extract as possible (excluding the MES buffer).

The reaction is assembled in the anaerobic chamber in assay vials that are filled with CO. The total reaction volume is small compared to the vial volume, so the reagents can be added before or after the vial is filled with CO, so long as a gas-tight Hamilton syringe is used and the reagents are kept anaerobic. The reaction (~60 ul total) consisted of the cell extract (except assay #1), CoA, Ti(III) citrate, MES (except assay #6), purified CODH/ACS, $^{14}C$-methyl-tetrahydrofolate, methyl-viologen, and ferredoxin. Additionally, purified MeTr was added to assays #1 and #4-6, and purified CFeSP was added to assay #1.

The reaction was carried out in an anaerobic chamber in a sand bath at 55° C. The final reagent added was the $^{14}C$-methyl-tetrahydrofolate, which started the reaction (t=0s). An initial sample was taken immediately, followed by samples at 30 minutes, 1 hour, and 2 hours. These time points are not exact, as the 6 conditions were run concurrently (since this experiment was primarily a qualitative one). The 15 μl samples were added to 15 μl of 1M HCl in scintillation vials. For the last sample, if less than 15 μl was left in the reactions, the assay vials were rinsed with the 15 ul of HCl to take the remainder of the reaction. A volume of 10 μl of cell extract was used for assay #2-5, and 26.4 μl of cell extract was used for assay #6.

Typical amounts of purified enzyme used in the assays is as follows: CODH/ACS=~0.2 nmoles; MeTr=0.2 nmoles; CFeSP=0.05 nmoles. Typical assay concentrations are used as follows: CODH/ACS=1 uM; Me-CFeSP=0.4 uM; MeTr=1 uM; Ferredoxin=3 uM; CoA=0.26 mM; $^{14}C$ methyl-THF=0.4 mM; methyl viologen=0.1 mM; and Ti(III)citrate=3 mM.

After counting the reaction mixtures, it was determined that the corrinoid Fe—S protein in ACS90 extracts was active with total activity approaching approximately ⅕ of the positive control and significantly above the negative control (no extract).

A non-radioactive synthesis assay can also be used. Optional non-radioactive assay conditions are as follows: Assay condition #1: 100 mM MES, pH6.0; 1 mM CoA; 1 mM Me-THF; 0.33 mM Ti(III) citrate, volume to 950 ul, +50 ul of extract; incubated under a CO atmosphere (Ar for control), at 55° C. These reactions should be carried out in the dark, as the corrinoid methyl carrier is light sensitive. Assay condition #2: 100 mM MES, pH6.0; 1 mM CoA; 1 mM Me-THF; 1 mM methyl viologen; volume to 950 ul, +50 ul of extract; incubated under a CO atmosphere, at 55° C., in the dark. The reaction was quenched with 10 μl of 10% formic acid, with samples taken at 1 hr, 3 hrs, and 6.5 hrs, and stored at −20°. Assay condition #3: 100 mM Tris, pH 7.6; 5 mM CoA; 7.5 mM Me-THF; 1 mM Me-viologen; volume to 90 μl, +10 μl extract; incubated under CO or Ar, at 55° C. in the dark for 1 hr, quenched with 10 μl 10% formic acid, and stored at −20° C.

In Lu et al., (J. Biol. Chem. 265:3124-3133. (1990)), the pH optimum for the synthesis reaction was found to be between 7.2-7.5. Lu et al. also found that CoA concentrations above 10 mM were inhibitory. Lu et al. described using methyl iodide as the methyl donor instead of Me-THF, and used 5-7.5 mM concentrations. Lu et al. also determined that DTT or other reducing agents were not necessary, although they did use ferredoxin as an electron carrier. Methyl viologen was substituted in the above-described reactions. In addition, Maynard et al., J. Biol. Inorg. Chem. 9:316-322 (2004), has determined that the electron carrier was not strictly necessary, but that failure to include one resulted in a time lag of the synthesis. Maynard et al. used 1 mM methyl viologen as electron carrier when one was used.

Methyltransferase Assay. Within the CODH-ACS operon is encoded an essential methyltransferase activity that catalyzes the transfer of $CH_3$ from methyl-tetrahydrofolate to the ACS complex as part of the synthesis of acetyl-CoA. This is the step that the methyl and carbonyl pathways join together. Within the operon in M. thermoacetica, the Mtr-encoding gene is Moth_1197 and comes after the main CODH and ACS subunits. Therefore, Mtr activity would constitute indirect evidence that the more proximal genes can be expressed.

Mtr activity was assayed by spectroscopy. Specifically, methylated CFeSP, with Co(III), has a small absorption peak at ~450 nm, while non-methylated CFeSP, with Co(I), has a large peak at ~390 nm. This spectrum is due to both the cobalt and iron-sulfur cluster chromophores. Additionally, the CFeSP can spontaneously oxidize to Co(II), which creates a broad absorption peak at ~470 nm (Seravalli et al., *Biochemistry* 38:5728-5735 (1999)). Recombinant methyltransferase is tested using *E. coli* cell extracts, purified CFeSP from *M. thermoacetica*, and methyl-tetrahydrofolate. The methylation of the corrinoid protein is observed as a decrease in the absorption at 390 nm with a concurrent increase in the absorption at 450 nm, along with the absence of a dominant peak at 470 nm.

Non-radioactive assays are also being developed using $^{13}C$-methanol. This should transfer to tetrahydrofolate and create a MTHF of molecular mass +1. Alternatively, the methyltransferase is thought to also work by transfer of the methanol methyl group to homocysteine to form methionine. This assay is also useful because methionine+1 mass is more readily detectable than MTHF+1 or some other possibilities. In addition to using $^{13}C$, deuterium can also be used as a tracer, both of which can be measured using mass spectrometry. These tracers can also be used in in vivo labeling studies. Other assay methods can be used to determine various intermediates or products including, for example, electron paramagnetic resonance (EPR), Mossbauer spectroscopy, Electron-Nuclear DOuble Resonance (ENDOR), infrared, magnetic circular dichroism (MCD), crystallography, X-ray absorption, as well as kinetic methods, including stopped flow and freeze-quench EPR.

FIG. 3B illustrates how methanol methyltransferase fits into a CODH/ACS ('syngas') pathway. Essentially, the methyl group of methanol is transferred via a cobabalamin-dependent process to tetrahydrofolate and then to the corrinoid-FeS protein of CODH/ACS (also a cobalamin protein) and that, in turn, donates the methyl group to the ACS reaction that results in acetate synthesis. The methanol methyltransferase complex consists of three gene products; two of these, MtaB and MtaC, (Moth_1209 and Moth_1208) are adjacent and were readily cloned. The third, MtaA, may be encoded by three different genes (Moth_2100, Moth_2102, and Moth_2346), and it unclear whether all three genes are required or whether a subset of the three can function. All cloning in *E. coli* was performed using the Lutz-Bujard vectors (Lutz and Bujard, *Nucleic Acids Res.* 25:1203-1210 (1997)).

The following assay can be used to determine the activity of MtaB that encodes a methanol methyltransferase gene product. A positive control for the latter can be performed with vanillate o-demethylation.

Methanol Methyltransferase reaction. An exemplary methanol methyl-transfer reaction has been described previously (Sauer and Thauer, *Eur. J. Biochem.* 249:280-285 (1997); Naidu and Ragsdale, *J. Bacteriol.* 183:3276-3281 (2001)). The reaction conditions are as follows: 50 mM MOPS/KOH, pH 7.0; 10 mM $MgCl_2$; 4 mM Ti(III) citrate; 0.2% dodecylmaltoside (replacing SDS, see Sauer and Thauer, *Eur. J. Biochem.* 253:698-705 (1998)); 25 µM hydroxycobalamin; 1% MeOH or 1 mM vanillate (depending on the methyl transferase version). These reactions are measured by spectrograph readings in the dark at 37° C. or 55° C. This assay tests the ability of MtaB or MtvB to transfer the methyl group to cobalamin from methanol or vanillate, respectively.

Example IX

*E. coli* CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, $NiCl_2$, Fe(II) $NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. each of these was added in 1 microliter increments to the same cuvette. Midway through the experiment a second cuvette was set up and used. The results are shown in Table II.

TABLE II

| Carbon Monoxide Concentrations, 36 hrs. | |
|---|---|
| Strain and Growth Conditions | Final CO concentration (micromolar) |
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table II indicate that the cultures grew whether or not a strain was cultured in the presence of CO or not. These results indicate that E. coli can tolerate exposure to CO under anaerobic conditions and that E. coli cells expressing the CODH-ACS operon can metabolize some of the CO.

These results demonstrate that E. coli cells, whether expressing CODH/ACS or not, were able to grow in the presence of saturating amounts of CO. Furthermore, these grew equally well as the controls in nitrogen in place of CO. This experiment demonstrated that laboratory strains of E. coli are insensitive to CO at the levels achievable in a syngas project performed at normal atmospheric pressure. In addition, preliminary experiments indicated that the recombinant E. coli cells expressing CODH/ACS actually consumed some CO, probably by oxidation to carbon dioxide.

Example X

Enhanced Yield of 1,4-Butanediol from Carbohydrates using CO/H$_2$

This example describes the generation of a microbial organism capable of producing 1,4-butanediol from carbohydrates (e.g., glucose) at a yield greater than 1 mol 1,4-butanediol/mol glucose. Synthesis gas is supplied as a secondary source of reducing equivalents to compliment the carbohydrate-based feedstock.

Escherichia coli is used as a target organism to engineer the 1,4-butanediol pathway shown in FIG. 6A. E. coli provides a good host for generating a non-naturally occurring microorganism capable of producing 1,4-butanediol from a mixed feedstock consisting of carbohydrates, CO, and/or H$_2$. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce 1,4-butanediol and extract reducing equivalents from CO and H$_2$, nucleic acids encoding the requisite enzymes are expressed in E. coli and various non-desirable genes are targeted for deletion using well known molecular biology techniques (see, for example, Sambrook, supra, 2001; Ausubel, supra, 1999). The construction of a host E. coli strain capable of synthesizing 1,4-butanediol from succinyl-CoA is described in (Burk et al., WO 2008/115840). Targeted gene deletions of lactate dehydrogenase (ldh), alcohol/aldehyde dehydrogenase (adhE), pyruvate formate lyase (pfl), succinate semialdehyde dehydrogenase (sad and gabD) are implemented for enhancing the yield of 1,4-butanediol.

Suitable host backgrounds include AB3 and ECKh-138 as described by Van Dien et al., (2009). Genes integrated into the chromosome or expressed via plasmids to enable 1,4-butanediol production from succinyl-CoA include succinyl-CoA reductase (aldehyde forming) [sucD, NP_904963.1, GI: 34540484, Porphyromonas gingivalis W83], 4-hydroxybutyrate dehydrogenase [4hbd, NP_904964.1, GI: 34540485, Porphyromonas gingivalis W83], 4-hydr mn oxybutyryl-CoA transferase [cat2, NP_906037.1, GI: 34541558, Porphyromonas gingivalis W83], and 4-hydroxybutyryl-CoA reductase (aldehyde forming) [GNM0025B—codon optimized variant of ald, AAT66436, GI: 49473535, Clostridium beijerinckii—described in Van Dien et al., (2009). Endogenous alcohol dehydrogenases can carry out the reduction of 4-hydroxybutyraldehyde to 1,4-butanediol. This step can be enhanced by overexpressing a native alcohol dehydrogenase such as (yqhD, NP 417484.1, GI: 16130909, Escherichia coli) or a non-native alcohol dehydrogenase such as (adhA, YP_162971.1, GI: 56552132, Zymomonas mobilis). PEP carboxykinase from E. coli [pck, NP_417862.1, GI: 16131280], H. influenzae [pckA, P43923.1, GI: 1172573], or another organism are expressed to improve the energetic efficiency of the engineered pathway.

1,4-Butanediol pathway genes are integrated into the chromosome as synthetic operons. This entails targeted integration using RecET-based 'recombineering' (Angrand et al., Nucleic Acids Res. 27.17:e16 (1999); Muyrers et al., Nucleic Acids Res. 27.6:1555-1557 (1999); Zhang et al., Nat. Genet. 20.2:123-128 (1998)). A potential issue with RecET-based integration of a cassette and removal of a FRT or loxP-bounded selectable marker by FLP or Cre is the production of a recombination scar at each integration site. While problems caused by this can be minimized by a number of methods, other means that do not leave genomic scars are available. The standard alternative is to introduce the desired genes using integrative 'suicide' plasmids coupled to counter-selection such as that allowed by the Bacillus sacB gene (Link et al., J. Bacteriol. 179.20:6228-6237 (1997)); in this way, markerless and scar less insertions at any location in the E. coli chromosome can be generated.

Carbon monoxide dehydrogenase activity is enabled by cloning the following genes from Clostridium carboxydivorans P7 (ZP_05391756.1, GI: 255524806; ZP_05391757.1, GI: 255524807; ZP_05391758.1, GI: 255524808; ZP_05392945, GI: 255526021) into the pZE13 vector (Expressys, Ruelzheim, Germany) under the PA1/lacO promoter. Alternatively, carbon monoxide dehydrogenase activity is enabled by cloning the following genes from Clostridium carboxydivorans P7 (ZP_05392944, GI: 255526020; ZP_05392945, GI: 255526021) into the pZE13 vector (Expressys, Ruelzheim, Germany) under the PA1/lacO promoter. In addition, ferredoxin and NAD(P)H:ferredoxin oxidoreductase activity is enabled by cloning the following genes from Clostridium carboxydivorans P7 (ZP_05392639.1, GI: 255525707; ZP_05392638.1, GI: 255525706; ZP_05392636.1, GI: 255525704; ZP_05392958.1, GI: 255526034) or from Helicobacter pylori (NP_207955.1; GI: 15645778; AAD07340.1, GI: 2313367) into the pZA33 vector (Expressys, Ruelzheim, Germany) under the PA1/lacO promoter. Hydrogenase activity is enabled by cloning the following genes from Ralstonia eutropha H16 (HoxF, NP_942727.1, GI: 38637753; HoxU, NP_942728.1, GI: 38637754; Hoxy, NP_942729.1, GI: 38637755; HoxH, NP_942730.1, GI: 38637756; HoxW, NP_942731.1, GI: 38637757; HoxI, NP_942732.1, GI: 38637758) into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques.

Cloned genes are verified by PCR and or restriction enzyme mapping to demonstrate construction and insertion into the expression vector. DNA sequencing of the presumptive clones is carried out to confirm the expected sequences of each gene. Expression of the cloned genes is monitored using SDS-PAGE of whole cell extracts. To optimize levels of soluble vs. pellet (potentially inclusion body origin) protein, the affect of titration of the promoter on these levels can be examined. If no acceptable expression is obtained, higher or lower copy number vectors or variants in promoter strength are tested. The three sets of plasmids are transformed into the 1,4-butanediol-producing host strain of E. coli to express the proteins and enzymes required for the extraction of reducing equivalents from H$_2$ and CO.

The resulting genetically engineered organism is cultured in glucose-containing medium following procedures well known in the art (see, for example, Sambrook et al., supra, 2001). The expression of the 1,4-butanediol synthesis and reducing equivalent extraction genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The assay for CO dehydrogenase activity is one of the simpler, reliable, and more versatile assays of enzymatic activities within the Wood-Ljungdahl pathway (Ragsdale and Wood, *J. Biol. Chem.* 260:3970-3977 (1985)). It will provide a measure of the activity of CODH in recombinant cells. This assay employs reduction of methyl viologen in the presence of CO. This is measured at 578 nm in stoppered, anaerobic, glass cuvettes. Some hydrogenase assays use electron acceptors such as methyl viologen and test the enzymatic activity relative to inhibitors such as cyanide (Ragsdale and Ljungdahl, Arch. Microbiol. 139:361-365 (1984); Menon and Ragsdale, *Biochemistry* 36:8484-8494 (1996)). Assays for hydrogenase activity that directly measure $H_2$ generation or loss with GC or $H_2$ electrodes can also be applied (Der et al., Anal. Biochem. 150:481-486 (1985)). The ability of the engineered *E. coli* strain to produce 1,4-butanediol is confirmed using HPLC, gas chromatography-mass spectrometry (GCMS), liquid chromatography-mass spectrometry (LCMS), or other suitable analytical methods using routine procedures well known in the art.

Microbial strains engineered to have a functional 1,4-butanediol synthesis and reducing equivalent extraction pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,4-butanediol. One modeling method is the bilevel optimization approach, OptKnock (Burgard et al., *Biotechnol. Bioengineer.* 84:647-657 (2003)), which is applied to select gene knockouts that collectively result in better production of 1,4-butanediol. Adaptive evolution also can be used to generate better producers of, for example, the succinyl-CoA intermediate of the 1,4-butanediol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 1,4-butanediol producer to further increase production.

Initial conditions employ strictly anaerobically grown cells provided with exogenous glucose as a carbon and energy source. Alternatively, or in addition to glucose, nitrate can be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et al., *Mol. Microbiol.* 47:793-805 (2003). Oxygen can also be provided as long as its intracellular levels are maintained below any inhibition threshold of the engineered enzymes. Anaerobic conditions are maintained by first sparging the medium with nitrogen, then CO and $H_2$, and finally sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art.

For large-scale production of 1,4-butanediol, the above organism is cultured in a fermenter using a medium known in the art to support growth of the organism under anaerobic or microaerobic conditions. Fermentations are performed in either a batch, fed-batch or continuous manner. Previous studies have shown that a rate-limiting step to syngas utilization can be the mass transfer of CO into the liquid phase (Do et al., *Biotechnol. Bioeng.* 97:279-286 (2007)). This is largely due to the relatively low solubility of CO in water. Continuously gas-sparged fermentations (i.e., with $H_2$ and CO) are performed in controlled fermenters with continuous off-gas analysis by mass spectrometry and periodic liquid sampling and analysis by GC and HPLC. 1,4-butanediol production, as well as detailed metabolite production, are quantified via GCMS or LCMS. All piping in these systems is glass or metal to maintain anaerobic conditions. The gas sparging is done using glass fits to decrease bubble size, maximize the surface to volume ratio, and improve mass transfer. Various sparging rates are tested, ranging from about 0.1 to 1 vvm (vapor volumes per minute). Agitation and impeller design are examined. We will also test methods such as moderate overpressure at 1.5 atm to improve mass transfer (Najafpour and Younesi, 38(1-2):223-228 (2006)). To obtain accurate measurements of gas uptake rates, periodic challenges are performed in which the gas flow is temporarily stopped, and the gas phase composition is monitored as a function of time. We also will evaluate other high mass transfer systems such as bubble columns, which allow hydrostatic overpressure and longer bubble retention times. Fermentation conditions are optimized to further improve the productivity and titer of the 1,4-butanediol producing strains. The data generated from fermentations are analyzed to discern the impact of each parameter on cell density and alcohol yield. The pH of the culture impacts the growth of the host and may also affect the bioavailability of some of the trace elements. Other parameters to be optimized include temperature, trace metals innoculum size, ionic strength and duration of fermentation.

Example XI

Engineering the Reverse TCA Cycle into an Isopropanol-Producing Organism

This example describes the generation of a microbial organism that has been engineered to produce isopropanol from glucose and $CO_2$. The organism contains a functional reverse TCA cycle and a pathway for producing isopropanol from acetyl-CoA as shown in FIG. 2b. Engineering a functional pathway to produce isopropanol from glucose and $CO_2$ at high yields will require the optimized expression of a combination of exogenous and/or endogenous genes.

Escherichia coli is used as a target organism for engineering an isopropanol-producing pathway that utilizes enzymes from the reduced TCA cycle to assimilate $CO_2$. E. coli provides a good host for generating a non-naturally occurring microorganism capable of producing isopropanol. E. coli is amenable to genetic manipulation and is known to be capable of producing various products, like ethanol, acetic acid, formic acid, lactic acid, and succinic acid, effectively under anaerobic or microaerobic conditions. Engineering a functional pathway to produce isopropanol from glucose and $CO_2$ at high yields will require the optimized expression of a combination of exogenous and/or endogenous genes.

To generate an E. coli strain engineered to produce isopropanol, nucleic acids encoding the enzymes utilized in the isopropanol pathway from acetyl-CoA are expressed in E. coli using well known molecular biology techniques (see, for example, Sambrook, supra, 2001; Ausubel supra, 1999; Roberts et al., supra, 1989). In particular, an E. coli strain is engineered to produce isopropanol from acetyl-CoA via the route outlined in Figure XX. Conversion of acetyl-CoA to acetoacetyl-CoA is catalyzed by acetoacetyl-CoA thiolase, an enzyme native to E. coli encoded by atoB (NP_416728). For the first stage of pathway construction, genes encoding enzymes to transform acetoacetyl-CoA to isopropanol are assembled onto a vector. In particular, the genes ctfAB (NP_149326.1 and NP_149327.1), adc (NP_149328.1), and adh (AAA23199.2) encoding acetoacetyl-CoA-transferase, acetoacetate decarboxylase and isopropanol dehydrogenase, respectively, are cloned into the pZE13 vector (Expressys, Ruelzheim, Germany), under the control of the PA1/lacO promoter. The vector is transformed into E. coli strain MG1655 to express the proteins and enzymes required for isopropanol synthesis from acetoacetyl-CoA.

The resulting genetically engineered organism is cultured in glucose containing medium following procedures well known in the art (see, for example, Sambrook et al., supra, 2001). The expression of isopropanol pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to produce isopropanol through this pathway is confirmed using HPLC, gas chromatography-mass spectrometry (GCMS) or liquid chromatography-mass spectrometry (LCMS).

Microbial strains engineered to have a functional isopropanol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers. After successful demonstration of enhanced isopropanol production via the activities of the exogenous enzymes, the genes encoding these enzymes are inserted into the chromosome of a wild type E. coli host using methods known in the art. Such methods include, for example, sequential single crossover (Gay et al., J. Bacteriol. 153:1424-1431 (1983) and Red/ET methods from GeneBridges (Zhang et al. (2001). Chromosomal insertion provides several advantages over a plasmid-based system, including greater stability and the ability to co-localize expression of pathway genes.

The isopropanol-overproducing host strain is further engineered to assimilate $CO_2$ via the reductive TCA cycle as shown in FIG. 2B. Many of the native E. coli enzymes are capable of operating in the reductive direction including aconitase, isocitrate dehydrogenase, succinyl-CoA synthetase, fumarate reductase, fumarase and malate dehydrogenase. To generate a strain with a functional RTCA cycle, nucleic acids encoding alpha-ketoglutarate synthase, pyruvate:ferredoxin oxidoreductase, ATP-citrate synthase, ferredoxin and ferredoxin:$NADP^+$ reductase are expressed in the isopropanol-producing host using well known molecular biology techniques (see, for example, Sambrook, supra, 2001; Ausubel supra, 1999; Roberts et al., supra, 1989).

In particular, the korAB (BAB21494 and BAB21495), por (YP_428946.1) genes encoding the alpha-ketoglutarate synthase and pyruvate:ferredoxin oxidoreductase, respectively, are cloned into the pZE13 vector (Expressys, Ruelzheim, Germany), under the control of the PA1/lacO promoter. This plasmid is then transformed into a host strain containing lacI$^Q$, which allows inducible expression by addition of isopropyl-beta-D-1-thiogalactopyranoside (IPTG). The genes aclAB (AAM72321.1 and AAM72322.1), fdx1 (BAE02673.1) and HP1164 (NP_207955.1) encoding ATP-citrate synthase, ferredoxin and ferredoxin:$NADP^+$ reductase, respectively, are cloned into the pZA33 vector (Expressys, Ruelzheim, Germany) under the PA1/lacO promoter. The two sets of plasmids are transformed into the isopropanol-producing E. coli strain, described above, to express the proteins and enzymes required for $CO_2$ assimilation to acetyl-CoA, and subsequently isopropanol, via the reductive TCA cycle.

The resulting genetically engineered organism is cultured in glucose-containing medium following procedures well known in the art (see, for example, Sambrook et al., supra, 2001). The expression of reductive TCA cycle genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to assimilate $CO_2$ through this pathway is confirmed using $^{13}C$ labeled bicarbonate, HPLC, gas chromatography-mass spectrometry (GCMS) or liquid chromatography-mass spectrometry (LCMS).

Microbial strains engineered to have a functional reductive TCA pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type E. coli host using methods known in the art. Such methods include, for example, sequential single crossover ((Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., *Biotechnol. Bioengineer.* 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, *Nat. Genet.* 36:1056-1058 (2004); Alper et al., *Science* 314: 1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example XII

Introducing the Syngas Utilization Pathway into an Isopropanol Producing Organism This example describes the generation of a microbial organism that has been engineered to produce isopropanol from glucose and $CO_2$. The organism contains a functional Wood Ljungdahl pathway for fixing carbon as shown in FIG. 4A and a pathway for producing isopropanol from acetyl-CoA as shown in FIG. 1B.

*Escherichia coli* is used as a target organism for engineering an isopropanol-producing pathway that utilizes enzymes from the Wood ljungdahl pathway to fix $CO_2$. *E. coli* provides a good host for generating a non-naturally occurring microorganism capable of producing isopropanol. *E. coli* is amenable to genetic manipulation and is known to be capable of producing various products, like ethanol, acetic acid, formic acid, lactic acid, and succinic acid, effectively under anaerobic or microaerobic conditions. Engineering a functional pathway to produce isopropanol from glucose and $CO_2$ at high yields will require the optimized expression of a combination of exogenous and/or endogenous genes.

To generate an *E. coli* strain engineered to produce isopropanol, nucleic acids encoding the enzymes utilized in the isopropanol pathway from acetyl-CoA are expressed in *E. coli* using well known molecular biology techniques (see, for example, Sambrook, supra, 2001; Ausubel supra, 1999; Roberts et al., supra, 1989). In particular, an *E. coli* strain is engineered to produce isopropanol from acetyl-CoA via the route outlined in FIG. 1B. Conversion of acetyl-CoA to acetoacetyl-CoA is catalyzed by acetoacetyl-CoA thiolase, an enzyme native to *E. coli* encoded by atoB (NP_416728). For the first stage of pathway construction, genes encoding enzymes to transform acetoacetyl-CoA to isopropanol are assembled onto a vector. In particular, the genes ctfAB (NP_149326.1 and NP_149327.1), adc (NP_149328.1), and adh (AAA23199.2) encoding acetoacetyl-CoA-transferase, acetoacetate decarboxylase and isopropanol dehydrogenase, respectively, are cloned into the pZE13 vector (Expressys, Ruelzheim, Germany), under the control of the PA1/lacO promoter. The vector is transformed into *E. coli* strain MG1655 to express the proteins and enzymes required for isopropanol synthesis from acetoacetyl-CoA.

The resulting genetically engineered organism is cultured in glucose containing medium following procedures well known in the art (see, for example, Sambrook et al., supra, 2001). The expression of isopropanol pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce isopropanol through this pathway is confirmed using HPLC, gas chromatography-mass spectrometry (GCMS) or liquid chromatography-mass spectrometry (LCMS).

Microbial strains engineered to have a functional isopropanol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers. After successful demonstration of enhanced isopropanol production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

The isopropanol-overproducing host strain is further engineered to assimilate carbon via the Wood Ljungdahl pathway as shown in FIG. 4A. The enzymes required to be active are formate dehydrogenase, Formyltetrahydrofolate synthetase, Methenyltetrahydrofolate cyclohydrolase, Methylenetetrahydrofolate dehydrogenase, Methylenetetrahydrofolate reductase, Methyltetrahydrofolate:corrinoid protein methyltransferase (AcsE), Corrinoid iron-sulfur protein (AcsD), Nickel-protein assembly protein (AcsF & CooC), Ferredoxin (Orf7), Acetyl-CoA synthase (AcsB & AcsC), Carbon monoxide dehydrogenase (AcsA), Pyruvate formate lyase (Pfl), and Pyruvate ferredoxin oxidoreductase (Por) or pyruvate dehydrogenase (PDH).

While *E. coli* naturally possesses the capability for some of the required transformations in the methyl branch (i.e., methenyltetrahydrofolate cyclohydrolase, methylenetetrahydrofolate dehydrogenase, methylenetetrahydrofolate reductase), it is thought that the methyl branch enzymes from acetogens may have significantly higher (50-100×) specific activities than those from non-acetogens (Morton et al., *Genetics and Molecular Biology of Anaerobic Bacteria*, M. Sebald, Ed., New York: Springer Verlag pp. 389-406 (1992)). Formate dehydrogenase also appears to be specialized for anaerobic conditions (Ljungdahl and Andreesen, *FEBS Lett.* 54:279-282 (1975)). Therefore, various non-native versions of each of these are expressed in the strain of *E. coli* capable of methanol and syngas utilization. For example, Moth_2312 and Moth_2314 (Accession numbers YP_431142 and YP_431144 respectively) encoding the alpha and beta subunits of formate dehydrogenase, Moth_0109 (GenBank No: YP_428991.1) encoding for formyltetrahydrofolate synthetase, Moth_1516 (Accession no: YP_430368.1) encoding for methenyltetrahydrofolate cyclohydrolase and methylenetetrahydrofolate dehydrogenase, and Moth_1191 (Accession no: YP_430048.1) encoding for methylenetetrahydrofolate reductase will be cloned and combined into an expression vector designed to express them as a set. Initially, a high or medium copy number vector will be chosen (using ColE1 or P15A replicons). The first promoter to be tested is a strongly constitutive promoter such as lambda pL or an IPTG-inducible version of this, pL-lacO (Lutz and Bujard, *Nucleic Acids Res.* 25:1203-1210 (1997)). To make an artificial operon, one 5' terminal promoter is placed upstream of the set of genes and each gene receives a consensus rbs element. The order of genes is based on the natural order whenever possible. Ultimately, the genes are integrated into the *E. coli* chromosome. Enzyme assays are performed as described in (Ljungdahl and Andreesen, supra; Yamamoto et al., *J. Biol. Chem.* 258:1826-1832 (1983); Lovell et al., *Arch. Microbiol.* 149:280-285 (1988); de Mata and Rabinowitz, *J. Biol. Chem.* 255:2569-2577 (1980); D'Ari and Rabinowitz, *J. Biol. Chem.* 266:25953-23958 (1991); Clark and Ljungdahl, *J. Biol. Chem.* 259:10845-10849 (1984); Clark and Ljungdahl, *Methods Enzymol.* 122:392-399 (1986)).

Expression of acetyl CoA synthase/CO dehydrogenase in a foreign host requires introducing many, if not all, of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes required for carbon-monoxide dehydrogenase/acetyl-CoA synthase activity typically reside in a limited region of the native genome that may be an extended operon (Ragsdale, *Crit. Rev. Biochem. Mol. Biol.* 39:165-195 (2004); Morton et al., *J. Biol. Chem.* 266:23824-23828 (1991); Roberts et al., *Proc. Nat. Acad. Sci. U.S.A.* 86:32-36 (1989)). Each of the genes in this operon from the acetogen, *M. thermoacetica*, has already been cloned and expressed actively in *E. coli* (Morton et al., *J. Biol. Chem.* 266:23824-23828 (1991); Roberts et al., supra; Lu et al., *J. Biol. Chem.* 268:5605-5614 (1993)). The protein sequences of these genes can be identified by the following GenBank accession numbers.

| Protein | GenBank ID | Organism |
|---|---|---|
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

Using standard PCR methods, the entire ACS/CODH operons are assembled into low or medium copy number vectors such as pZA33-S (P15A-based) or pZS13-S (pSC101-based). The structures and sequences of the cloned genes are confirmed. Expression is monitored via protein gel electrophoresis of whole-cell lysates grown under strictly anaerobic conditions with the requisite metals (Ni, Zn, Fe) and coenzyme $B_{12}$ provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products—most of which interact with each other.

*E. coli* possesses native pyruvate formate lyase activity. The resulting genetically engineered organism is cultured in glucose-containing medium following procedures well known in the art (see, for example, Sambrook et al., supra, 2001). The expression of the methyl/carbonyl branch genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to assimilate carbon through this pathway is confirmed using $^{13}C$ labeled bicarbonate, HPLC, gas chromatography-mass spectrometry (GCMS) or liquid chromatography-mass spectrometry (LCMS). Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Microbial strains engineered to have a functional W-L pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., *Biotechnol. Bioengineer.* 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, *Nat. Genet.* 36:1056-1058 (2004); Alper et al., *Science* 314: 1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example XIII

Engineering the Methanol Utilization Pathway into an Isopropanol Producing Organism This Example shows how an organism is engineered to utilize methanol in an isopropanol producing organism.

The first step in the cloning and expression process is to express in *E. coli* the minimal set of genes (e.g., MtaA, MtaB, and MtaC) necessary to produce Methyl-THF from methanol (FIG. 4B). These methyltransferase activities require Coenzyme $B_{12}$ (cobalamin) as a cofactor. In *Moorella thermoacetica*, a cascade of methyltransferase proteins mediate incorporation of methanol derived methyl groups into the acetyl-CoA synthase pathway. Recent work (Das et al., *Proteins* 67:167-176 (2007)) suggests that MtaABC are encoded by Moth_1208-09 and Moth_2346. These genes are cloned via proof-reading PCR and linked together for expression in a high-copy number vector such as pZE22-S under control of the repressible PA1-lacO1 promoter (Lutz and Bujard, *Nucleic Acids Res.* 25:1203-1210 (1997). Cloned genes are verified by PCR and or restriction enzyme mapping to demonstrate construction and insertion of the 3-gene set into the expression vector. DNA sequencing of the presumptive clones is carried out to confirm the expected sequences of each gene. Once confirmed, the final construct is expressed in *E. coli* K-12 (MG1655) cells by addition of IPTG inducer between 0.05 and 1 mM final concentration. Expression of the cloned genes is monitored using SDS-PAGE of whole cell extracts. To optimize levels of soluble vs. pellet (potentially inclusion body origin) protein, the affect of titration of the promoter on these levels can be examined. If no acceptable expression is obtained, higher or lower copy number vectors or variants in promoter strength are tested.

To determine if expression of the MtaABC proteins from *M. thermoacetica* confers upon *E. coli* the ability to transfer methyl groups from methanol to tetrahydrofolate (THF) the recombinant strain is fed methanol at various concentrations. Activity of the methyltransferase system is assayed anaerobically as described for vanillate as a methyl source in *M. thermoacetica* (Naidu and Ragsdale, *J. Bacteriol.* 183:3276-3281 (2001) or for *Methanosarcina barkeri* methanol methyltransferase (Sauer et al., *Eur. J. Biochem.* 243:670-677 (1997); Tallant et al., *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996)). For a positive control, *M. thermoacetica* cells are cultured in parallel and assayed anaerobically to confirm endogenous methyltransferase activity. Demonstration of dependence on exogenously added coenzyme $B_{12}$ confirms methanol:corrinoid methyltransferase activity in *E. coli*.

Once methyltransferase expression is achieved, further work is performed towards optimizing the expression. Titrating the promoter in the expression vector enables the testing of a range of expression levels. This is then used as a guide towards the expression required in single-copy, or enables the determination of whether or not a single-copy of these genes allows sufficient expression. If so, the methyltransferase genes are integrated into the chromosome as a single, synthetic operon. This entails targeted integration using RecET-based 'recombineering' (Angrand et al., *Nucleic Acids Res.* 27:e16 (1999); Muyrers et al., *Nucleic Acids Res.* 27:1555-1557 (1999); Zhang et al., *Nat. Genet.* 20:123-128 (1998)). A potential issue with RecET-based integration of a cassette and removal of a FRT or loxP-bounded selectable marker by FLP or Cre is the production of a recombination scar at each integration site. While problems caused by this can be minimized by a number of methods, other means that do not leave genomic scars are available. The standard alternative, is to introduce the desired genes using integrative 'suicide' plasmids coupled to counter-selection such as that allowed by the *Bacillus* sacB gene (Link et al., *J. Bacteriol.* 179:6228-6237 (1997); in this way, markerless and scar less insertions at any location in the *E. coli* chromosome can be generated. The final goal is a strain of *E. coli* K-12 expressing methanol:corrinoid methyltransferase activity under an inducible promoter and in single copy (chromosomally integrated).

Expression of acetyl CoA synthase/CO dehydrogenase in a foreign host requires introducing many, if not all, of the following proteins and their corresponding activities. Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes required for carbon-monoxide dehydrogenase/acetyl-CoA synthase activity typically reside in a limited region of the native genome that may be an extended operon (Ragsdale, *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989)).

Each of the genes in this operon from the acetogen, *M. thermoacetica*, has already been cloned and expressed actively in *E. coli* (Morton et al., *J. Biol. Chem.* 266:23824-23828 (1991); Roberts et al., *Proc. Natl. Acad. Sci. U.S.A.* 86:32-36 (1989); Lu et al., *J. Biol. Chem.* 268:5605-5614 (1993)). The protein sequences of these genes can be identified by the following GenBank accession numbers.

| Protein | GenBank ID | Organism |
| --- | --- | --- |
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

Using standard PCR methods, the entire ACS/CODH operons are assembled into low or medium copy number vectors such as pZA33-S (P15A-based) or pZS13-S (pSC101-based). The structures and sequences of the cloned genes are confirmed. Expression is monitored via protein gel electrophoresis of whole-cell lysates grown under strictly anaerobic conditions with the requisite metals (Ni, Zn, Fe) and coenzyme $B_{12}$ provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products—most of which interact with each other.

*E. coli* possesses native pyruvate formate lyase activity. The resulting genetically engineered organism is cultured in glucose-containing medium following procedures well known in the art (see, for example, Sambrook et al., supra, 2001). The expression of the exogenous genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to assimilate carbon through this pathway is confirmed using $^{13}C$ labeled bicarbonate, HPLC, gas chromatography-mass spectrometry (GCMS) or liquid chromatography-mass spectrometry (LCMS). Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Microbial strains engineered to have a functional methanol utilization pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., *Biotechnol. Bioengineer.* 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, *Nat. Genet.* 36:1056-1058 (2004); Alper et al., *Science* 314: 1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example XIV

Engineering Cobalamin Synthesis into an Organism

This example describes engineering de novo $B_{12}$ synthetic capability into an organism. One enzyme of the Wood-Ljungdahl pathway, ACS/CODH, uses cobalamin (vitamin $B_{12}$) to function. $B_{12}$ is synthesized de novo in some organisms but must be supplied exogenously to others. Still other organisms such as *S. cerevisiae* lack the ability to efficiently uptake $B_{12}$.

$B_{12}$ biosynthetic pathways have been characterized in several organisms including *Salmonella typhimurium* LT2 (Roth et al., *J. Bacteriol.* 175:3303-3316 (1993), *Lactobacillus reuteri* CRL1098 (Santos et al., *Microbiology* 154:81-93 (2008) and *Bacillus megaterium* (Brey et al., *J. Bacteriol.* 167:623-

630 (1986)). Bacterial $B_{12}$ biosynthesis pathways involve 20-30 genes clustered together in one or more operons. Two cobalamin biosynthesis pathways: late-insertion (aerobic only) and early-insertion (anaerobic) have been described (Scott, A. I., *J. Org. Chem.* 68:2529-2539 (2003)). The final products of the biosynthesis of vitamin $B_{12}$ are 5'-deoxyadenosylcobalamin (coenzyme $B_{12}$) and methylcobalamin (MeCbl). Vitamin $B_{12}$ is defined as cyanocobalamin (CNCbl) which is the form commonly prepared in industry. In this example, $B_{12}$ refers to all three analogous molecules.

The anaerobic cobalamin biosynthesis pathway has been well-characterized in *Salmonella typhimurium* LT2 (Roth et al., *J. Bacteriol.* 175:3303-3316 (1993)). Pathway genes are clustered in a large operon termed the cob operon. A plasmid containing the following 20 genes from the cob operon (pAR8827) was transformed into *E. coli* and conferred the ability to synthesize cobalamin de novo (Raux et al., *J. Bacteriol.* 178:753-767 (1996)). To further improve yield of the cobyric acid precursor, the known regulatory elements of cbiA were removed and the RBS altered. The genes and corresponding GenBank identifiers and gi numbers are listed below.

| Protein | GenBank ID | GI Number | Organism |
| --- | --- | --- | --- |
| cysG | NP_462380.1 | 16766765 | *Salmonella typhimurium* |
| cbiK | NP_460970.1 | 16765355 | *Salmonella typhimurium* |
| cbiL | NP_460969.1 | 16765354 | *Salmonella typhimurium* |
| cbiH | NP_460972.1 | 16765357 | *Salmonella typhimurium* |
| cbiF | NP_460974.1 | 16765359 | *Salmonella typhimurium* |
| cbiG | NP_460973.1 | 16765358 | *Salmonella typhimurium* |
| cbiD | NP_460977.1 | 16765362 | *Salmonella typhimurium* |
| cbiJ | NP_460971.1 | 16765356 | *Salmonella typhimurium* |
| cbiE | NP_460976.1 | 16765361 | *Salmonella typhimurium* |
| cbiT | NP_460975.1 | 16765360 | *Salmonella typhimurium* |
| cbiC | NP_460978.1 | 16765363 | *Salmonella typhimurium* |
| cbiA | NP_460980.1 | 16765365 | *Salmonella typhimurium* |
| fldA | NP_459679.1 | 16764064 | *Salmonella typhimurium* |
| cobA | P31570.1 | 399274 | *Salmonella typhimurium* |
| cbiP | AAA27268.1 | 154436 | *Salmonella typhimurium* |
| cbiB | Q05600.1 | 543942 | *Salmonella typhimurium* |
| cobU | NP_460963.1 | 16765348 | *Salmonella typhimurium* |
| cobT | NP_460961.1 | 16765346 | *Salmonella typhimurium* |
| Cobs | AAA27270.1 | 154438 | *Salmonella typhimurium* |
| cobC | NP_459635.1 | 16764020 | *Salmonella typhimurium* |
| cysG | NP_462380.1 | 16766765 | *Salmonella typhimurium* |

Some organisms unable to synthesize $B_{12}$ de novo are able to catalyze some steps of the pathway. *E. coli*, for example, is unable to synthesize the corrin ring structure but encodes proteins that catalyze several reactions in the pathway (Raux et al., *J. Bacteriol.* 178:753-767 (1996)). The cysG gene encodes a functional CysG, a multifunctional enzyme that converts uroporphyrinogen III to precorrin-2 (Warren et al. 1990; Woodcock et al. 1998). The proteins encoded by cobTSU transform cobinamide to cobalamin and introduce the 5'-deoxyadenosyl group (Raux et al., *J. Bacteriol.* 178: 753-767 (1996)).

| Protein | GenBank ID | GI Number | Organism |
| --- | --- | --- | --- |
| cobT | NP_416495.1 | 16129932 | *Escherichia coli* K12 sp. |
| cobs | NP_416496.1 | 16129933 | *Escherichia coli* K12 sp. |
| cobU | NP_416497.1 | 16129934 | *Escherichia coli* K12 sp. |
| cysG | NP_417827.1 | 16131246 | *Escherichia coli* K12 sp. |

*S. cerevisiae* is not able to synthesize $B_{12}$ de novo, nor is it able to uptake the vitamin at detectable levels. However, the *S. cerevisiae* genome encodes two proteins, Met1p and Met8p, that catalyze several $B_{12}$ pathway reactions. Met1p is analogous to the uroporphyrinogen III transmethylase CysG of *S. typhimurium*, which catalyzes the first step of B12 biosynthesis from uroporphyrinogen 111 (Raux et al., *Biochem. J.* 338(Pt 3): 701-708 (1999)). The Met8p protein is a bifunctional protein with uroporphyrinogen III transmethylase activity and cobaltochelatase activity analogous to the CysG of *B. megaterium* (Raux et al., supra (1999)).

| Protein | GenBank ID | GI Number | Organism |
| --- | --- | --- | --- |
| Met1p | NP_012995.1 | 6322922 | *Saccharomyces cerevisiae* |
| Met8p | NP_009772.1 | 6319690 | *Saccharomyces cerevisiae* |

Any or all of these genes can be introduced into an organism deficient or inefficient in one or more components of cobalamin synthesis to enable or increase the efficiency of cobalamin synthesis.

Example XV

Engineering Enhanced Cobalamin Uptake Capability in an Organism

This example describes engineering $B_{12}$ uptake capability into a host organism. $B_{12}$ uptake requires a specific transport system (Sennett et al., *Annu. Rev. Biochem.* 50:1053-1086 (1981)).

The $B_{12}$ transport system of *E. coli* has been extensively studied. High-affinity transport across the outer membrane is calcium-dependent and mediated by a 66 kDa outer membrane porin, BtuB (Heller et al., *J. Bacteria* 161:896-903 (1985)). BtuB interacts with the TonB energy transducing system (TonB-ExbB-ExbD), facilitating energy-dependent translocation and binding to periplasmic binding protein BtuF (Letain and Postle, 1997; Chimento et al. 2003). Transport across the inner membrane is facilitated by an ABC type uptake system composed of BtuF, BtuD (ATP binding component) and BtuC (permease) (Locher et al., *Science* 296: 1091-1098 (2002)). Crystal structures of the BtuCDF complex are available (Hvorup et al., *Science* 317:1387-1390 (2007); Locher et al. supra). An additional protein, BtuE, is coexpressed in the btuCED operon, but this protein is not required for B12 transport and its function is unknown (Rioux and Kadner, *Mol. Gen. Genet.* 217:301-308 (1989)). The btuCED operon is constitutively expressed. The GenBank identifiers and GI numbers of the genes associated with $B_{12}$ transport are listed below.

| Protein | GenBank ID | GI Number | Organism |
| --- | --- | --- | --- |
| btuB | NP_418401.1 | 16131804 | *Escherichia coli* K12 sp. MG1655 |
| btuC | NP_416226.1 | 16129667 | *Escherichia coli* K12 sp. MG1655 |
| btuD | NP_416224.1 | 16129665 | *Escherichia coli* K12 sp. MG1655 |
| btuF | NP_414700.1 | 16128151 | *Escherichia coli* K12 sp. MG1655 |
| tonB | NP_415768.1 | 16129213 | *Escherichia coli* K12 sp. MG1655 |
| exbB | NP_417479.1 | 16130904 | *Escherichia coli* K12 sp. MG1655 |

| Protein | GenBank ID | GI Number | Organism |
| --- | --- | --- | --- |
| exbD | NP_417478.1 | 16130903 | Escherichia coli K12 sp. MG1655 |

The $B_{12}$ uptake capability of an organism can be further improved by overexpressing genes encoding the requisite transport proteins, and reducing or eliminating negative regulatory control. Overexpressing the btuBCDF genes leads to increased binding of B12 to membranes and increased rate of uptake into cells. Another strategy is to remove regulatory control. The btuB mRNA translation is directly repressed by B12 at the 5' UTR (Nahvi et al., Chem. Biol. 9:1043 (2002)). This interaction may induce mRNA folding to block ribosome access to the translational start. Mutation or elimination of the $B_{12}$ binding site removes inhibition and improves the efficiency of $B_{12}$ uptake (U.S. Pat. No. 6,432,686 (2002)). These strategies were successfully employed to improve $B_{12}$ uptake capability in 1,3-PDO producing microorganisms (WO/1999/058686) and (U.S. Pat. No. 6,432,686 (2002)). A recent patent application describes improving the efficiency of $B_{12}$ uptake (WO/2008/152016) by deleting negative regulatory proteins such as C. glutamicum btuR2.

*S. typhimurium* possesses both high and low affinity transporters for $B_{12}$. The high affinity transporter is encoded by btuB (Rioux and Kadner, *J. Bacteriol.* 171:2986-2993 (1989)). Like *E. coli* transport across the periplasmic membrane is predicted to occur via an ABC transport system, although this has not been characterized to date. The $B_{12}$ binding protein is encoded by btuD and btuE, and btuC is predicted to encode the permease.

| Protein | GenBank ID | GI Number | Organism |
| --- | --- | --- | --- |
| btuB | AAA27031.1 | 153891 | Salmonella typhimurium LT2 |
| btuC | NP_460306.1 | 16764691 | Salmonella typhimurium LT2 |
| btuD | NP_460308.1 | 16764693 | Salmonella typhimurium LT2 |
| btuE | AAL20266.1 | 16419860 | Salmonella typhimurium LT2 |

Any or all of these genes can be introduced into an organism deficient in one or more components of cobalamin uptake to enable or increase the efficiency cobalamin uptake.

Method for quantifying $B_{12}$ in the culture medium. To quantify the amount of $B_{12}$ in the culture medium, cell free samples are run on HPLC. Cobalamin quantification is achieved by comparing peak area ratios at 278 nm and 361 num with standards, then applying peak areas to standard curves of cobalamin.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring microbial organism having a reductive TCA pathway and comprising three exogenous nucleic acids that encode an ATP-citrate lyase, a fumarate reductase, and an alpha-ketoglutarate: ferredoxin oxidoreductase.

2. A non-naturally occurring microbial organism having a reductive TCA pathway and comprising three exogenous nucleic acids that encode a citrate lyase, a fumarate reductase, and an alpha-ketogtutarate:ferredoxin oxidoreductase.

3. The non-naturally occurring microbial organism of claim 1 or claim 2, further comprising an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H: ferredoxin oxidoreductase, ferredoxin, and combinations thereof.

4. The non-naturally occurring microbial organism of claim 1 or claim 2, further comprising a 1,3-butanediol pathway, said 1,3-butanediol pathway converting acetyl-CoA to 1,3-butanediol, wherein said 1,3-butanediol pathway comprises at least three enzymes selected from the group consisting of 1) Acetoacetyl-CoA thiotase (AtoB), 2) Acetoacetyl-CoA reductase (CoA-dependent, alcohol forming), 3) 3-oxobutyraldehyde reductase (aldehyde reducing), 4) 4-hydroxy,2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

5. The non-naturally occurring microbial organism of claim 1 or claim 2, further comprising a 1,4-butanediol pathway, said 1,4-butanediol pathway converting acetyl-CoA to 1,4-butanediol, wherein said 1,4-butanediol pathway comprises at least five enzymes selected from the group consisting of 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

6. The non-naturally occurring microbial organism of claim 1 or claim 2, further comprising a 4-hydroxybutyrate pathway, said 4-hydroxybutyrate pathway converting acetyl-CoA to 4-hydroxybutyrate, wherein said 4-hydroxybutyrate pathway comprises at least five enzymes selected from the group consisting of 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

7. The non-naturally occurring microbial organism of claim 1 or claim 2, further comprising an exogenous nucleic acid encoding an enzyme selected from carbon monoxide dehydrogenase, hydrogenase, NAD(P)H:ferredoxin oxidoreductase, ferredoxin, and combinations thereof.

8. The non-naturally occurring microbial organism of claim 7, wherein said microbial organism utilizes a carbon feedstock selected from CO, $CO_2$ and $H_2$, synthesis gas comprising CO and $H_2$, and synthesis gas comprising CO, $CO_2$, and $H_2$.

* * * * *